US010668072B2

(12) United States Patent
Reynolds et al.

(10) Patent No.: US 10,668,072 B2
(45) Date of Patent: *Jun. 2, 2020

(54) LIQUID FORMULATIONS OF (S)-N-(5-((R)-2-(2,5-DIFLUOROPHENYL)-PYRROLIDIN-1-YL)-PYRAZOLO[1,5-A]PYRIMIDIN-3-YL)-3-HYDROXYPYRROLIDINE-1-CARBOXAMIDE

(71) Applicant: Loxo Oncology, Inc., Stamford, CT (US)

(72) Inventors: Mark Reynolds, Stamford, CT (US); Steven A. Smith, Stamford, CT (US)

(73) Assignee: Loxo Oncology, Inc., Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/199,739

(22) Filed: Nov. 26, 2018

(65) Prior Publication Data

US 2019/0216814 A1    Jul. 18, 2019

Related U.S. Application Data

(63) Continuation of application No. 15/622,544, filed on Jun. 14, 2017, now Pat. No. 10,137,127, which is a continuation of application No. PCT/US2017/025939, filed on Apr. 4, 2017.

(60) Provisional application No. 62/329,561, filed on Apr. 29, 2016, provisional application No. 62/323,452, filed on Apr. 15, 2016, provisional application No. 62/318,041, filed on Apr. 4, 2016.

(51) Int. Cl.
*A61K 31/519* (2006.01)
*A61K 47/12* (2006.01)
*A61K 47/40* (2006.01)

(52) U.S. Cl.
CPC ............ *A61K 31/519* (2013.01); *A61K 47/12* (2013.01); *A61K 47/40* (2013.01)

(58) Field of Classification Search
None
See application file for complete search history.

(56) References Cited

U.S. PATENT DOCUMENTS

| | | | |
|---|---|---|---|
| 5,430,021 A | 7/1995 | Rudnic et al. |
| 5,760,068 A | 6/1998 | Talley et al. |
| 5,844,092 A | 12/1998 | Presta et al. |
| 5,877,016 A | 3/1999 | Presta et al. |
| 5,910,574 A | 6/1999 | Presta et al. |
| 6,025,166 A | 2/2000 | Presta et al. |
| 6,027,927 A | 2/2000 | Presta et al. |
| 6,153,189 A | 11/2000 | Presta et al. |
| 6,534,085 B1 | 3/2003 | Zeligs |
| 7,384,632 B2 | 6/2008 | Devaux et al. |
| 7,491,794 B2 | 2/2009 | Blatt et al. |
| 7,514,446 B2 | 4/2009 | Davis-Ward et al. |
| 7,550,470 B2 | 6/2009 | Fraley |
| 7,612,067 B2 | 11/2009 | Barbosa et al. |
| 7,615,383 B2 | 11/2009 | Devaux et al. |
| 7,863,289 B2 | 1/2011 | Spevak et al. |
| 8,026,247 B2 | 9/2011 | Bold et al. |
| 8,106,167 B2 | 1/2012 | Wild, Jr. et al. |
| 8,114,989 B2 | 2/2012 | Wang et al. |
| 8,119,592 B2 | 2/2012 | Beigelman et al. |
| 8,148,107 B2 | 4/2012 | Macdonald et al. |
| 8,299,021 B2 | 10/2012 | Blatt et al. |
| 8,299,057 B2 | 10/2012 | Lombardi Borgia et al. |
| 8,338,417 B2 | 12/2012 | Li et al. |
| 8,399,442 B2 | 3/2013 | Berdini et al. |
| 8,450,322 B2 | 5/2013 | Andrews et al. |
| 8,501,756 B2 | 8/2013 | Artman, III et al. |
| 8,513,263 B2 | 8/2013 | Haas et al. |
| 8,552,002 B2 | 10/2013 | Ding et al. |
| 8,568,998 B2 | 10/2013 | Mani |
| 8,637,256 B2 | 1/2014 | Ernst |
| 8,637,516 B2 | 1/2014 | Fan et al. |
| 8,642,035 B2 | 2/2014 | Luehrsen |
| 8,673,347 B2 | 3/2014 | Traversa et al. |
| 8,691,221 B2 | 4/2014 | Pavone et al. |
| 8,791,123 B2 | 7/2014 | Allen et al. |
| 8,815,901 B2 | 8/2014 | Furet et al. |
| 8,865,698 B2 | 10/2014 | Haas et al. |
| 8,911,734 B2 | 12/2014 | Latham et al. |
| 8,912,194 B2 | 12/2014 | Ciomei |
| 8,912,204 B2 | 12/2014 | Ibrahim et al. |
| 8,933,084 B2 | 1/2015 | Andrews |
| 8,937,071 B2 | 1/2015 | Eidam et al. |
| 8,946,226 B2 | 2/2015 | Ciomei et al. |

(Continued)

FOREIGN PATENT DOCUMENTS

| AU | 2015/101722 | 5/2016 |
|---|---|---|
| CN | 1938311 | 3/2007 |

(Continued)

OTHER PUBLICATIONS

Adriaenssens et al., "Nerve Growth Factor is a Potential Therapeutic Target in Breast Cancer," Cancer Res., 2008, 68(2):346-351.
Agaram et al., "Recurrent NTRK1 gene fusions define a novel subset of locally aggressive lipofibromatosis-like neural tumors," Am. J. Surg. Pathol, Oct. 2016, 40(10): 1407-1416.
Agaram, et al., "Abstract 33: NTRK1 Associated Gene Fusions in Pediatric Fibroblastic Myofibroglastic Neoplasms: A Molecular Study of 58 Cases," 105th Annual Meeting of the United States and Canadian Academy of Pathology, 2016, 12A.
Aisner et al., "ROS1 and ALK fusions in colorectal cancer, with evidence of intra-tumoral heterogeneity for molecular drivers.", Mal. Cancer Res., 12(1): 111-8, 2014.

(Continued)

*Primary Examiner* — Leslie A. Royds Draper
(74) *Attorney, Agent, or Firm* — Meunier Carlin & Curfman LLC

(57) ABSTRACT

A liquid formulation of (S)—N-(5-((R)-2-(2,5-difluorophenyl)pyrrolidin-1-yl)-pyrazolo[1,5-a]pyrimidin-3-yl)-3-hydroxypyrrolidine-1-carboxamide, pharmaceutically acceptable salts thereof, or a combination thereof and the use of the liquid formulation in the treatment of pain, cancer, inflammation, and certain infectious diseases are disclosed.

22 Claims, 13 Drawing Sheets

Specification includes a Sequence Listing.

(56) References Cited

U.S. PATENT DOCUMENTS

| | | |
|---|---|---|
| 9,006,256 B2 | 4/2015 | Matsui |
| 9,035,063 B2 | 5/2015 | Eidam et al. |
| 9,102,671 B2 | 8/2015 | Molteni et al. |
| 9,127,013 B2 | 9/2015 | Haas et al. |
| 9,187,489 B2 | 11/2015 | Takeda et al. |
| 9,227,975 B2 | 1/2016 | Andrews et al. |
| 9,242,977 B2 | 1/2016 | Takeuchi et al. |
| 9,260,437 B2 | 2/2016 | Ibrahim et al. |
| 9,273,051 B2 | 3/2016 | Chen et al. |
| 9,346,788 B2 | 5/2016 | Wu et al. |
| 9,447,104 B2 | 9/2016 | Haas et al. |
| 9,447,135 B2 | 9/2016 | Rohr et al. |
| 9,469,876 B2 | 10/2016 | Kuslich |
| 9,493,476 B2 | 11/2016 | Andrews et al. |
| 9,511,050 B2 | 12/2016 | Toretsky et al. |
| 9,670,207 B2 | 6/2017 | Sasmal et al. |
| 9,676,783 B2 | 6/2017 | Haas et al. |
| 9,682,979 B2 | 6/2017 | Allen et al. |
| 9,701,681 B2 | 6/2017 | Kim et al. |
| 9,718,822 B2 | 8/2017 | Andrews et al. |
| 9,750,744 B2 | 9/2017 | Andrews et al. |
| 9,782,400 B2 | 10/2017 | Yao et al. |
| 9,782,414 B2 | 10/2017 | Arrigo et al. |
| 9,782,415 B2 | 10/2017 | Allen et al. |
| 9,795,611 B2 | 10/2017 | Andrews et al. |
| 9,796,723 B2 | 10/2017 | Andrews et al. |
| 9,796,724 B2 | 10/2017 | Allen et al. |
| 9,840,519 B2 | 12/2017 | Andrews et al. |
| 9,902,741 B2 | 2/2018 | Andrews et al. |
| 1,000,578 A1 | 6/2018 | Haas et al. |
| 1,001,160 A1 | 7/2018 | Andrews et al. |
| 1,004,599 A1 | 8/2018 | Cox et al. |
| 1,004,709 A1 | 8/2018 | Haas et al. |
| 10,045,991 B2 * | 8/2018 | Cox .................. A61K 9/08 |
| 1,013,712 A1 | 11/2018 | Reynolds et al. |
| 10,137,127 B2 * | 11/2018 | Reynolds .............. A61K 47/12 |
| 1,017,286 A1 | 1/2019 | Arrigo et al. |
| 2005/0209195 A1 | 9/2005 | Menta et al. |
| 2006/0089362 A1 | 4/2006 | Seno et al. |
| 2006/0094699 A1 | 5/2006 | Kampen et al. |
| 2006/0128725 A1 | 6/2006 | Guzi et al. |
| 2006/0211696 A1 | 9/2006 | Hibi et al. |
| 2007/0025540 A1 | 2/2007 | Travis |
| 2007/0042941 A1 | 2/2007 | Hirashima et al. |
| 2007/0082900 A1 | 4/2007 | Guzi et al. |
| 2007/0082902 A1 | 4/2007 | Paruch et al. |
| 2007/0184117 A1 | 8/2007 | Gregory et al. |
| 2007/0225270 A1 | 9/2007 | Guzi et al. |
| 2007/0281951 A1 | 12/2007 | Guzi et al. |
| 2009/0041717 A1 | 2/2009 | Macdonald et al. |
| 2009/0099167 A1 | 4/2009 | Bold et al. |
| 2009/0130229 A1 | 5/2009 | Lanzi et al. |
| 2009/0227556 A1 | 9/2009 | Obaishi |
| 2010/0029633 A1 | 2/2010 | Allen et al. |
| 2010/0152219 A1 | 6/2010 | Block et al. |
| 2010/0297115 A1 | 11/2010 | Blaustein |
| 2010/0324065 A1 | 12/2010 | Ibrahim et al. |
| 2011/0053934 A1 | 3/2011 | Angell et al. |
| 2011/0166122 A1 | 7/2011 | Andrews et al. |
| 2011/0195948 A1 | 8/2011 | Haas et al. |
| 2011/0268725 A1 | 11/2011 | Shelton |
| 2011/0301157 A1 | 12/2011 | Bold et al. |
| 2012/0108568 A1 | 5/2012 | Allen et al. |
| 2013/0029925 A1 | 1/2013 | Vandier et al. |
| 2013/0203776 A1 | 8/2013 | Andrews et al. |
| 2013/0217662 A1 | 8/2013 | Andrews et al. |
| 2014/0121239 A1 | 5/2014 | Aftab |
| 2014/0194403 A1 | 7/2014 | Haas et al. |
| 2014/0227287 A1 | 8/2014 | Kamohara et al. |
| 2014/0243332 A1 | 8/2014 | Davare |
| 2014/0315199 A1 | 10/2014 | Rhodes et al. |
| 2014/0336236 A1 | 11/2014 | Cronin et al. |
| 2015/0005499 A1 | 1/2015 | Haas et al. |
| 2015/0018336 A1 | 1/2015 | Chen et al. |
| 2015/0031667 A1 | 1/2015 | Allen et al. |
| 2015/0051222 A1 | 2/2015 | Barbugian et al. |
| 2015/0073036 A1 | 3/2015 | Hawryluk et al. |
| 2015/0166564 A1 | 6/2015 | Allen et al. |
| 2015/0218132 A1 | 8/2015 | Wu |
| 2015/0218652 A1 | 8/2015 | Doebele et al. |
| 2015/0283132 A1 | 10/2015 | Lim et al. |
| 2015/0306086 A1 | 10/2015 | Wilcoxen |
| 2015/0315657 A1 | 11/2015 | Rhodes et al. |
| 2015/0336970 A1 | 11/2015 | Andrews et al. |
| 2016/0000783 A1 | 1/2016 | Takeuchi et al. |
| 2016/0009785 A1 | 1/2016 | Lipson et al. |
| 2016/0010068 A1 | 1/2016 | Bastian et al. |
| 2016/0032396 A1 | 2/2016 | Diehn et al. |
| 2016/0032402 A1 | 2/2016 | Jagani et al. |
| 2016/0032404 A1 | 2/2016 | Schweighofer et al. |
| 2016/0108123 A1 | 4/2016 | Freeman et al. |
| 2016/0108380 A1 | 4/2016 | Iavarone et al. |
| 2016/0137654 A1 | 5/2016 | Arrigo et al. |
| 2016/0145237 A1 | 5/2016 | Hu et al. |
| 2016/0228441 A1 | 8/2016 | Haas et al. |
| 2016/0251357 A1 | 9/2016 | Andrews et al. |
| 2016/0263086 A1 | 9/2016 | Toretsky et al. |
| 2016/0272725 A1 | 9/2016 | Stransky et al. |
| 2016/0305943 A1 | 10/2016 | Takeuchi et al. |
| 2016/0367547 A1 | 12/2016 | Yao et al. |
| 2017/0107232 A1 | 4/2017 | Andrews et al. |
| 2017/0112842 A1 | 4/2017 | Andrews et al. |
| 2017/0112849 A1 | 4/2017 | Andrews et al. |
| 2017/0114059 A1 | 4/2017 | Andrews et al. |
| 2017/0114067 A1 | 4/2017 | Haas et al. |
| 2017/0114068 A1 | 4/2017 | Andrews et al. |
| 2017/0114069 A1 | 4/2017 | Allen et al. |
| 2017/0114415 A1 | 4/2017 | Doebele et al. |
| 2017/0119770 A1 | 5/2017 | Allen et al. |
| 2017/0165267 A1 | 6/2017 | Arrigo et al. |
| 2017/0224662 A1 | 8/2017 | Motheram et al. |
| 2017/0260589 A1 | 9/2017 | Nanda et al. |
| 2017/0281632 A1 | 10/2017 | Cox et al. |
| 2017/0283435 A1 | 10/2017 | Andrews et al. |
| 2017/0296544 A1 | 10/2017 | Reynolds et al. |
| 2018/0021342 A1 | 1/2018 | Arrigo et al. |
| 2018/0030548 A1 | 2/2018 | Nanda et al. |
| 2018/0030549 A1 | 2/2018 | Nanda et al. |
| 2018/0119228 A1 | 5/2018 | Nanda et al. |
| 2018/0127427 A1 | 5/2018 | Haas et al. |
| 2018/0133222 A1 | 5/2018 | Cox et al. |
| 2018/0140604 A1 | 5/2018 | Tuch et al. |
| 2018/0142306 A1 | 5/2018 | Nanda et al. |
| 2018/0207162 A1 | 7/2018 | Arrigo et al. |
| 2018/0263984 A1 | 9/2018 | Allen et al. |
| 2019/0031684 A1 | 1/2019 | Andrews et al. |
| 2019/0076436 A1 | 3/2019 | Andrews et al. |
| 2019/0076437 A1 | 3/2019 | Andrews et al. |
| 2019/0151322 A1 | 5/2019 | Andrews et al. |
| 2019/0169193 A1 | 6/2019 | Andrews et al. |
| 2019/0211017 A1 | 7/2019 | Haas et al. |
| 2019/0216814 A1 | 7/2019 | Reynolds et al. |
| 2019/0218222 A1 | 7/2019 | Reynolds et al. |
| 2019/0247398 A1 | 8/2019 | Zhao et al. |
| 2019/0365763 A1 | 12/2019 | Allen et al. |

FOREIGN PATENT DOCUMENTS

| | | |
|---|---|---|
| CN | 101119996 | 2/2008 |
| CN | 101208093 | 6/2008 |
| EA | 009517 | 2/2008 |
| EP | 0810217 | 12/1997 |
| EP | 1873157 | 1/2008 |
| EP | 1948633 | 8/2011 |
| EP | 2986736 | 2/2016 |
| EP | 2558490 | 12/2016 |
| EP | 3266795 | 10/2018 |
| JP | H10120683 | 5/1998 |
| JP | 2004-087707 | 3/2004 |
| JP | 2004-277337 | 10/2004 |
| JP | 2005-008581 | 1/2005 |
| JP | 2006-518364 | 8/2006 |
| JP | 2007-504276 | 3/2007 |
| JP | 2007-514712 | 6/2007 |

(56) References Cited

FOREIGN PATENT DOCUMENTS

| | | |
|---|---|---|
| JP | 2008-523034 | 7/2008 |
| JP | 2008-285464 | 11/2008 |
| JP | 2009-502734 | 1/2009 |
| JP | 2009-511487 | 3/2009 |
| JP | 2009-541242 | 11/2009 |
| JP | 2010-508315 | 3/2010 |
| JP | 2011-520887 | 7/2011 |
| JP | 2012-506446 | 3/2012 |
| JP | 2012-507569 | 3/2012 |
| JP | 2013-226108 | 11/2013 |
| JP | 2014-082984 | 5/2014 |
| WO | WO 1998/49167 | 11/1998 |
| WO | WO 2003/080064 | 10/2003 |
| WO | WO 2004/022561 | 3/2004 |
| WO | WO 2004/052286 | 6/2004 |
| WO | WO 2004/052315 | 6/2004 |
| WO | WO 2004/074290 | 9/2004 |
| WO | WO 2004/082458 | 9/2004 |
| WO | WO 2004/087707 | 10/2004 |
| WO | WO 2004/089415 | 10/2004 |
| WO | WO 2004/089471 | 10/2004 |
| WO | WO 2005/044835 | 5/2005 |
| WO | WO 2005/049033 | 6/2005 |
| WO | WO 2005/051366 | 6/2005 |
| WO | 2005/077954 | 8/2005 |
| WO | WO 2006/052913 | 5/2006 |
| WO | WO 2006/087538 | 8/2006 |
| WO | WO 2006/115452 | 11/2006 |
| WO | WO 2006/123113 | 11/2006 |
| WO | WO 2006/131051 | 12/2006 |
| WO | WO 2006/131952 | 12/2006 |
| WO | WO 2007/002325 | 1/2007 |
| WO | WO 2007/002433 | 1/2007 |
| WO | WO 2007/013673 | 2/2007 |
| WO | WO 2007/015824 | 2/2007 |
| WO | WO 2007/022999 | 3/2007 |
| WO | WO 2007/024680 | 3/2007 |
| WO | WO 2007/025090 | 3/2007 |
| WO | WO 2007/025540 | 3/2007 |
| WO | WO 2007/038314 | 4/2007 |
| WO | WO 2007/044410 | 4/2007 |
| WO | WO 2007/044449 | 4/2007 |
| WO | WO 2007/044893 | 4/2007 |
| WO | WO 2007/048066 | 4/2007 |
| WO | WO 2007/057399 | 5/2007 |
| WO | WO 2007/062805 | 6/2007 |
| WO | WO 2007/084815 | 7/2007 |
| WO | WO 2007/087245 | 8/2007 |
| WO | WO 2007/102679 | 9/2007 |
| WO | WO 2007/103308 | 9/2007 |
| WO | WO 2007/110344 | 10/2007 |
| WO | WO 2007/113000 | 10/2007 |
| WO | WO 2007/129161 | 11/2007 |
| WO | WO 2007/136103 | 11/2007 |
| WO | 2007/147647 | 12/2007 |
| WO | WO 2008/016131 | 2/2008 |
| WO | WO 2008/021924 | 2/2008 |
| WO | WO 2008/030579 | 3/2008 |
| WO | WO 2008/031551 | 3/2008 |
| WO | WO 2008/037477 | 4/2008 |
| WO | WO 2008/052734 | 5/2008 |
| WO | WO 2008/058126 | 5/2008 |
| WO | WO 2008/079903 | 7/2008 |
| WO | WO 2008/079906 | 7/2008 |
| WO | WO 2008/079909 | 7/2008 |
| WO | WO 2008/080001 | 7/2008 |
| WO | WO 2008/080015 | 7/2008 |
| WO | WO 2008/115974 | 9/2008 |
| WO | WO 2008/116898 | 10/2008 |
| WO | WO 2008/155421 | 12/2008 |
| WO | WO 2009/007748 | 1/2009 |
| WO | WO 2009/012283 | 1/2009 |
| WO | WO 2009/013126 | 1/2009 |
| WO | WO 2009/014637 | 1/2009 |
| WO | WO 2009/017838 | 2/2009 |
| WO | WO 2009/052145 | 4/2009 |
| WO | WO 2009/053442 | 4/2009 |
| WO | WO 2009/060197 | 5/2009 |
| WO | 2009/070567 | 6/2009 |
| WO | WO 2009/071480 | 6/2009 |
| WO | WO 2009/092049 | 7/2009 |
| WO | WO 2009/118411 | 10/2009 |
| WO | WO 2009/140128 | 11/2009 |
| WO | WO 2009/143018 | 11/2009 |
| WO | WO 2009/143024 | 11/2009 |
| WO | WO 2009/152083 | 12/2009 |
| WO | WO 2010/012733 | 2/2010 |
| WO | WO 2010/031816 | 3/2010 |
| WO | WO 2010/033941 | 4/2010 |
| WO | WO 2010/048314 | 4/2010 |
| WO | WO 2010/051549 | 5/2010 |
| WO | WO 2010/058006 | 5/2010 |
| WO | WO 2010/093928 | 8/2010 |
| WO | WO 2010/111527 | 9/2010 |
| WO | WO 2010/145998 | 12/2010 |
| WO | WO 2011/006074 | 1/2011 |
| WO | WO 2011/092120 | 8/2011 |
| WO | WO 2011/130340 | 10/2011 |
| WO | WO 2011/133637 | 10/2011 |
| WO | WO 2011/146336 | 11/2011 |
| WO | WO 2012/024650 | 2/2012 |
| WO | WO 2012/034091 | 3/2012 |
| WO | WO 2012/034095 | 3/2012 |
| WO | WO 2012/053606 | 4/2012 |
| WO | WO 2012/101029 | 8/2012 |
| WO | WO 2012/101032 | 8/2012 |
| WO | WO 2012/109075 | 8/2012 |
| WO | WO 2012/113774 | 8/2012 |
| WO | WO 2012/116217 | 8/2012 |
| WO | WO 2012/139930 | 10/2012 |
| WO | WO 2012/143248 | 10/2012 |
| WO | WO 2012/152763 | 11/2012 |
| WO | WO 2012/158413 | 11/2012 |
| WO | WO 2013/014039 | 1/2013 |
| WO | WO 2013/050446 | 4/2013 |
| WO | WO 2013/050448 | 4/2013 |
| WO | WO 2013/059740 | 4/2013 |
| WO | WO 2013/074518 | 5/2013 |
| WO | WO 2013/102059 | 7/2013 |
| WO | WO 2013/174876 | 11/2013 |
| WO | WO 2013/183578 | 12/2013 |
| WO | 2014/016433 | 1/2014 |
| WO | WO 2014/011900 | 1/2014 |
| WO | WO 2014/019908 | 2/2014 |
| WO | WO 2014/036387 | 3/2014 |
| WO | WO 2014/047572 | 3/2014 |
| WO | WO 2014/071358 | 5/2014 |
| WO | WO 2014/072220 | 5/2014 |
| WO | WO 2014/078322 | 5/2014 |
| WO | WO 2014/078323 | 5/2014 |
| WO | WO 2014/078325 | 5/2014 |
| WO | WO 2014/078328 | 5/2014 |
| WO | WO 2014/078331 | 5/2014 |
| WO | WO 2014/078372 | 5/2014 |
| WO | WO 2014/078378 | 5/2014 |
| WO | WO 2014/078408 | 5/2014 |
| WO | WO 2014/078417 | 5/2014 |
| WO | WO 2014/078454 | 5/2014 |
| WO | WO 2014/083567 | 6/2014 |
| WO | WO 2014/130975 | 8/2014 |
| WO | WO 2014/134096 | 9/2014 |
| WO | WO 2014/152777 | 9/2014 |
| WO | WO 2014/160521 | 10/2014 |
| WO | WO 2014/184069 | 11/2014 |
| WO | WO 2014/194127 | 12/2014 |
| WO | WO 2015/017528 | 2/2015 |
| WO | WO 2015/017533 | 2/2015 |
| WO | WO 2015/039006 | 3/2015 |
| WO | WO 2015/057873 | 4/2015 |
| WO | WO 2015/058129 | 4/2015 |
| WO | WO 2015/061572 | 4/2015 |
| WO | WO 2015/064621 | 5/2015 |
| WO | WO 2015/108992 | 7/2015 |
| WO | WO 2015/112806 | 7/2015 |

(56) References Cited

FOREIGN PATENT DOCUMENTS

| | | |
|---|---|---|
| WO | WO 2015/124697 | 8/2015 |
| WO | WO 2015/161274 | 10/2015 |
| WO | WO 2015/161277 | 10/2015 |
| WO | WO 2015/175788 | 11/2015 |
| WO | WO 2015/183836 | 12/2015 |
| WO | WO 2015/183837 | 12/2015 |
| WO | WO 2015/184443 | 12/2015 |
| WO | WO 2015/191666 | 12/2015 |
| WO | WO 2015/191667 | 12/2015 |
| WO | WO 2016/011141 | 1/2016 |
| WO | WO 2016/011144 | 1/2016 |
| WO | WO 2016/011147 | 1/2016 |
| WO | WO 2016/022569 | 2/2016 |
| WO | WO 2016/027754 | 2/2016 |
| WO | WO 2016/075224 | 5/2016 |
| WO | WO 2016/077841 | 5/2016 |
| WO | WO 2016/081450 | 5/2016 |
| WO | WO 2016/097869 | 6/2016 |
| WO | WO 2016/187508 | 11/2016 |
| WO | WO 2016/196141 | 12/2016 |
| WO | WO 2016/196671 | 12/2016 |
| WO | WO 2017/001491 | 1/2017 |
| WO | WO 2017/004342 | 1/2017 |
| WO | WO 2017/075107 | 5/2017 |
| WO | WO 2017/155018 | 9/2017 |
| WO | WO 2017/184597 | 10/2017 |
| WO | WO 2017/201156 | 11/2017 |
| WO | WO 2017/201241 | 11/2017 |
| WO | WO 2018/081417 | 5/2018 |
| WO | WO 2018/170381 | 9/2018 |
| WO | WO 2019/005796 | 1/2019 |
| WO | WO 2019/084285 | 5/2019 |

OTHER PUBLICATIONS

Alassiri et al., "ETV6-NTRK3 is Expressed in a Subset of ALK-Negative Inflammatory Myofibroblastic Tumors," Am J Surg Pathol., Aug. 2016, 40(8): 1051-1061.
Albaugh et al., "Discovery of GNF-5837, a Selective TRK Inhibitor with Efficacy in Rodent Cancer Tumor Models," ACS Medicinal Chemistry Letters, 2012, 3(2): 140-145.
Ali et al., "Comprehensive Genomic Profiling Identifies a Subset of Crizotinib-Responsive ALK-Rearranged Non-Small Cell Lung Cancer Not Detected by Fluorescence In Situ Hybridization.", Oncologist, 21(6): 762-70, 2016.
Alvarez-Breckenridge et al., "Clinical and radiographic response following targeting of BCAN-NTRKI fusion in glioneuronal tumor," NPJ Precision Oncology, Mar. 2017, 5 pages.
Amatu et al., "NTRK gene fusions as novel targets of cancer therapy across multiple tumour types", ESMD Open, 1-9, 2016.
American Association for Cancer Research, "TRK Inhibitor Shows Early Promise," Cancer Discovery, 6(1), Jan 1, 2016, XP009194480.
American Cancer Society,"Sarcoma: Adult Soft Tissue Cancer," Jun. 2014, retrieved on Apr. 27, 2015, http://www.cancer.org/cancer/sarcoma-adultsofttissuecancer/detailedguide/sarcoma-adult-soft-tissue-cancer-key-statistics, 45 pages.
Andreason et al., "ETV6 Gene Rearrangements Characterize a Morphologically Distinct Subset of Sinonasal Low-grade Non-intestinal-type Adenocarcinoma," Am. J. Surg. Pathol, Nov. 2017, 41(11):1552-1560.
Arce et al., "Secretory carcinoma of the breast containing the ETV6-NTRK3 fusion gene in a male: case report and review of the literature," World J. Surg. Oncol, Jun. 2005, 3:35.
Ardini et al., "The TPM3-NTRK1 rearrangement is a recurring event in colorectal carcinoma and is associated with tumor sensitivity to TRKA kinase inhibition," Mol. Oncol. 8(8): 1495-1507, 2014.
Asaumi et al., "Expression of neurotrophins and their receptors (TRK) during fracture healing," Bone, 2000, 26(6):625-633.
Awad et al., "Acquired resistance to crizotinib from a mutation in CD74-ROS1.", N. Engl. J Med, 368(25): 2395-401, 2013.

Bailey, Justin J., et al. "Tropomyosin receptor kinase inhibitors: an updated patent review for 2010-2016—Part II." Expert opinion on therapeutic patents 27.7 (2017): 831-849.
Bardelli et al., "Mutational Analysis of the Tyrosine Kinome in Colorectal Cancers," Science, May 2003, 300(5621):949.
Bartenstein et al., "Lipofibromatosis-like neural tumor: Case report of a unique infantile presentation," JAAD Case Reports, 4(2):185-188, 2018.
Baughn et al., "Abstract 5115: Whole-Genome Mate Pair Sequencing Reflex Test to Characterize Chromosome Rearrangements in Hematologic Neoplasia," Blood, 2017, 130: 5115.
Bavle et al., "Abstract GENE-04: Pediatric Malignant Epithelioid Glioneuronal Tumor: Pathological, Clinical, and Molecular Characterization of a Rare and Deadly Malignancy," Neuro-Oncology, Jun. 2017, iv18-iv19.
Behrens et al., "Go 6976 is a potent inhibitor of neurotrophin-receptor intrinsic tyrosine kinase," J Neurochem., Mar. 1999, 72(3):919-924.
Beimfohr et al., "NTRK.1 re-arrangement in papillary thyroid carcinomas of children after the Chernobyl reactor accident," Int. J Cancer, Mar. 15, 1999;80(6):842-847.
Bender et al., Abstract HG-024: Multiple Novel Fusion Genes with the RTK-RAS-PBK Signalling Axis Highlight its Central Role in the Turmorigenesis of Pediatric Gioblastoma, Neuro-oncology, Jun. 2014, 145.
Bensinger et al., "Transplantation of allogeneic peripheral blood stem cells mobilized by recombinant human granulocyte colony stimulating factor," Stem Cells, Jan. 1996;14(1):90-105.
Bensinger et al., "Transplantation of allogeneic peripheral blood stem cells mobilized by recombinant human granulocyte colony-stimulating factor [see comments].," Blood, Mar. 15, 1995;85(6):1655-8.
Bertrand et al., "The crystal structures of TrkA and TrkB suggest key regions for achieving selective inhibition," Journal of molecular biology, Oct. 26, 2012;423(3):439-53.
Birch et al., "Chromosome 3 anomalies investigated by genome wide SNP analysis of benign, low malignant potential and low grade ovarian serous tumours.", PLoS One, 6(12): e28250, 2011.
Bonanno et al., Journal of Thoracic Oncology, vol. 11, No. 4, Supp. Suppl. 1, pp. S67. Abstract No. 28P; 6th European Lung Cancer Conference, ELCC 2016, Geneva, Switzerland.
Bongarzone et al., "Age-related activation of the tyrosine kinase receptor protooncogenes RET and NTRK.1 in papillary thyroid carcinoma," J Clin. Endocrinol. Metab., May 1996, 81(5):2006-2009.
Bouhana et al., "Abstract #1798: Identification of Pan-Trk Inhibitors for the Treatment of Trk-Driven Cancers," Poster, Presented at Proceedings of the AACR 103rd Annual Meeting, Apr. 15, 2012.
Bourgeois et al., "Molecular Detection of the ETV6-NTRK3 Gene Fusion Differentiates Congenital Fibrosarcoma From Other Childhood Spindle Cell Tumors," Am. J Surg. Pathol., Jul. 2000, 24(7):937-946.
Branford, S., et al. "High frequency of point mutations clustered within the adenosine triphosphate-binding region of BCR/ABL in patients with chronic myeloid leukemia or Ph-positive acute lymphoblastic leukemia who develop imatinib (STI571) resistance," Blood, May 2002, 99, 3472-3475.
Brastianos et al., "Abstract OS06.4: Identification of Novel NTRK Fusion in Glioneuronal Tumors and Radiographic Response Following Therapy with an NTRK Inhibitor," Neuro-Oncology, May 2017, iii11, 1 page, Meeting Info: 5th Quadrennial Meeting of the World Federation of Neuro-Oncology Societies, WFNOS. Zurich, Switzerland, 2017.
Brenca et al., "Transcriptome sequencing identifies ETV6-NTRK3 as a gene fusion involved in GIST," J. Pathol. 238(4):543-549, 2016.
Brinner et al., "A rapid and general method for asymmetric synthesis of 2-substituted pyrrolidines using ter-butanesulfinamide," Organic & Biomolecular Chemistry, Jan. 2005, 3(11): 2109.
Brodeur, "Neuroblastoma: biological insights into a clinical enigma," Nat. Rev. Cancer, 2003, 3:203-216.
Bruse et al., "Improvements to Bead Based Oligonucleotide Ligation SNP Genotyping Assays," Biotechniques, Nov. 2008, 45:559-571.

(56) References Cited

OTHER PUBLICATIONS

Brzezianska et al., "Rearrangements of NTRK.1 oncogene in papillary thyroid carcinoma," Neuroendocrinology Letters, 2007, 28(3):221-229.
Burris et al., "Pharmacokinetics (PK) of LOXO-101 During the First-in-Human Phase I Study in Patients with Advanced Solid Tumors," Interim Update AACR Annual Meeting, Mar. 2015, Philadelphia, PA., 1 page.
Butti et al., "A sequence analysis of the genomic regions involved in the rearrangements between TPM3 and NTRK1 genes producing TRK oncogenes in papillary thyroid carcinomas," Genomics. 28(1):15-24, 1995.
Caira, "Crystalline Polymorphism of Organic Compounds," Topics in Current Chemistry, Feb. 1999, 198: 163-208.
Cajaiba et al., "Expanding the spectrum of ALK-rearranged renal cell carcinomas in children: Identification of a novel HOOK1-ALK fusion transcript.", Genes Chromosomes Cancer, 55(10): 814-7, 2016.
Calabresi and Chabner, Goodman & Gilnnan's The Pharmacological Basis of Therapeutics, 10th ed., 2001, ne: 1388, para 2, lines 4-5.
Calero et al., "Sunitinib suppress neuroblastoma growth through degradation of MYCN and inhibition of angiogenesis," PLoS One, Apr. 23, 2014;9(4):e95628. doi: 10.1371/iournal.pone.0095628. eCollection 2014.
Camoratto et al., "CEP-751 inhibits TRK receptor tyrosine kinase activity in vitro exhibits anti-tumor activity," Int. J Cancer, Aug. 1997, 72:673-679.
Campos et al., "Enantioselective, palladium-catalyzed alpha-arylation ofN-Boc-pyrrolidine," J. Am. Chem Soc., 2006, 128:3538-3539.
Cancer.gov [online] "National Cancer Institute: Oral TRK Inhibitor LOXO-101 (Larotrectinib) for Treatment of Advanced Pediatric Solid or Primary Central Nervous System Tumors," ClinicalTrials. gov Identifier: NCT02637687, [retrieved on Jul. 17, 2017] Retrieved from the Internet: URL<https://www.cancer.gov/about-cancer/treatment/clinical-trials/search/view?cdrid=78 1 000>, 5 pages.
Cancer.sanger.ac.uk [online]. "COSMIC, Catalog of Somatic Mutations in Cancer: Cosmic» Mutation» Overview» NTRK.1 p.V321M / c.961G>A," Catalog of Somatic Mutations in Cancer (COSMIC) database, [retrieved on Jul. 17, 2017] Retrieved from the Internet: URL<cancer.sanger.ac.uk/cosmic/mutation/ overview?id=1259646>, 1 page.
Cancer.sanger.ac.uk [online]. "COSMIC, Catalog of Somatic Mutations in Cancer: Cosmic» Mutation» Overview» NTRK.1 p. D679N / c.2035G>A," Catalog of Somatic Mutations in Cancer (COSMIC) database, [retrieved on Jul. 17, 2017] Retrieved from the Internet: URL<cancer.sanger.ac.uk/cosmic/mutation/overview?id=897427>, 1 page.
Cancer.sanger.ac.uk [online]. "COSMIC, Catalog of Somatic Mutations in Cancer: Cosmic» Mutation» Overview» NTRK.3 p. D537Y / c.1609G>T," Catalog of Somatic Mutations in Cancer (COSMIC) database, [retrieved on Jul. 17, 2017] Retrieved from the Internet: URL<cancer.sanger.ac.uk/cosmic/mutation/ overview?id=966118>, 1 page.
Cancer.sanger.ac.uk [online]. "COSMIC, Catalog of Somatic Mutations in Cancer: Cosmic» Mutation» Overview» NTRK.3 p. D609V / c.1826A>T," Catalog of Somatic Mutations in Cancer (COSMIC) database, [retrieved on Jul. 17, 2017] Retrieved from the Internet: URL:<cancer.sanger.ac.uk/cosmic/mutation/ overview?id=124878>, 1 page.
Cancer.sanger.ac.uk [online]. "COSMIC, Catalog of Somatic Mutations in Cancer: Cosmic» Mutation» Overview» NTRK.3 p. G608S / c.1822G>a," Catalog of Somatic Mutations in Cancer (COSMIC) database, [retrieved on Jul. 17, 2017] Retrieved from the Internet: URL<cancer.sanger.ac.uk/cosmic/mutation/ overview?id=88799>, 1 page.
Cancer.sanger.ac.uk [online]. "COSMIC, Catalog of Somatic Mutations in Cancer: Cosmic» Mutation» Overview» NTRK.3 p. L282M / c.844C>a," Catalog of Somatic Mutations in Cancer (COSMIC) database, [retrieved on Jul. 17, 2017] Retrieved from the Internet: URL<cancer.sanger.ac.uk/cosmic/mutation/ overview?id=401588>, 1 page.
Cancer.sanger.ac.uk [online]. "COSMIC, Catalog of Somatic Mutations in Cancer: Cosmic» Mutation» Overview» NTRK.3 p.V539M I c.1615G>A," Catalog of Somatic Mutations in Cancer (COSMIC) database, [retrieved on Jul. 17, 2017] Retrieved from the Internet: URL<cancer. sanger.ac.uk/cosmic/mutation/ overview?id=1708512>, 1 page.
Capparelli et al., "Stromal neuregulin-1 modulates the response to MEK inhibitors in WT BRAF/WT.NRAS (WT/WT) melanomas", Pigment Cell Melanoma Res. vol. 30, No. 5, pp. e61, 2017.
Caria et al., "Cytogenetic and molecular events in adenoma and well-differentiated thyroid follicular-cell neoplasia," Cancer Genet. Cytogenet., 2010, 203:21-29.
Carpinelli et al., "PHA-739358, a potent inhibitor of Aurora kinases with a selective target inhibition profile relevant to cancer," Mol Cancer Ther, Dec. 2007;6(12 Pt 1):3158-3168.
Carvalho et al., Neuro-Oncology1 7:iiil-iii40, 2015, Abstract No. HG-09, 1 page.
Catalog of Somatic Mutations in Cancer (COSMIC) database, cancer.sanger.ac.uk/cosmic/mutation/overview?id=1517968, downloaded on May 31, 2016, 2 pages.
Catalog of Somatic Mutations in Cancer (COSMIC) database, cancer.sanger.ac.uk/cosmic/mutation/overview?id=1636266, downloaded on May 31, 2016, 2 pages.
Catalog of Somatic Mutations in Cancer (COSMIC) database, cancer.sanger.ac.uk/cosmic/mutation/overview?id=1688778, downloaded on May 31, 2016, 2 pages.
Catalog of Somatic Mutations in Cancer (COSMIC) database, cancer.sanger.ac.uk/cosmic/mutation/overview?id=3711772, downloaded on May 31, 2016, 2 pages.
Catalog of Somatic Mutations in Cancer (COSMIC) database, cancer.sanger.ac.uk/cosmic/mutation/overview?id=471203, downloaded on May 31, 2016, 2 pages.
Catalog of Somatic Mutations in Cancer (COSMIC) database, cancer.sanger.ac.uk/cosmic/mutation/overview?id=48622, downloaded on May 31, 2016, 2 pages.
Catic et al., "A novel cytogenetic and molecular characterization of renal metanephric adenoma, identification of partner genes involved in translocation t(9;15)(p24;q24)," Cancer Genet. 214-215:915, doi: 10.1016/j.cancergen.2017.03.001, 2017.
Catic et al., "Abstract 1537: The frequency of a novel KANK1 and NTRK3translocation and BRAFV600E mutation in patients diagnosed with metanephric adenoma utilizing molecular mechanisms," 2017 Annual Meeting of the American Society of Clinical Oncology, 2017, 1 page.
Chang-Qi et al., "Brain derived neurotrophic factor (BDNF) contributes to the pain hypersensitivity following surgical incision in the rats," Molecular Pain, 2008, 4:27.
Chaudhuri et al., "Early Detection of Molecular Residual Disease in Localized Lung Cancer by Circulating Tumor DNA Profiling," Cancer Discov, Dec. 2017, 7(12):1394-1403.
Chen et al.,"40: The landscape of kinase fusions in 445 Chinese NSCLC patients," Annals of Oncology, Oct. 2017, 28(7): vii16, 1 page.
Cherry et al., "Recent kinase and kinase inhibitor X-ray structures: mechanisms of inhibition and selectivity insights," Curr Med Chem. Mar. 2004;ll(6):663-73.
Chiang et al., "NTRK Fusions Define a Novel Uterine Sarcoma Subtype with Features of Fibrosarcoma," Am. J. Surg. Pathol. doi: 10.1097IPAS.0000000000001055, 2018.
Chintakuntlawar et al., "High-grade transformation of acinic cell carcinoma: an inadequately treated entity?" Oral Surg Oral Med Oral Pathol Oral Radiol, May 2016, 121(5):542-549.
Chmielecki et al., "Abstract LB-178: Genomic profiling of 1239 diverse pediatric cancers identifies novel discoveries across tumors", Cancer Research, vol. 76, No. 14, Supp. Supplement. Abstract No. LB-178. 107th Annual meeting of the American Association for Cancer Research, AACR. New Orleans, LA Apr. 16-20, 2016.
Chmielecki et al., "Genomic Profiling of a Large Set of Diverse Pediatric Cancers Identifies Known and Novel Mutations across Tumor Spectra.", Cancer Research, 77(2): 509-519, 2017.

(56) References Cited

OTHER PUBLICATIONS

Cho et al., "Expression of mRNA for brain-derived neurotrophic factor in the dorsal root ganglion following peripheral inflammation," Brain Research, 1997, 749:358-362.
Choi et al., "(R)-2-Phenylpyrrolidine Substituted Irnidazopy ridazines: A New Class of Potent and Selective Pan-TRK Inhibitors," ACS medicinal chemistry letters, Mar. 2015 I 9;6(5):562-7.
Chung et al., "Infantile fibrosarcoma," Cancer, Aug. 1976, 38(2):729-739.
Church et al., "Abstract ST16: A Novel EML4-NTRK3 Translocation in Infantile Fibrosarcoma and Congenital Mesoblastic Nephroma Requires a New Approach to Conventional Diagnostic Algorithms," J Molecular Diag, 2015, 816.
Church et al., "Recurrent EML4-NTRK3 fusions in infantile fibrosarcoma and congenital mesoblastic nephroma suggest a revised testing strategy," Mod. Pathol. 31(3), 463-473, 2018.
Cocce et al., "Identification of ZCCHC8 as fusion partner of ROS1 in a case of congenital glioblastoma multiforme with a t(6;12)(q21;q24.3)", Genes Chromosomes Cancer, 55(9): 677-87, 2016.
Coebergh et al., "Abstract 490: Identification of oncogenic gene fusions in primary colon cancers," Cancer Research, Jul. 2017, DOI: 10.1158/1538-7445.AM2017-490, 2 pages.
Comina-Mendez and Turner, "Predicting Relapse with Circulating Tumor DNA Analysis in Lung Cancer," CancerDiscov, Dec. 2017, 7(12): 1368-1370.
Cook et al., "Somatic chromosomal engineering identifies BCAN-NTRK1 as a potent glioma driver and therapeutic target," Nat. Comm. 8(15987). DOI 10.1038/ncomms15987, 2017.
Creancier et al., "Chromosomal rearrangements involving the NTRK.1 gene in colorectal carcinoma," Cancer Lett., Awmst 2015, 365(1):107-111.
Crescenzo et al., "Convergent mutations and kinase fusions lead to oncogenic STAT3 activation in anaplastic large cell lymphoma.", Cancer Cell., 27(4): 516-32, 2015.
Croucher et al., "TrkB inhibition by GNF-4256 slows growth and enhances chemotherapeutic efficacy in neuroblastoma xenografts," Cancer Chemother Pharmacol. Jan. 2015;75(1):131-41. doi:10.1007/s00280-014-2627-1. Epub Nov. 14, 2014.
Cruz, "Lung cancer: epidemiology, etiology and prevention," Clinics in Chest Medicine, 2011, 32(4): 1-61.
Cui et al., "Abstract #MA 07.09: ALK/ROSl/Inhibitor TPX-0005 Effectively Overcomes Clinical Resistance Solvent Front Mutations," Abstracts, Nov. 2017, p. S1829.
Cui et al., "Use of capture-based next-generation sequencing to detect ALK fusion in plasma cell-free DNA of patients with non-small-cell lung cancer", Oncotarget, 2771-2780, 2016.
Dacie et al., "ALK FISH patterns and the detection of ALK fusions by next generation sequencing in lung adenocarcinoma", Oncotarget, vol. 7, No. 50, pp. 82943-82952, 2016.
Dang et al., "Expression of nerve growth factor receptors is correlated with progression and prognosis of human pancreatic cancer," J. Gastroenterology and Hepatology, 2006, 21(5): 850-858.
Das et al., "Synergistic Effects of Crizotinib and Temozolomide in Experimental FIG-ROS1 Fusion-Positive Glioblastoma.", Cancer Growth Metastasis, 8:51-60, 2015.
Davare et al., "Foretinib is a potent inhibitor of oncogenic ROS1 fusion proteins.", Proc. Natl. Acad Sci. USA., 110(48): 19519-24, 2013.
Davare et al., "Structural insight into selectivity and resistance profiles of ROSI tyrosine kinase inhibitors.", Proc. Natl. Acad Sci. USA., 112(39): E5381-90, 2015.
Davidson et al., "Expression and activation of the nerve growth factor receptor TrkA in serous ovarian carcinoma," Clin. Cancer Res., 2003, 9(6):2248-2259.
Davies and Dobele, "Molecular pathways: ROS1 fusion proteins in cancer.", Clin. Cancer Res, 19(15): 4040-4045, 2013.
Davies et al., "Identifying and targeting ROS1 gene fusions in non-small cell lung cancer.", Clin Cancer Res 18: 4570-4579, 2012.

Davies et al., "Resistance to ROSI inhibition mediated by EGFR pathway activation in non-small cell lung cell," PLoS One, 2013, 8(12):e82236, 13 pages.
Davis et al., "Infantile NTRK-associated Mesenchymal Tumors," Pediatr. Dev. Pathol. 21(1):68-78, 2018.
De Smith et al., "Clonal and microclonal mutational heterogeneity in high hyperdiploid acute lymphoblastic leukemia", Oneatarget., 7(45) 72733-72745, 2016.
Deihimi et al., "BRCA2, EGFR, and NTRK mutations in mismatch repair-deficient colorectal cancers with MSH2 or MLH1 mutations," Oncotarget. Jun 20;8(25):39945-39962, 2017.
Delafoy et al., "Role of nerve growth factor in the trinitrobenzene sulfonic acid-induced colonic hypersensitivity," Pain, 2003, 105:489-497.
Demaria et al., "Development of tumor-infiltrating lymphocytes in breast cancer after neoadjuvant paclitaxel chemotherapy," Clin Cancer Res, Oct. 2001;7(10):3025-30.
Di Mola et al., "Nerve growth factor and Trk high affinity receptor (TrkA) gene expression in inflammatory bowel disease," Gut, 2000, 46(5):670-678.
Diner et al., "Preparation of 3-substituted-1-isopropyl-1H-pyrazolo[3,4-d]pyrimidin-4-amines as RET kinase inhibitors," J. Med. Chem., May 2012, 55 (10), 4872-4876.
Dionne et al., "Cell cycle-independent death of prostate adenocarcinoma is induced by the trk tyrosine kinase inhibitor CEP-751 (KT6587)," Clin. Cancer Research, 1998, 4(8):1887-1898.
Doebele et al., "Abstract 8023: NTRK1 gene fusions as a novel oncogene target in lung cancer," 2013 Annual Meeting of the American Society of Clinical Oncology, Chicago, IL, 2013, 1 page.
Doebele et al., "An oncogenic NTRK fusion in a soft tissue sarcoma patient with response to the tropomysin-related kinase (TRK) inhibitor LOXO-101," Cancer Discovery, Jul. 2015, 5(10):1049-1057.
Doebele et al., "Phase II Trial of Stereotactic Body Radiation Therapy Combined with Erlotinib for Patients with Limited but Progressive Metastatic Non-Small-Cell Lung Cancer," J. Clin. Oncol., 2014, 32:9 pages.
Dolle et al., "Nerve growth factor-induced migration of endothelial cells," J. Pharmacol Exp Ther, 2005, 315(3):1220-1227.
Dolomanov et al., "OLEX2: a complete structure solution, refinement and analysis program," J Annl Cryst. 2009, 42, 339-341.
Dou et al., "Increased nerve growth factor and its receptors in atopic dermatitis: an immunohistochemical study," Archives of Dermatological Research, 2006, 298(1):31-37.
Drexler et al., "Pathobiology of NPM-ALK and variant fusion genes in anaplastic large cell lymphoma and other lymphomas," Leukemia, Sep. 2000, 14:1533-1559.
Drilon et al., "A Novel Crizotinib-Resistant Solvent-Front Mutation Responsive to Cabozantinib Therapy in a Patient with ROSI-Rearranged Lung Cancer.", Clin. Cancer Res., 22(10): 2351-8, 2016.
Drilon et al., "A phase 1 study of oral LOXO 292 in adult patients with advanced solid tumors, including RET-fusion non-small cell lung cancer, medullary thyroid cancer and other tumors with increased RET activity," Annals of oncology Developmental Therapeutics, Sep. 2017, 28(5):138.
Drilon et al., "Abstract CT007: Entrectinib, an oral pan-Trk, ROSI, and ALK inhibitor in TKI-naive patients with advanced solid tumors harboring gene rearrangements: Updated phase I results," Cancer research, 76(14), AACR 107th Annual Meeting, Apr. 2016, URL <http://cancerres.aacrjournals.org/content/76/14 Supplement/CT007.short>, 5 pages.
Drilon et al., "Entrectinib, an oral pan-Trk, ROSI, and ALK inhibitor in TK1-naive patients with advanced solid tumors harboring gene rearrangements," Cancer research, vol. 76, No. 14, Supp. Supplement., Abstract No. 15 CT007; Presented at the 107th Annual Meeting of the American Association for Cancer Research, AACR 2016. New Orleans, LA; Apr. 16-20, 2016, 35 pages.
Drilon et al., "What hides behind the MASC: clinical response and acquired resistance to entrectinib after ETV6-NTRK3 identification in a mammary analogue secretory carcinoma (MASC)," Annals of Oncology., Feb. 15, 2016, 27(5):920-926.

(56) References Cited

OTHER PUBLICATIONS

Du et al., "Expression of NGF family and their receptors in gastric carcinoma: a cDNA microarray study," World Journal of Gastroenterology, http://www.wjgnet.com/1007-9327/full/v9/i7/1431.htm, Jul. 2003, 9(7):1431-1434.
Duranti et al., "Homologation of Mexiletine alkyl chain and stereoselective blockade of skeletal muscle sodium channels," Euro. J. Med. Chem., 2000, 35:147-156.
Durham et al. "Diverse and Targetable Kinase Alterations Drive Histiocytic Neoplasms," Blood. 126(23):481, 2015.
Edgren et al., Cancer Res. 75(15 Supplement): 4793, 2015; Abstract only, 3 pages.
Eguchi et al., "Absence of t(12;15) associated ETV6-NTRK3 fusion transcripts in pediatric acute leukemias," Med Pediatr. Oncol., Oct. 2001, 37:417.
Eguchi et al., "Fusion of ETV6 to neurotrophin-3 receptor TRKC in acute myeloid leukemia with t(12;15)(p13;q25)," Blood, 1999, 93(4):1355-1363.
Eisenhauer et al., "New response evaluation criteria in solid tumours: revised RECIST guideline (version 1.1)," Eur J Cancer, Jan. 2009, 45(2):228-247.
Ellison et al., "Abstract 013: Genetic alterations in uncommon low-grade neural tumors—BRAF, FGFR1, and MYB/MYBL1 mutations occur frequently and align with morphology," Neuropathology and Applied Neurobiology, 2016, 42(S1): 18.
Elvin et al., "319: Genomic profiling of uterine leiomyosarcomas reveal frequent alterations in Akt/mammalian target of rapamycin (mTOR) pathway genes and other actionable genomic abnormalities linked to targeted therapies," Poster Session—Molecular Targeted Agents I, Nov. 2014, 1 page.
Endometrial Cancer Gene Database, ecgene.bioinfominzhao.org/gene_mutation.cgi?gene=4915, downloaded on May 31, 2016, 13 pages.
Engman et al., "Syngeneic transplant in mantle cell lymphoma: a rare event and review of the literature," Clin Adv Hematol Oncol. May 2009;7(5):321-3.
Esmo, "TRK Cancer-Causing Mutation Discovered in 1982 Finally Target of Clinical Trials: Matching drugs to long-overlooked oncogene," European Society of Medical Oncology, Jan. 2015, 2 pages.
Essand et al., "Genetically engineered T cells for the treatment of cancer," J Intern Med. Feb. 2013;273(2):166-81. doi: 10.1111/joim.12020.
Estrada-Bernal et al., "Abstract#: C65: TRK kinase domain mutations that induce resistance to a pan-TRK inhibitor," Poster, Presented at Proceedings of the AACR-NCI-EORTC International Conference: Molecular Targets and Cancer Therapeutics, Boston MA, Nov. 5-9, 2015; Mol Cancer Ther, Dec. 2015, 14(12)(Suppl. 2): 1 page.
Estrada-Bernal et al., "Abstract#: LB-118: Identification of TRKA and TRKB kinase domain mutations that induce resistance to a pan-TRK inhibitor," Poster, Presented at Proceedings of the 107th Annual Meeting of the American Association for Cancer Research, New Orleans LA, Apr. 16-20, 2016; Cancer Res, Jul. 2016, 76(14): 1 page.
Euthus et al., "ETV6-NTRK3—Trk-ing the primary event in human secretory breast cancer," Cancer Cell, 2002, 2(5):347-348.
Evans et al., "Antitumor activity of CEP-751 (KT-6587) on human neuroblastoma and medulloblastomaxenografts," Clin. Cancer Res., Nov. 1999, 5(11):3594-3602.
Extended European Search Report in European Application No. 13197815.7, dated Apr. 1, 2014, 5 pages.
Extended European Search Report in European Application No. 16166461.0, dated Sep. 28, 2016, 5 pages.
Extended European Search Report in European Application No. 17163978.4, dated Jul. 17, 2017, 5 pages.
Extended European Search Report in European Application No. 17199899.0, dated Feb. 26, 2018, 7 pages.
Extended European Search Report in European Application No. 18151233.6, dated Jun. 26, 2018, 6 pages.
Extended European Search Report in European Application No. 18208279.2, dated Jun. 27, 2019, 10 pages.
Facchinetti et al., "Crizotinib-Resistant ROS1 Mutations Reveal a Predictive Kinase Inhibitor Sensitivity Model for ROS1- and ALK-Rearranged Lung Cancers.", Clin. Cancer Res., 22(24): 5983-5991, 2016
Farago et al., "Abstract MINB0.09: Clinical Response to Entrectinib in a Patient with NTRK1-Rearranged Non-small cell Lung Cancer," J Thoracic Oncol, Sep. 2015, 10(9-S2): S374-S375.
Farago et al., "Durable clinical response to entrectinib in NTRK1-rearranged non-small cell lung cancer," J. Thorac Oncol. 10(12):1670-1674, 2015.
Farhat et al., "Primary benign and malignant thyroid neoplasms with signet ring cells: cytologic, histologic, and molecular features," Am. J. Clin. Pathol., 148(3):251-258, 2017.
Fernandez-Cuesta et al., "Abstract 1531: Cross-entity mutation analysis of lung neuroendocrine tumors sheds light into their molecular origin and identifies new therapeutic targets," AACR Annual Meeting 2014, Apr. 2014, URL <http://cancerres.aacrjournals.org/content/7 4/19 Supplement/1531.short>, 5 pages.
Flannery et al., "Immunomodulation: NK cells activated by interferon-conjugated monoclonal antibody against human osteosarcoma," Eur J Cancer Clin Oncol. Jun. 1984;20(6):791-8.
Forghieri et al., Abstract P137: Chronic Eosinophilic Leukemia with ETV6-NTRK3 Fusion Transcript in an Elderly Patient Affected with Pancreatic Carcinoma, Haemologica, 2010, 95(s3): S125-S126.
Frattini et al., "The integrated landscape of driver genomic alterations in glioblastoma," Nature Genet., 2013, 45:1141-1149.
Freund-Michel and Frossard, "The nerve growth factor and its receptors in airway inflammatory diseases," Pharmacology & Therapeutics, 2008, 117(1):52-76.
Frey et al., "7-Aminopyrazolo[1,5-a]pyrimidines as potent multitargeted receptor tyrosine kinase inhibitors," J. Med. Chem, Jul. 2008, 51(13):3777-3787.
Fu et al., "The Frequency and Clinical Implication of ROS1 and RET Rearrangements in Resected Stage IIIA-N2 Non-Small Cell Lung Cancer Patients.", PLoS One, 10(4):e0124354, 2015.
Fuse et al., "Mechanisms of Resistance to NTRK Inhibitors and Therapeutic Strategies in NTRK1-Rearranged Cancers," Mol. Cancer Ther., Oct. 2017; 16(10); 2130-43.
Gainor et al., "Patterns of Metastatic Spread and Mechanisms of Resistance to Crizotinib in ROS1-Positive Non-Small-Cell Lung Cancer", JCO Precis Oneal. 10.1200/PO.1 7.00063, 2017.
Gang et al., "The landscape of fusion transcripts in spitzoid melanoma and biologically indeterminate spitzoid tumors by RNA sequencing.", Mod Pathol., 29(4): 359-69, 2016.
Gao et al., "Driver fusions and their implications in the development and treatment of human cancers," Cell Rep. 23(1):227-238.e3, 2018.
Gatalica et al., "Abstract A047: Molecular characterization of the malignancies with targetable NTRK gene fusions," American Association for Cancer Research, Jan. 2018, 2 pages.
Gaudet et al., "Allele-specific PCR in SNP genotyping," Methods Mol Biol. 2009;578:415-24. doi: 10.1007/978-1-60327-411-126.
Gavrin et al., "Synthesis of Pyrazolo[1,5-[alphapyrimidoinone Regioisomers," J Org Chem, Feb. 2007, 72(3): 1043-1046.
Geiger et al., "Functional Characterization of Human Cancer-Derived TRKB Mutations," PLoS One, Feb. 17, 2011, 6(2):e16871.
Geiger et al., "The neurotrophic receptor TrkB in anoikis resistance and metastasis: a perspective," J Cancer Res., Aug. 2005, 65(16):7033-7036.
GenBank Accession No. AAB33109.1, "trkB [*Homo sapiens*]," Jul. 27, 1995, 1 page.
GenBank Accession No. AAB33111.1"trkC [*Homo sapiens*]," Jul. 27, 1995, 1 page.
GenBank Accession No. NM_002529, "high affinity nerve growth factor receptor isoform 2 precursor [*Homo sapiens*]," May 11, 2014, 4 pages.
GenBank Accession No. NM_001007792 "*Homo sapiens*neurotrophic tyrosine kinase, receptor, type 1 (NTRK1), transcript variant 3, mRNA," May 10, 2014, 5 pages.

(56) References Cited

OTHER PUBLICATIONS

GenBank Accession No. NM_001012338, "*Homo sapiens* neurotrophic tyrosine kinase, receptor, type 3 (NTRK3), transcript variant 1, mRNA," May 10, 2014, 6 pages.
GenBank Accession No. NM_006180, "*Homo sapiens* neurotrophic tyrosine kinase, receptor, type 2 (NTRK2), transcript variant a, mRNA," May 12, 2014, 9 pages.
GenBank Accession No. NP 001007793, "high affinity nerve growth factor receptor isoform 3 [*Homo sapiens*]," May 10, 2014, 3 pages.
GenBank Accession No. NP_ 002520 "high affinity nerve growth factor receptor isoform 2 precursor [*Homo sapiens*]," May 11, 2014, 4 pages.
GenBank Accession No. NP_001007157, "NT-3 growth factor receptor isoform c precursor [*Homo sapiens*]," May 10, 2014, 3 pages.
GenBank Accession No. NP_001012331.1, "high affinity nerve growth factor receptor isoform 1 precursor [*Homo sapiens*]," May 10, 2014, 4 pages.
GenBank Accession No. NP_001012338, "NT-3 growth factor receptor isoform a precursor [*Homo sapiens*]," May 10, 2014, 3 pages.
GenBank Accession No. NP_006171, "BDNF/NT-3 growth factors receptor isoform a precursor [*Homo sapiens*]," May 12, 2014, 4 pages.
GenBank Accession No. S76473.1, "trkB [human, brain, mRNA, 3194 nt]," Jul. 27, 1995, 2 pages.
GenBank Accession No. S76475.1, "trkC [human, brain, mRNA, 2715 nt]," Jul. 27, 1995, 2 pages.
Genevois et al., "Dependence receptor TrkC is a putative colon cancer tumor suppressor," Proc. Nat. Acad. Sci. U.S.A. Feb. 19, 2013, 110(8):3017-3022.
Giacomini et al., "Breakpoint Analysis of Transcriptional and Genomic Profiles Uncovers Novel Gene Fusions Spanning Multiple Human Cancer Types", PLoS Gene.t, 9(4): e1003464, 2013.
Gimm et al., "Mutation analysis of NTRK.2 and NTRK.3, encoding 2 tyrosine kinase receptors, in sporadic human medullary thyroid carcinoma reveals novel sequence variants," International Journal of Cancer, Apr. 1, 2001, 92(1):70-74.
Greco et al., "Chromosome I rearrangements involving the genes TPR and NTRK1 produce structurally different thyroid-specific TRK oncogenes," Genes Chromosomes Cancer. 19(2):112-23, 1997.
Greco et al., "Rearrangements of NTRK1 gene in papillary thyroid carcinoma," Molecular and Cellular Endocrinology, 2010, 321(1):44-49.
Greco et al., "The DNA rearrangement that generates the TRK-T3 oncogene involves a novel gene on chromosome 3 whose product has a potential coiled-coil domain," Mol. Cell. Biol. 15(11):6118-6127, 1995.
Greco et al., "TRK-T1 is a novel oncogene formed by the fusion of TPR and TRK genes in human papillary thyroid carcinomas," Oncogene. 7(2):237-42, 1992.
Green & Wuts, eds, "Protective Groups in Organic Synthesis," John Wiley & Sons Inc, May 8, 1999.
Groisberg et al., "Clinical next-generation sequencing in sarcomas", Journal of Clinical Oncology, vol. 34, Supp. Supplement 15; Abstract No. 11046; 2016 Annual Meeting of the American Society of Clinical Oncology, ASCO 2016, Chicago, IL. Jun. 3-7, 2016.
Gruber-Olipitz et al., "Neurotrophin 3/TrkC-regulated proteins in the human medulloblastoma cell line DAOY," J. Proteome Research, 2008, 7(5):1932-1944.
Gu et al., "Lung adenocarcinoma harboring concomitant SPTBN1-ALK fusion, c-Met overexpression, and HER-2 amplification with inherent resistance to crizotinib, chemotherapy, and radiotherapy.", J Hematol Oneal, 9(1): 66, 2016.
Gwak et al., "Attenuation of mechanical hyperalgesia following spinal cord injury by administration of antibodies to nerve growth factor in the rat." Neurosci. Lett., 2003, 336:117-120.
Hainsworth et al., "Lung Adenocarcinoma with Anaplastic Lymphoma Kinase (ALK) Rearrangement Presenting as Carcinoma of Unknown Primary Site: Recognition and Treatment Implications.", Drugs Real World Outcomes, 3: 115-120, 2016
Hakimi et al., "Minimally invasive approaches to prostate cancer: a review of the current literature.", Urol. J., 4: 130-137, 2007.
Hallberg and Palmer, "The role of the ALK receptor in cancer biology.", Ann. Oncology, 27 (Suppl 3):iii4-iii15. doi: 10.1093/annonc/mdw301, 2016.
Haller et al., "Paediatric and adult soft tissue sarcomas with NTRK.1 gene fusions: a subset of spindle cell sarcomas unified by a prominent myopericytic/haemangiopericytic pattern," J Pathol, Apr. 2016, 238(5):700-710.
Hamdouchi et al "Imidazo[1,2-b]pyridazines, novel nucleus with potent and broad spectrum activity against human picornavimses: design, synthesis, and biological evaluation" J Med Chem., Sep. 25, 2003;46(20):4333-4341.
Hansen et al., "Autophagic cell death induced by TrkA receptor activation in human glioblastoma cells," J. of Neurochemistry, 2007, 103:259-275.
Harada et al., "Role and Relevance of TrkB Mutations and Expression in Non-Small Cell Lung Cancer," Clinical Cancer Research, Jan. 17, 2011, 17(9):2638-2645.
Harris et al., "Multicenter Feasibility Study of Tumor Molecular Profiling to Inform Therapeutic Decisions in Advanced Pediatric Solid Tumors: The Individualized Cancer Therapy (iCat) Study," JAMA Oncol, Jan. 2016; 10.1001/jamaoncol.2015.5689, 8 pages.
Harwood et al., "Experimental organic chemistry—Principles and practice," Experimental Chemistry—Organic Chemistry and Reaction, Jan. 1, 1989, 127-132.
Hayashi et al., "Crizotinib treatment for refractory pediatric acute myeloid leukemia with RAN-binding protein 2-anaplastic lymphoma kinase fusion gene.", Blood Cancer J, 6(8): e456, 2016.
Hechtman et al., "Identification of targetable kinase alterations in patients with colorectal carcinoma that are preferentially associated with wild-type RAS/RAF," Mol. Cancer Res. 14(3):296-301, 2016.
Hechtman et al., Abstract 1837: Pan-TRK IHC is an Efficient and Reliable Screening Assay for Targetable NTRK Fusions, Annual Meeting Abstracts, 2017, 457A.
Herzberg et al., "NGF involvement in pain induced by chronic constriction injury of the rat sciatic nerve," Neuroreport, 1997, 8:1613-1618.
Hinrichs et al., "Exploiting the curative potential of adoptive T-cell therapy for cancer," Immunol Rev. Jan. 2014;257(1):56-71.doi: 10. 1 1 1 1/imr. 12132
Hobbs et al., "Effects of T-Cell Depletion on Allogeneic Hematopoietic Stem Cell Transplantation Outcomes in AML Patients," J Clin Med. Mar. 19, 2015;4(3):488-503. doi: 10.3390/jcm4030488.
Holla et al., "ALK: a tyrosine kinase target for cancer therapy", Cold Spring Harb Mol Case Study, 3(1):a001115. doi: 10.1101/mcs. a001115, 20 pages, 2017.
Hong et al., "Clinical Safety and activity from a Phase 1 study of LOXO-101, a selective TRKA/B/C inhibitor, in solid-tumor patients with NTRK gene fusions," 2016 AACR Annual Meeting, Apr. 17, 2016, 32 pages.
Hong et al., Abstract PR13: Clinical safety and activity from a phase 1 study of LOXO-101, a selective TRKA/B/C inhibitor, in solid-tumor patients with NTRK gene fusions, Molecular Cancer Therapeutics 2015:14(12 Supplement 2):PR13.; Abstract only, 4 pages.
Hornick et al., "Expression of ROSI predicts ROSI gene rearrangement in inflammatory myofibroblastic tumors.", Mod Pathol., 28(5): 732-9, 2015.
Hover et al., "Abstract TMOD-07: NTRK3 Gene Fusions Drive Tumorigenesis in Novel Models of Pediatric HighGrade Glioma," Neuro-Oncology, Jun. 2017, iv49.
Howell et al., "Dynamic allele-specific hybridization. A new method for scoring single nucleotide polymorphisms," Nat Biotechnol. 1999 Jan;17(1):87-8.
Hu et al., "Decrease in bladder overactivity with REN1820 in rats with cyclophosphamide induced cystitis," J. Urology, 2005, 173(3):1016-1021.
Hu et al., "Identification of brain-derived neurotrophic factor as a novel angiogenic protein in multiple myeloma" Cancer Genetics and Cytogenetics, 2007, 178:1-10.

(56) References Cited

OTHER PUBLICATIONS

Huehls et al., "Bispecific T-cell engagers for cancer immunotherapy," Immunol Cell Biol. Mar. 2015;93(3):290-6. doi: 10.1038/icb.2014.93. Epub Nov. 4, 2014.
Hyrcza et al., "Abstract OFP-06-007: Comparison of ultrastructural features between pediatric Mammary Analogue Secretory Carcinoma (MASC) of the salivary glands and Pediatric Secretory Breast Carcinoma (SBC) reveals similar pathological features," Virchows Arch, Sep. 2016, 469(S1): S17.
Hyrcza et al., vol. 469, Supp. Supplement 1, pp. S17. Abstract No. OFP-1997-7; 31st International Congress of the International Academy of Pathology and the 28th Congress of the European Society of Pathology, Cologne, Germany. Sep. 25-29, 2016.
Igaz et al., "Biological and clinical significance of the JAK-STAT pathway; lessons from knockout mice," Inflamm. Res., 2001, 50:435-441.
Ihle et al., "The Roles of Jaks and Stats in Cytokine Signaling," Canc. J. Sci. Am., 1998, 4(1):84-91.
Ihuegbu et al., "Non-invasive detection of crizotinib resistance in ALK-rearranged lung adenocarcinoma directs treatment with next-generation ALK inhibitors", J Clin. Oncology, vol. 34, Supp. Supplement 15, Abstract No. e20643, 2016 Annual Meeting of the American Society of Clinical Oncology, Chicago, IL, 2016.
Ikeda et al., "Basic Science", Annals of Oncology. vol. 28 (suppl_10): xl x6.10.1093/annonc/mdx652, 2017.
Imamura et al., "Allogeneic hematopoietic stem cell transplantation in adult acute lymphoblastic leukemia: potential benefit of medium-dose etoposide conditioning," Exp Hematol Oncol, Jul. 16, 2015;4:20. doi: 10.1186/s40164-015-0015-0. eCollection 2015.
Iniguez-Ariza et al., "Abstract 6087: NTRK.1-3-point mutations in poor prognosis thyroid cancers," J Clinical Oncology, May 2017, 35(15): 6087.
Isdori et al., "Advancement in high dose therapy and autologous stem cell rescue in lymphoma," World J Stem Cells, Aug. 2015, 7(7):1039-1046.
Iyama et al., "Identification of Three Novel Fusion Oncogenes, SQSTM1/NTRK3, AFAP1L2/RET, and PPFIBP2/RET, in Thyroid Cancers of Young Patients in Fukushima," Thyroid. 27(6):811-818, 2017.
Iyer et al., "AZ64 inhibits TrkB and enhances the efficacy of chemotherapy and local radiation in neuroblastoma xenografts," Cancer Chemother Pharmacol. Sep. 2015;70(3):477-86. doi: 10.1007/s00280-012-1879-x. Epub May 24, 2012.
Iyer, R., "Entrectinib is a potent inhibitor of Trk-driven neuroblastomas in a xenograft mouse model." Cancer letters 372.2 (2016): 179-186. (Year: 2016).
Jaggar et al., "Inflammation of the rat urinary bladder is associated with a referred thermal hyperalgesia which is nerve growth factor dependent," Br. J. Anaesth, 1999, 83:442-448.
Jencks and Regenstein, "Ionization Constants of Acids and Bases," Handbook of Biochemistry and Molecular Biology, 3rd ed., G.D. Fassman, CRC Press, 1976, 1: 305-347.
Jin et al., "TrkC plays an essential role in breast tumor growth and metastasis," Carcinogenesis, 2010, 31(11):1939-1947.
Johnson et al., "Comprehensive Genomic Profiling of 282 Pediatric Low- and High-Grade Gliomas Reveals Genomic Drivers, Tumor Mutational Burden, and Hypermutation Signatures.", Oncologist. 22(12): 1478-1490, 2017.
Jones et al., "Recurrent somatic alterations of FGFR1 and NTRK.2 in pilocytic astrocytoma," Nature Genetics, 2013, 45:927-932.
Kao et al., "Recurrent BRAF Gene Fusions in a Subset of Pediatric Spindle Cell Sarcomas," Am. J. Surg. Pathol. 42(1):28-38, 2018.
Karachialiou et al., "Real-time liquid biopsies become a reality in cancer treatment", Ann. Transl. Med, 3(3):36, 2016.
Katayama et al., "Cabozantinib Overcomes Crizotinib Resistance in ROS1 Fusion-Positive Cancer", Clin. Cancer Res., 21 (I): 166-7 4, 2015.
Katayama et al., "Mechanisms of Acquired Crizotinib Resistance in ALK Rearranged Lung Cancers," Sci Transl Med, Feb. 2012, 4(120): 120ra17.
Katayama et al., "Therapeutic targeting of anaplastic lymphoma kinase in lung cancer: a paradigm for precision cancer medicine.", Clin Cancer Res, 21(10): 2227-35, 2015.
Keysar et al., "A patient tumor transplant model of Squamous cell cancer identifies PBK inhibitors as candidate therapeutics in defined molecular bins," Molecular Oncology, 2013, 7(4):776-790.
Kim et al., "Mammaglobin-A is a target for breast cancer vaccination", Oncolmmunology 5(2):e1069940, 2016.
Kim et al., "NTRK.1 fusion in glioblastoma multiforme," PloS One, 2014, 9(3): e91940.
Kim et al., "SEC31A-ALK Fusion Gene in Lung Adenocarcinoma", Cancer Res Treat, 48(1): 398-402,2016.
Klijn et al., "A comprehensive transcriptional portrait of human cancer cell lines," Nat Biotechnol., 2015, 33(3):306-312.
Knezevich et al., "A novel ETV6-NTRK.3 gene fusion in congenital fibrosarcoma," Nat Genet, Feb. 1998:18(2):184-187.
Knezevich et al., "ETV6-NTRK3 gene fusions and trisomy 11 establish a histogenetic link between mesoblastic nephroma and congenital fibrosarcoma," Cancer Res, Nov. 1998:58(22):5046-5048.
Koboldt et al., "The next-generation sequencing revolution and its impact on genomics," Cell, Sep. 26, 2013;155(1):27-38. doi: 10.1016/j.cell.2013.09.006.
Kohsaka et al., Pediatric soft tissue tumor of the upper arm with LMNA-NTRK1 fusion, Hum. Pathol. 72:167-173,2017.
Kolokythas et al., "Nerve growth factor and tyrosine kinase A receptor in oral squamous cell carcinoma: is there an association with perineural invasion?" J. Oral Maxillofacial Surgery, 2010, 68(6):1290-1295.
Konicek et al., Cancer research, vol. 76, No. 14, Supp. Supplement. Abstract No. 2647; 107th Annual Meeting of the American Association for Cancer Research, AACR 2016. New Orleans, LA; Apr. 16-20, 2016; Abstract only, 3 pages.
Kralik et al., "Characterization of a newly identified ETV6-NTRK3 fusion transcript in acute myeloid leukemia," Diagn. Pathol. 6:19, 2011.
Kremer et al., "The safety and efficacy of a JAK inhibitor in patients with active rheumatoid arthritis: Results of a double-blind, placebo-controlled phase IIa trial of three dosage levels of CP-690,550 versus placebo," Arth. & Rheum., 2009, 60:1895-1905.
Kruttgen et al., "The dark side of the NGF family: neurotrophins in neoplasias," Brain Pathology, 2006, 16:304-310.
Kubler et al., "Self-adjuvanted mRNA vaccination in advanced prostate cancer patients: a first-in-man phase I/IIa study.", J. Immunother Cancer 3 :26, 2015.
Kusano et al., "Two Cases of Renal Cell Carcinoma Harboring a Novel STRN-ALK Fusion Gene.", Am J SurgPathol. 40(6): 761-9, 2016.
Lamb et al., "Nerve growth factor and gastric hyperalgesia in the rat," Neurogastrenterol. Motil., 2003, 15:355-361.
Lannon et al., "ETV6-NTRK3: a chimeric protein tyrosine kinase with transformation activity in multiple cell lineages," Semin Cancer Biol, Jun. 2005:15(3):215-223.
Lansky et al., "The measurement of performance in childhood cancer patients," Cancer, 1987, 60(7):1651-1651.
Lecht et al., "Angiostatic effects ofK252a, a Trk inhibitor, in murine brain capillary endothelial cells," Mol Cell Biochem, Jun. 2010;339(1-2):201-13. doi: 10.1007/s11010-010-0386-9. Epub Feb. 11, 2010.
Lee et al., "Identification of ROS1 rearrangement in gastric adenocarcinoma.", Cancer, 119(9): 1627-1635, 2013.
Leeman-Neill et al., "ETV6-NTRK3 is a common chromosomal rearrangement in radiation-associated thyroid cancer," Cancer, 2014, 120(6):799-807.
Leukemia, Wikipedia the Free Encyclopedia, Dec. 8, 2001, https://en.wikipedia.org/wiki/Leukemia, 15 pages.
Leyvraz et al., Abstract No. 897. Meeting Info: 33. Deutscher Krebskongress, DKK. Berlin, Germany, 2018.
Lezcano et al., "Regular transfusion lowers plasma free hemoglobin in children with sickle-cell disease at risk for stroke," Am. J. Surg. Pathol. doi: 10.1097/P AS.0000000000001070, 2018.
Li et al., "Brain derived neurotrophic factor (BDNF) contributes to the pain hypersensitivity following surgical incision in the rats," Molecular Pain, 2008, 4(28):1-11.

(56) References Cited

OTHER PUBLICATIONS

Li et al., "Combinational Analysis of FISH and Immunohistochemistry Reveals Rare Genomic Events in ALK Fusion Patterns in NSCLC that Responds to Crizotinib Treatment", J Thorac. Oneal., 12(1):94-101. doi: 10.1016/i .itho.2016.08.145, 2017.
Li et al., "Correlation of expressions of GFAP, NT-3, TRK and NCAM with neurotropic molecular mechanism and clinical factors in adenoid cystic carcinoma of salivary gland," Chinese Journal of Cancer Prevention and Treatment, 2009, 16(6): 428-430 (with English abstract).
Li et al., "In vivo sensitized and in vitro activated B cells mediate tumor regression in cancer adoptive immunotherapy," J Immunol, Sep. 1, 2009;183(5):3195-203. doi:.10.4049/jimmunol.0803773. Epub Aug. 10, 2009.
Li et al., "Lumbar 5 ventral root transection-induced upregulation of nerve growth factor in sensory neurons and their target tissues: a mechanism in neuropathic pain," Mol. Cell. Neurosci., 2003, 23:232-250.
Li et al., "TRK inhibitor attenuates the BDNF/TrkB-induced protection of neuroblastoma cells from etoposide in vitro and in vivo," Cancer Biol. Ther., Feb. 2015, 16(3):477-483.
Lin et al., "HG-48. Integrated sequencing of pediatric pilocytic Astrocytoma with anaplasia reveals molecular features of both Lowand high-grade glial tumors", Neuro-Oneol, vol. 18, Supp. Supplement 3, pp. iii58, Abstract No. HG-48; 17th International Symposium on Pediatric Neuro-Oncology, ISPNO 2016. Liverpool, UK, Jun. 12, 2016-Jun. 15, 2016.
Lin et al., Neuro-Oncol, vol. 18, Supp. Supplement 3, pp. iii58, Abstract No. HG-48; 17th International Symposium on Pediatric Neuro-Oncology, ISPNO 2016. Liverpool, UK, Jun. 12, 2016-Jun. 15, 2016.
Linch et al., "Systemic treatment of soft-tissue sarcoma [mdash] gold standard and novel therapies," Nature Reviews Clinical Oncology, 2014, 11(4):187-202.
Loh et al., "Treatment of infantile fibrosarcoma with chemotherapy and surgery: results from the Dana-Farber Cancer Institute and Children's Hospital, Boston," J Pediatr Hematol Oncol, Dec. 2002:24(9):722-726.
Lorigan et al., "Phase III trial of two investigational schedules of ifosfamide compared with standard-dose doxombicin in advanced or metastatic soft tissue sarcoma: a European Organisation for Research and Treatment of Cancer Soft Tissue and Bone Sarcoma Group Study," J. Clin Oncol., 2007, 25(21):3144-3150.
Lovly et al., "Inflammatory myofibroblastic tumors harbor multiple potentially actionable kinase fusions," Cancer Discov., 2014, 4(8):889-895.
Lu et al., "Targeted next generation sequencing identifies somatic mutations and gene fusions in papillary thyroid carcinoma," Oncotarget. 8(28):45784-45792, 2017.
Ma and Woolf, "The progressive tactile hyperalgesia induced by peripheral inflammation is nerve growth factor dependent," Neuroreport, 1997, 8:807-810.
Ma et al., "Responses to crizotinib in patients with ALK-positive lung adenocarcinoma who tested immunohistochemistry (IHC)-positive and fluorescence in situ hybridization (FISH)-negative", Oncotarget, 7(39), 64410-64420, 2016.
Macleod, et al., "Abstract 0294: Gene Targets ofETV6-NTRK3 Fusion," Haematologica, 14th Congress of the European Hematology Association,2009, 94(s2): 116.
Majweskaetal., CancerResearch, vol. 76, No. 14, Supp. Supplement. Abstract No. 3190. 107th Annual meeting of the American Association for Cancer Research, Aacr. New Orleans, LA Apr. 16-20, 2016.
Makretsov et al., "A fluorescence in situ hybridization study ofETV6-NTRK3 fusion gene in secretory breast carcinoma," Genes, Chromosomes and Cancer, Jun. 2004:40(2):152-157.
Marchetti et al., "Frequent mutations in the neurotrophic tyrosine receptor kinase gene family in large cell neuroendocrine carcinoma of the lung," Human Mutation, 2008, 29(5):609-616.
Marras et al., "Genotyping SNPs with molecular beacons," Methods Mol Biol, 2003;212:111-28.
Marras et al., Single Nucleotide Polymorphism: Methods and Protocols. Methods in Molecular Biology, Kwok, P.-Y., Ed., Totowa, NJ, Humana Press, vol. 212, pp. 111-128, 2003.
Martin-Zanca et al., "A human oncogene formed by the fusion of truncated tropomyosin and protein tyrosine kinase sequences," Nature, 1986, 319:743-748.
Matayoshi, "Actions of brain-derived neurotrophic factor on spinal nociceptive transmission during inflammation in the rat," J. Physiol., 2005, 569:685-695.
McCahon et al., "Non-Resectable Congenital Tumors with the ETV6-NTRK3 Gene Fusion Are Highly Responsive to Chemotherapy," Med. Pediatr. Oncol., May 2003, 40(5):288-292.
McCarthy et al., "Tropomyosin receptor kinase inhibitors: a patent update 2009-2013," Expert Opin TherPat. Jul. 2014;24(7):731-44. doi: 10.1517/13543776.2014.910195. Epub May 8, 2014.
McMahon et al., "The biological effects of endogenous nerve growth factor on adult sensory neurons revealed by a trkA-1gG fusion molecule," Nat. Med., 1995, 1:774-780.
McMahon., "VEGF Receptor Signaling in Tumor Angiogenesis," The Oncologist, 2000, 5(1): 3-10.
Mekinist, Highlights of Prescribing Information, Initial Approval 2013, revised Nov. 2015, Novartis Pharmaceuticals Com., 27 pages.
Melo-Jorge et al., The Chagas' disease parasite *Trypanosoma cmzi* exploits nerve growth factor receptor TrkA to infect mammalian hosts Cell Host & Microbe, 2007, 1(4):251-261.
Meyer et al., "Remarkable leukemogenic potency and quality of a constitutively active neurotrophin receptor, delta TrkA," Leukemia, 2007, 21:2171-2180.
Milione et al., "Identification and characterization of a novel SCYL3-NTRK1 rearrangement in a colorectal cancer patient," Oncotarget, 8(33):55353-55360, 2017.
Miranda et al., "Functional characterization of NTRK1 mutations Identified in melanoma," Genes Chromosomes & Cancer, Jun. 26, 2014, 53(10):875-880.
Montagnoli et al., "Anti-proliferative effects of GW441756, a novel inhibitor of NGF receptor tyrosine kinase a (TRKA), in human sarcoma," Italian Journal of Anatomy and Embryology, Nov. 10 2010, 115:117.
Montalli et al., "Mammaglobin and DOG-1 expression in polymorphous low-grade adenocarcinoma: an appraisal of its origin and morphology," J Oral Pathol Med., Mar. 2017, 46(3):182-187.
Morissette et al., "High-throughput crystallization: polymorphs, salts, co-crystals and solvates of pharmaceutical solids," Adv. Drug Deliv Rev, 2004, 56: 375-300.
Mulligan, "RET revisited: expanding the oncogenic portfolio.", Nature Reviews Cancer, 14, 173-186,2014.
Murakami et al., "Integrated molecular profiling of juvenile myelomonocytic leukemia", Blood, blood-2017-07-798157; DOI: 10.1182/blood-2017-07-798157, 2018.
Myers, "Synthesis of Chiral Amines by Asymmetric Additions to tert-Butylsulfinimines (Ellman Auxiliary)," Chem 115, retrieved on May 18, 2016, retrieved from the Internet. URL: <faculty.chemistry. harvard.edu/files/myers/files/15-ellman auxiliarv.pelf>, 6 pages.
Nagasubmamanian et al., "Brief Report: Infantile Fibrosarcoma With NTRK3-ETV6 Fusion Successfully Treated with the Tropomyosin-Related Kinase Inhibitor LOXO-101," Pediatric Blood & Cancer, 2016, DOI 10.1002, 3 pages.
Nagasubramanian et al., "Infantile Fibrosarcoma With NTRK3-ETV6 Fusion Successfully Treated With the Tropomyosin-Related Kinase Inhibitor LOXO-101," Pediatr Blood Cancer., Aug. 2016, 63(8):1468-70.
Nakagawara, "Trk receptor tyrosine kinases: a bridge between cancer and neural development," Cancer Letters, 2001, 169(2):107-114.
Nakano et al., "Novel Oncogenic KLC1-ROS1 Fusion in Pediatric Low Grade Glioma", Pediatr Blood Cancer. vol. 64, S54-S55 Suppe. 4. 013-1-7, 2017.
Narayanan et al., "Discovery and preclinical characterization of novel small molecule TRK and ROS1 tyrosine kinase inhibitors for

(56) References Cited

OTHER PUBLICATIONS the treatment of cancer and inflammation," PLoS One, Dec. 26, 2013;8(12):e83380. doi: 10.1371/journal.pone.0083380. eCollection 2013.
National Cancer Institute at the National Institutes of Health, posted on or before Jan. 5, 2000,n retrieved on Jan. 13, 2015, http://www.cancer.gov/, 2 pages.
National Comprehensive Cancer Network, posted on or before Dec. 3, 1998, retrieved on Jan. 13, 2015, http://www.nccn.org/, 1 page.
NCT02050919, "Sorafenib Tosylate, Combination Chemotherapy, Radiation Therapy, and Surgery in Treating Patients with High-Risk Stage IIB-IV Soft Tissue Sarcoma," ClinicalTrials.gov, Last Updated Dec. 16, 2015, https://www.clinicaltrials.gov/ct2/show/NCT02050919, 5 pages.
NCT02122913, "Oral TRK Inhibitor LOXO-101 for Treatment of Advanced Adult Solid Tumors," ClinicalTrials.gov, Last Updated Dec. 7, 2015, https://clinicaltrials.gov/ct2/show/NCT02122913.
Ni et al., "siRNA interference with a proliferation-inducing ligand gene in the Sgr-7901 gastric carcinoma cell line," Asian Pacific Journal of Cancer Prevention, 2012, 13:1511-1514.
Ni et al., "Tyrosine receptor kinase Bis a drug target in astrocytomas," Neuro Oncol., Jan 2017, 19(1):22-30.
NIH National Cancer Institute [online], "progression (pm-GREH-shun)," NCI Dictionary of Cancer Terms, retrieved on Sep. 17, 2018, URL: <https://www.cancer.gov/publications/dictionaries/cancer-terms/def/progression>, 1 page.
NIH National Cancer Institute [online], "recurrence (ree-KER-ents)," NCI Dictionary of Cancer Terms, retrieved on Sep. 21, 2018, URL: <https://www.cancer.gov/publications/dictionaries/cancer-terms/def/recurrence>, 1 page.
NIH National Cancer Institute [online], "relapse (REE-laps)," NCI Dictionary of Cancer Terms, retrieved on Sep. 17, 2018, URL: <https://www.cancer.gov/publications/dictionaries/cancer-terms/def/relapse>, 1 page.
NIH, "List of Cancer-causing Agents Grows," National Institute of Environmental Health Sciences, https://www.niehs.nih.gov/news/newsroom/releases/2005/january31/index.cfm, 4 pages.
Nikiforova et al., Abstract No. 5. Meeting Info: 84th Annual Meeting of the American Thyroid Association. Coronado, CA, United States, 2014.
Nollau et al., "Methods for detection of point mutations: performance and quality assessment. IFCC Scientific Division, Committee on Molecular Biology Techniques," Clin Chem. Jul. 1997;43(7):1114-28.
Obianyo et al., "Novel small molecule activators of the Trk family of receptor tyrosine kinases. BiochimBiophys Acta, 1834:2214-2218," BiochimBiophys Acta, Oct. 2013, 1834(10):2213-2218.
Ocgene.bioinfo-minzhao.org [online]. "Ovarian Cancer Gene Database, Gene ID: 4914," [retrieved on Jul. 17, 2017] Retrived from the Internet: URL<ocgene.bioinfominzhao.org/gene mutation.cgi?gene=4914>, 13 pages.
Oken et al., "Toxicity and response criteria of the Eastern Cooperative Oncology Group," Am J Clin Oncol, 1982, 5:649-655.
Olivier, "The Invader assay for SNP genotyping," Mutat Res, Jun. 3, 2005;573(1-2): 103-10.
Orbach et al., "Conservative strategy in infantile fibrosarcoma is possible: The European paediatric Soft tissue sarcoma Study Group experience," Eur J Cancer, Apr. 2016, 57:1-9.
Orbach et al., "Infantile fibrosarcoma: management based on the European experience," J Clin Oncol, Jan. 2010, 28(2):318-323.
O'Shea, "Jaks, STATs, cytokine signal transduction, and immunoregulation: are we there yet?" Immunity, 1997, 7:1-11.
Otsubo et al., "Sporadic pediatric papillary thyroid carcinoma harboring the ETV6/NTRK3 fusion in oncogene in a 7-year-old Japanese girl: a case report and review of literature," J. Pediatr. Endocrinol. Metab. 28;31(4):461-467, 201.
Ott et al., "An immunogenic personal neoantigen vaccine for patients with melanoma.", Nature 547: 217-221, 2017.
Ou et al., "Emergence of novel and dominant acquired EGFR solvent-front mutations at Gly796 (G796S/R) together with C797S/R and L792F/H mutations in one EGFR (L858R/T790M) NSCLC patient who progressed on osimertinib," Lung Cancer, 2017, 108: 228-231.
Ou et al., "Identification of a novel TMEM106B-ROS1 fusion variant in lung adenocarcinoma by comprehensive genomic profiling.", Lung Cancer, 88(3):352-4, 2015.
Ou et al., "Next-Generation Sequencing Reveals a Novel NSCLC ALK Fl 174V Mutation and Confirms ALK G1202R Mutation Confers High-Level Resistance to Alectinib (CH5424802/RO5424802) in ALK-Rearranged NSCLC Patients Who Progressed on Crizotinib," Journal of Thoracic Oncology, Apr. 2014, 9: 549-553.
Ovarian Cancer Gene Database, ocgene.bioinfo-minzhao.org/gene_mutation.cgi?gene=49 1 4, downloaded on May 31, 2016, 14 pages.
Ovarian Cancer Gene Database, ocgene.bioinfo-minzhao.org/gene_mutation.cgi?gene=4916, downloaded on May 31, 2016, 21 pages.
Pan et al., Laboratory Investigation, vol. 96, Supp. Suppl. 1, pp. 367A, Abstract No. 1450, 105th Annual Meeting of the United States and Canadian Academy of Pathology, Seattle, WA, 2016.
Panagopoulos et al., "Recurrent fusion of the genes FN1 and ALK in gastrointestinal leiomyomas", Modem Pathology 29: 1415-1423, 2016.
Pao, W., et al. "Acquired resistance of lung adenocarcinomas to gefitinib or erlotinib is associated with a second mutation in the EGFR kinase domain," PLoS Med, Feb. 2005, 2(3), e73.
Papatsoris et al., "Manipulation of the nerve growth factor network in prostate cancer," Exper Opin Invest Drugs, 2007, 16(3):303-309.
Park et al., "Genomic alterations in BCL2L1 and DLC1 contribute to drug sensitivity in gastric cancer," Proc. Natl. Acad. Sci. U.S.A., Oct. 2015, 112(40):12492-12497.
Park et al., "NTRK1 fusions for the therapeutic intervention of Korean patients with colon cancer," Oncotarget. 7(7):8399-412, 2016.
Patani et al., "Bioisosterism: A rational approach in Drug Design," Chem Rev., Dec. 1996, 96(8):3147-3176.
Patapoutian et al., "Trk receptors: mediators of neurotrophin action," Current Opinion in Neurobiology, 2001, 11:272-280.
Pavlick et al., "Identification of NTRK fusions in pediatric mesenchymal tumors," Pediatr Blood Cancer, Aug. 2017, 64(8). doi: 10.1002/pbc.26433. Epub Jan. 18, 2017.
PCT International Preliminary Report on Patentability in International Application No. PCT/US2009/057729, dated Mar. 22, 2011, 7 pages.
PCT International Preliminary Report on Patentability in International Application No. PCT/US2009/061519, dated Apr. 26, 2011, 6 pages.
PCT International Preliminary Report on Patentability in International Application No. PCT/US2010/041538, dated Jan. 10, 2012, 7 pages.
PCT International Preliminary Report on Patentability in International Application No. PCT/US201 1/036452, dated Nov. 29, 2012, 6 pages.
PCT International Preliminary Report on Patentability in International Application No. PCT/US2015/060953, dated May 16, 2017, 7 pages.
PCT International Preliminary Report on Patentability in International Application No. PCT/US2016/035327, dated Dec. 14, 2017, 9 pages.
PCT International Preliminary Report on Patentability in International Application No. PCT/US2016/058951, dated May 11, 2018, 11 pages.
PCT International Preliminary Report on Patentability in International Application No. PCT/US2017/033257, dated Nov. 20, 2018, 8 pages.
PCT International Preliminary Report on Patentability in International Application. No. PCT/US2017/058518, dated Apr. 30, 2019, 8 pages.
PCT International Search Report and Written Opinion in International Application No. PCT/US2009/0161519, dated Feb. 2, 2010, 8 pages.
PCT International Search Report and Written Opinion in International Application No. PCT/US2009/057729, dated Feb. 4, 2010, 10 pages.

(56) References Cited

OTHER PUBLICATIONS

PCT International Search Report and Written Opinion in International Application No. PCT/US2010/041538, dated Oct. 1, 2010, 10 pages.
PCT International Search Report and Written Opinion in International Application No. PCT/US2011/036452, dated Aug. 18, 2011, 9 pages.
PCT International Search Report and Written Opinion in International Application No. PCT/US2015/060953, dated Feb. 8, 2016, 12 pages.
PCT International Search Report and Written Opinion for International Application No. PCT/US2016/035327, dated Aug. 18, 2016, 15 pages.
PCT International Search Report and Written Opinion in International Application No. PCT/US2016/058951, dated Feb. 7, 2017, 20 pages.
PCT International Search Report and Written Opinion in International Application No. PCT/US2017/025932, dated May 31, 2017, 16 pages.
PCT International Search Report and Written Opinion in International Application No. PCT/US2017/025939, dated May 31, 2017, 16 pages.
PCT International Search Report and Written Opinion in International Application No. PCT/US2017/033257, dated Jul. 24, 2017, 13 pages.
PCT International Search Report and Written Opinion in International Application No. PCT/US2017/058518, dated May 2, 2018, 17 pages.
PCT International Search Report and Written Opinion in International Application No. PCT/US2018/022833, dated Aug. 13, 2018.
PCT International Search Report and Written Opinion in International Application No. PCT/US2018/039502, dated Apr. 16, 2018, 16 pages.
PCT International Search Report and Written Opinion in International Application No. PCT/US2018/057542, dated Mar. 6, 2019, 19 pages.
PCT International Search Report and Written Opinion in International Application No. PCT/US2019/024961, dated Jul. 23, 2019, 13 pages.
Pediatric Cancer Gene Database, pedican.bioinfominzhao.org/gene_mutation.cgi?gene=4914, downloaded on May 31, 2016, 6 pages.
Pediatric Cancer Gene Database, pedican.bioinfominzhao.org/gene_mutation.cgi?gene=4915, downloaded on May 31, 2016, 5 pages.
Pediatric Cancer Gene Database, pedican.bioinfominzhao.org/gene_mutation.cgi?gene=4916, downloaded on May 31, 2016, 9 pages.
Perales et al., "Fast Cars and No Brakes: Autologous Stem Cell Transplantation as a Platform for Novel Immunotherapies," Biol Blood Marrow Transplant, Jan. 2016;22(1):17-22. doi:.10.1016/j.bbmt.2015.10.014. Epub Oct. 17, 2015.
Perez-Pinera et al., "The Trk tyrosine kinase inhibitor K252a regulates growth of lung adenocarcinomas," Molecular and Cellular Biochemistry, 2007, 295(1&2):19-26.
Perrault et al., "The Synthesis of N-Aryl-5(S)-aminomethyl-2-oxazolidinone Antibacterials and Derivatives in One Step from Aryl Carbamates," Org. Process Res. Dev., 2003, 7:533-546.
Peus et al., "Appraisal of the Karnofsky Performance Status and proposal of simple algorithmic system for its evaluation," BMC Med Inform and Decision Making, 2013, 13:72.
Picarsic et al., "Molecular characterization of sporadic pediatric thyroid carcinoma with the DNA/RNA ThyroSeq v2 next-generation sequencing assay," Pediatr. Dev. Pathol, Mar. 2016, 19(2):115-122.
Pierottia and Greco, "Oncogenic rearrangements of the NTRK1/NGF receptor," Cancer Letters, 2006, 232:90-98.
Pinedo et al., "Translational Research: the Role of VEGF in Tumor Angiogenesis," The Oncologist, 2000, 5(1): 1-2.
Pinski et al., "Trk receptor inhibition induces apoptosis of proliferating but not quiescent human osteoblasts," Cancer Res, 2002, 62:986-989.

Plosker, "Sipuleucel-T: in metastatic castration-resistant prostate cancer.", Drugs 71(1): 101-108, 2011.
Ponsaerts et al., "Cancer immunotherapy using RNA-loaded dendritic cells," Clin. Exp. Immunol., Dec. 2003, 134:378-384.
Prabhakaran et al., "Novel TLE4-NTRK2 fusion in a ganglioglioma identified by array-CGH and confirmed by NGS: Potential for a gene targeted therapy," Neuropathology, Mar. 2018, doi:10.1111/neup.12458.
Prasad et al., "NTRK fusion oncogenes in pediatric papillary thyroid carcinoma in northeast United States," Cancer, Apr. 2016, 122(7):1097-1107.
PubChem, "Larotrectinib," https://pubchem.ncbi.nlm.nih.gov/compound/46188928, retrived on Apr. 29, 2019, 20 pages.
Pulciani et al., "Oncogenes in solid human tumours," Nature, 1982, 300(5892):539-542.
Qaddoumi et al., "Genetic alterations in uncommon low-grade neuroepithelial tumors: BRAF, FGFR1, and MYB mutations occur at high frequency and align with morphology," Acta Neuropathol, Jun. 2016, 131(6):833-845.
Qiu et al., "Next generation sequencing (NGS) in wild type GISTs", J Clin. Oneal. 35: 15 _suppl, e22507-e22507,2017.
Ramer and Bisby, "Adrenergic innervation of rat sensory ganglia following proximal or distal painful sciatic neuropathy: distinct mechanisms revealed by anti-NGF treatment," Eur. J. Neurosci., 1999, 11:837-846.
Rausch et al., "mRNA vaccine CV9103 and CV9104 for the treatment of prostate cancer.", Human Vaccinimmunother 10(11): 3146-52, 2014.
Raychaudhuri et al., K252a, a high-affinity nerve growth factor receptor blocker, improves psoriasis: an in vivo study using the severe combined immunodeficient mouse-human skin model, J. Investigative Dermatology, 2004, 122(3):812-819.
Reshmi et al., "Abstract 477: Genomic and Outcome Analyses of Philadelphia Chromosome like (Ph-like) NCI Standard Risk B-Acute Lymphoblastic Leukemia (SR B-ALL) Patients Treated on Children's Oncology Group (COG) AALL0331," Blood, 2017, 130(S1): 477.
Reungwetwattana et al., "Targeted therapies in development for non-small cell lung cancer," J Carcinog, Dec. 2013, 12:22, doi: 10.4103/1477-3163.123972. eCollection 2013.
Reuther et al., "Identification and characterization of an activating TrkA deletion mutation in acute myeloid leukemia," Mol. Cell. Biol. 2000, 20:8655-8666.
Ricarte-Filho et al., "Identification of kinase fusion oncogenes in post-Chernobyl radiation-induced thyroid cancers," J. Clin. Invest, Nov. 2013, 123(11): 4935-4944.
Ricci et al., Neurotrophins and neurotrophin receptors in human lung cancer, Am. J. Respiratory Cell and Molecular Biology, Oct. 2001, 25(4): 439-446.
Richard et al., "Syngeneic stem cell transplant for spent-phase polycythaemia vera: eradication of myelofibrosis and restoration of normal haematopoiesis," Br. J Haematol., Apr. 2002, 117(1):245-246.
Rimkunas et al., "Analysis of receptor tyrosine kinase ROS1-positive tumors in non-small cell lung cancer: identification of a FIG-ROS1 fusion.", Clin. Cancer Res., 18: 4449-58, 2012.
Ritterhouse et al., "ROS1 Rearrangement in Thyroid Cancer.", Thyroid, 26(6): 794-7, 2016.
Ro et al., "Effect of NGF and anti-NGF on neuropathic pain in rats following chronic constriction injury of the sciatic nerve," Pain, 1999, 79:265-274.
Roberts et al., "Targetable kinase-activating lesions in Ph-like acute lymphoblastic leukemia," N. Engl J Med, Sep. 2014, 371(11):1005-1015.
Roberts et al., Blood, vol. 128, No. 22. Abstract No. 278, 58th Annual Meeting of the American Society of Hematology, ASH 2016. San Diego, CA, United States. Dec. 3, 2016-Dec. 6, 2016, 2 pages.
Roblin et al., "Topical TrkA Kinase Inhibitor CT327 is an Effective, Novel Therapy for the Treatment of Pmritus due to Psoriasis: Results from Experimental Studies, and Efficacy and Safety of CT327 in a Phase 2b Clinical Trial in Patients with Psoriasis," Acta Denn. Venereal., 2015, 95:542-548.

(56) References Cited

OTHER PUBLICATIONS

Rosenbaum et al., "Next Generation Sequencing Reveals Genomic Heterogenity of ALK Fusion Breakpoints in Non -Small Cell Lung Cancer", Laboratory Investigation, vol. 96, Supp. Suppl. 1, pp. 481A-482A, Abstract No. 1914, 105th Annual Meeting of the United States and Canadian Academy of Pathology, Seattle, WA, 2016.
Roskoski, Jr. et al., "Classification of small molecule protein kinase inhibitors based upon the structures of their drug-enzyme complexes," Pharmacological Research, 2016, 103: 26-48.
Ross et al., "New routes to targeted therapy of intrahepatic cholangiocarcinomas revealed by next-generation sequencing," Oncologist, 2014, 19:235-242.
Rossi et al., "Abstract 84: RNA-Sequencing Identifies ETV6-NTRAK3 as a Gene Fusion Involved in Gastrointestinal Stromal Tumors," Meeting Info: 105th Annual Meeting of the United States and Canadian Academy of Pathology, Seattle, WA, Annual Meeting Abstracts, 24A.
Rubin et al., "Congenital mesoblastic nephroma t(12;15) is associated with ETV6-NTRK3 gene fusion: cytogenetic and molecular relationship to congenital (infantile) fibrosarcoma," Am. J. Pathol, Nov. 1998, 153(5):1451-1458.
Rubin et al., "Growth, survival and migration: the Trk to cancer," Cancer Treat Res, 2003, 115:1-18.
Russo et al., "Acquired Resistance to the Trk Inhibitor Entrectinib in Colorectal Cancer," Cancer Discovery, Jan. 1, 2016, 6(1):36-44.
Rutkowski et al., "Treatment of advanced dermatofibrosarcoma protuberans with imatinib mesylate with or without surgical resection," J. Eur. Acad. Dermatol. Venereol., 2011, 25:264-270.
Sahin et al., "Personalized RNA mutanome vaccines mobilize poly-specific therapeutic immunity against cancer.", Nature 547: 222-226, 2017.
Saborowski et al., "Mouse model of intrahepatic cholangiocarcinoma validates FIG-ROS as a potent fusion oncogene and therapeutic target.", Proc. Natl. Acad Sci. USA, 110(48): 19513-19518, 2013.
Santoro et al., "Doxombicin versus CYVADIC versus doxombicin plus ifosfamide in first-line treatment of advanced soft tissue sarcomas: a randomized study of the European Organization for Research and Treatment of Cancer Soft Tissue and Bone Sarcoma Group," J. Clin Oncol., 1995, 13(7):1537-1545.
Saragovi et al., "A TrkA-selective, fast internalizing nerve growth factor-antibody complex induces trophic but not neuritogenic signals," J Biol Chem, Dec. 25, 1998;273(52):34933-34940.
Sartore-Bianchi et al., "Sensitivity to Entrectinib Associated with a Novel LMNA-NTRK1 Gene Fusion in Metastatic Colorectal Cancer," J. Natl. Cancer Inst, Nov. 2015, 108(1). doi: 10.1093/inci/div306.
Sassolas et al., "Oncogenic alterations in papillary thyroid cancers of young patients," Thyroid Jan. 2012, 22(1):17-26.
Scaruffi et al., "Detection of DNA polymorphisms and point mutations of high-affinity nerve growth factor receptor (TrkA) in human neuroblastoma," Int. J. Oneal., May 1999, 14:935-938.
Schmidt et al., "Heilmittelchemische untersuchungen in der Heterocyclischen Rihe. Pyrazolo-(3,4-D)-Pyrimidine (Medicinal chemical studies in the heterocyclic series. Pyrazolo-(3,4-D)-Pyrimidine)," Helvetica Chimica, Verlag Helvetica Chimica Acta, Jan. 1956, 39: 986-991 (with English Abstract).
Schmidt, Charles. "Combinations on trial." Nature 552.7685 (Dec. 21, 2017): S67-S69.
Schram et al., "Abstract LB-302: Potential role of larotrectinib (LOXO-101), a selective pan-TRK inhibitor, in NTRK fusion-positive recurrent glioblastoma, "Cancer Research, Jul. 2017, DOI: 10.1158/1538-7445.AM2017-LB-302, 2 pages.
Schrock et al., "Gastrointestinal tumours, non-colorectal", Annals of Oncology. vol. 27, Suppl 6, 6130, 2016.
Shah et al., "Cardiac metastasis and hypertrophic osteoarthropathy in recurrent infantile fibrosarcoma," Pediatr. Blood Cancer, Jul. 2012, 59(1):179-181.
Shaver et al., "Diverse, Biologically Relevant, and Targetable Gene Rearrangements in Triple-Negative Breast Cancer and Other Malignancies.", Cancer Res, 76(16): 4850-60, 2016.
Shaw et al., "Ceritinib in ALK-rearranged non-small-cell lung cancer," N Engl J Med, Mar. 27, 2014;370(13):1189-97. doi: 10.1056/NEJMoal311 107.
Shaw et al., "Crizotinib in ROSI-rearranged non-small-cell lung cancer," N Engl J Med, Nov. 20, 2014;371(21):1963-71. doi: 10.1056/NEJMoa1406766. Epub Sep. 27, 2014.
Shaw et al., "Tyrosine kinase gene rearrangements in epithelial malignancies," Nat Rev Cancer, Nov. 2013, 13(11):772-787.
Sheldrick, "A short history of SHELX," Acta Crystallogr A, Jan. 2008, 64(Ptl): 112-122.
Shelton et al., "Nerve growth factor mediates hyperalgesia and cachexia in auto-immune arthritis," Pain, 2005, 116:8-16.
Sheng et al., "Congenital-infantile fibrosarcoma. A clinicopathologic study of 10 cases and molecular detection of the ETV6-NTRK3 fusion transcripts using paraffin-embedded tissues," Am. J Clin. Pathol., Mar. 2001, 115:348-355.
Sigal, et al., "Activity of Entrectinib in a Patient with the First Reported NTRK Fusion in Neuroendocrine Cancer," J. Natl. Compr. Cane. Netw, Nov. 2017, 15(11): 1317-1322.
Silverman, The Organic Chemistry of Drug Design and Drug Action, Second Edition, 2007, 20-21.
Sims et al., Abstract P280: Profiling abscopal regression in a pediatric fibrosarcoma with a novel EML4-NTRK3 fusion using immunogenomics and high-dimensional histopathology, J mmunotherapy of Cancer, Nov. 2016, 4(S1): 73.
Skalova et al., "Mammary Analogue Secretory Carcinoma of Salivary Glands: Molecular Analysis of 25 ETV6 Gene Rearranged Tumors with Lack of Detection of Classical ETV6-NTRK3 Fusion Transcript by Standard RT-PCR: Report of 4 Cases Harboring ETV6-X Gene Fusion," Am. J. Surg. Pathol, Jan. 2016, 40(1):3-13.
Skalova et al., "Molecular Profiling of Mammary Analog Secretory Carcinoma Revealed a Subset of Tumors Harboring a Novel ETV6-RET Translocation: Report of 10 Cases," Am. J. Surg. Pathol, Feb. 2018, 42(2):234-246.
Skalova et al., "Newly described salivary gland tumors," Modem Pathology, Jan. 2017, 30, S27-S43.
Sleijfer et al., "Prognastic and predictive factors for outcome to firs-line ifosfamide-containing chemotherapy for adult patients with advanced soft tissue sarcomas: an exploratory, retrospective analysis on large series from the European Organization for Research and Treatment of Cancer-Soft Tissue and Bone Sarcoma Group," Eur J. Cancer, 2010, 46(1):72-83.
Sleijfer et al., "Using single-agent therapy in adult patients with advanced soft tissue sarcoma can still be considered standard care," Oncologist, 2005, 10(10):833-841.
Smith et al., "Annotation of human cancers with EGFR signaling-associated protein complexes using proximity ligation assays," Sci Signal, 2015, 8(359):ra4, 12 pages.
Sohrabji et al., "Estrogen-BDNF interactions: implications for neurodegenerative diseases," Frontiers in Neuroendocrinology, 2006, 27(4):404-414.
Song et al., "Molecular Changes Associated with Acquired Resistance to Crizotinib in ROS1-Rearranged Non-Small Cell Lung Cancer.", Clin. Cancer Res., 21(10): 2379-87, 2015.
Stephens et al., "Trk receptors use redundant signal transduction pathways involving SHC and PLC-gamma 1 to mediate NGF responses," Neuron, Mar. 1994, 12(3):691-705.
Stransky et al., "The landscape of kinase fusions in cancer," Nature comm., 2014, 5:4846.
Subramaniam et al., Abstract 2019: RNA-Seq analysis of glioma tumors to reveal targetable gene fusions, 2017 Annual Meeting of the American Society of Clinical Oncology,2017, 1 page.
Sun et al., "P-loop conformation governed crizotinib resistance in G2032R-mutated ROSI tyrosine kinase: clues from free energy landscape," PLoS computational biology, Jul. 17, 2014, 10(7): e1003729.
Tacconelli et al., "TrkA alternative splicing: a regulated tumor-promoting switch in human neuroblastoma," Cancer Cell, 2004, 6:347-360.

(56) References Cited

OTHER PUBLICATIONS

Tafinlar, Highlights of Prescribing Information, GlaxoSmithKline, Jan. 2014, 41 pages.
Tahira et al., "dbQSNP: a database of SNPs in human promoter regions with allele frequency information determined by single-strand conformation polymorphism-based methods," Hum Mutat, Aug. 2005;26(2):69-77.
Taipale et al., "Chaperones as thermodynamic sensors of drug-target interactions reveal kinase inhibitor specificities in living cells," Nat Biotech, 2013, 31(7):630-637.
Tan et al., "Genetic landscape of ALK+ non-small cell lung cancer (NSCLC) patients (pts) and response to ceritinib in ASCEND-I", J Clin. Oncology, vol. 34, Supp. Supplement 15, Abstract No. 9064, 2016 Annual Meeting of the American Society of Clinical Oncology, Chicago, IL, 2016.
Tanaka et al., "Brain-derived neurotrophic factor (BDNF)-induced tropomyosin-related kinase B (Trk B) signaling is a potential therapeutic target for peritoneal carcinomatosis arising from colorectal cancer," PLoS One May 6, 2014, 9(5):e96410.
Tannenbaum, et al., "Abstract 749: Characterization of a Novel Fusion Gene, EML4-NTRK3, in Infantile Fibrosarcoma," Pediatr Blood Cancer, DOI 10.1002/pbc, 1 page.
Tannenbaum-Dvir et al., "Characterization of a novel fusion gene EML4-NTRK3 in a case of recurrent congenital fibrosarcoma," Cold Spring Harb. Mol. Case Stud., Oct. 2015 1(1):a000471.
Tarate et al., "Oral Solid Self-Emulsifying Formulations: A Patent Review," Recent Patents on Drug Delivery & Formulation, 2014, 8(2):126-143.
Taylor et al., "Abstract 794: Characterization of NTRK fusions and Therapeutic Response to NTRK Inhibition in Hematologic Malignancies," Blood, 2017, 130: 794.
The Cancer Genome Atlas Network, "Comprehensive Molecular Characterization of Human colon and Rectal Cancer," Nature, Jan. 2013, 487(7407): 330-337.
Theodosiou et al., "Hyperalgesia due to nerve damage: role of nerve growth factor," Pain, 1999, 81:245-255.
Thiele, "On Trk—the TrkB signal transduction pathway is an increasingly important target in cancer biology," Clinical Cancer Research, 2009, 105(19):5962-5967.
Thompson et al., "Brain-derived neurotrophic factor is an endogenous modulator of nociceptive responses in the spinal cord," Proc. Natl. Acad. Sci. USA, 1999, 96:7714-7718.
Thress et al., "Identification and preclinical characterization of AZ-23, a novel, selective, and orally bioavailable inhibitor of the Trk kinase pathway," Mol Cancer Ther, Jul. 2009:8(7):1818-27. doi: 10.1158/1535-7163.MCT-09-0036. Epub Jun. 9, 2009.
Truzzi et al., "Neurotrophins and their receptors stimulate melanoma cell proliferation and migration," J. Investigative Dermatology, 2008, 128(8):2031-2040.
Truzzi et al., "Neurotrophins in healthy and diseased skin," Dermato-Endocrinology, 2008, 3(1):32-36.
Tognon et al., "Expression of the ETV6-NTRK3 gene fusion as a primary event in human secretory breast carcinoma," Cancer Cell, Nov. 2002, 2(5):367-376.
Turtle et al., "Artificial antigen-presenting cells for use in adoptive immunotherapy," Cancer J, Jul.-Aug. 2010;16(4):374-81. doi: 10.1097/PP0.0b013e3181eb33a6.
UniProtKB/Swiss-Prot: P04629.4, "RecName: Full=High affinity nerve growth factor receptor; AltName: Full=Neurotrophic tyrosine kinase receptor type 1; AltName: Full=TRK.1-transforming tyrosine kinase protein; AltName: Full=Tropomyosin-related kinase A; AltName: Full=Tyrosine kinase receptor; AltName: Full=Tyrosine kinase receptor A; Short=Trk-A; AltName: Full=gp140trk; AltName: Full=p140-TrkA; Flags: Precursor," May 14, 2014, 28 pages, available at URL<https://www.ncbi.nlm.nih.gov/protein/947304027sat=18&satkey=12407077>.
UniProtKB/Swiss-Prot: Q16288.2, "RecName: Full=NT-3 growth factor receptor; AltName: Full=GP145-TrkC; Short=Trk-C; AltName: Full=Neurotrophic tyrosine kinase receptor type 3; AltName: Full=TrkC tyrosine kinase; Flags: Precursor," May 14, 2014, 13 pages, available at URL<www.ncbi.nlm.nih.gov/protein/1340353357report=genbank&log$=protalign&blast_rank=O&RID=0>.
UniProtKB/Swiss-Prot: Q16620.1, "RecName: Full=BDNF/NT-3 growth factors receptor; AltName: Full=GP145-TrkB; Short=Trk-B; AltName: Full=Neurotrophic tyrosine kinase receptor type 2; AltName: Full=TrkB tyrosine kinase; AltName: Full=Tropomyosin-related kinase B; Flags: Precursor," May 14, 2014, 17 pages, available at URL<www.ncbi.nlm.nih.gov/protein/24975607report=genbank&log$=protalign&blast_rank=O&R ID=0>.
Vaishnavi et al., "Oncogenic and drug-sensitive NTRK1 rearrangements in lung cancer.", Nature Med 19: 1469-1472, 2013.
Vaishnavi et al., "TRK.ing Down an Old Oncogene in a New Era of Targeted Therapy," Cancer Discovery, Jan. 2015, 5(1):25-34.
Van Gurp et al., "Phase 1 dose-escalation study of CP-690 550 in stable renal allograft recipients: preliminary findings of safety, tolerability, effects on lymphocyte subsets and pharmacokinetics," Am. J. Transpl., 2008, 8:1711-1718.
Van Noesel et al., "Pediatric neuroblastomas: genetic and epigenetic 'danse macabre'," Gene, 2004, 325:1-15.
Vanden et al., "Endocrine and neuroendocrine tumours", Annals of Oncology, vol. 27, Supp. Supplement 6. Abstract No. 427PD' 4pt European Society for Medical Oncology Congress, ESMO 2016; Copenhagen, Denmark; Oct. 7-11, 2016.
Vippagunta et al., "Crystalline Solids" Advanced Drug Delivery Rev., 2001, 48(1): 3-26.
Vogelstein and Kinzler, The Genetic Basis of Human Cancer, 2nd ed., 2002, ng 3, col. 1, para 2.
Wadhwa et al., "Expression of the neurotrophin receptors Trk A and Trk Bin adult human astrocytoma and glioblastoma," Journal of Biosciences, 2003, 28(2):181-188.
Walch et al., "Role of neurotrophins and neurotrophins receptors in the in vitro invasion and heparanase production of human prostate cancer cells," Clin. Exp. Metastasis, 1999, 17:307-314.
Walther et al., "Cytogenetic and single nucleotide polymorphism array findings in soft tissue tumors in infants," Cancer Genet, Jul.-Aug. 2013, 206(7-8): 299-303.
Wang et al., "Design, synthesis and biological evaluation of novel 4-arylaminopyrimidine derivatives possessing a hydrazone moiety as dual inhibitors of L1196M ALK and ROS1.", Eur. J Med Chem., 123, 80-99, 2016.
Wang et al., "Identification of 4-aminopyrazolylpyrimidines as potent inhibitors of Trk kinases," J Med Chem, Aug. 14, 2008;51(15):4672-84. doi: 10.1021/jm800343j. Epub Jul. 23, 2008.
Wang et al., "Identification of NTRK3 fusions in childhood melanocytic neoplasms," J. Mol. Diagn, May 2017, 19(3):387-396.
Wang et al., "T cells sensitized with breast tumor progenitor cell vaccine have therapeutic activity against spontaneous HER2/neu tumors," Breast Cancer Res Treat, Jul. 2012;134(1):61-70. doi: 10.1007/s10549-011-1912-5. Epub Dec. 16, 2011.
Wang et al., "Trk kinase inhibitors as new treatments for cancer and pain," Expert Opin. Ther Patents, Mar. 2009, 19(3):305-319.
Wang, "Pan-cancer analysis of ROSI genomic aberrations", University of Hong Kong, Pokfulam, Hong Kong SAR (Thesis), 44 pages, 2015.
Watanbe et al., "Cryptic t(12;15)(p13;q26) producing the ETV6-NTRK3 fusion gene and no loss of IGF2 imprinting in congenital mesoblastic nephroma with trisomy 11: fluorescence in situ hybridization and IGF2 allelic expression analysis," Cancer Genet. Cytogenet, Jul. 2002, 136(1):10-16.
Wei et al., "Abstract #2136: Entrectinib is Effective Against the Gatekeeper and Other Emerging Resistance Mutations in NTRK-, ROSI- and ALK-Rearranged Cancers," Poster, Presented at Proceedings of the 107th Annual Meeting of the American Association for Cancer Research, New Orleans LA, Apr. 16-20, 2016; Cancer Res, Jul. 2016, 76(14): 1 page.
Wei et al., "Abstract 78: Entrectinib, a highly potent pan-Trk, and ALK inhibitor, has broad-spectrum, histology-agnostic anti-tumor activity in molecularly defined cancers," 28thEORTC-NCI-AACR Symposium on Molecular Targets and Cancer Therapeutics, Munich, Germany, 2016, 1 page.
Weinstein, "Cancer. Addiction to oncogenes—the Achilles heal of cancer," Science, Jul. 2002, 297(5578):63-64.

(56) References Cited

OTHER PUBLICATIONS

Wen et al, "Updated response assessment criteria for high-grade gliomas: response assessment in neuro-oncology working group," J Clin Oncol, Apr. 2010, 28(11): 1963-1972.

Wiesner et al., "Kinase fusions are frequent in Spitz tumours and spitzoid melanomas," Nature Comm., 2014, 5:3116.

Winski et al., "LOXO-101, a pan-TRK inhibitor, for the treatment of TRK-driven cancers," 26th EORTC-NCI-AACR Symposium on Molecular Targets and Cancer Therapeutics, Barcelona, Spain, 2014, 175.

Wittwer et al., "High-resolution genotyping by amplicon melting analysis using LCGreen," Clin Chem, Jun. 2003;49(6 Pt 1):853-60.

Wlodarska et al., "ALK-Positive Anaplastic Large Cell Lymphoma with the Variant EEF1G-, RNF213- and Atic-ALK Fusions is Featured by Copy Number Gain of the Rearranged ALK Gene", Blood, vol. 126(23): 3654, 57th Annual Meeting of the American Society of Hematology, San Diego, CA, 2015.

Won et al., "Post-crizotinib management of effective ceritinib therapy in a patient with ALK-positive non-small cell lung cancer", BMC Cancer, 16: 568, 2016.

Wong et al., "Evaluation of a Congenital Infantile Fibrosarcoma by Comprehensive Genomic Profiling Reveals an LMNA-NTRK.1 Gene Fusion Responsive to Crizotinib," J Natl Cancer Inst, Nov. 2016, 108(1) pii: div307.

Woodward, "Bi-allelic SNP genotyping using the TaqMan® assay," Methods Mol Biol., 2014;1145:67-74. doi: 10.1007/978-1-4939-0446-4 6.

Woolf et al., "Letter to Neuroscience: Nerve Growth Factor Contributes to the Generation of Inflammatory Sensory Hypersensitivity," Neuroscience, 1994, 62:327-331.

Wu et al., "The genomic landscape of diffuse intrinsic pontine glioma and pediatric non-brainstem high-grade glioma," Nature Genetics, 2014, 444-450.

Wu et al., "The landscape of fusion transcripts in spitzoid melanoma and biologically indeterminate spitzoid tumors by RNA sequencing," Modern Pathol., Apr. 2016, 29(4):359-369.

Xalkori, Highlights of Prescribing Information, Pfizer Labs, Initial approval 2011, revised Mar. 2016, 20 pages.

Yakirevich et al., "Colorectal Adenocarcinoma with ALK Rearrangement: Clinicopathologic and Molecular Characteristics", Laboratory Investigation, vol. 96, Supp. Suppl. 1, pp. 209A, Abstract No. 827, 105th Annual Meeting of the United States and Canadian Academy of Pathology, Seattle, WA, 2016.

Yakirevich et al., "Oncogenic ALK Fusion in Rare and Aggressive Subtype of Colorectal Adenocarcinoma as a Potential Therapeutic Target.", Clin Cancer Res, 22(15): 3831-40, 2016.

Yamamoto et al., "ALK, ROS1 and NTRK3 gene rearrangements in inflammatory myofibroblastic tumours.", Histopathology, 69(1): 72-83, 2016.

Yamamoto et al., "Anaplastic lymphoma kinase-positive squamous cell carcinoma of the lung: A case report.", Mal Clin. Oneal. 5(1): 61-63, 2016.

Yanai et al., "A rare case of bilateral stage IV adrenal neuroblastoma with multiple skin metastases in a neonate: diagnosis, management, and outcome," J Pediatr. Surg., Dec. 2004, 39(12):1782-1783.

Yeh et al., "NTRK.3 kinase fusions in Spitz tumours," J Pathol., Nov. 2016, 240(3): 282-290.

Yilmaz et al., "Theraputic targeting of Trk supresses tumor proliferation and enhances cisplatin activity inHNSCC," Cancer Biology and Therapy, 2010, 10(6):644-653.

Ying et al., "Atypical negative ALK FISH accompanied by immunohistochemistry positivity harbored various ALK rearrangements in NSCLC patients and respond to targeted therapy.", J Clin. Oncology, vol. 34, Supp. Supplement 15, Abstract No. e20506, 2016 Annual Meeting of the American Society of Clinical Oncology, Chicago, IL, 2016.

Yu et al., "Denaturing high performance liquid chromatography: high throughput mutation screening in familial hypertrophic cardiomyopathy and SNP genotyping in motor neurone disease," J Clin Pathol, MAy 2005;58(5):479-85.

Yu et al., "Detection of ALK rearrangements in lung cancer patients using a homebrew PCR assay", Oncotarget, 8(5): 7722-7728, 2016.

Yuzugullu et al., "NTRK.2 activation cooperates with PTEN deficiency in T-ALL through activation of both the PBK-AKT and JAK-STAT3 pathways," Cell Discov., Sep. 2016, 2: 16030.

Zage et al., "The selective Trk inhibitor A2623 inhibits brain-derived neurotrophic factor-mediated neuroblastoma cell proliferation and signaling and is synergistic with topotecan," Cancer, Mar. 2011, 117(6):1321-1391.

Zahn et al., "Effect of blockade of nerve growth factor and tumor necrosis factor on pain behaviors after plantar incision," J. Pain, 2004, 5:157-163.

Zehir et al., "Mutational landscape of metastatic cancer revealed from prospective clinical sequencing of 10,000 patients," Nat. Med, Jun. 2017, 23(6):703-713.

Zelboraf, Highlights of Prescribing Information, Genentech USA, Initial Approval 2011, revised Aug. 2015, 18 pages.

Zhang et al., "A novel multiplex tetra-primer ARMS-PCR for the simultaneous genotyping of six single nucleotide polymorphisms associated with female cancers," PLoS One, Apr. 17, 2013;8(4):e62126. doi: 10.1371/iournal.pone.0062126. Print 2013.

Zhang et al., "Expression of nerve growth factor receptors and their prognostic value in human pancreatic cancer," Oncology Reports, 2005, 14:161-171.

Zhang et al., "Novel Phenotypic and Genetic Analysis oft-Cell Prolymphocytic Leukemia (T-PLL)," Blood, 2014, 124(21):1682.

Zhang et al., "Whole-genome sequencing identifies genetic alterations in pediatric low-grade gliomas," Nat. Genet., Jun. 2013, 45(6): 602-612.

Zheng et al., "Anchored multiplex PCR for targeted next-generation sequencing," Nature Med., Dec. 2014, 20(12):1479-1486.

Zhu et al., "TPD52L1-ROS1, a new ROSI fusion variant in lung adenosquamous cell carcinoma identified by comprehensive genomic profiling", Lung Cancer, 97:48-50, doi: 10.1016/j.lungcan.2016.04. 013, 2012.

Ziemiecki et al., "Oncogenic activation of the human trk proto-oncogene by recombination with the ribosomal large subunit protein L7a," EMBO J, Jan. 1990, 9(1):191-196.

Zou et al., "PF-06463922 is a potent and selective next-generation ROS1/ALK inhibitor capable of blocking crizotinib-resistant ROS1 mutations.", Proc. Natl. Acad Sci. USA., 112(11): 3493-8, 2015.

Braga, Dario, et al. "Crystal polymorphism and multiple crystal forms." Struct Bond (2009) 132:25-50. Springer-Verlag Berlin Heidelberg.

Center for Drug Evaluation and Research. https://www.accessdata. fda.gov/drugsatfda_docs/nda/2018/210861Orig1s000_ 2117100rig1s000ChemR.pdf, 2017.

Camidge, D. Ross, William Pao, and Lecia V. Sequist. "Acquired resistance to TKIs in solid tumours: learning from lung cancer." Nature reviews Clinical oncology 11.8 (2014): 473.

Communication pursuant to Rule 114(2) EPC, issued by the European Patent Office in EP Application No. 15808300.6 dated May 24, 2019. 9 pages.

Hilfiker, Rolf, Fritz Blatter, and Markus von Raumer. "Relevance of solid-state properties for pharmaceutical products." Polymorphism in the pharmaceutical industry (2006): 1-19.

JoVE Science Education Database. Organic Chemistry. Purifying Compounds by Recrystallization. JoVE, Cambridge, MA (2019).

PCT International Preliminary Report on Patentability in International Application No. PCT/US2018/022833, dated Sep. 26, 2019, 8 pages.

\* cited by examiner

Unpolarised light

Polarised light

```
SEQ ID NO: 1
PRT
Homo sapiens
Wildtype TrkA protein precursor

Amino acids 1-32 encode the signal sequence 1 mlrggrrgql gwhswaagpg sllawlilas agaapcpdac cphgssglrc trdgaldslh
 61 hlpgaenlte lyienqqhlq hlelrdlrgl gelrnltivk sglrfvapda fhftprlsrl
121 nlsfnalesl swktvqgisl qelvlsgnpl hcscalrwlq rweeeglggv peqklqchgq
181 gplahmpnas cgvptlkvqv pnasvdvgdd vllrcqvegr gleqagwilt eleqsatvmk
241 sgglpslglt lanvtsdlnr knvtcwaend vgraevsvqv nvsfpasvql htavemhhwc
301 ipfsvdgqpa pslrwlfngs vlnetsfift eflepaanet vrhgclrlnq pthvnngnyt
361 llaanpfgqa sasimaafmd npfefnpedp ipvsfspvdt nstsgdpvek kdetpfgvsv
421 avglavfacl flstlllvln kcgrrnkfgi nrpavlaped glamslhfmt lggsslspte
481 gkgsglqghi ienpqyfsda cvhhikrrdi vlkwelgega fgkvflaech nllpeqdkml
541 vavkalkeas esarqdfqre aelltmlqhq hivrffgvct egrpllmvfe ymrhgdlnrf
601 lrshgpdakl laggedvapg plglgqllav asqvaagmvy laglhfvhrd latrnclvgq
661 glvvkigdfg msrdiystdy yrvggrtmlp irwmppesil yrkfttesdv wsfgvvlwei
721 ftygkqpwyq lsnteaidci tqgrelerpr acppevyaim rgcwqrepqq rhsikdvhar
781 lqalaqappv yldvlg www.ncbi.nlm.nih.gov/protein/94730402?report=genbank&log$=protalign&bl
ast_rank=0&RID=0
```

FIG. 11

SEQ ID NO: 2
PRT
Homo sapiens
Wildtype TrkB protein precursor
Amino acids 1-31 encode the signal sequence

```
  1 msswirwhgp amarlwgfcw lvvgfwraaf acptsckcsa sriwcsdpsp givafprlep
 61 nsvdpenite ifianqkrle iineddveay vglrnltivd sglkfvahka flknsnlqhi
121 nftrnkltsl srkhfrhldl selilvgnpf tcscdimwik tlqeaksspd tqdlyclnes
181 skniplanlq ipncglpsan laapnltvee gksitlscsv agdpvpnmyw dvgnlvskhm
241 netshtqgsl ritnissdds gkqiscvaen lvgedqdsvn ltvhfaptit flesptsdhh
301 wcipftvkgn pkpalqwfyn gailneskyi ctkihvtnht eyhgclqidn pthmnngdyt
361 liakneygkd ekqisahfmg wpgiddganp nypdviyedy gtaandigdt tnrsneipst
421 dvtdktgreh lsvyavvvia svvgfcllvm lfllklarhs kfgmkgpasv isndddsasp
481 lhhisngsnt pssseggpda viigmtkipv ienpqyfgit nsqlkpdtfv qhikrhnivl
541 krelgegafg kvflaecynl cpeqdkilva vktlkdasdn arkdfhreae lltnlqhehi
601 vkfygvcveg dplimvfeym khgdlnkflr ahgpdavlma egnppteltq sqmlhiaqqi
661 aagmvylasq hfvhrdlatr nclvgenllv kigdfgmsrd vystdyyrvg ghtmlpirwm
721 ppesimyrkf ttesdvwslg vvlweiftyg kqpwyqlsnn eviecitqgr vlqrprtcpq
781 evyelmlgcw qrephmrkni kgihtllqnl akaspvyldi lg
``` www.ncbi.nlm.nih.gov/protein/2497560?report=genbank&log$=protalign&bla
st_rank=0&RID=0

FIG. 12

SEQ ID NO: 3
PRT
Homo sapiens
Wildtype TrkC protein precursor
Amino acids 1-31 encode signal sequence

```
  1 mdvslcpakc sfwrifllgs vwldyvgsvl acpancvcsk teincrrpdd gnlfpllegq
 61 dsgnsngnas initdisrni tsihienwrs lhtlnavdme lytglqklti knsglrsiqp
121 rafaknphlr yinlssnrlt tlswqlfqtl slrelqleqn ffncscdirw mqlwqeqgea
181 klnsqnlyci nadgsqlplf rmnisqcdlp eisvshvnlt vregdnavit cngsgsplpd
241 vdwivtglqs inthqtnlnw tnvhainlti vnvtsedngf tltciaenvv gmsnasvalt
301 vyypprvvsl eepelrlehc iefvvrgnpp ptlhwlhngq plreskiihv eyyqegeise
361 gcllfnkpth ynngnytlia knplgtanqt inghflkepf pestdnfilf devsptppit
421 vthkpeedtf gvsiavglaa facvllvvlf vminkygrrs kfgmkgpvav isgeedsasp
481 lhhinhgitt pssldagpdt vvigmtripv ienpqyfrqg hnchkpdtyv qhikrrdivl
541 krelgegafg kvflaecynl sptkdkmlva vkalkdptla arkdfqreae lltnlqhehi
601 vkfygvcgdg dplimvfeym khgdlnkflr ahgpdamilv dgqprqakge lglsqmlhia
661 sqiasgmvyl asqhfvhrdl atrnclvgan llvkigdfgm srdvystdyy rlfnpsgndf
721 ciwcevgght mlpirwmppe simyrkftte sdvwsfgvil weiftygkqp wfqlsntevi
781 ecitqgrvle rprvcpkevy dvmlgcwqre pqqrlnikei ykilhalgka tpiyldilg
``` www.ncbi.nlm.nih.gov/protein/134035335?report=genbank&log$=protalign&b
last_rank=0&RID=0

FIG. 13

LIQUID FORMULATIONS OF (S)-N-(5-((R)-2-(2,5-DIFLUOROPHENYL)-PYRROLIDIN-1-YL)-PYRAZOLO[1,5-A] PYRIMIDIN-3-YL)-3-HYDROXYPYRROLIDINE-1-CARBOXAMIDE

CROSS-REFERENCE TO RELATED APPLICATIONS

This application is a continuation of U.S. application Ser. No. 15/622,544, filed Jun. 14, 2017, which claims priority to PCT/US2017/025939, filed Apr. 4, 2017; which claims priority to U.S. Provisional Application Ser. No. 62/318,041, filed Apr. 4, 2016; 62/323,452, filed Apr. 15, 2016; and 62/329,561, filed Apr. 29, 2016, each of which is incorporated by reference in its entirety herein.

BACKGROUND

1. Field of the Invention

The present disclosure relates to liquid formulations of (S)—N-(5-((R)-2-(2,5-difluorophenyl)-pyrrolidin-1-yl)-pyrazolo[1,5-a]pyrimidin-3-yl)-3-hydroxypyrrolidine-1-carboxamide (Formula I), pharmaceutically acceptable salts thereof, or a combination thereof and to the use of the liquid formulations in the treatment of pain, inflammation, cancer, and certain infectious diseases.

2. Description of the Related Art

Trk's are the high affinity receptor tyrosine kinases activated by a group of soluble growth factors called neurotrophins (NT). The Trk receptor family has three members—TrkA, TrkB and TrkC. Among the neurotrophins are (i) nerve growth factor (NGF) which activates TrkA, (ii) brain-derived neurotrophic factor (BDNF) and NT-4/5 which activate TrkB and (iii) NT3 which activates TrkC. Trk's are widely expressed in neuronal tissue and are implicated in the maintenance, signaling and survival of neuronal cells (Patapoutian, A. et al., Current Opinion in Neurobiology, 2001, 11, 272-280).

Recent literature has shown that overexpression, activation, amplification and/or mutation of Trk's are associated with many cancers including neuroblastoma (Brodeur, G. M., Nat. Rev. Cancer 2003, 3, 203-216), ovarian cancer (Davidson., B. et al., Clin. Cancer Res. 2003, 9, 2248-2259), breast cancer (Kruettgen et al., Brain Pathology 2006, 16: 304-310), prostate cancer (Dionne et al., Clin. Cancer Res. 1998, 4(8): 1887-1898), pancreatic cancer (Dang et al., Journal of Gastroenterology and Hepatology 2006, 21(5): 850-858), multiple myeloma (Hu et al., Cancer Genetics and Cytogenetics 2007, 178: 1-10), astrocytoma amd medulloblastoma (Kruettgen et al., Brain Pathology 2006, 16: 304-310), glioma (Hansen et al., Journal of Neurochemistry 2007, 103: 259-275), melanoma (Nakagawara, A. (2001) Cancer Letters 169:107-114; Meyer, J. et al. (2007) Leukemia, 1-10; Pierottia, M. A. and Greco A., (2006) Cancer Letters 232:90-98; Eric Adriaenssens, E. et al. Cancer Res (2008) 68:(2) 346-351), thyroid carcinoma (Brzezianska et al., Neuroendocrinology Letters 2007, 28(3), 221-229), lung adenocarcinoma (Perez-Pinera et al., Molecular and Cellular Biochemistry 2007, 295(1&2), 19-26), large cell neuroendocrine tumors (Marchetti et al., Human Mutation 2008, 29(5), 609-616), and colorectal cancer (Bardelli, A., Science 2003, 300, 949). In preclinical models of cancer, Trk inhibitors are efficacious in both inhibiting tumor growth and stopping tumor metastasis. In particular, non-selective small molecule inhibitors of TrkA, TrkB, TrkC and Trk/Fc chimeras were efficacious in both inhibiting tumor growth and stopping tumor metastasis (Nakagawara, A. (2001) Cancer Letters 169:107-114; Meyer, J. et al. (2007) Leukemia, 1-10; Pierottia, M. A. and Greco A., (2006) Cancer Letters 232: 90-98; Eric Adriaenssens, E. et al. Cancer Res (2008) 68:(2) 346-351). Therefore, an inhibitor of the Trk family of kinases is expected to have utility in the treatment of cancer.

In addition, inhibitors of the Trk/neurotrophin pathway have been demonstrated to be effective in numerous pre-clinical animal models of pain. For example, antagonistic NGF and TrkA antibodies (for example, RN-624) have been shown to be efficacious in inflammatory and neuropathic pain animal models and in human clinical trials (Woolf, C. J. et al. (1994) Neuroscience 62, 327-331; Zahn, P. K. et al. (2004) J. Pain 5, 157-163; McMahon, S. B. et al., (1995) Nat. Med. 1, 774-780; Ma, Q. P. and Woolf, C. J. (1997) Neuroreport 8, 807-810; Shelton, D. L. et al. (2005) Pain 116, 8-16; Delafoy, L. et al. (2003) Pain 105, 489-497; Lamb, K. et al. (2003) Neurogastroenterol. Motil. 15, 355-361; Jaggar, S. I. et al. (1999) Br. J. Anaesth. 83, 442-448). Additionally, recent literature indicates after inflammation, BDNF levels and TrkB signaling is increased in the dorsal root ganglion (Cho, L. et al. Brain Research 1997, 749, 358) and several studies have shown antibodies that decrease signaling through the BDNF/TrkB pathway inhibit neuronal hypersensitization and the associated pain (Chang-Qi, L et al. Molecular Pain 2008, 4:27).

It has been shown that NGF secreted by tumor cells and tumor invading macrophages directly stimulates TrkA located on peripheral pain fibers. Using various tumor models in both mice and rats it was demonstrated that neutralizing NGF with a monoclonal antibody inhibits cancer related pain to a degree similar or superior to the highest tolerated dose of morphine. In addition, activation of the BDNF/TrkB pathway has been implicated in numerous studies as a modulator of various types of pain including inflammatory pain (Matayoshi, S., J. Physiol. 2005, 569: 685-95), neuropathic pain (Thompson, S. W., Proc. Natl. Acad. Sci. USA 1999, 96:7714-18) and surgical pain (Li, C.-Q. et al., Molecular Pain, 2008, 4(28), 1-11). Because TrkA and TrkB kinases may serve as a mediator of NGF driven biological responses, inhibitors of TrkA and/or other Trk kinases may provide an effective treatment for chronic pain states.

The current treatment regimens for pain conditions utilize several classes of compounds. The opioids (such as morphine) have several drawbacks including emetic, constipatory and negative respiratory effects, as well as the potential for addictions. Non-steroidal anti-inflammatory analgesics (NSAIDs, such as COX-1 or COX-2 types) also have drawbacks including insufficient efficacy in treating severe pain. In addition, COX-1 inhibitors can cause ulcers of the mucosa. Accordingly, there is a continuing need for new and more effective treatments for the relief of pain, especially chronic pain.

In addition, inhibition of the neurotrophin/Trk pathway has been shown to be effective in treatment of pre-clinical models of inflammatory diseases. For example, inhibition of the neurotrophin/Trk pathway has been implicated in preclinical models of inflammatory lung diseases including asthma (Freund-Michel, V; Frossard, N.; Pharmacology & Therapeutics (2008), 117(1), 52-76), interstitial cystitis (Hu Vivian Y; et. al. The Journal of Urology (2005), 173(3), 1016-21), inflammatory bowel diseases including ulcerative colitis and Crohn's disease (Di Mola, F. F, et. al., Gut (2000), 46(5), 670-678) and inflammatory skin diseases such as atopic dermatitis (Dou, Y.-C.; et. al. Archives of Dermatological Research (2006), 298(1), 31-37), eczema and psoriasis (Raychaudhuri, S. P.; et. al. Journal of Investigative Dermatology (2004), 122(3), 812-819).

The neurotrophin/Trk pathway, particularly BDNF/TrkB, has also been implicated in the etiology of neurodegenerative diseases including multiple sclerosis, Parkinson's disease and Alzheimer's disease (Sohrabji, Farida; Lewis, Danielle K. Frontiers in Neuroendocrinology (2006), 27(4), 404-414). Modulation of the neutrophin/Trk pathway may have utility in treatment of these and related diseases.

The TrkA receptor is also thought to be critical to the disease process in the infection of the parasitic infection of *Trypanosoma cruzi* (Chagas disease) in human hosts (de Melo-Jorge, M. et al. *Cell Host & Microbe* (2007), 1(4), 251-261). Thus, TrkA inhibition may have utility in treating Chagas disease and related protozoan infections.

Trk inhibitors may also find use in treating disease related to an imbalance of the regulation of bone remodeling, such as osteoporosis, rheumatoid arthritis, and bone metastases. Bone metastases are a frequent complication of cancer, occurring in up to 70 percent of patients with advanced breast or prostate cancer and in approximately 15 to 30 percent of patients with carcinoma of the lung, colon, stomach, bladder, uterus, rectum, thyroid, or kidney. Osteolytic metastases can cause severe pain, pathologic fractures, life threatening hypercalcemia, spinal cord compression, and other nerve-compression syndromes. For these reasons, bone metastasis is a serious and costly complication of cancer. Therefore, agents that can induce apoptosis of proliferating osteoblasts would be highly advantageous. Expression of TrkA and TrkC receptors has been observed in the bone forming area in mouse models of bone fracture (K. Asaumi, et al., Bone (2000) 26(6) 625-633). In addition, localization of NGF was observed in almost all bone forming cells (K. Asaumi, et al.). Recently, it was demonstrated that a pan-Trk inhibitor inhibits the tyrosine signaling activated by neurotrophins binding to all three of the Trk receptors in human hFOB osteoblasts (J. Pinski, et al., (2002) 62, 986-989). These data support the rationale for the use of Trk inhibitors for the treatment of bone remodeling diseases, such as bone metastases in cancer patients.

Several classes of small molecule inhibitors of Trk kinases said to be useful for treating pain or cancer are known (*Expert Opin. Ther. Patents* (2009) 19(3)).

International Patent Application Publications WO 2006/115452 and WO 2006/087538 describe several classes of small molecules said to be inhibitors of Trk kinases which could be useful for treating pain or cancer.

Pyrazolo[1,5-a]pyrimidine compounds are known. For example, International Patent Application Publication WO 2008/037477 discloses pyrazolo[1,5-a]pyrimidine compounds bearing an alkyl, aryl or heterocyclic group at the 3-position. These compounds are asserted to be PI3K and/or mTOR Lipid Kinase inhibitors.

PCT Patent Publication No. WO 2008/058126 discloses pyrazolo[1,5-a]pyrimidine compounds bearing a phenyl group at the 3-position. These compounds are asserted to be Pim-kinase inhibitors.

U.S. Patent Publication No. 2006/0094699 discloses pyrazolo[1,5-a]pyrimidine compounds bearing a —C(═O)NH-phenyl, —C(═O)(4-methylpiperidinyl) or —C(═O)NMe (CH$_2$-trimethylpyrazolyl) group at the 3-position for use in combination therapy with a glucocorticoid receptor agonist.

PCT Patent Publication Nos. WO 2010/033941, WO 2010/048314, WO 2011/006074, and WO 2011/146336 disclose compounds which exhibit Trk family protein tyrosine kinase inhibition, and which are useful in the treatment of pain, cancer, inflammation, neurodegenerative diseases and certain infectious diseases.

WO 2010/048314 discloses in Example 14A a hydrogen sulfate salt of (S)—N-(5-((R)-2-(2,5-difluorophenyl)-pyrrolidin-1-yl)-pyrazolo[1,5-a]pyrimidin-3-yl)-3-hydroxypyrrolidine-1-carboxamide. WO 2010/048314 does not disclose the particular form of the hydrogen sulfate salt described herein when prepared according to the method of Example 14A in that document. In particular, WO 2010/048314 does not disclose crystalline form (I-HS) as described below.

All documents, including scientific articles, patent publications and applications, and the like, referenced in the present disclosure are hereby incorporated by reference in their entirety.

SUMMARY

Provided herein is a liquid formulation comprising a solubilizing agent and (S)—N-(5-((R)-2-(2,5-difluorophenyl)-pyrrolidin-1-yl)-pyrazolo[1,5-a]pyrimidin-3-yl)-3-hydroxypyrrolidine-1-carboxamide having the formula (I):

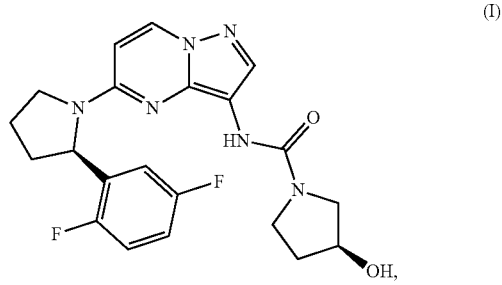 [SMILES: O=C(Nc1cnn2ccc(N3CCC[C@@H]3c3cc(F)ccc3F)nc12)N1CC[C@H](O)C1]

(I)

a pharmaceutically acceptable salt thereof, or a combination thereof.

In some embodiments, the compound of formula (I), a pharmaceutically acceptable salt thereof, or a combination thereof, is present in an amount from about 0.5 wt. % to about 7 wt. %. For example, the compound of formula (I), a pharmaceutically acceptable salt thereof, or a combination thereof can be present in the liquid formulation in an amount of about 1.5 wt. % to about 2.5 wt. %.

In some embodiments, the compound of formula (I), the pharmaceutically acceptable salt thereof, or the combination thereof, has a concentration of about 5 mg/mL to about 50 mg/mL in the liquid formulation. For example, the compound of formula (I), the pharmaceutically acceptable salt thereof, or the combination thereof, can have a concentration of about 15 mg/mL to about 35 mg/mL in the liquid formulation. In some embodiments, the compound of formula (I), the pharmaceutically acceptable salt thereof, or the combination thereof, has a concentration of about 20 mg/mL in the liquid formulation.

The solubilizing agent can be selected from the group consisting of a cyclodextrin, a glycol, a glycerol, and combinations thereof. In some embodiments, the solubilizing agent includes a cyclodextrin. For example, the solubilizing agent can be selected from the group consisting of a β-cyclodextrin derivative, a γ-cyclodextrin, and combinations thereof. In some embodiments, the solubilizing agent includes a hydroxy alkyl-γ-cyclodextrin. The solubilizing agent can include a β-cyclodextrin selected from the group consisting of a hydroxy alkyl-β-cyclodextrin, a sulfoalkyl ether-β-cyclodextrin, and combinations thereof. In some embodiments, the solubilizing agent includes hydroxypropyl-β-cyclodextrin.

In some embodiments, the solubilizing agent is present in the liquid formulation in an amount of about 5 wt. % to about 35 wt. %. For example, the solubilizing agent can be present in the liquid formulation in an amount of about 13 wt. % to about 17 wt. %.

The liquid formulation can further include a buffer. In some embodiments, the buffer includes at least one of a citrate buffer, a lactate buffer, a phosphate buffer, a maleate buffer, a tartarate buffer, a succinate buffer, or an acetate buffer. In some embodiments, the buffer includes at least one of lithium lactate, sodium lactate, potassium lactate, calcium lactate, lithium phosphate, sodium phosphate, potassium phosphate, calcium phosphate, lithium maleate, sodium maleate, potassium maleate, calcium maleate, lithium tartarate, sodium tartarate, potassium tartarate, calcium tartarate, lithium succinate, sodium succinate, potassium succinate, calcium succinate, lithium acetate, sodium acetate, potassium acetate, or calcium acetate. The buffer can be a citrate buffer. The citrate buffer can include at least one of lithium citrate monohydrate, sodium citrate monohydrate, potassium citrate monohydrate, calcium citrate monohydrate, lithium citrate dihydrate, sodium citrate dihydrate, potassium citrate dihydrate, calcium citrate dihydrate, lithium citrate trihydrate, sodium citrate trihydrate, potassium citrate trihydrate, calcium citrate trihydrate, lithium citrate tetrahydrate, sodium citrate tetrahydrate, potassium citrate tetrahydrate, calcium citrate tetrahydrate, lithium citrate pentahydrate, sodium citrate pentahydrate, potassium citrate pentahydrate, calcium citrate pentahydrate, lithium citrate hexahydrate, sodium citrate hexahydrate, potassium citrate hexahydrate, calcium citrate hexahydrate, lithium citrate heptahydrate, sodium citrate heptahydrate, potassium citrate heptahydrate, or calcium citrate heptahydrate. In some embodiments, the buffer includes at least one of sodium citrate monohydrate, potassium citrate monohydrate, calcium citrate monohydrate, sodium citrate dihydrate, potassium citrate dihydrate, calcium citrate dihydrate, sodium citrate trihydrate, potassium citrate trihydrate, calcium citrate trihydrate, sodium citrate tetrahydrate, potassium citrate tetrahydrate, calcium citrate tetrahydrate, sodium citrate pentahydrate, potassium citrate pentahydrate, calcium citrate pentahydrate, sodium citrate hexahydrate, potassium citrate hexahydrate, calcium citrate hexahydrate, sodium citrate heptahydrate, potassium citrate heptahydrate, or calcium citrate heptahydrate.

In some embodiments, the buffer includes sodium citrate dihydrate.

The buffer can be present in the liquid formulation in an amount of about 0.1 wt. % to about 5 wt. %.

In some embodiments, the formulation has a pH of about 2 to about 7. For example, the formulation can have a pH of about 3 to about 4. In some embodiments, the formulation has a pH of about 3.5.

In some embodiments, the pH of the liquid formulation is adjusted. In some such embodiments, the formulation includes a base. For example, the base can include one or more of a citrate, a lactate, a phosphate, a maleate, a tartarate, a succinate, an acetate, a carbonate, and a hydroxide. In some embodiments, the formulation includes at least one of lithium lactate, sodium lactate, potassium lactate, calcium lactate, lithium phosphate, sodium phosphate, potassium phosphate, calcium phosphate, lithium maleate, sodium maleate, potassium maleate, calcium maleate, lithium tartarate, sodium tartarate, potassium tartarate, calcium tartarate, lithium succinate, sodium succinate, potassium succinate, calcium succinate, lithium acetate, sodium acetate, potassium acetate, calcium acetate, sodium carbonate, potassium carbonate, calcium carbonate, sodium bicarbonate, potassium bicarbonate, calcium bicarbonate, sodium hydroxide, potassium hydroxide, calcium hydroxide, or combinations thereof. In some embodiments, the base includes a citrate. The citrate can include at least one of lithium citrate monohydrate, sodium citrate monohydrate, potassium citrate monohydrate, calcium citrate monohydrate, lithium citrate dihydrate, sodium citrate dihydrate, potassium citrate dihydrate, calcium citrate dihydrate, lithium citrate trihydrate, sodium citrate trihydrate, potassium citrate trihydrate, calcium citrate trihydrate, lithium citrate tetrahydrate, sodium citrate tetrahydrate, potassium citrate tetrahydrate, calcium citrate tetrahydrate, lithium citrate pentahydrate, sodium citrate pentahydrate, potassium citrate pentahydrate, calcium citrate pentahydrate, lithium citrate hexahydrate, sodium citrate hexahydrate, potassium citrate hexahydrate, calcium citrate hexahydrate, lithium citrate heptahydrate, sodium citrate heptahydrate, potassium citrate heptahydrate, or calcium citrate heptahydrate. In some embodiments, the liquid formulation includes at least one of sodium citrate monohydrate, potassium citrate monohydrate, calcium citrate monohydrate, sodium citrate dihydrate, potassium citrate dihydrate, calcium citrate dihydrate, sodium citrate trihydrate, potassium citrate trihydrate, calcium citrate trihydrate, sodium citrate tetrahydrate, potassium citrate tetrahydrate, calcium citrate tetrahydrate, sodium citrate pentahydrate, potassium citrate pentahydrate, calcium citrate pentahydrate, sodium citrate hexahydrate, potassium citrate hexahydrate, calcium citrate hexahydrate, sodium citrate heptahydrate, potassium citrate heptahydrate, or calcium citrate heptahydrate.

In some embodiments, the base includes sodium citrate dihydrate.

In some embodiments, the formulation includes about 0.1 wt. % to about 5 wt. % of a base such as citrate (e.g., sodium citrate dihydrate).

The liquid formulation can further include a sweetener. In some embodiments, the sweetener includes a sugar. The sugar can include sucrose. In some embodiments, the sweetener includes an intense sweetener. The intense sweetener can include sucralose.

In some embodiments, the sweetener is present in the liquid formulation in an amount of about 30 wt. % to about 70 wt. %. For example, the sweetener can be present in the liquid formulation in an amount of about 45 wt. % to about 55 wt. %.

The liquid formulation can further include a bitterness masking agent. In some embodiments, the bitterness masking agent is present in the liquid formulation in an amount of about 0.01 wt. % to about 2 wt. %. For example, the bitterness masking agent can be present in the liquid formulation in an amount of about 0.2 wt. % to about 0.5 wt. %.

The liquid formulation can further include a flavoring agent. The flavoring agent can include at least one of a natural flavoring agent, a natural fruit flavoring agent, an artificial flavoring agent, an artificial fruit flavoring agent, or a flavor enhancer. In some embodiments, the flavoring agent is present in the liquid formulation in an amount of about 0.01 wt. % to about 2 wt. %. For example, the flavoring agent can be present in the liquid formulation in an amount of about 0.01 wt. % to about 0.1 wt. %.

In some embodiments, the liquid formulation further includes a coloring agent.

In some embodiments, the liquid formulation is prepared from a pharmaceutically acceptable salt of the compound of formula (I). For example, the liquid formulation can be prepared from the hydrogen sulfate salt of the compound of formula (I).

In some embodiments, the liquid formulation is prepared from a crystalline form of the compound of formula (I). In some embodiments, the crystalline form has the formula (I-HS):

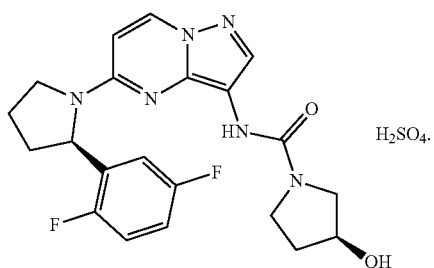

I-HS

Also provided herein is a liquid formulation including (S)—N-(5-((R)-2-(2,5-difluorophenyl)-pyrrolidin-1-yl)-pyrazolo[1,5-a]pyrimidin-3-yl)-3-hydroxypyrrolidine-1-carboxamide having the formula (I):

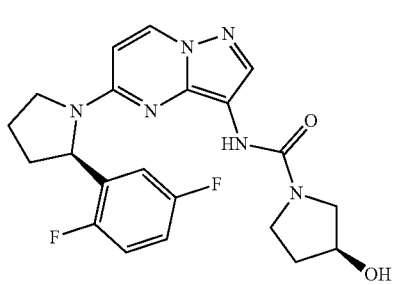

(I)

a pharmaceutically acceptable salt thereof, or a combination thereof. The liquid formulation also includes a solubilizing agent and a buffer. The liquid formulation has a pH of about 2.5 to about 5.5. The compound of formula (I), the pharmaceutically acceptable salt thereof, or the combination thereof, has a concentration of about 15 mg/mL to about 35 mg/mL in the liquid formulation.

In some embodiments, the liquid formulation has a pH of about 3 to about 4.

In some embodiments, the buffer includes sodium citrate dihydrate.

Also provided herein is a liquid formulation including (S)—N-(5-((R)-2-(2,5-difluorophenyl)-pyrrolidin-1-yl)-pyrazolo[1,5-a]pyrimidin-3-yl)-3-hydroxypyrrolidine-1-carboxamide having the formula (I):

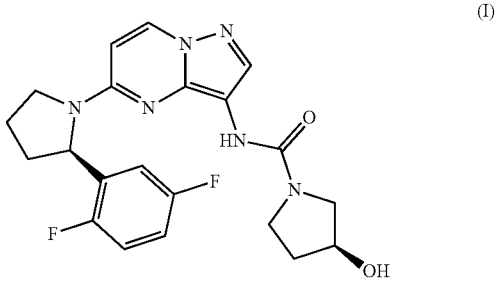 [SMILES: O=C(Nc1cnn2ccc(N3CCC[C@@H]3c3cc(F)ccc3F)nc12)N1CC[C@H](O)C1]

(I)

a pharmaceutically acceptable salt thereof, or a combination thereof. The liquid formulation also includes a solubilizing agent and a base. The liquid formulation has a pH of about 2.5 to about 5.5. In some embodiments, the base includes a citrate (e.g., sodium citrate). The compound of formula (I), the pharmaceutically acceptable salt thereof, or the combination thereof, has a concentration of about 15 mg/mL to about 35 mg/mL in the liquid formulation.

In some embodiments, the liquid formulation has a pH of about 3 to about 4.

In some embodiments, the base includes sodium citrate dihydrate.

Also provided herein is a liquid formulation including (S)—N-(5-((R)-2-(2,5-difluorophenyl)-pyrrolidin-1-yl)-pyrazolo[1,5-a]pyrimidin-3-yl)-3-hydroxypyrrolidine-1-carboxamide having the formula (I):

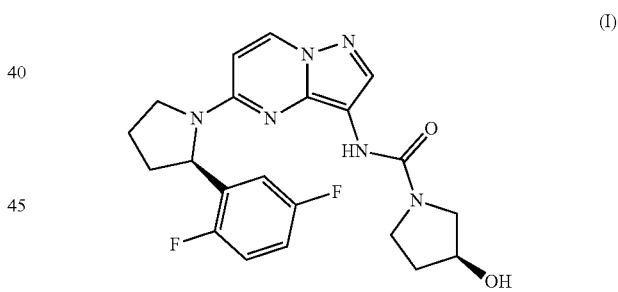

(I)

a pharmaceutically acceptable salt thereof, or a combination thereof. The liquid formulation includes a solubilizing agent, a buffer, a sweetener, a bitterness masking agent, and a flavoring agent. The liquid formulation has a pH of about 3 to about 4. The compound of formula (I), the pharmaceutically acceptable salt thereof, or the combination thereof, has a concentration of about 15 mg/mL to about 35 mg/mL in the liquid formulation.

In some embodiments, the buffer includes sodium citrate dihydrate.

In some embodiments, the sweetener includes sucrose.

Also provided herein is a liquid formulation including (S)—N-(5-((R)-2-(2,5-difluorophenyl)-pyrrolidin-1-yl)-pyrazolo[1,5-a]pyrimidin-3-yl)-3-hydroxypyrrolidine-1-carboxamide having the formula (I):

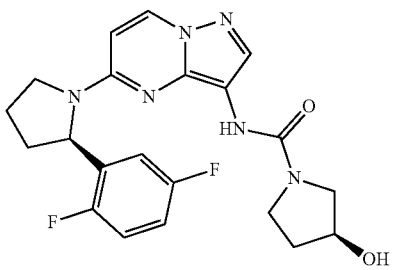

(I)

a pharmaceutically acceptable salt thereof, or a combination thereof. The liquid formulation includes a solubilizing agent, a base, a sweetener, a bitterness masking agent, and a flavoring agent. The liquid formulation has a pH of about 3 to about 4. In some embodiments, the base includes a citrate (e.g., sodium citrate). The compound of formula (I), the pharmaceutically acceptable salt thereof, or the combination thereof, has a concentration of about 15 mg/mL to about 35 mg/mL in the liquid formulation.

In some embodiments, the base includes sodium citrate dihydrate.

In some embodiments, the sweetener includes sucrose.

Also provided herein is a liquid formulation including (S)—N-(5-((R)-2-(2,5-difluorophenyl)-pyrrolidin-1-yl)-pyrazolo[1,5-a]pyrimidin-3-yl)-3-hydroxypyrrolidine-1-carboxamide having the formula (I):

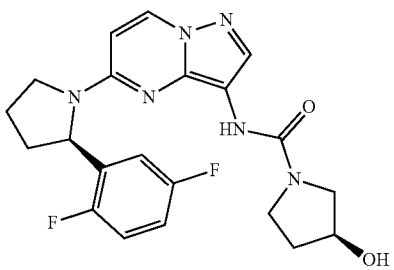

(I)

a pharmaceutically acceptable salt thereof, or a combination thereof. The liquid formulation includes a solubilizing agent present in an amount of about 5 wt. % to about 35 wt. % and a buffer present in an amount of about 0.1 wt. % to about 5 wt. %. The liquid formulation has a pH of about 2.5 to about 5.5. The compound of formula (I), the pharmaceutically acceptable salt thereof, or the combination thereof, has a concentration of about 20 mg/mL to about 30 mg/mL in the liquid formulation.

Also provided herein is a liquid formulation including (S)—N-(5-((R)-2-(2,5-difluorophenyl)-pyrrolidin-1-yl)-pyrazolo[1,5-a]pyrimidin-3-yl)-3-hydroxypyrrolidine-1-carboxamide having the formula (I):

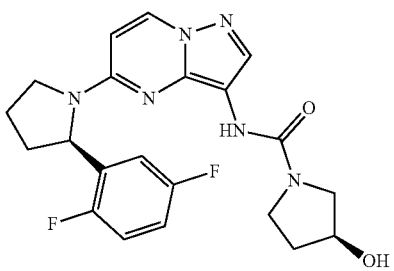

(I)

a pharmaceutically acceptable salt thereof, or a combination thereof. The liquid formulation includes a solubilizing agent present in an amount of about 5 wt. % to about 35 wt. %; a buffer present in an amount of about 0.1 wt. % to about 5 wt. %; a sweetener present in an amount of about 30 wt. % to about 70 wt. %; a bitterness masking agent present in an amount of about 0.2 wt. % to about 0.5 wt. %; and a flavoring agent present in an amount of about 0.01 wt. % to about 2 wt. %. The liquid formulation has a pH of about 2.5 to about 5.5. The compound of formula (I), the pharmaceutically acceptable salt thereof, or the combination thereof, has a concentration of about 20 mg/mL to about 30 mg/mL in the liquid formulation.

Also provided herein is a liquid formulation including (S)—N-(5-((R)-2-(2,5-difluorophenyl)-pyrrolidin-1-yl)-pyrazolo[1,5-a]pyrimidin-3-yl)-3-hydroxypyrrolidine-1-carboxamide having the formula (I):

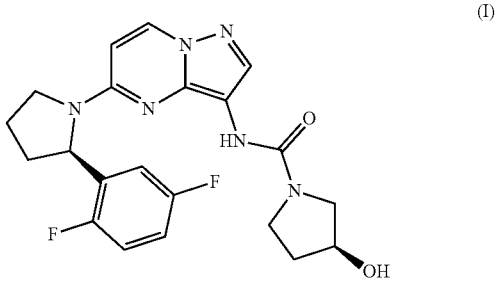 [SMILES: O=C(Nc1cnn2ccc(N3CCC[C@@H]3c3cc(F)ccc3F)nc12)N1CC[C@H](O)C1]

(I)

a pharmaceutically acceptable salt thereof, or a combination thereof. The liquid formulation includes a solubilizing agent present in an amount of about 5 wt. % to about 35 wt. %; a base present in an amount of about 0.1 wt. % to about 5 wt. %; a sweetener present in an amount of about 30 wt. % to about 70 wt. %; a bitterness masking agent present in an amount of about 0.2 wt. % to about 0.5 wt. %; and a flavoring agent present in an amount of about 0.01 wt. % to about 2 wt. %. The liquid formulation has a pH of about 2.5 to about 5.5. The compound of formula (I), the pharmaceutically acceptable salt thereof, or the combination thereof, has a concentration of about 20 mg/mL to about 30 mg/mL in the liquid formulation.

Also provided herein is a liquid formulation including (S)—N-(5-((R)-2-(2,5-difluorophenyl)-pyrrolidin-1-yl)-pyrazolo[1,5-a]pyrimidin-3-yl)-3-hydroxypyrrolidine-1-carboxamide having the formula (I):

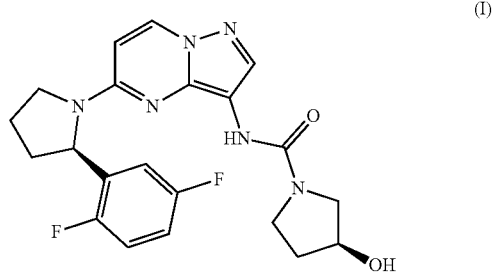 [SMILES: O=C(Nc1cnn2ccc(N3CCC[C@@H]3c3cc(F)ccc3F)nc12)N1CC[C@H](O)C1]

(I)

a pharmaceutically acceptable salt thereof, or a combination thereof. The liquid formulation includes a solubilizing agent present in an amount of about 5 wt. % to about 35 wt. %. The liquid formulation also includes a buffer including sodium citrate dihydrate present in an amount of about 0.1 wt. % to about 5 wt. %. The liquid formulation also includes a sweetener including sucrose present in an amount of about 30 wt. % to about 70 wt. %. The liquid formulation also includes a bitterness masking agent is present in an amount of about 0.2 wt. % to about 0.5 wt. %. The liquid formulation also includes a flavoring agent present in an amount of about 0.01 wt. % to about 2 wt. %. The liquid formulation has a pH of about 3 to about 4. The compound of formula (I), the pharmaceutically acceptable salt thereof, or the combination thereof, has a concentration of about 20 mg/mL to about 30 mg/mL in the liquid formulation.

Also provided herein is a liquid formulation including (S)—N-(5-((R)-2-(2,5-difluorophenyl)-pyrrolidin-1-yl)-pyrazolo[1,5-a]pyrimidin-3-yl)-3-hydroxypyrrolidine-1-carboxamide having the formula (I):

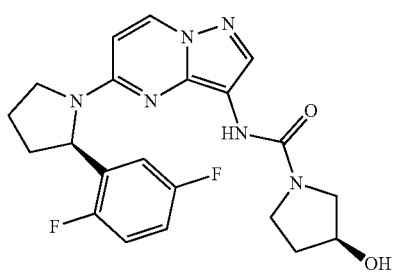

(I)

a pharmaceutically acceptable salt thereof, or a combination thereof. The liquid formulation includes a solubilizing agent present in an amount of about 5 wt. % to about 35 wt. %. The liquid formulation also includes a base including sodium citrate dihydrate present in an amount of about 0.1 wt. % to about 5 wt. %. The liquid formulation also includes a sweetener including sucrose present in an amount of about 30 wt. % to about 70 wt. %. The liquid formulation also includes a bitterness masking agent is present in an amount of about 0.2 wt. % to about 0.5 wt. %. The liquid formulation also includes a flavoring agent present in an amount of about 0.01 wt. % to about 2 wt. %. The liquid formulation has a pH of about 3 to about 4. The compound of formula (I), the pharmaceutically acceptable salt thereof, or the combination thereof, has a concentration of about 20 mg/mL to about 30 mg/mL in the liquid formulation.

Also provided herein is a liquid formulation including (S)—N-(5-((R)-2-(2,5-difluorophenyl)-pyrrolidin-1-yl)-pyrazolo[1,5-a]pyrimidin-3-yl)-3-hydroxypyrrolidine-1-carboxamide having the formula (I):

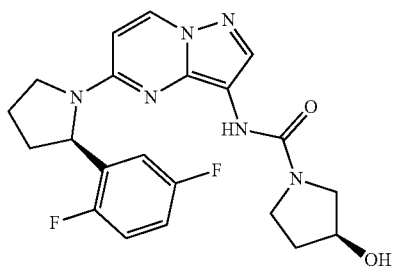

(I)

a pharmaceutically acceptable salt thereof, or a combination thereof. The liquid formulation includes a solubilizing agent present in an amount of about 5 wt. % to about 35 wt. %. The liquid formulation also includes sodium citrate dihydrate present in an amount of about 0.1 wt. % to about 5 wt. %. The liquid formulation also includes a sweetener including sucrose present in an amount of about 30 wt. % to about 70 wt. %. The liquid formulation also includes a bitterness masking agent is present in an amount of about 0.2 wt. % to about 0.5 wt. %. The liquid formulation also includes a flavoring agent present in an amount of about 0.01 wt. % to about 2 wt. %. The liquid formulation has a pH of about 3 to about 4. The compound of formula (I), the pharmaceutically acceptable salt thereof, or the combination thereof, has a concentration of about 20 mg/mL to about 30 mg/mL in the liquid formulation.

The liquid formulations provided herein can be prepared from a crystalline form of the compound of formula (I) having the formula (I-HS):

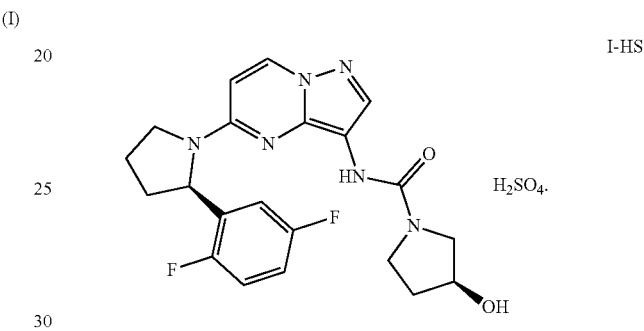

I-HS

In some embodiments, the crystalline form can be characterized by having XRPD diffraction peaks (2θ degrees) at 18.4±0.2, 20.7±0.2, 23.1±0.2, and 24.0±0.2. In some embodiments, the crystalline form is characterized by having XRPD diffraction peaks (2θ degrees) at 10.7±0.2, 18.4±0.2, 20.7±0.2, 23.1±0.2, and 24.0±0.2. In some embodiments, the crystalline form is characterized by having XRPD diffraction peaks (2θ degrees) at 10.7±0.2, 18.4±0.2, 19.2±0.2, 20.2±0.2, 20.7±0.2, 21.5±0.2, 23.1±0.2, and 24.0±0.2. In some embodiments, the crystalline form is characterized by having XRPD diffraction peaks (2θ degrees) at 10.7±0.2, 15.3±0.2, 16.5±0.2, 18.4±0.2, 19.2±0.2, 19.9±0.2, 20.2±0.2, 20.7±0.2, 21.5±0.2, 22.1±0.2, 23.1±0.2, 24.0±0.2. 24.4±0.2, 25.6±0.2, 26.5±0.2, 27.6±0.2, 28.2±0.2, 28.7±0.2, 30.8±0.2, and 38.5±0.2.

Also provided herein is a method of treating a cancer in a patient in need thereof. The method includes identifying a patient in need thereof having dysphagia and administering to the patient a therapeutically effective amount of a liquid formulation provided herein.

Also provided herein is a method of treating a cancer in a patient in need thereof, which includes identifying a patient in need thereof having dysphagia, determining if the cancer is mediated by a Trk kinase and if the cancer is determined to be mediated by a Trk kinase, administering to the patient a therapeutically effective amount of a liquid formulation provided herein. Also provided herein is a method of treating a cancer in a patient in need thereof, which includes identifying a patient in need thereof having dysphagia, identifying that the cancer is mediated by a Trk kinase administering to the patient a therapeutically effective amount of a liquid formulation provided herein.

Also provided herein is a method of treating cancer in a patient in need thereof, which includes administering to the patient a therapeutically effective amount of a liquid formulation as provided herein.

In some embodiments, the cancer is selected from the group consisting of a head and neck cancer, a throat cancer, an esophageal cancer, or combinations thereof.

In some embodiments, the patient is an infant, a child, an adolescent, or an elderly patient.

Also provided herein is a method for treating cancer in a subject in need thereof. The method includes determining if the cancer is associated with and/or exhibits one or more of overexpression, activation, amplification, and mutation of a Trk kinase and if the cancer is determined to be associated with and/or exhibits one or more of overexpression, activation, amplification, and mutation of a Trk kinase, administering to the subject a therapeutically effective amount of a liquid formulation as provided herein. Also provided herein is a method for treating cancer in a subject in need thereof. The method includes identifying that the cancer is associated with and/or exhibits one or more of overexpression, activation, amplification, and mutation of a Trk kinase and administering to the subject a therapeutically effective amount of a liquid formulation as provided herein.

Also provided herein is a method for treating cancer in a subject in need thereof, which includes determining if the cancer is mediated by a Trk kinase, and if the cancer is determined to be mediated by a Trk kinase, administering to the subject a therapeutically effective amount of a liquid formulation as provided herein. Also provided herein is a method for treating cancer in a subject in need thereof, which includes identifying the cancer as mediated by a Trk kinase, and administering to the subject a therapeutically effective amount of a liquid formulation as provided herein.

Also provided herein is a method of treating a subject. The method includes performing an assay on a sample obtained from the subject to determine whether the subject has a dysregulation of a NTRK gene, a Trk protein, or expression or level of the same. The method also includes administering to a subject determined to have a dysregulation of a NTRK gene, a Trk protein, or expression or activity, or level of the same a therapeutically effective amount of a liquid formulation as provided herein.

In some embodiments, the dysregulation of a NTRK gene, a Trk protein, or expression or level of the same is a chromosome translocation that results in the translation of a Trk fusion protein. The Trk fusion protein can be selected from the group consisting of: TP53-TrkA, LMNA-TrkA, CD74-TrkA, TFG-TrkA, TPM3-TrkA, NFASC-TrkA, BCAN-TrkA, MPRIP-TrkA, TPR-TrkA, RFWD2-TrkA, IRF2BP2-TrkA, SQSTM1-TrkA, SSBP2-TrkA, RABGAP1L-TrkA, C18ORF8-TrkA, RNF213-TrkA, TBC1D22A-TrkA, C20ORF112-TrkA, DNER-TrkA, ARHGEF2-TrkA, CHTOP-TrkA, PPL-TrkA, PLEKHA6-TrkA, PEAR1-TrkA, MRPL24-TrkA, MDM4-TrkA, LRRC71-TrkA, GRIPAP1-TrkA, EPS15-TrkA, DYNC2H1-TrkA, CEL-TrkA, EPHB2-TrkA, TGF-TrkA, NACC2-TrkB, QKI-TrkB, AFAP1-TrkB, PAN3-TrkB, SQSTM1-TrkB, TRIM24-TrkB, VCL-TrkB, AGBL4-TrkB, DAB2IP-TrkB, ETV6-TrkC, BTBD1-TrkC, LYN-TrkC, RBPMS-TrkC, EML4-TrkC, HOMER2-TrkC, TFG-TrkC, FAT1-TrkC, and TEL-TrkC.

In some embodiments, the dysregulation of a NTRK gene, a Trk protein, or expression or activity of the same is one or more point mutation in the gene. The NTRK gene can be a NTRK1 gene, and the one or more point mutations in the NTRK1 gene can result in the translation of a TrkA protein having substitutions are one or more of the following amino acid positions: 33, 336, 337, 324, 420, 444, 517, 538, 649, 682, 683, 702, and 1879.

In some embodiments, the one or more point mutations in the NTRK1 gene results in the translation of a TrkA protein having one or more of the following amino acid substitutions: R33W, A336E, A337T, R324Q, R324W, V420M, R444Q, R444W, G517R, G517V, K538A, R649W, R649L, R682S, V683G, R702C, and C1879T.

The features and advantages described in this summary and the following detailed description are not all-inclusive. Many additional features and advantages will be apparent to one of ordinary skill in the art in view of the drawings, specification, and claims hereof.

BRIEF DESCRIPTION OF THE DRAWINGS

FIG. 11 is a sequence listing for an exemplary wildtype TrkA polypeptide (SEQ ID NO: 1).

FIG. 12 is a sequence listing for an exemplary wildtype TrkA polypeptide (SEQ ID NO: 2).

FIG. 13 is a sequence listing for an exemplary wildtype TrkA polypeptide (SEQ ID NO: 3).

DETAILED DESCRIPTION

Figure 1:
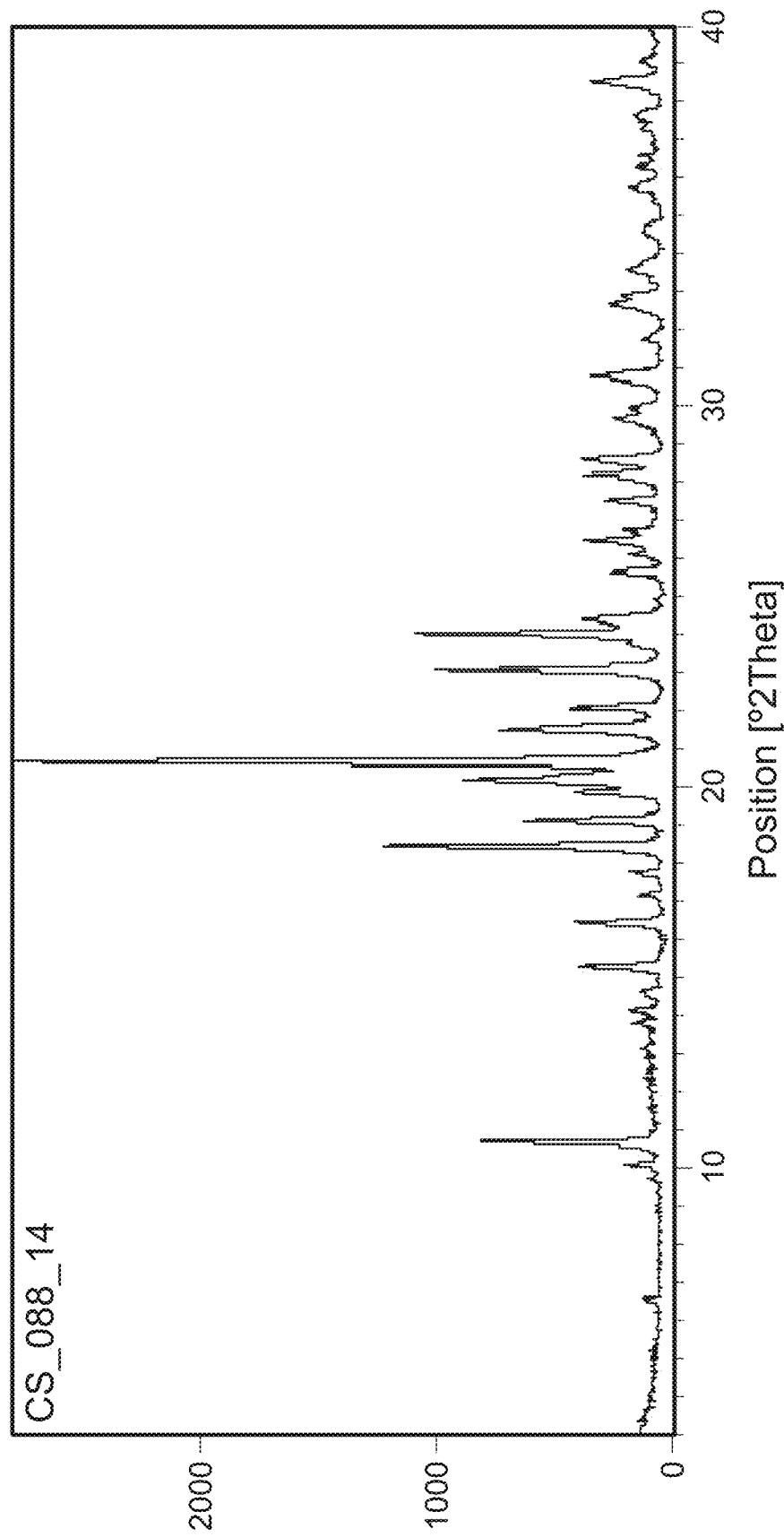
FIG. 1 illustrates an X-ray powder diffraction (XRPD) pattern of crystalline form (I-HS) prepared according to Example 2, according to one embodiment.

The present disclosure relates to liquid formulations of (S)—N-(5-((R)-2-(2,5-difluorophenyl)-pyrrolidin-1-yl)- pyrazolo[1,5-a]pyrimidin-3-yl)-3-hydroxypyrrolidine-1-carboxamide, a pharmaceutically acceptable salt thereof, or combinations thereof, and to the use of the liquid formulations in the treatment of pain, inflammation, cancer, and certain infectious diseases.

Provided herein is a liquid formulation including a solubilizing agent and (S)—N-(5-((R)-2-(2,5-difluorophenyl)pyrrolidin-1-yl)-pyrazolo[1,5-a]pyrimidin-3-yl)-3-hydroxypyrrolidine-1-carboxamide having the formula (I):

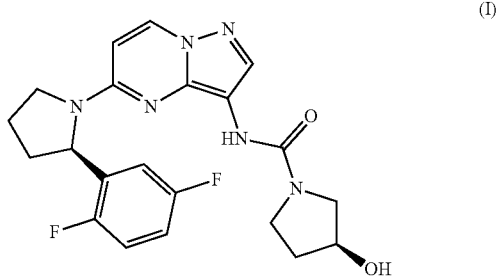 [SMILES: O=C(Nc1cnn2ccc(N3CCC[C@@H]3c3cc(F)ccc3F)nc12)N1CC[C@H](O)C1]

a pharmaceutically acceptable salt thereof, or a combination thereof.

In some embodiments, the compound of formula (I), a pharmaceutically acceptable salt thereof, or a combination thereof, can be present in the liquid formulation in an amount from about 0.5 wt. % to about 7%, about 1 wt. % to about 3 wt. %, or about 1.5 wt. % to about 2.5 wt. %. For example, the compound of formula (I), a pharmaceutically acceptable salt thereof, or a combination thereof can be present in the liquid formulation in an amount of about 0.5 wt. %, 1 wt. %, 2 wt. %, 3 wt. %, 4 wt. %, 5 wt. %, 6 wt. %, or about 7 wt. %. In some embodiments, the compound of formula (I), a pharmaceutically acceptable salt thereof, or a combination thereof can be present in the liquid formulation in an amount of about 2 wt. %.

In some embodiments, the compound of formula (I), a pharmaceutically acceptable salt thereof, or a combination thereof, has a concentration of about 5 mg/mL to about 50 mg/mL, about 15 mg/mL to about 35 mg/mL, or about 20 mg/mL to about 30 mg/mL in the liquid formulation. For example, the compound of formula (I), a pharmaceutically acceptable salt thereof, or a combination thereof can have a concentration of about 5 mg/mL, 10 mg/mL, 15 mg/mL, 20 mg/mL, 25 mg/mL, 30 mg/mL, 35 mg/m, 40 mg/mL, 45 mg/mL, or about 50 mg/mL in the liquid formulation. In some embodiments, the compound of formula (I), a pharmaceutically acceptable salt thereof, or a combination thereof can be present at a concentration of about 20 mg/mL in the liquid formulation.

The formulations provided herein can include a solubilizing agent that functions to increase the solubility of the compound of formula (I), a pharmaceutically acceptable salt thereof, or a combination thereof. A solubilizing agent is a polar organic compound having one or more hydroxyl groups. The solubilizing agent is also capable of achieving a higher concentration of the compound of formula (I) (e.g., the free base) in aqueous solution compared to an aqueous phase dissolution of the compound of formula (I) in a similar pH range without the solubilizing agent. The solubilizing agent can include, for example, a cyclodextrin, a glycol, a glycerol, a polyethylene glycol, a self-emulsifying drug delivery system (SEDDS), or a combination thereof.

In some embodiments, the cyclodextrin can include an α-cyclodextrin, β-cyclodextrin derivative, a δ-cyclodextrin derivative, a γ-cyclodextrin, or a combination derivative thereof. For example, the solubilizing agent can include a cyclodextrin. The solubilizing agent can include a β-cyclodextrin derivative, a γ-cyclodextrin, or a mixture thereof. For example, the solubilizing agent can include a hydroxy alkyl-γ-cyclodextrin. In some embodiments, the solubilizing agent includes a β-cyclodextrin including at least one of a hydroxy alkyl-β-cyclodextrin (e.g., hydroxypropyl-β-cyclodextrin) or a sulfoalkyl ether-β-cyclodextrin (e.g., sulfobutyl ether-β-cyclodextrin). For example, the liquid the solubilizing agent can include hydroxypropyl-β-cyclodextrin. In some embodiments, the cyclodextrin is CAVASOL® W7 HP (hydroxypropyl-β-cyclodextrin). In some embodiments, the cyclodextrin is KLEPTOSE® HP (hydroxypropyl-β-cyclodextrin). In some embodiments, the cyclodextrin is CAVAMAX® W7 (β-cyclodextrin). In some embodiments, the cyclodextrin is CAPTISOL® (sulfoalkyl ether-β-cyclodextrin). In some embodiments, the cyclodextrin is CAVASOL® W7 M (methyl-β-cyclodextrin). In some embodiments, the cyclodextrin is CAVASOL® W8 HP (hydroxypropyl-γ-cyclodextrin). In some embodiments, the cyclodextrin is CAVAMAX® W8 (γ-cyclodextrin). In some embodiments, the cyclodextrin is CAVAMAX® W6 (α-cyclodextrin).

SEDDS are isotropic mixtures of oils, surfactants, solvents and co-solvents/surfactants, that can be used to improve the oral absorption of highly lipophilic drug compounds. See, e.g., Tarate, B. et al., *Recent Patents on Drug Delivery & Formulation* (2014) Vol. 8.

In some embodiments, the poly(ethylene glycol) molecule is a linear polymer. The molecular weight of the linear chain PEG may be between about 1,000 Da and about 100,000 Da. For example, a linear chain PEG used herein can have a molecular weight of about 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, or 1,000 Da. In some embodiments, the molecular weight of the linear chain PEG is between about 1,000 Da and about 50,000 Da. In some embodiments, the molecular weight of the linear chain PEG is between about 1,000 Da and about 40,000 Da. In some embodiments, the molecular weight of the linear chain PEG is between about 5,000 Da and about 40,000 Da. In some embodiments, the molecular weight of the linear chain PEG is between about 5,000 Da and about 20,000 Da.

In some embodiments, the poly(ethylene glycol) molecule is a branched polymer. The molecular weight of the branched chain PEG may be between about 1,000 Da and about 100,000 Da. For example, a branched chain PEG used herein can have a molecular weight of about 100,000 Da, 95,000 Da, 90,000 Da, 85,000 Da, 80,000 Da, 75,000 Da, 70,000 Da, 65,000 Da, 60,000 Da, 55,000 Da, 50,000 Da, 45,000 Da, 40,000 Da, 35,000 Da, 30,000 Da, 25,000 Da, 20,000 Da, 15,000 Da, 10,000 Da, 9,000 Da, 8,000 Da, 7,000 Da, 6,000 Da, 5,000 Da, 4,000 Da, 3,000 Da, 2,000 Da, or 1,000 Da. In some embodiments, the molecular weight of the branched chain PEG is between about 1,000 Da and about 50,000 Da. In some embodiments, the molecular weight of the branched chain PEG is between about 1,000 Da and about 40,000 Da. In some embodiments, the molecular weight of the branched chain PEG is between about 5,000 Da and about 40,000 Da. In some embodiments, the molecular weight of the branched chain PEG is between about 5,000 Da and about 20,000 Da.

In some embodiments, the solubilizing agent can be present in the liquid formulation in an amount of about 5 wt. % to about 35 wt. %, about 10 wt. % to about 25 wt. %, about 10 wt. % to about 20 wt. %, or about 13 wt. % to about 17 wt. %. For example, the solubilizing agent can be present at about 5 wt. %, 7 wt. %, 10 wt. %, 13 wt. %, 15 wt. %, 17 wt. %, 20 wt. %, 23 wt. %, 26 wt. %, 30 wt. % or about 35 wt. %. In some embodiments, the solubilizing agent is present in the liquid formulation in an amount of 15 wt. %.

A buffer can be added to the liquid formulation to adjust the pH of the formulation to a desired pH. In some embodiments, a buffer can be added in an amount to adjust the pH of the formulation to a pH of about 2 to about 7, about 2.5 to about 5.5, or about 3 to about 4. For example, a buffer can be added in an amount to adjust the pH of the formulation to a pH of about 2.0, 2.5, 3.0, 3.5, 4.0, 4.5, 5.0, 6.0, or about 7.0. In some embodiments, a buffer can be added in an amount to adjust the pH of the formulation to a pH of about 3.5. In some embodiments, the buffer includes a citrate buffer, a lactate buffer, a phosphate buffer, a maleate buffer, a tartrate buffer, a suucinate buffer, an acetate buffer, or a combination thereof. In some embodiments, the buffer includes lithium lactate, sodium lactate, potassium lactate, calcium lactate, lithium phosphate, sodium phosphate, potassium phosphate, calcium phosphate, lithium maleate, sodium maleate, potassium maleate, calcium maleate, lithium tartrate, sodium tartrate, potassium tartrate, calcium tartrate, lithium succinate, sodium succinate, potassium succinate, calcium succinate, lithium acetate, sodium acetate, potassium acetate, calcium acetate, or combinations thereof. In some embodiments, the buffer is a citrate buffer. For example, the citrate buffer can include at least one of lithium citrate monohydrate, sodium citrate monohydrate, potassium citrate monohydrate, calcium citrate monohydrate, lithium citrate dihydrate, sodium citrate dihydrate, potassium citrate dihydrate, calcium citrate dihydrate, lithium citrate trihydrate, sodium citrate trihydrate, potassium citrate trihydrate, calcium citrate trihydrate, lithium citrate tetrahydrate, sodium citrate tetrahydrate, potassium citrate tetrahydrate, calcium citrate tetrahydrate, lithium citrate pentahydrate, sodium citrate pentahydrate, potassium citrate pentahydrate, calcium citrate pentahydrate, lithium citrate hexahydrate, sodium citrate hexahydrate, potassium citrate hexahydrate, calcium citrate hexahydrate, lithium citrate heptahydrate, sodium citrate heptahydrate, potassium citrate heptahydrate, calcium citrate heptahydrate, or mixtures thereof. The buffer can include sodium citrate monohydrate, potassium citrate monohydrate, calcium citrate monohydrate, sodium citrate dihydrate, potassium citrate dihydrate, calcium citrate dihydrate, sodium citrate trihydrate, potassium citrate trihydrate, calcium citrate trihydrate, sodium citrate tetrahydrate, potassium citrate tetrahydrate, calcium citrate tetrahydrate, sodium citrate pentahydrate, potassium citrate pentahydrate, calcium citrate pentahydrate, sodium citrate hexahydrate, potassium citrate hexahydrate, calcium citrate hexahydrate, sodium citrate heptahydrate, potassium citrate heptahydrate, or calcium citrate heptahydrate. In some embodiments, the buffer includes sodium citrate dihydrate.

In some embodiments, the buffer is present in the liquid formulation in an amount of about 0.1 wt. % to about 5 wt. %, about 0.3 wt. % to about 4 wt. %, about 0.5 wt. % to about 3.5 wt. %, about 0.6 wt. % to about 3 wt. %, 0.7 wt. % to about 2.5 wt. %, about 0.7 wt. % to about 2.0 wt. %, or about 0.7 wt. % to about 1.5 wt. %. For example, the buffer can be present in the liquid formulation in an amount of about 0.1 wt. %, 0.3 wt. %, 0.5 wt. %, 0.7 wt. %, 0.9 wt. %, 1.1 wt. %, 1.5 wt. %, 2.0 wt. %, 2.5 wt. %, 3.0 wt. %, 3.5 wt. %, 4.0 wt. %, or about 5 wt. %. In some embodiments, the buffer is present in the liquid formulation in an amount of about 0.9 wt. %.

The pH of the liquid formulation can be adjusted to a desired pH. In some embodiments, the pH of the formulation can be adjusted to a pH of about 2 to about 7, about 2.5 to about 5.5, or about 3 to about 4. For example, the pH of the formulation can be adjusted to a pH of about 2.0, 2.5, 3.0, 3.5, 4.0, 4.5, 5.0, 6.0, or about 7.0. In some embodiments, the pH of the formulation is adjusted to a pH of about 3.5. In some such embodiments, where the pH of the liquid formulation is adjusted to a desired pH, the liquid formulation includes a base. In some embodiments, the base is selected from a citrate, a lactate, a phosphate, a maleate, a tartrate, a succinate, an acetate, a carbonate, a hydroxide, or a combination thereof. In some embodiments, the base includes lithium lactate, sodium lactate, potassium lactate, calcium lactate, lithium phosphate, sodium phosphate, potassium phosphate, calcium phosphate, lithium maleate, sodium maleate, potassium maleate, calcium maleate, lithium tartrate, sodium tartrate, potassium tartrate, calcium tartrate, lithium succinate, sodium succinate, potassium succinate, calcium succinate, lithium acetate, sodium acetate, potassium acetate, calcium acetate, sodium carbonate, potassium carbonate, calcium carbonate, sodium bicarbonate, potassium bicarbonate, calcium bicarbonate, sodium hydroxide, potassium hydroxide, calcium hydroxide, or combinations thereof. In some embodiments, the base includes a citrate. For example, the citrate can include at least one of lithium citrate monohydrate, sodium citrate monohydrate, potassium citrate monohydrate, calcium citrate monohydrate, lithium citrate dihydrate, sodium citrate dihydrate, potassium citrate dihydrate, calcium citrate dihydrate, lithium citrate trihydrate, sodium citrate trihydrate, potassium citrate trihydrate, calcium citrate trihydrate, lithium citrate tetrahydrate, sodium citrate tetrahydrate, potassium citrate tetrahydrate, calcium citrate tetrahydrate, lithium citrate pentahydrate, sodium citrate pentahydrate, potassium citrate pentahydrate, calcium citrate pentahydrate, lithium citrate hexahydrate, sodium citrate hexahydrate, potassium citrate hexahydrate, calcium citrate hexahydrate, lithium citrate heptahydrate, sodium citrate heptahydrate, potassium citrate heptahydrate, calcium citrate heptahydrate, or mixtures thereof. The base can include sodium citrate monohydrate, potassium citrate monohydrate, calcium citrate monohydrate, sodium citrate dihydrate, potassium citrate dihydrate, calcium citrate dihydrate, sodium citrate trihydrate, potassium citrate trihydrate, calcium citrate trihydrate, sodium citrate tetrahydrate, potassium citrate tetrahydrate, calcium citrate tetrahydrate, sodium citrate pentahydrate, potassium citrate pentahydrate, calcium citrate pentahydrate, sodium citrate hexahydrate, potassium citrate hexahydrate, calcium citrate hexahydrate, sodium citrate heptahydrate, potassium citrate heptahydrate, or calcium citrate heptahydrate. In some embodiments, the base includes sodium citrate dihydrate.

In some embodiments, the base is present in the liquid formulation in an amount of about 0.1 wt. % to about 5 wt. %, about 0.3 wt. % to about 4 wt. %, about 0.5 wt. % to about 3.5 wt. %, about 0.6 wt. % to about 3 wt. %, 0.7 wt. % to about 2.5 wt. %, about 0.7 wt. % to about 2.0 wt. %, or about 0.7 wt. % to about 1.5 wt. %. For example, the base can be present in the liquid formulation in an amount of about 0.1 wt. %, 0.3 wt. %, 0.5 wt. %, 0.7 wt. %, 0.9 wt. %, 1.1 wt. %, 1.5 wt. %, 2.0 wt. %, 2.5 wt. %, 3.0 wt. %, 3.5 wt. %, 4.0 wt. %, or about 5 wt. %. In some embodiments, the base is present in the liquid formulation in an amount of about 0.9 wt. %. For example, the citrate is present in the liquid formulation in an amount of about 0.1 wt. % to about 5 wt. %, about 0.3 wt. % to about 4 wt. %, about 0.5 wt. % to about 3.5 wt. %, about 0.6 wt. % to about 3 wt. %, 0.7 wt. % to about 2.5 wt. %, about 0.7 wt. % to about 2.0 wt. %, or about 0.7 wt. % to about 1.5 wt. %. In some embodiments, the citrate can be present in the liquid formulation in an amount of about 0.1 wt. %, 0.3 wt. %, 0.5 wt. %, 0.7 wt. %, 0.9 wt. %, 1.1 wt. %, 1.5 wt. %, 2.0 wt. %, 2.5 wt. %, 3.0 wt. %, 3.5 wt. %, 4.0 wt. %, or about 5 wt. %. For example, the citrate is present in the liquid formulation in an amount of about 0.9 wt. %.

The liquid formulation can have a pH of about 2 to about 8, about 2.5 to about 6, about 3 to about 4, or about 3 to about 4. For example, the liquid formulation can have a pH of about 2, 2.5, 3.0, 3.5, 4.0, 4.5, or about 5. In some embodiments, the formulation can have a pH of about 3.5.

A sweetener can be added to the liquid formulation to make it less bitter or palatable, or both. Sweeteners suitable for inclusion in the formulation can include, both natural and artificial sweeteners. In some embodiments, the sweetener is an artificial sweetener and can include intense or high-intensity sweeteners. Intense sweeteners are commonly used as sugar substitutes or sugar alternatives as they are many times sweeter than sugar but contribute only a few to no calories when added to food. Exemplary intense sweeteners include sorbitol, sucrose, saccharins such as sodium saccharin, cyclamates such as sodium cyclamates, aspartame, sucralose, thaumatin, and acesulfam K. In some embodiments, the sweetener is a natural sugar. For example, sugars such as monosaccharides, disaccharides and polysaccharides can be used in the liquid formulations provided herein. The sugars can include xylose, ribose, glucose, mannose, galactose, fructose, dextrose, sucrose, maltose, partially hydrolyzed starch or corn syrup, and sugar alcohols such as sorbitol, xylitol, mannitol, glycerin, and combination thereof. In some embodiments, the liquid formulation further comprises a sweetener. The sweetener can include a sugar. For example, the sweetener can include sucrose. For example, the sweetener can be ORA-SWEET®, a sweetener that includes purified water, sucrose, glycerin, sorbitol, and flavoring; is buffered with citric acid and sodium phosphate; and is preserved with methylparaben and potassium sorbate. The sweetener can also include an intense sweetener. The intense sweetener can include sucralose. For example, the sweetener can be ORA-SWEET SF®, a sugar free sweetener that includes purified water, glycerin, sorbitol, sodium saccharin, xanthan gum, and flavoring; is buffered with citric acid and sodium citrate; and is preserved with methylparaben (0.03%), potassium sorbate (0.1%), and propylparaben (0.008%).

In some embodiments, the sweetener includes one or more of sucrose, glycerin, sorbitol, and flavoring. In some such embodiments, the sweetener further includes citric acid and sodium phosphate. In some such embodiments, the sweetener can include a preservative, such as methylparaben and potassium sorbate. For example, the sweetener includes sucrose, glycerin, sorbitol, flavoring, citric acid, sodium phosphate, methylparaben, and potassium sorbate. In some embodiments, the sweetener includes one or more of glycerin, sorbitol, sodium saccharin, xanthan gum, and flavoring. In some such embodiments, the sweetener further includes citric acid and sodium citrate. In some such embodiments, the sweetener includes a preservative, such as methylparaben, potassium sorbate, and propylparaben. For example, the sweetener can include glycerin, sorbitol, sodium saccharin, xanthan gum, flavoring, citric acid and sodium citrate, methylparaben (0.03%), potassium sorbate (0.1%), and propylparaben (0.008%).

In some embodiments, the sweetener is present in the liquid formulation in an amount of about 30 wt. % to about 70 wt. %, about 35 wt. % to about 65 wt. %, about 40 wt. % to about 60 wt. %, or about 45 wt. % to about 55 wt. %. For example, the sweetener can be present in the liquid formulation in an amount of about 30 wt. %, 35 wt. %, 40 wt. %, 45 wt. %, 50 wt. %, 55 wt. %, 60 wt. %, 65 wt. %, or about 70 wt. %. In some embodiments, the sweetener is present in the liquid formulation in an amount of about 50 wt. %.

In some embodiments, the liquid formulation further comprises a bitterness masking agent. The bitterness masking agent can include 231a12 natural masking type flavor (Abelei®), 231a39 natural bitterness masking type flavor (Abelei®), bitterness masking flavor, nat (FONA®), and FINATECH Taste Modifier Flavor, Nat.

The bitterness masking agent can be present in the liquid formulation in an amount of about 0.01 wt. % to about 2 wt. %, about 0.1 wt. % to about 1.0 wt. %, or about 0.2 wt. % to about 0.5 wt. %. For example, the bitterness masking agent can be present in the liquid formulation in an amount of about 0.01 wt. %, 0.1 wt. %, 0.2 wt. %, 0.3 wt. %, 0.4 wt. %, 0.5 wt. %, 0.7 wt. %, 1.0 wt. %, 1.5 wt. %, or 2.0 wt. %. In some embodiments, the bitterness masking agent is present in the liquid formulation in an amount of about 0.4 wt. %.

A flavoring agent can be included in the liquid formulation so that the final formulation has a substantially non-bitter and palatable taste. The flavoring agent can include at least one of a natural flavoring agent, a natural fruit flavoring agent, an artificial flavoring agent, an artificial fruit flavoring agent, flavor enhancers, or mixtures thereof. Exemplary flavoring agents can be found, for example in US CFR 21 § 172.515 (Apr. 1, 2015), which is incorporated by reference in its entirety. For example, cinnamon, raspberry, orange, maple, butterscotch, *glycyrrhiza* (licorice) syrup, fruit, berry, vanilla, acacia syrup, coca, chocolate-mint, wild cherry, walnut, eriodictyon, bubblegum, grapefruit, lime, marshmellow, gurana, coffee, peach, lemon, fennel, apricot, honey, mint, wintergreen, and cherry. In some embodiments, the flavoring agent can include a FONATECH® natural taste modifier flavoring agent. The flavoring agent can be present in the liquid formulation in an amount of about 0.01 wt. % to about 2 wt. %, about 0.01 wt. % to about 0.1 wt. %, or about 0.2 wt. % to about 0.5 wt. %. For example, the flavoring agent can be present in an amount of about 0.01 wt. %, 0.1 wt. %, 0.2 wt. %, 0.3 wt. %, 0.4 wt. %, 0.5 wt. %, 0.7 wt. %, 1.0 wt. %, 1.5 wt. %, or 2.0 wt. %. In some embodiments, the flavoring agent can be present in the liquid formulation in an amount of about 0.5 wt. %.

The liquid formulation can also include a coloring agent.

The liquid formulations provided herein can be prepared from a crystalline form of the compound of formula (I). The crystalline form can the formula (I-HS):

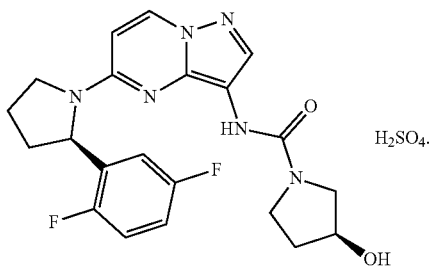

I-HS

Also provided herein is a liquid formulation including (S)—N-(5-((R)-2-(2,5-difluorophenyl)pyrrolidin-1-yl)-pyrazolo[1,5-a]pyrimidin-3-yl)-3-hydroxypyrrolidine-1-carboxamide having the formula (I):

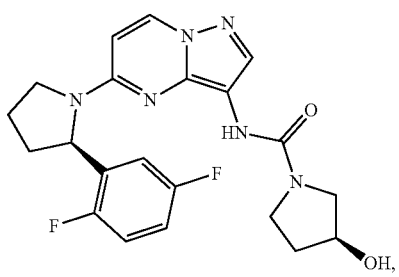

(I)

a pharmaceutically acceptable salt thereof, or a combination thereof, a solubilizing agent and a buffer. In some embodiments, the formulation has a pH of about 2.5 to about 5.5. In some embodiments, the compound of formula (I) has a concentration of about 15 mg/mL to about 35 mg/mL. In some embodiments, the formulation has a pH of about 3 to about 4 and the compound of formula (I), or a pharmaceutically acceptable salt thereof, or a combination thereof, is present at a concentration of about 15 mg/mL to about 35 mg/mL in the liquid formulation. The buffer can include sodium citrate dihydrate.

Also provided herein is a liquid formulation including (S)—N-(5-((R)-2-(2,5-difluorophenyl)pyrrolidin-1-yl)-pyrazolo[1,5-a]pyrimidin-3-yl)-3-hydroxypyrrolidine-1-carboxamide having the formula (I):

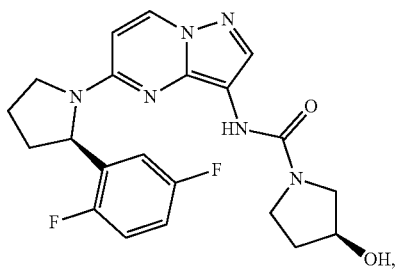

(I)

a pharmaceutically acceptable salt thereof, or a combination thereof, a solubilizing agent and a base. In some embodiments, the formulation has a pH of about 2.5 to about 5.5. In some embodiments, the compound of formula (I) has a concentration of about 15 mg/mL to about 35 mg/mL. In some embodiments, the formulation has a pH of about 3 to about 4 and the compound of formula (I), or a pharmaceutically acceptable salt thereof, or a combination thereof, is present at a concentration of about 15 mg/mL to about 35 mg/mL in the liquid formulation. The base can include sodium citrate dihydrate.

Also provided herein is a liquid formulation including (S)—N-(5-((R)-2-(2,5-difluorophenyl)pyrrolidin-1-yl)-pyrazolo[1,5-a]pyrimidin-3-yl)-3-hydroxypyrrolidine-1-carboxamide having the formula (I):

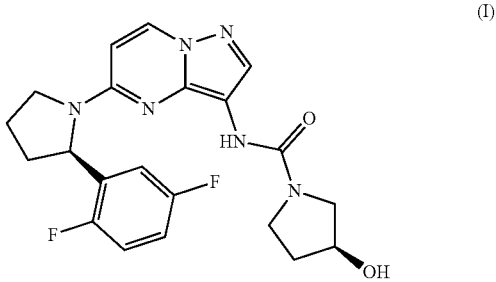 [SMILES: O=C(Nc1cnn2ccc(N3CCC[C@@H]3c3cc(F)ccc3F)nc12)N1CC[C@H](O)C1]

(I)

a pharmaceutically acceptable salt thereof, or a combination thereof, a solubilizing agent, a buffer, a sweetener, a bitterness masking agent, and a flavoring agent. In some embodiments, the formulation has a pH of about 3 to about 4 and the compound of formula (I), or a pharmaceutically acceptable salt thereof, or a combination thereof, is present at a concentration of about 15 mg/mL to about 35 mg/mL in the liquid formulation. In some embodiments, the buffer includes sodium citrate dihydrate. In some embodiments, the sweetener includes sucrose.

Also provided herein is a liquid formulation including (S)—N-(5-((R)-2-(2,5-difluorophenyl)pyrrolidin-1-yl)-pyrazolo[1,5-a]pyrimidin-3-yl)-3-hydroxypyrrolidine-1-carboxamide having the formula (I):

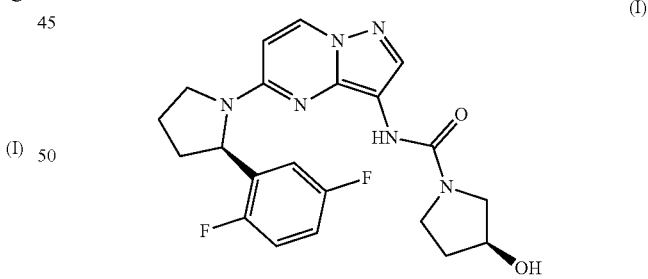

(I)

a pharmaceutically acceptable salt thereof, or a combination thereof, a solubilizing agent, a base, a sweetener, a bitterness masking agent, and a flavoring agent. In some embodiments, the formulation has a pH of about 3 to about 4 and the compound of formula (I), or a pharmaceutically acceptable salt thereof, or a combination thereof, is present at a concentration of about 15 mg/mL to about 35 mg/mL in the liquid formulation. In some embodiments, the base includes sodium citrate dihydrate. In some embodiments, the sweetener includes sucrose.

Also provided herein is a liquid formulation including (S)—N-(5-((R)-2-(2,5-difluorophenyl)pyrrolidin-1-yl)-pyrazolo[1,5-a]pyrimidin-3-yl)-3-hydroxypyrrolidine-1-carboxamide having the formula (I):

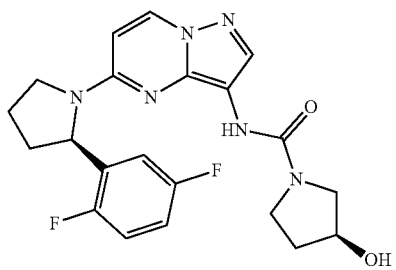

(I)

a pharmaceutically acceptable salt thereof, or a combination thereof, a solubilizing agent, a buffer, a sweetener, a bitterness masking agent, and flavoring agent, wherein the formulation has a pH of about 3 to about 4.

Also provided herein is a liquid formulation including (S)—N-(5-((R)-2-(2,5-difluorophenyl)pyrrolidin-1-yl)-pyrazolo[1,5-a]pyrimidin-3-yl)-3-hydroxypyrrolidine-1-carboxamide having the formula (I):

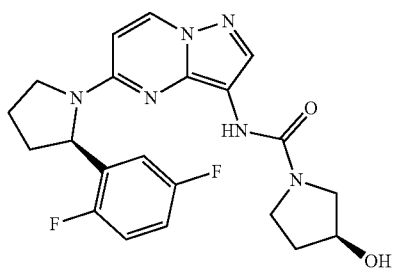

(I)

a pharmaceutically acceptable salt thereof, or a combination thereof, a solubilizing agent, a base, a sweetener, a bitterness masking agent, and flavoring agent, wherein the formulation has a pH of about 3 to about 4.

Also provided herein is a liquid formulation including (S)—N-(5-((R)-2-(2,5-difluorophenyl)pyrrolidin-1-yl)-pyrazolo[1,5-a]pyrimidin-3-yl)-3-hydroxypyrrolidine-1-carboxamide having the formula (I):

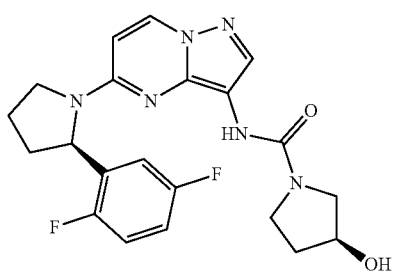

(I)

a pharmaceutically acceptable salt thereof, or a combination thereof, a solubilizing agent, a buffer, a sweetener, a bitterness masking agent, and a flavoring agent, wherein the compound of formula (I) has a concentration of about 15 mg/mL to about 35 mg/mL in the liquid formulation.

Also provided herein is a liquid formulation including (S)—N-(5-((R)-2-(2,5-difluorophenyl)pyrrolidin-1-yl)-pyrazolo[1,5-a]pyrimidin-3-yl)-3-hydroxypyrrolidine-1-carboxamide having the formula (I):

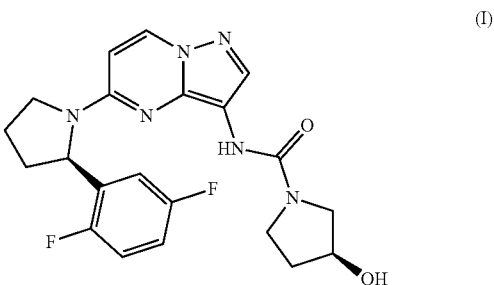 [SMILES: O=C(Nc1cnn2ccc(N3CCC[C@@H]3c3cc(F)ccc3F)nc12)N1CC[C@H](O)C1]

(I)

a pharmaceutically acceptable salt thereof, or a combination thereof, a solubilizing agent, a base, a sweetener, a bitterness masking agent, and a flavoring agent, wherein the compound of formula (I) has a concentration of about 15 mg/mL to about 35 mg/mL in the liquid formulation.

Also provided herein is a liquid formulation including:

(a) (S)—N-(5-((R)-2-(2,5-difluorophenyl)pyrrolidin-1-yl)-pyrazolo[1,5-a]pyrimidin-3-yl)-3-hydroxypyrrolidine-1-carboxamide having the formula (I):

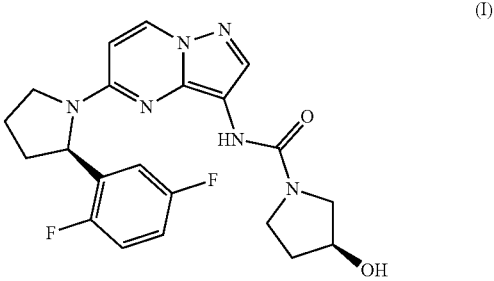 [SMILES: O=C(Nc1cnn2ccc(N3CCC[C@@H]3c3cc(F)ccc3F)nc12)N1CC[C@H](O)C1]

(I)

a pharmaceutically acceptable salt thereof, or a combination thereof;

(b) a solubilizing agent present in an amount of about 5 wt. % to about 35 wt. %; and (c) a buffer present in an amount of about 0.1 wt. % to about 5 wt. %. In some embodiments, the buffer comprises sodium citrate dehydrate. In some embodiments, the formulation also includes a sweetener present in an amount of about 30 wt. % to about 70 wt. %. In some embodiments, the sweetener comprises sucrose. In some embodiments, the formulation also includes a bitterness masking agent present in an amount of about 0.2 wt. % to about 0.5 wt. %. In some embodiments, the formulation also includes a flavoring agent present in an amount of about 0.01 wt. % to about 2 wt. %. In some embodiments, the formulation has a pH of about 3 to about 4. In some embodiments, the compound of formula (I) has a concentration of about 20 mg/mL to about 30 mg/mL in the liquid formulation.

Also provided herein is a liquid formulation including:
(a) (S)—N-(5-((R)-2-(2,5-difluorophenyl)pyrrolidin-1-yl)-pyrazolo[1,5-a]pyrimidin-3-yl)-3-hydroxypyrrolidine-1-carboxamide having the formula (I):

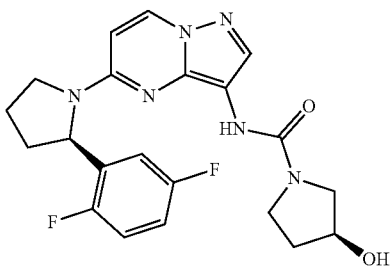

(I)

a pharmaceutically acceptable salt thereof, or a combination thereof;
(b) a solubilizing agent present in an amount of about 5 wt. % to about 35 wt. %; and
(c) a base present in an amount of about 0.1 wt. % to about 5 wt. %. In some embodiments, the base comprises sodium citrate dehydrate. In some embodiments, the formulation also includes a sweetener present in an amount of about 30 wt. % to about 70 wt. %. In some embodiments, the sweetener comprises sucrose. In some embodiments, the formulation also includes a bitterness masking agent present in an amount of about 0.2 wt. % to about 0.5 wt. %. In some embodiments, the formulation also includes a flavoring agent present in an amount of about 0.01 wt. % to about 2 wt. %. In some embodiments, the formulation has a pH of about 3 to about 4. In some embodiments, the compound of formula (I) has a concentration of about 20 mg/mL to about 30 mg/mL in the liquid formulation.

Also provided herein is a liquid formulation including:
(a) (S)—N-(5-((R)-2-(2,5-difluorophenyl)pyrrolidin-1-yl)-pyrazolo[1,5-a]pyrimidin-3-yl)-3-hydroxypyrrolidine-1-carboxamide having the formula (I):

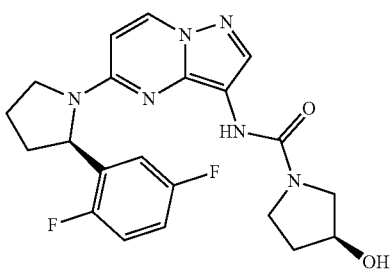

(I)

a pharmaceutically acceptable salt thereof, or a combination thereof;
(b) a solubilizing agent (e.g., a cyclodextrin such as a hydroxypropyl-β-cyclodextrin) present in an amount of about 5 wt. % to about 35 wt. %; and
(c) a buffer (e.g., a citrate buffer such as sodium citrate) present in an amount of about 0.1 wt. % to about 5 wt. %;
(d) a sweetener (e.g., a sweetener comprising sucrose or an intense sweetener) present in an amount of about 30 wt. % to about 70 wt. %;
(e) a bitterness masking agent present in an amount of about 0.2 wt. % to about 0.5 wt. %; and
(f) a flavoring agent present in an amount of about 0.01 wt. % to about 2 wt. %. In some embodiments, the formulation has a pH of about 3 to about 4. In some embodiments, the compound of formula (I) has a concentration of about 20 mg/mL to about 30 mg/mL in the liquid formulation.

Also provided herein is a liquid formulation including:
(a) (S)—N-(5-((R)-2-(2,5-difluorophenyl)pyrrolidin-1-yl)-pyrazolo[1,5-a]pyrimidin-3-yl)-3-hydroxypyrrolidine-1-carboxamide having the formula (I):

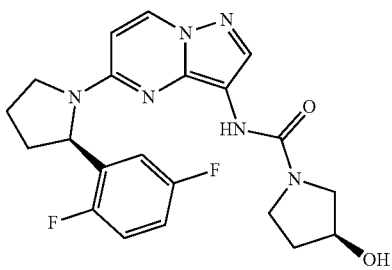

(I)

a pharmaceutically acceptable salt thereof, or a combination thereof;
(b) a solubilizing agent (e.g., a cyclodextrin such as a hydroxypropyl-β-cyclodextrin) present in an amount of about 5 wt. % to about 35 wt. %; and
(c) a base (e.g., a citrate such as sodium citrate) present in an amount of about 0.1 wt. % to about 5 wt. %;
(d) a sweetener (e.g., a sweetener comprising sucrose or an intense sweetener) present in an amount of about 30 wt. % to about 70 wt. %;
(e) a bitterness masking agent present in an amount of about 0.2 wt. % to about 0.5 wt. %; and
(f) a flavoring agent present in an amount of about 0.01 wt. % to about 2 wt. %. In some embodiments, the formulation has a pH of about 3 to about 4. In some embodiments, the compound of formula (I) has a concentration of about 20 mg/mL to about 30 mg/mL in the liquid formulation.

Also provided herein is a liquid formulation including:
(a) (S)—N-(5-((R)-2-(2,5-difluorophenyl)pyrrolidin-1-yl)-pyrazolo[1,5-a]pyrimidin-3-yl)-3-hydroxypyrrolidine-1-carboxamide having the formula (I):

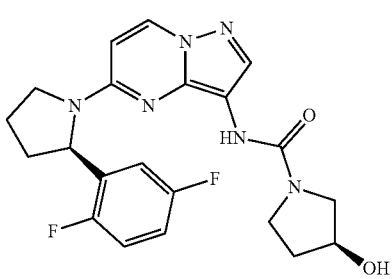

(I)

a pharmaceutically acceptable salt thereof, or a combination thereof;
(b) hydroxypropyl-β-cyclodextrin present in an amount of about 5 wt. % to about 35 wt. %; and
(c) a sodium citrate present in an amount of about 0.1 wt. % to about 5 wt. %;
(d) a sucrose or an intense sweetener present in an amount of about 30 wt. % to about 70 wt. %;

(e) a bitterness masking agent present in an amount of about 0.2 wt. % to about 0.5 wt. %; and
(f) a flavoring agent present in an amount of about 0.01 wt. % to about 2 wt. %. In some embodiments, the formulation has a pH of about 3 to about 4. In some embodiments, the compound of formula (I) has a concentration of about 20 mg/mL to about 30 mg/mL in the liquid formulation.

Also provided herein is a liquid formulation including:
(a) (S)—N-(5-((R)-2-(2,5-difluorophenyl)pyrrolidin-1-yl)-pyrazolo[1,5-a]pyrimidin-3-yl)-3-hydroxypyrrolidine-1-carboxamide having the formula (I):

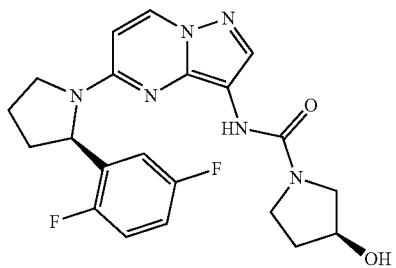

(I)

a pharmaceutically acceptable salt thereof, or a combination thereof;
(b) hydroxypropyl-β-cyclodextrin present in an amount of about 5 wt. % to about 35 wt. %; and
(c) sodium citrate dihydrate present in an amount of about 0.1 wt. % to about 5 wt. %;
(d) a sucrose or an intense sweetener present in an amount of about 30 wt. % to about 70 wt. %;
(e) a bitterness masking agent present in an amount of about 0.2 wt. % to about 0.5 wt. %; and
(f) a flavoring agent present in an amount of about 0.01 wt. % to about 2 wt. %. In some embodiments, the formulation has a pH of about 3 to about 4. In some embodiments, the compound of formula (I) has a concentration of about 20 mg/mL to about 30 mg/mL in the liquid formulation.

In some embodiments, the liquid formulation is prepared from a pharmaceutically acceptable salt of the compound of formula (I). For example, the pharmaceutically acceptable salt is a hydrogen sulfate salt. In some embodiments, the liquid formulation is prepared from a crystalline form of the compound of formula (I). For example, the crystalline form of the compound of formula (I) can have the formula (I-HS):

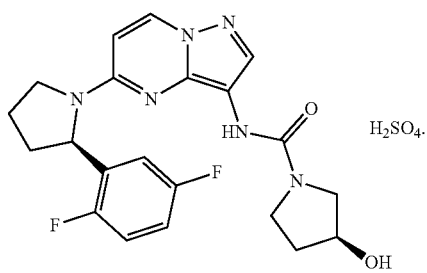

I-HS

In some embodiments, crystalline form (I-HS) is characterized by having XRPD diffraction peaks (2θ degrees) at 18.4±0.2, 20.7±0.2, 23.1±0.2, and 24.0±0.2. In some embodiments, crystalline form (I-HS) is characterized by having XRPD diffraction peaks (2θ degrees) at 10.7±0.2, 18.4±0.2, 20.7±0.2, 23.1±0.2, and 24.0±0.2. In some embodiments, crystalline form (I-HS) is characterized by having XRPD diffraction peaks (2θ degrees) at 10.7±0.2, 18.4±0.2, 19.2±0.2, 20.2±0.2, 20.7±0.2, 21.5±0.2, 23.1±0.2, and 24.0±0.2. In some embodiments, crystalline form (I-HS) is characterized by having XRPD diffraction peaks (2θ degrees) at 10.7±0.2, 15.3±0.2, 16.5±0.2, 18.4±0.2, 19.2±0.2, 19.9±0.2, 20.2±0.2, 20.7±0.2, 21.5±0.2, 22.1±0.2, 23.1±0.2, 24.0±0.2. 24.4±0.2, 25.6±0.2, 26.5±0.2, 27.6±0.2, 28.2±0.2, 28.7±0.2, 30.8±0.2, and 38.5±0.2.

Figure 8:
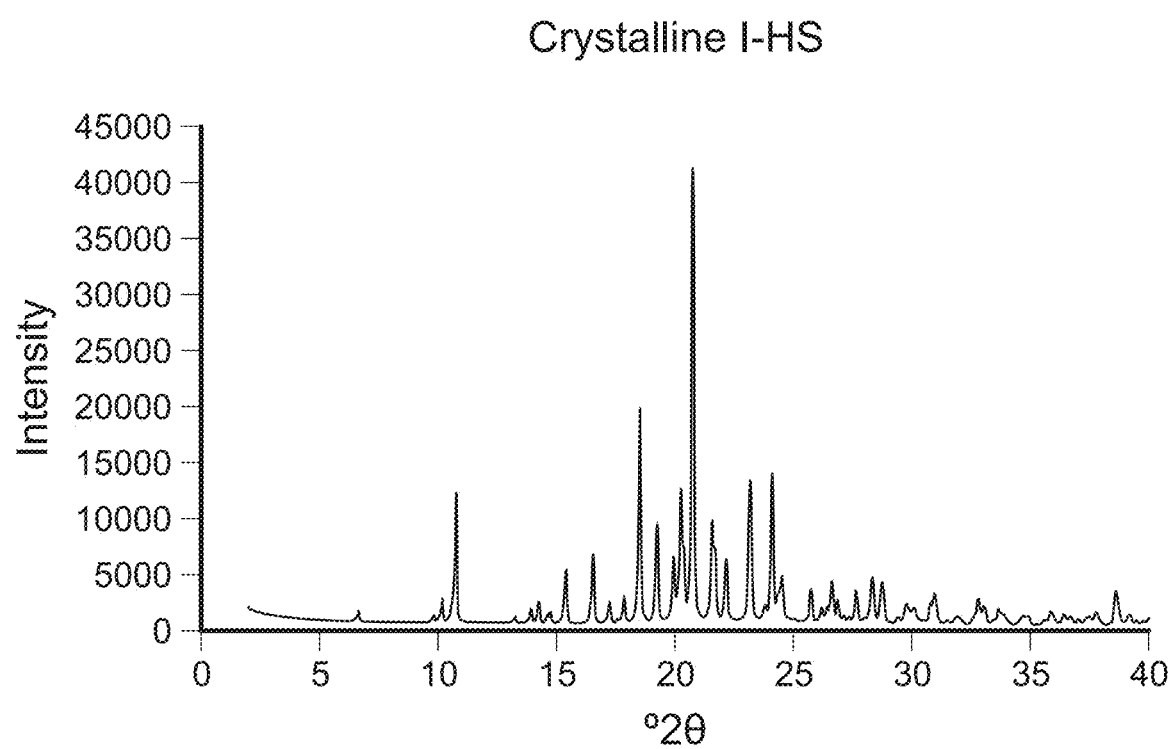
FIG. 8 illustrates an X-ray powder diffraction (XRPD) pattern of crystalline form (I-HS).

In some embodiments, the crystalline form (I-HS) has XRPD pattern substantially as shown in FIG. 1 or FIG. 8.

In some embodiments, the crystalline form exhibits an onset to maximum of about 193 to about 205° Celsius, as measured by differential scanning calorimetry. In some embodiments, the crystalline form (I-HS) exhibits a heat of melting of about 2.415 mW, as measured by differential scanning calorimetry.

Also provided herein is a method of treating cancer in a patient in need thereof. The method includes administering to the patient a therapeutically effective amount of a liquid formulation provided herein.

In some embodiments, the cancer results in dysphagia or difficulty swallowing. For example, the cancer can be a head and neck cancer, a mouth cancer, a throat cancer, or an esophageal cancer. In some embodiments, a patient having cancer develops difficulty swallowing due to one or more of fibrosis in the throat, esophagus, or mouth; infections of the mouth or esophagus (e.g., from radiation therapy or chemotherapy), swelling or narrowing of the throat or esophagus (e.g., from radiation therapy or surgery); physical changes to the mouth, jaws, throat, or esophagus from surgery; mucositis, which is soreness, pain or inflammation in the throat, esophagus, or mouth; xerostomia, commonly referred to as dry mouth (e.g., from radiation therapy or chemotherapy).

In some embodiments, the patient is an infant, a child, an adolescent, or an elderly patient.

In some embodiments, the patient has a dysphagia. The dysphagia can be an oropharyngeal dysphagia. Oropharyngeal dysphagia can arise due to cancer (e.g., certain cancers and some cancer treatments, such as radiation, can cause difficulty swallowing), neurological disorders (e.g., certain disorders, such as multiple sclerosis, muscular dystrophy and Parkinson's disease, can cause dysphagia), neurological damage (e.g., sudden neurological damage, such as from a stroke or brain or spinal cord injury, that effects one's ability to swallow), and pharyngeal diverticula.

In some embodiments, the patient has a neurological disorders (e.g., certain disorders, such as multiple sclerosis, muscular dystrophy and Parkinson's disease, can cause dysphagia), neurological damage (e.g., sudden neurological damage, such as from a stroke or brain or spinal cord injury, that effects one's ability to swallow), and pharyngeal diverticula.

Also provided herein is a method of treating cancer in a patient in need thereof with dysphagia (e.g., difficulty swallowing). The method includes identifying a patient in need thereof with dysphagia. The method further includes administering to the patient a therapeutically effective amount of a liquid formulation described herein.

In some embodiments, the dysphagia is an oropharyngeal dysphagia.

Also provided herein is a method of treating cancer in a patient in need thereof with dysphagia. The method includes identifying a patient in need thereof with dysphagia. The method further includes determining if the cancer is mediated by a Trk kinase. If the cancer is determined to be mediated by a Trk kinase, administering to the patient a therapeutically effective amount of a liquid formulation described herein. Also provided herein is a method of treating cancer in a patient in need thereof with dysphagia. The method includes identifying a patient in need thereof with dysphagia. The method further includes identifying the cancer as mediated by a Trk kinase, and administering to the patient a therapeutically effective amount of a liquid formulation described herein.

In some embodiments, the dysphagia is an oropharyngeal dysphagia. Oropharyngeal dysphagia can arise due to cancer (e.g., certain cancers and some cancer treatments, such as radiation, can cause difficulty swallowing), neurological disorders (e.g., certain disorders, such as multiple sclerosis, muscular dystrophy and Parkinson's disease, can cause dysphagia), neurological damage (e.g., sudden neurological damage, such as from a stroke or brain or spinal cord injury, that effects one's ability to swallow), and pharyngeal diverticula.

Crystalline Form of the Compound of Formula (I)

As discussed herein the liquid formulations can be prepared from a crystalline form of (S)—N-(5-((R)-2-(2,5-difluorophenyl)-pyrrolidin-1-yl)-pyrazolo[1,5-a]pyrimidin-3-yl)-3-hydroxypyrrolidine-1-carboxamide (Formula I), a pharmaceutically acceptable salt thereof, or combinations thereof. In some embodiments, the crystalline form is crystalline form (I-HS).

As illustrated in FIG. 1, in some embodiments, the crystalline form (I-HS) can be characterized by its X-ray powder diffraction pattern (XRPD). The XRPD was carried out on a D5000 X-ray diffractometer with a CuKα1, 0.1540562 nm long, fine focus sealed tube source from Siemens by scanning samples between 3 and 40° 2-theta at a step size of 0.0200° 2-theta and a time per step of 1 second. The effective scan speed was 0.0200°/s with an instrument voltage 40 kV and a current setting of 40 mA. Samples were analyzed using a divergence slit having a size of 2 mm in reflection mode under the following experimental conditions.

In some embodiments, crystalline form (I-HS) has an XRPD pattern with at least the 20 characteristic peaks (2θ degrees±0.3), as listed in Table 1.

TABLE 1

XRPD peaks of crystalline form (I-HS)

| Position [°2-θ] | FWHM [°2-θ] | d-spacing [Å] | Relative Intensity [%] |
|---|---|---|---|
| 10.63 | 0.12 | 8.32 | 27.44 |
| 15.25 | 0.14 | 5.81 | 12.24 |
| 16.39 | 0.13 | 5.40 | 13.92 |
| 18.37 | 0.13 | 4.82 | 43.65 |
| 19.08 | 0.14 | 4.65 | 19.60 |
| 19.79 | 0.11 | 4.48 | 9.83 |
| 20.15 | 0.25 | 4.40 | 25.09 |
| 20.61 | 0.13 | 4.31 | 100.00 |
| 21.47 | 0.21 | 4.14 | 24.71 |
| 22.01 | 0.12 | 4.03 | 14.45 |
| 23.04 | 0.15 | 3.86 | 33.01 |
| 23.97 | 0.12 | 3.71 | 38.52 |
| 24.35 | 0.21 | 3.65 | 10.05 |
| 25.58 | 0.13 | 3.48 | 8.11 |
| 26.48 | 0.17 | 3.36 | 9.76 |
| 27.50 | 0.14 | 3.24 | 7.70 |
| 28.17 | 0.17 | 3.16 | 11.60 |
| 28.58 | 0.19 | 3.12 | 10.85 |
| 30.77 | 0.29 | 2.90 | 8.48 |
| 38.47 | 0.21 | 2.34 | 10.97 |

In some embodiments, the crystalline form (I-HS) has an XRPD pattern with at least the 8 characteristic peaks (2θ degrees±0.3), which comprises peaks having a relative intensity greater than or equal to about 15%, as listed in Table 2.

TABLE 2

XRPD peaks of crystalline form (I-HS)

| Position [°2-θ] | FWHM [°2-θ] | d-spacing [Å] | Relative Intensity [%] |
|---|---|---|---|
| 10.63 | 0.12 | 8.32 | 27.44 |
| 18.37 | 0.13 | 4.82 | 43.65 |
| 19.08 | 0.14 | 4.65 | 19.60 |
| 20.15 | 0.25 | 4.40 | 25.09 |
| 20.61 | 0.13 | 4.31 | 100.00 |
| 21.47 | 0.21 | 4.14 | 24.71 |
| 23.04 | 0.15 | 3.86 | 33.01 |
| 23.97 | 0.12 | 3.71 | 38.52 |

In some embodiments, the crystalline form (I-HS) has an XRPD pattern with at least the 5 characteristic peaks (2θ degrees±0.3), which comprises peaks having a relative intensity greater than or equal to about 25%, as listed in Table 3.

TABLE 3

XRPD peaks of crystalline form (I-HS)

| Position [°2-θ] | FWHM [°2-θ] | d-spacing [Å] | Relative Intensity [%] |
|---|---|---|---|
| 10.63 | 0.12 | 8.32 | 27.44 |
| 18.37 | 0.13 | 4.82 | 43.65 |
| 20.61 | 0.13 | 4.31 | 100.00 |
| 23.04 | 0.15 | 3.86 | 33.01 |
| 23.97 | 0.12 | 3.71 | 38.52 |

In some embodiments, the crystalline form (I-HS) has an XRPD pattern with at least the 4 characteristic peaks (2θ degrees±0.3), which comprises peaks having a relative intensity greater than or equal to about 30%, as listed in Table 4.

TABLE 4

XRPD peaks of crystalline form (I-HS)

| Position [°2-θ] | FWHM [°2-θ] | d-spacing [Å] | Relative Intensity [%] |
|---|---|---|---|
| 18.37 | 0.13 | 4.82 | 43.65 |
| 20.61 | 0.13 | 4.31 | 100.00 |
| 23.04 | 0.15 | 3.86 | 33.01 |
| 23.97 | 0.12 | 3.71 | 38.52 |

In certain embodiments, crystalline form (I-HS) has an XRPD pattern that is substantially the same XRPD pattern as shown in FIG. 1.

In some embodiments, crystalline form (I-HS) is characterized by having XRPD diffraction peaks (2θ degrees) at about 18.4, 20.6, 23.0, and 24.0. In some embodiments, crystalline form (I-HS) is characterized by having XRPD diffraction peaks (2θ degrees) at about 10.6, 18.4, 20.6, 23.0, and 24.0. In some embodiments, crystalline form (I-HS) is characterized by having XRPD diffraction peaks (2θ degrees) at about 10.6, 18.4, 19.1, 20.2, 20.6, 21.5, 23.0, and 24.0. In some embodiments, crystalline form (I-HS) is characterized by having XRPD diffraction peaks (2θ degrees) at about 10.6, 15.3, 16.4, 18.4, 19.1, 19.8, 20.2, 20.6, 21.5, 22.0, 23.0, 24.0, 24.4, 25.6, 26.5, 27.5, 28.2, 28.6, 30.8, and 38.5.

In certain embodiments, crystalline form (I-HS) has an XRPD pattern that is substantially the same XRPD pattern as shown in FIG. 8.

In some embodiments, crystalline form (I-HS) has an XRPD pattern with at least the 20 characteristic peaks (2θ degrees±0.3), as listed in Table 5.

TABLE 5

XRPD peaks of crystalline form (I-HS)

| Position (°2θ) | Relative Intensity (%) |
|---|---|
| 10.76 | 29.85 |
| 15.38 | 13.22 |
| 16.52 | 16.46 |
| 18.50 | 48.07 |
| 19.22 | 22.92 |
| 19.92 | 16.05 |
| 20.26 | 30.80 |
| 20.74 | 100.00 |
| 21.56 | 23.78 |
| 22.16 | 15.51 |
| 23.16 | 32.52 |
| 24.10 | 33.89 |
| 24.50 | 12.14 |
| 25.72 | 8.89 |
| 26.50 | 10.88 |
| 27.62 | 8.61 |
| 28.32 | 11.44 |
| 28.74 | 10.73 |
| 30.92 | 8.23 |
| 38.60 | 8.88 |

In some embodiments, the crystalline form (I-HS) has an XRPD pattern with at least the 8 characteristic peaks (2θ degrees±0.3), which comprises peaks having a relative intensity greater than or equal to about 15%, as listed in Table 6.

TABLE 6

XRPD peaks of crystalline form (I-HS)

| Position (°2θ) | Relative Intensity (%) |
|---|---|
| 10.76 | 29.85 |
| 18.50 | 48.07 |
| 19.22 | 22.92 |
| 20.26 | 30.80 |
| 20.74 | 100.00 |
| 21.56 | 23.78 |
| 23.16 | 32.52 |
| 24.10 | 33.89 |

In some embodiments, the crystalline form (I-HS) has an XRPD pattern with at least the 5 characteristic peaks (2θ degrees±0.3), which comprises peaks having a relative intensity greater than or equal to about 25%, as listed in Table 7.

TABLE 7

XRPD peaks of crystalline form (I-HS)

| Position (°2θ) | Relative Intensity (%) |
|---|---|
| 10.76 | 29.85 |
| 18.50 | 48.07 |
| 20.74 | 100.00 |

TABLE 7-continued

XRPD peaks of crystalline form (I-HS)

| Position (°2θ) | Relative Intensity (%) |
|---|---|
| 23.16 | 32.52 |
| 24.10 | 33.89 |

In some embodiments, the crystalline form (I-HS) has an XRPD pattern with at least the 4 characteristic peaks (2θ degrees±0.3), which comprises peaks having a relative intensity greater than or equal to about 30%, as listed in Table 8.

TABLE 8

XRPD peaks of crystalline form (I-HS)

| Position (°2θ) | Relative Intensity (%) |
|---|---|
| 18.50 | 48.07 |
| 20.74 | 100.00 |
| 23.16 | 32.52 |
| 24.10 | 33.89 |

In some embodiments, crystalline form (I-HS) is characterized by having XRPD diffraction peaks (2θ degrees) at about 18.5, 20.7, 23.2, and 24.1. In some embodiments, crystalline form (I-HS) is characterized by having XRPD diffraction peaks (2θ degrees) at about 10.8, 18.5, 20.7, 23.2, and 24.1. In some embodiments, crystalline form (I-HS) is characterized by having XRPD diffraction peaks (2θ degrees) at about 10.8, 18.5, 19.2, 20.3, 20.7, 21.6, 23.2, and 24.1. In some embodiments, crystalline form (I-HS) is characterized by having XRPD diffraction peaks (2θ degrees) at about 10.8, 15.4, 16.5, 18.5, 19.2, 19.9, 20.3, 20.7, 21.6, 22.2, 23.2, 24.1, 24.5, 25.7, 26.5, 27.6, 28.3, 28.7, 30.9, and 38.6.

In some embodiments, given the XRPD patterns provided in FIGS. 1 and 8, crystalline form (I-HS) is characterized by having XRPD peaks (2θ degrees) as shown in Table 9.

TABLE 9

XRPD peaks of crystalline form (I-HS)

| FIG. 1 | FIG. 29 | Difference | Average |
|---|---|---|---|
| 10.76 | 10.63 | 0.13 | 10.70 |
| 15.38 | 15.25 | 0.13 | 15.32 |
| 16.52 | 16.39 | 0.13 | 16.46 |
| 18.50 | 18.37 | 0.13 | 18.44 |
| 19.22 | 19.08 | 0.14 | 19.15 |
| 19.92 | 19.79 | 0.13 | 19.86 |
| 20.26 | 20.15 | 0.11 | 20.21 |
| 20.74 | 20.61 | 0.13 | 20.68 |
| 21.56 | 21.47 | 0.09 | 21.52 |
| 22.16 | 22.01 | 0.15 | 22.09 |
| 23.16 | 23.04 | 0.12 | 23.10 |
| 24.10 | 23.97 | 0.13 | 24.04 |
| 24.50 | 24.35 | 0.15 | 24.43 |
| 25.72 | 25.58 | 0.14 | 25.65 |
| 26.50 | 26.48 | 0.02 | 26.49 |
| 27.62 | 27.50 | 0.12 | 27.56 |
| 28.32 | 28.17 | 0.15 | 28.25 |
| 28.74 | 28.58 | 0.16 | 28.66 |
| 30.92 | 30.77 | 0.15 | 30.85 |
| 38.60 | 38.47 | 0.13 | 38.54 |

In some embodiments, crystalline form (I-HS) is characterized by having XRPD diffraction peaks (2θ degrees) at 18.4±0.2, 20.7±0.2, 23.1±0.2, and 24.0±0.2. In some embodiments, crystalline form (I-HS) is characterized by having XRPD diffraction peaks (2θ degrees) at 10.7±0.2, 18.4±0.2, 20.7±0.2, 23.1±0.2, and 24.0±0.2. In some embodiments, crystalline form (I-HS) is characterized by having XRPD diffraction peaks (2θ degrees) at 10.7±0.2, 18.4±0.2, 19.2±0.2, 20.2±0.2, 20.7±0.2, 21.5±0.2, 23.1±0.2, and 24.0±0.2. In some embodiments, crystalline form (I-HS) is characterized by having XRPD diffraction peaks (2θ degrees) at 10.7±0.2, 15.3±0.2, 16.5±0.2, 18.4±0.2, 19.2±0.2, 19.9±0.2, 20.2±0.2, 20.7±0.2, 21.5±0.2, 22.1±0.2, 23.1±0.2, 24.0±0.2. 24.4±0.2, 25.6±0.2, 26.5±0.2, 27.6±0.2, 28.2±0.2, 28.7±0.2, 30.8±0.2, and 38.5±0.2.

It will be understood that the 2-theta values of the X-ray powder diffraction patterns for crystalline form (I-HS) may vary slightly from one instrument to another and also depending on variations in sample preparation and batch to batch variation, and so the values quoted are not to be construed as absolute. It will also be understood that the relative intensities of peaks may vary depending on orientation effects so that the intensities shown in the XRPD trace included herein are illustrative and not intended to be used for absolute comparison. Accordingly, it is to be understood that the phrase "substantially the same XRPD pattern as shown in FIG. 1 or FIG. 8" means that for comparison purposes, at least 90% of the peaks shown in FIG. 1 or FIG. 8 are present. It is to be understood that the relative peak positions may vary ±0.3 degrees from the peak positions shown in FIG. 1 or FIG. 8. It is to be further understood that for comparison purposes some variability in peak intensities from those shown in FIG. 1 and FIG. 8 is allowed.

Figure 2:
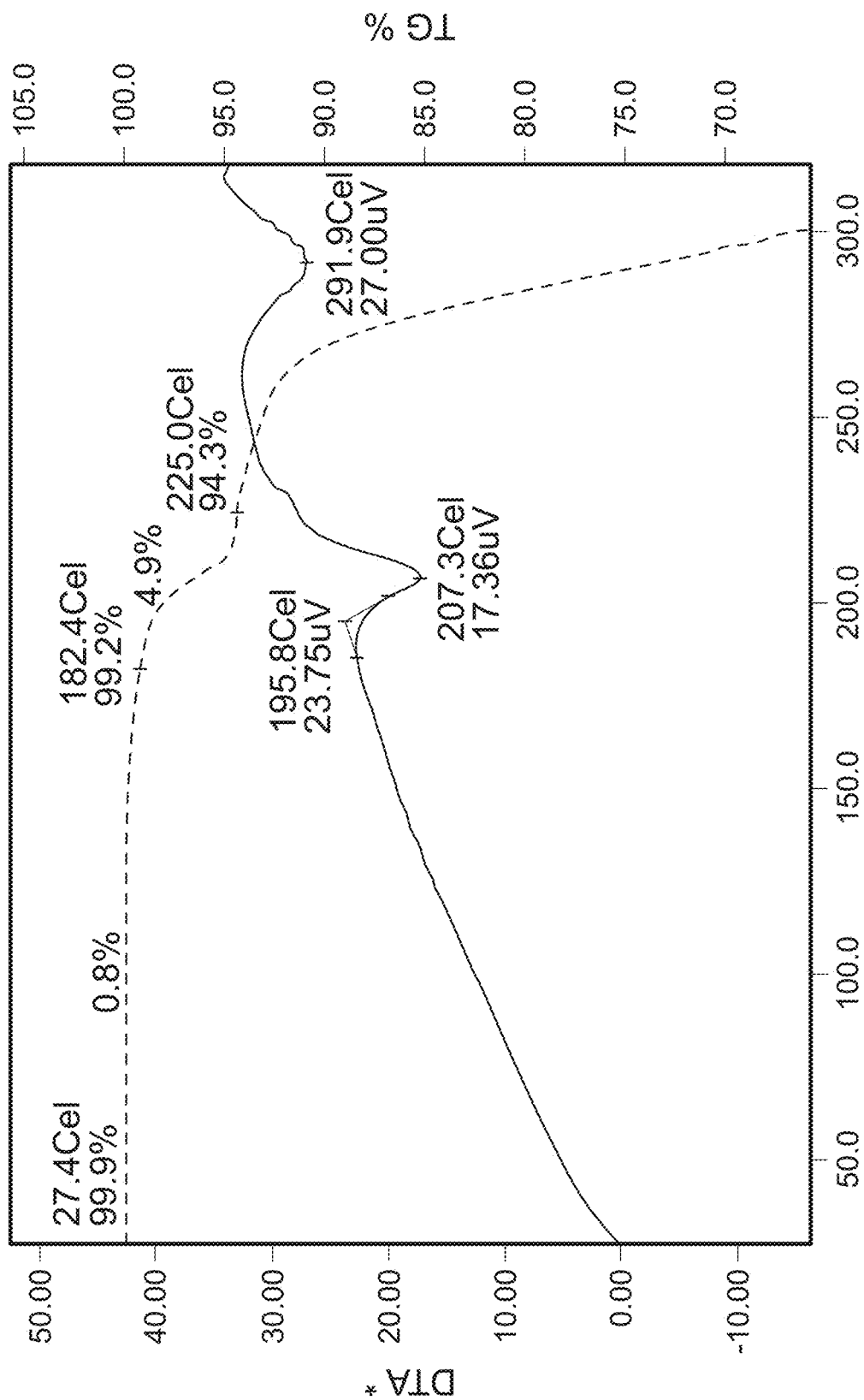
FIG. 2 illustrates a simultaneous thermogravimetric/differential thermal analyzer (TG/DTA) profile of crystalline form (I-HS) prepared according to Example 2, according to one embodiment.

FIG. 2 illustrates a simultaneous thermogravimetric/differential thermal analyzer (TG/DTA) profile of crystalline form (I-HS), according to one embodiment. For the analysis about 5 mg of crystalline form (I-HS) was weighed into an open aluminum pan and loaded into a simultaneous thermogravimetric/differential thermal analyzer (TG/DTA) and held at room temperature. The sample was then heated at a rate of 10° Celsius/min from 25° Celsius to 3000 Celsius during which time the change in sample weight was recorded along with any differential thermal events. Nitrogen was used as the purge gas at a flow rate of 100 cm$^3$/min. The TG/DAT profile of crystalline form (I-HS) shows an initial weight loss of 0.8% between 27.4° Celsius to 182.40 Celsius, which is followed by 4.9% weight loss in the TG curve between 182.4° Celsius to 225.00 Celsius, also seen as an endotherm in the DTA curve. These weight losses could be decomposition of the material.

Figure 3:
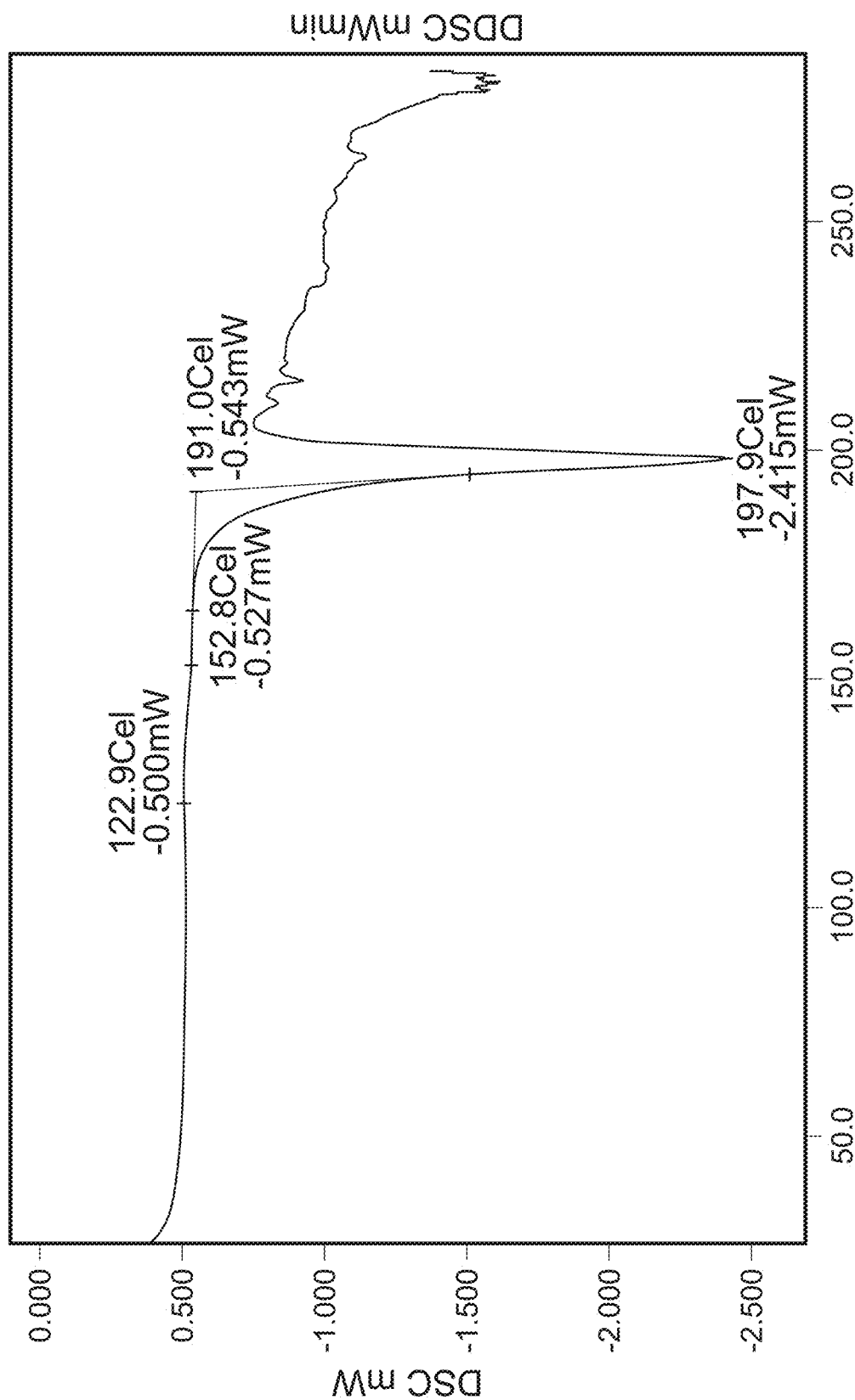
FIG. 3 illustrates a differential scanning calorimetry (DSC) profile of crystalline form (I-HS) prepared according to Example 2, according to one embodiment.

FIG. 3 illustrates a differential scanning calorimetry (DSC) profile of crystalline form (I-HS), according to one embodiment. DSC analysis of the sample was performed using a Seiko DSC6200 differential scanning calorimeter (equipped with a cooler). About 5 mg of crystalline form (I-HS) was weighed into an aluminum DSC pan and sealed non-hermetically with a pierced aluminum lid. The sample pan was then loaded into a Seiko DSC6200 (equipped with a cooler), cooled, and held at 250 Celsius. Once a stable heat-flow response was obtained, the sample and reference were heated to 2700 Celsius at a scan rate of 10° Celsius/min while monitoring the resulting heat flow response. In some embodiments, crystalline form (I-HS) has a DSC thermogram substantially as shown in FIG. 3. As used herein, "substantially as shown in FIG. 3" means that the temperatures of the endothermic event shown in FIG. 3 can vary by about +5° C.

As shown in FIG. 3, the DSC thermogram of the crystalline form (I-HS) indicates a small endothermic change in the baseline between 122.9° Celsius to 152.80 Celsius, followed by a sharp endotherm that corresponds to the melting of the crystalline form (I-HS) at an onset temperature of melting of 190.8° Celsius, a peak temperature of melting of 197.9° Celsius and a heat of melting of 2.415 mW. The transition following the melting endotherm may be caused by the decomposition of the melted crystalline form (I-HS).

Figure 4A:
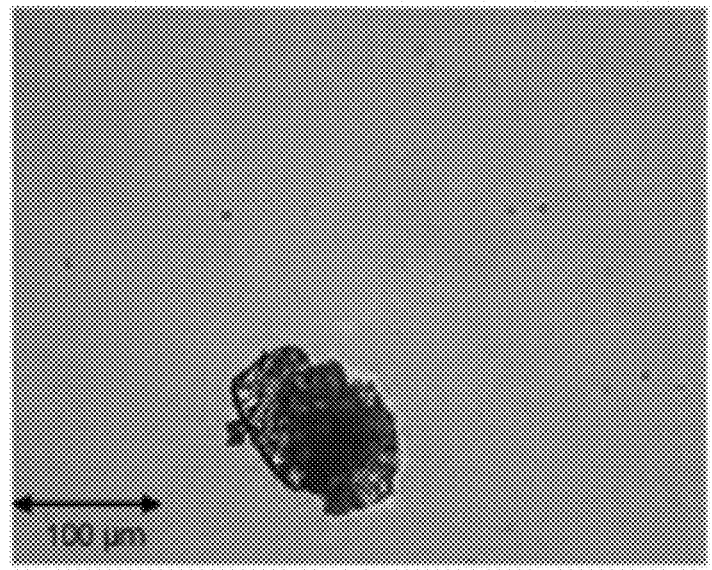
FIGS. 4A and 4B illustrate polarized light microscopy (PLM) images of crystalline form (I-HS) prepared according to Example 2 under (A) unpolarized and (B) polarized light, according to some embodiments.
Figure 4B:
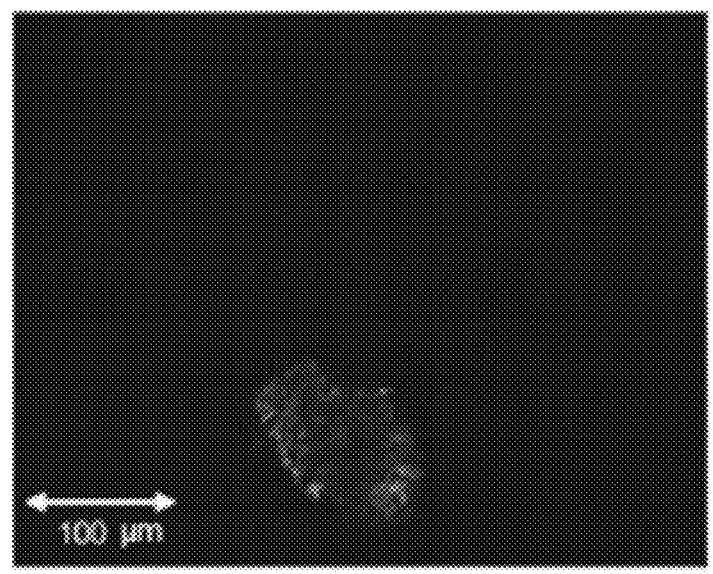

FIGS. 4A and 4B illustrate polarized light microscopy (PLM) images of crystalline form (I-HS) under (A) unpolarized and (B) unpolarized light, according to some embodiments. The presence of crystallinity (birefringence) was determined using an Olympus BX50 polarizing microscope, equipped with a Motic camera and image capture software (Motic Images Plus 2.0). All images were recorded using the 20× objective. The crystalline form (I-HS) exhibits birefringence when examined under polarized light without exhibiting a definite morphology or agglomerates.

Figure 5:
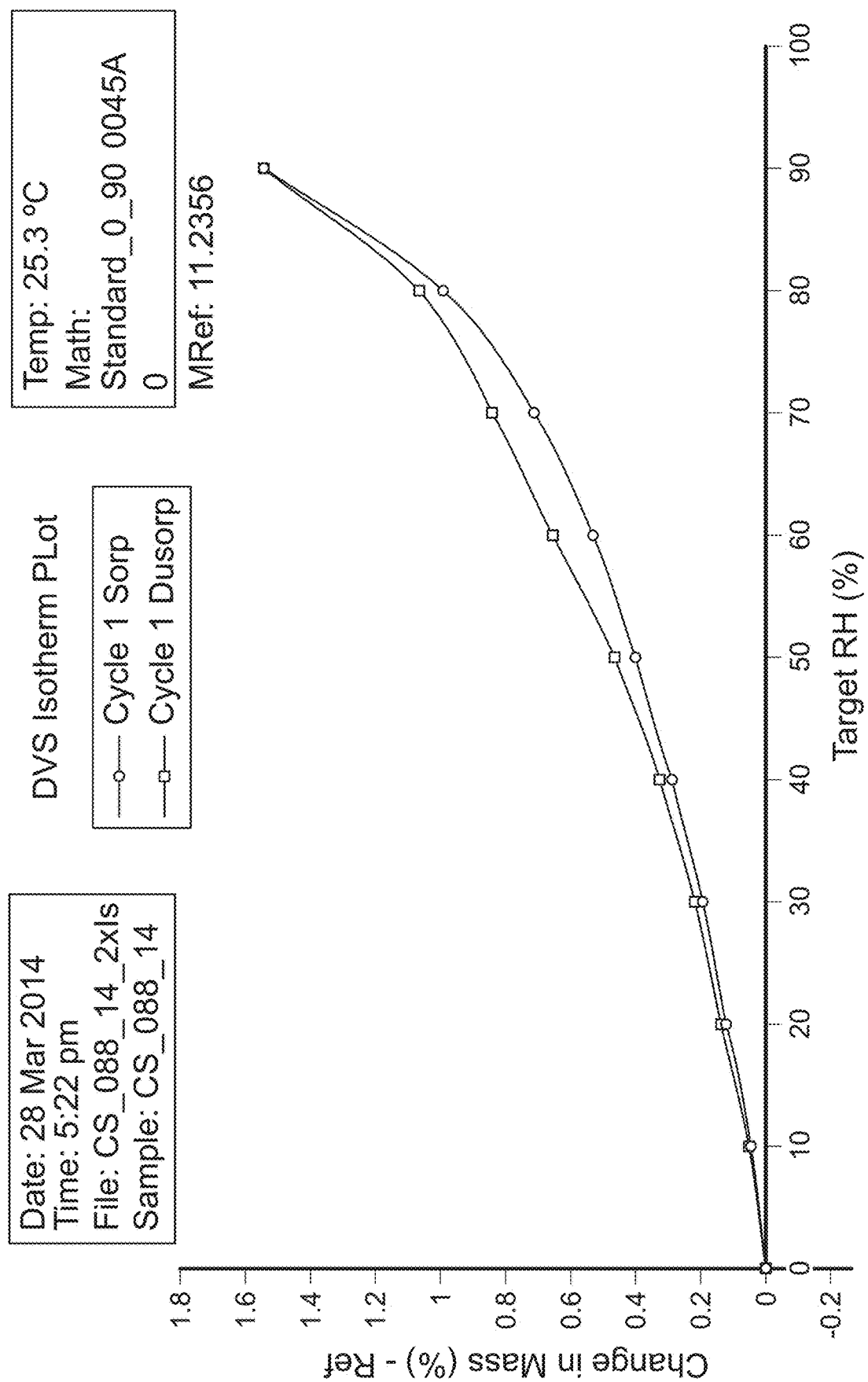
FIG. 5 illustrates a dynamic vapor sorption (DVS) isotherm profile of crystalline form (I-HS) prepared according to Example 2, according to one embodiment.

FIG. 5 illustrates a dynamic vapor sorption (DVS) isotherm profile of crystalline form (I-HS), according to one embodiment. For the DVS measurement a sample of crystalline form (I-HS) was cycled through changing humidity conditions to determine its hygroscopicity. The sample was analyzed using a Surface Measurement System DVS-1 Dynamic Vapor Sorption System. About 10 mg of crystalline form (I-HS) was placed into a mesh vapor sorption balance pan and loaded into a dynamic vapor sorption balance as part of the Surface Measurement System. Data was collected in 1 minute intervals. Nitrogen was used as the carrier gas. The sampled crystalline form (I-HS) was subjected to a ramping profile from 20-90% relative humidity (RH) at 10% increments, maintaining the sample at each step until a stable weight had been achieved (99.5% step completion). After completion of the sorption cycle, the sample was dried using the same procedure, but all the way down to 0% RH and finally taken back to the starting point of 20% RH. The weight change during the sorption/desorption cycles were plotted, allowing for the hygroscopic nature of the sample to be determined.

As shown in FIG. 5, crystalline form (I-HS) appears to be non-hygroscopic. A small increase in mass of about 1.7% was observed between 0% and 90% RH during the sorption cycle. In addition, a very small hysteresis was observed between sorption and desorption cycles. The XRPD pattern of crystalline form (I-HS) post DVS analysis (not shown) being similar to its pre-DVS XRPD pattern shown in FIG. 1 or FIG. 29 indicates that no change in the crystalline form (I-HS) occurred during DVS.

Figure 6:
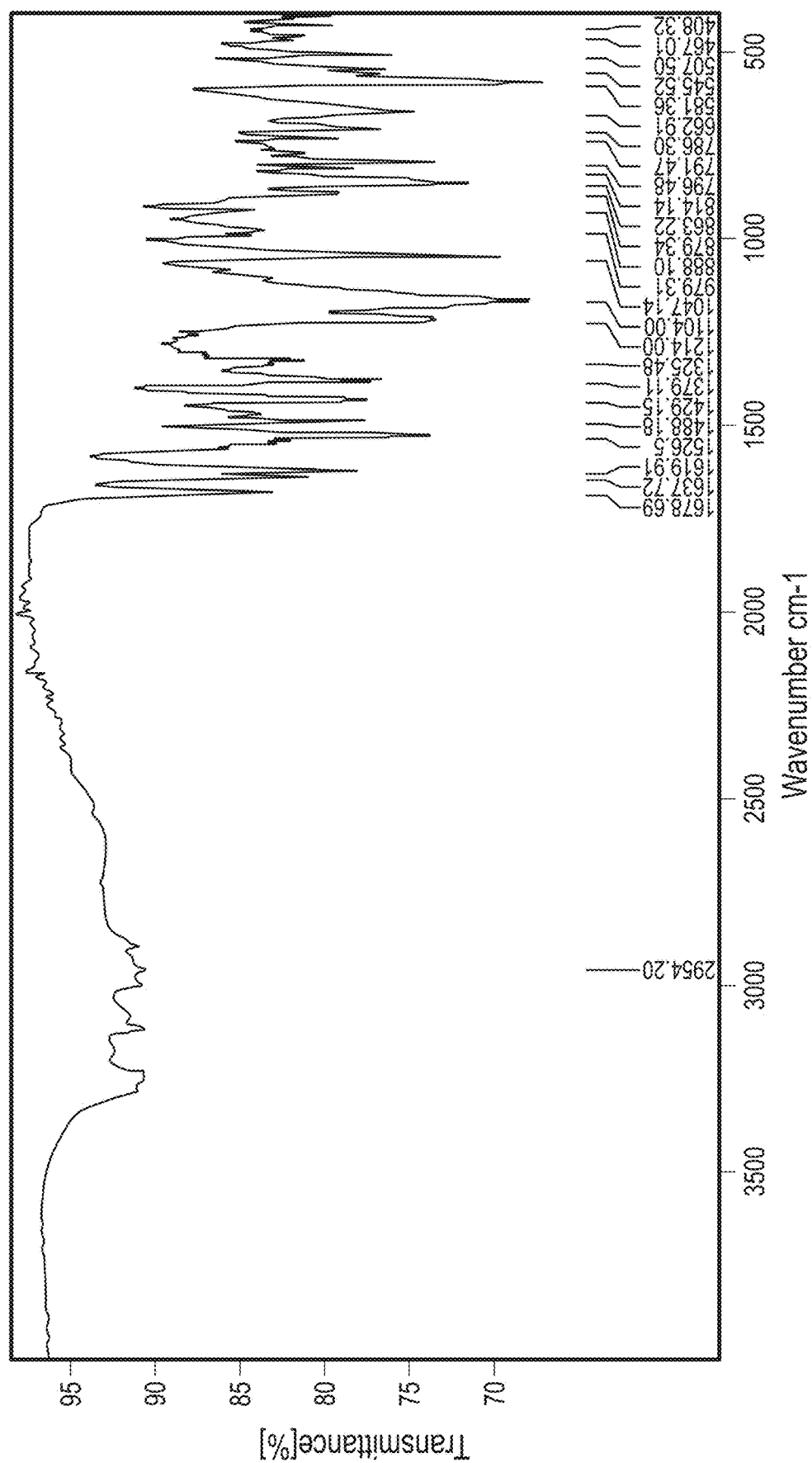
FIG. 6 illustrates an infrared (IR) spectroscopy profile of crystalline form (I-HS) prepared according to Example 2, according to one embodiment.

FIG. 6 illustrates an infrared (IR) spectroscopy profile of crystalline form (I-HS) for the compound of Formula I, according to one embodiment. IR spectroscopy was carried out on a Bruker ALPHA P spectrometer. Sufficient material of crystalline form (I-HS) was placed onto the center of the plate of the spectrometer with a transmittance spectrum being obtained using a resolution of 4 cm$^{-1}$, a background scan time of 16 scans, a sample scan time of 16 scans, and collecting data from 4000 cm$^{-1}$ to 400 cm$^{-1}$. The observed IR spectrum of crystalline form (I-HS) is shown in FIG. 6.

The crystalline form (I-HS) has a number of properties that make it surprisingly superior to the amorphous form of (S)—N-(5-((R)-2-(2,5-difluorophenyl)-pyrrolidin-1-yl)-pyrazolo[1,5-a]pyrimidin-3-yl)-3-hydroxypyrrolidine-1-carboxamide hydrogen sulfate (AM(HS)). For example, the crystalline form (I-HS) has properties which contribute to its manufacturability and production of a commercial product. As shown in Example 8, the crystalline form (I-HS) has better flow properties as compared to the amorphous API (AM(HS)) as evidenced by the Carr's and Hausner Index. For example, the crystalline form (I-HS) exhibits a Carr Index value of greater than 20%. In some embodiments, the crystalline form (I-HS) exhibits a Hausner ratio of less than 1.35 (e.g., a value of between about 1.26 to about 1.34). The differences in flow properties can make the development of a solid oral dosage form more difficult for the amorphous API vs. the crystalline API.

The crystalline form (I-HS) also evidenced better stability in an accelerated stability study conducted in an LDPE bag at 40° C./75% RH for five weeks. While neither the AM(HS) or crystalline form (I-HS) exhibited a significant changes in chemical impurity levels over the course of the study, the study did reveal that the crystalline form (I-HS) has stable physicochemical properties. The amorphous API, on the other hand, converted into a crystalline form substantially similar to the crystalline form (I-HS) by XRPD, DSC, TGA, KF and polarized light microscopy. Additionally, the amorphous API changed to an agglomerated powder with reduced flow properties over the course of the stability testing. Such changes in the physical properties of the compound, including a change from an amorphous power to a crystalline material and/or an agglomerated powder with reduced flow, on storage would make it nearly impossible to manufacture a solid oral dosage form for patient use based on the amorphous compound. The properties observed for the crystalline form (I-HS), however, are consistent with that desired for a commercial product, including having both a stable physical and chemical structure.

The crystalline form (I-HS), as noted previously, is non-hygroscopic. As used herein, "non-hygroscopic" refers to a compound exhibiting less than a 2% weight gain at 25° C. and 80% RH after 24 to 48 hours (see, e.g., Example 10). The AM(HS) compound, however, was found to deliquesce upon exposure to humidity. Given this tendency, use of the AM(HS) compound would require significant handling precautions during storage and manufacture to prevent this change in form from occurring whereas the crystalline form (I-HS) requires no such precautions during manufacture of the API. This stability to humidity would also be expected to carry over to any solid oral dosage product prepared using the crystalline form (I-HS).

A crystalline form (e.g., I-HS) can provide an improved impurity profile versus the amorphous API. The ability to control an impurity profile can be important for patient safety, developing a repeatable manufacturing process, and meeting requirements by regulatory agencies prior to use in humans. Additional properties and characteristics of the polymorph can be found in U.S. application Ser. No. 14/943,014, which is hereby incorporated by reference in its entirety.

The liquid formulations provided herein, including (S)—N-(5-((R)-2-(2,5-difluorophenyl)-pyrrolidin-1-yl)-pyrazolo[1,5-a]pyrimidin-3-yl)-3-hydroxypyrrolidine-1-carboxamide (Formula I), exhibit Trk family protein tyrosine kinase inhibition, and can be used in the treatment of pain, inflammation, cancer, and certain infectious diseases.

Some embodiments include the use of a liquid formulation as provided herein for the treatment of disorders and diseases which can be treated by inhibiting TrkA, TrkB and/or TrkC kinases, such as a TrkA, TrkB and/or TrkC mediated condition, such as one or more conditions described herein, including a Trk-associated cancer. In some embodiments, the liquid formulations can be useful in the treatment of pain, including chronic and acute pain. In some embodiments, the liquid formulations can be useful in the treatment of multiple types of pain including inflammatory pain, neuropathic pain, surgical pain, and pain associated with cancer, surgery and bone fracture. In addition, the liquid formulations can be useful for treating inflammation, active and chronic neurodegenerative diseases and certain infectious diseases.

The ability of a compound of Formula (I), a pharmaceutically acceptable salt form thereof, or the crystalline form (I-HS) to act as TrkA, TrkB and/or TrkC inhibitors may be demonstrated by the assays described in Examples A and B as disclosed in U.S. Pat. No. 8,513,263, issued on Aug. 20, 2013, which is incorporated herein by reference.

In some embodiments, provided herein is a method for treating a patient diagnosed with a TRK-associated cancer, comprising administering to the patient a therapeutically effective amount of a liquid formulation provided herein. Trk family of neurotrophin receptors, TrkA, TrkB, and TrkC (encoded by NTRK1, NTRK2, and NTRK3 genes, respectively) and their neurotrophin ligands regulate growth, differentiation and survival of neurons. Dysregulation in a NTRK gene, a Trk protein, or expression or activity, or level of the same, such as translocations involving the NTRK kinase domain, mutations involving the TRK ligand-binding site, amplifications of a NTRK gene, Trk mRNA splice variants, and Trk autocrine/paracrine signaling are described in a diverse number of tumor types and may contribute to tumorigenesis. Recently NTRK1 fusions were described in a subset of adenocarcinoma lung cancer patients[2]. Translocations in NTRK1, NTRK2, and NTRK3 that lead to the production of constitutively-active TrkA, TrkB, and TrkC fusion proteins are oncogenic and prevalent in a wide array of tumor types, including lung adenocarcinoma, thyroid, head and neck cancer, glioblastoma, and others.

In some embodiments, the dysregulation in a NTRK gene, a Trk protein, or expression or activity, or level of the same, includes overexpression of wild-type TrkA, TrkB, or TrkC (e.g., leading to autocrine activation). In some embodiments, the dysregulation in a NTRK gene, a Trk protein, or expression or activity, or level of the same, includes overexpression, activation, amplification or mutation in a chromosomal segment comprising the NTRK1, NTRK2, or NTKR3 gene or a portion thereof. In some embodiments, the dysregulation of a NTRK gene, a Trk protein, or expression or activity, or level of the same, includes one or more chromosome translocations or inversions resulting in NTRK1, NTRK2, or NTRK3 gene fusions, respectively. In some embodiments, the dysregulation of a NTRK gene, a Trk protein, or expression or activity, or level of the same, is a result of genetic translocations in which the expressed protein is a fusion protein containing residues from a non-TrkA partner protein and TrkA, a non-TrkB partner protein and TrkB, or a non-TrkC partner protein and TrkC proteins, and include a minimum of a functional TrkA, TrkB, or TrkC kinase domain, respectively.

In some embodiments, a TrkA fusion protein is one of the TrkA fusion proteins shown in Table 10, where:

TABLE 10

Exemplary TrkA Fusion Proteins and Cancers

| Fusion Protein | Non-TrkA Fusion Partner | Non-limiting Exemplary Trk- and Synonyms of Associated Cancer(s) |
|---|---|---|
| TP53-TrkA[1,11] | Tumor Protein P53 | Spitzoid Melanoma, Spitz tumors |
| LMNA-TrkA[1,12] | Lamin A/C | Spitzoid Melanoma, Spitz tumors, Undifferentiated Sarcoma, Adult Soft Tissue Sarcoma (e.g., Soft Tissue Sarcoma Metastatic to Lung), Soft Tissue Fibrosarcoma, Spindle Cell Sarcoma[G], Congenital Infantile Fibrosarcoma[H], Pediatric haemangiopericytoma-like sarcoma[I], Colorectal Cancer[K] |
| CD74-TrkA[2] | MHC class II invariant chain | Non-Small Cell Lung Cancer (NSCLC) Lung adenocarcimona |
| TFG-TrkA (TRK-T3)[3] | TRK-Fused Gene | Papillary Thyroid Carcinoma (PTC), Soft Tissue Solitary Fibrous Tumor |
| TPM3-TrkA[3] | Tropomyosin 3 | Lung Cancer, Papillary Thyroid Carcinoma (PTC), Acute Myeloid Leukemia (AML), Sarcoma, Pediatric Gliomas, Colorectal Cancer (CRC), Soft Tissue Schwannoma, Spitzoid melanocytic tumors[J] |
| NFASC-TrkA[4] | Neurofascin | Gliobastoma multiforme (GBM); Glioblastoma |
| BCAN-TrkA[4] | Brevican | Glioblastoma multiforme (GBM) |
| MPRIP-TrkA[5,E] | Myosin Phosphatase Rho Interacting Protein or Rho Interacting Protein 3 | Non-small cell lung cancer (NSCLC), Lung adenocarcinoma |
| TPR-TrkA (TRK-T1 or TRK-T2)[3] | Translocated Promoter Region, Nuclear Basket Protein | Papillary Thyroid Carcinoma (PTC), Colorectal Cancer (CRC)[A], Non-small cell lung cancer (NSCLC) |
| RFWD2-TrkA[6] | Ring Finger and WD Repeat Domain 2 | Large Cell Neuroendrocine Cancer (LCNEC); NSCLC |
| IRF2BP2-TrkA[7] | Interferon Regulatory Factor 2 Binding Protein 2 | Thyroid Cancer; Thyroid Gland Carcinoma |
| SQSTM1-TrkA[7] | Sequestosome 1 | Thyroid Cancer (e.g., Papillary Thyroid Cancer), Thyroid Gland Carcinoma, Soft TissueFibrosarcoma, Non-small-cell lung cancer[L] |
| SSBP2-TrkA[7] | Single-Stranded DNA Binding Protein 2 | Thyroid Cancer (e.g., Papillary Thyroid Cancer); Thyroid Gland Carcinoma |
| RABGAP1L-TrkA[8] | RAB GTPase Activating Protein 1-Like | Intrahepatic Cholangicarcinoma (ICC) |
| C18ORF8-TrkA[9] | Chromosome 18 Open Reading Frame 8 | Non-Small Cell Lung Cancer (NSCLC) |
| RNF213-TrkA[9] | Ring Finger Protein 213 | Non-Small Cell Lung Cancer (NSCLC) |
| TBC1D22A-TrkA[9] | TBC1 Domain Family, Member 22A | Non-Small Cell Lung Cancer (NSCLC) |
| C20ORF112-TrkA[9] | Chromosome 20 Open Reading Frame 112 | Non-Small Cell Lung Cancer (NSCLC) |
| DNER-TrkA[9] | Delta/Notch-Like EGF Repeat Containing | Non-Small Cell Lung Cancer (NSCLC) |
| ARHGEF2-TrkA[13] | Rho Guanine Nucleotide Exchange Factor 2 | Glioblastoma |
| CHTOP-TrkA[13] | Chromatin Target of PRMT1 | Glioblastoma |
| PPL-TrkA[13] | Periplakin | Thyroid Carcinoma |
| PLEKHA6-TrkA | Pleckstrin Homology Domain-Containing Family A Member 6 | |
| PEAR1-TrkA | Platelet Endothelial Aggregation Receptor 1 | |
| MRPL24-TrkA | 39S Ribosomal Protein L24, Mitochondrial | |
| MDM4-TrkA | Human Homolg of Mouse Double Minute 4 | |
| LRRC71-TrkA | Leucine Rich Repeat Containing 71 | |
| GRIPAP1-TrkA | GRIP1 Associated Protein 1 | |
| EPS15-TrkA | Epidermal Growth Factor Receptor Substrate 15 | |

TABLE 10-continued

Exemplary TrkA Fusion Proteins and Cancers

| Fusion Protein | Non-TrkA Fusion Partner | Non-limiting Exemplary Trk- and Synonyms of Associated Cancer(s) |
|---|---|---|
| DYNC2H1-TrkA[B] | Dynein, Cytoplasmic 2, Heavy Chain 1 | Sarcoma |
| CEL-TrkA | Carboxyl Ester Lipase | Pancreatic adenocarcinoma sample[D] |
| EPHB2-TrkA[B] | EPH Receptor B2 | Lower Grade Glioma |
| TGF-TrkA[C] | Transforming Growth Factor | Papillary Thyroid Cancer |
| NELL1-TrkA[F] | Cytoplasmic Protein That Contains Epidermal Growth Factor (Egf)-Like Repeats | Non-Small Cell Lung Cancer (NSCLC) |
| EPL4-TrkA[F] | EPH-Related Receptor Tyrosine Kinase Ligand 4/ Ephrin-A4 Protein | Non-Small Cell Lung Cancer (NSCLC) |
| CTNND2-TrkA[F] | Catenin (Cadherin-Associated Protein), Delta 2 | Non-Small Cell Lung Cancer (NSCLC) |
| TCEANC2-TrkA[F] | Transcription Elongation Factor A (SII) N-Terminal And Central Domain | Non-Small Cell Lung Cancer (NSCLC) |

[A] Créancier et al., Cancer Lett. 365(1): 107-111, 2015.J
[B] U.S. patent application Pub. No. 2015/0315657.
[C] U.S. patent application Pub. No. 2015/0283132.
[D] Egren et al., Cancer Res. 75(15 Supplement): 4793, 2015.
[E] U.S. patent application Pub. No. 2015/0073036.
[F] P.C.T. Patent Application Publication No. WO2015184443A1.
[G] Haller et al., The Journal of pathology 238.5 (2016): 700-710.
[H] Wong et al., J Natl Cancer Inst 2016; 108: djv307.
[I] Haller et al., J. Pathol. 238(5): 700-10.
[J] Wu et al., Mod Pathol. 2016 April; 29(4): 359-69.
[K] Konicek et al., Cancer research, Vol. 76, No. 14, Supp. Supplement. Abstract Number: 2647; 107th Annual Meeting of the American Association for Cancer Research, AACR 2016. New Orleans, LA; 16-20 Apr. 2016.
[L] Drilon et al., Cancer research, Vol. 76, No. 14, Supp. Supplement. Abstract Number: CT007; 107th Annual Meeting of the American Association for Cancer Research, AACR 2016. New Orleans, LA; 16-20 Apr. 2016.

In some embodiments, the dysregulation of a NTRK gene, a Trk protein, or expression or activity, or level of the same, includes one or more deletions, insertions, or point mutation(s) in a TrkA protein. In some embodiments, the dysregulation of a NTRK gene, a Trk protein, or expression or activity, or level of the same, includes a deletion of one or more residues from the TrkA protein, resulting in constitutive activity of the TrkA kinase domain. In some embodiments, the deletion includes a deletion of amino acids 303-377 in TrkA isoform 2.

In some embodiments, the dysregulation of a NTRK gene, a Trk protein, or expression or activity, or level of the same, includes at least one point mutation in a NTRK1 gene that results in the production of a TrkA protein that has one or more amino acid substitutions as compared to the wildtype TrkA protein (see, for example, the point mutations listed in Table 11). An exemplary wildtype TrkA polypeptide is SEQ ID NO: 1, an exemplary wildtype TrkB polypeptide is SEQ ID NO: 2, and an exemplary TrkC polypeptide is SEQ ID NO: 3.

TABLE 11

Activating TrkA Point Mutations[A]

| Point Mutation | Rationale | Exemplary Isoform in which Mutation is Present (if known) |
|---|---|---|
| R33W[B] | | NP_001007793.1[F] |
| A336E | Near NGF Binding Site | Reference TrkA sequence |
| A337T | Near NGF Binding Site | Reference TrkA sequence |
| R324Q or R324W | Near NGF Binding Site | Unknown |
| V420M | Close to Membrane | Reference TrkA sequence |
| R444Q or R444W | Close to Membrane | Reference TrkA sequence |
| G517R or G517V | P-Loop | Reference TrkA sequence |
| K538A | Activating | Reference TrkA sequence |
| V573M[E] | | Reference TrkA sequence |
| F589L[E] | | Reference TrkA sequence |
| G595R or G667C[D] | Catalytic Domain | Reference TrkA sequence |
| F598L[E] | | Unknown |
| R649W or R649L | Arginine may stabilize auto-inhibited conformation. | Reference TrkA sequence |
| R682S | Activation Loop | Reference TrkA sequence |
| V683G | Activation Loop | Reference TrkA sequence |
| R702C | Exposed, may form face-to-face disulfide linked dimer | Reference TrkA sequence |

TABLE 11-continued

Activating TrkA Point Mutations[A]

| Point Mutation | Rationale | Exemplary Isoform in which Mutation is Present (if known) |
| --- | --- | --- |
| Q627X[C], Q597X[C], Q633X[C] | | NP_001012331.1[G], NP_001007793.1[F], and Reference TrkA sequence, respectively |

[A]Reference TrkA sequence is UniProtKB/Swiss-Prot: P04629.4, and can be found at URL: www.ncbi.nlm.nih.gov/protein/94730402?report=genbank&log$=protalign&blast_rank=0&RID=0 (SEQ ID NO. 1)
[B]Zhang et al., Blood 124(21): 1682, 2014. Mutation found in T-cell prolymphocytic leukemia.
[C]Park et al., Proc. Natl. Acad. Sci. U.S.A. 112(40): 12492-12497, 2015. Mutation found in colorectal cancer.
[D]Russo et al., Cancer Discov. January; 6(1): 36-44, 2016.
[E]PCT Application No. WO2016196141A1.
[F]www.ncbi.nlm.nih.gov/protein/56118210?report=genbank&log$=protalign&blast_rank=3&RID=0
[G]www.ncbi.nlm.nih.gov/protein/59889558

In some embodiments, the dysregulation of a NTRK gene, a Trk protein, or expression or activity, or level of the same, includes a splice variation in a TrkA mRNA which results in an expressed protein that is an alternatively spliced variant of TrkA having at least one residue deleted (as compared to a wild-type TrkA protein) resulting in constitutive activity of the TrkA kinase domain. In some embodiments, an alternatively spliced form of TrkA with constitutive activity has deletions of exons 8, 9, and 11 resulting in an expressed protein missing residues 192-284 and 393-398 relative to TrkA Isoform 2, has a deletion of exon 10 in TrkA, or has a deletion in a NTRK1 gene that encodes a TrkA protein with a 75 amino acid deletion in the transmembrane domain (Reuther et al., Mol. Cell Biol. 20:8655-8666, 2000).

Cancers identified as having dysregulation of a NTRK gene, a Trk protein, or expression or activity, or level of the same, (see references cited herein and also the www.cancer.gov and www.nccn.org websites) include:

(A) Cancers wherein the dysregulation of a NTRK gene, a Trk protein, or expression or activity, or level of the same, includes one or more chromosome translocations or inversions resulting in TrkA fusion proteins, e.g., including:

| Cancer | Standard of Care |
| --- | --- |
| Non-Small Cell Lung Cancer[2] | radiotherapy (e.g., radioiodide therapy, external-beam radiation, or radium 223 therapy), chemotherapeutics as single agents (e.g., afatinib dimaleate, bevacizumab, carboplatin, cetuximab, cisplatin, crizotinib, erlotinib, gefitinib, gemcitabine, methotrexate, paclitaxel, or pemetrexed) or combinations (e.g., carboplatin-paclitaxel, gemcitabine-paclitaxel, or chemoradiation) |
| Papillary Thyroid Carcinoma[14] | Radiotherapies (e.g., radioiodide therapy or external-beam radiation) and chemotherapeutics (e.g., sorafenib, sunitinib, or pazopanib) |
| Glioblastoma Multiforme[15] | Chemotherapeutics (e.g., bevacizumab, everolimus, lomustine, or temozolomide) |
| Colorectal Carcinoma[16] | Chemotherapeutics as single agents (e.g., aflibercept, bevacizumab, capecitabine, cetuximab, fluorouracil, irinotecan, leucovorin, oxaliplatin, panitumumab, or regorafenib) or combinations (e.g., folfox, folfiri, capox, folfiri-bevacizumab, folfiri-cetuximab, or xelox) |
| Melanoma[12] | Chemotherapeutics (e.g., aldesleukin, dabrafenib, dacarbazine, interferon alfa-2b, ipilimumab, peginterferon alfa-2b, trametinib, or vemurafenib) |

(B) Cancers wherein the dysregulation of a NTRK gene, a Trk protein, or expression or activity, or level of the same, includes one or more deletions, insertions, or mutations in the TrkA protein, e.g., including:

| Cancer | Standard of care |
| --- | --- |
| Acute Myeloid leukemia[17,18] | Chemotherapeutics as single agents (e.g., arsenic trioxide, cyclophosphamide, cytarabine, daunorubicin, doxorubicin, or vincristine) or combinations (e.g., ADE) |
| Large Cell Neuroendocrine Carcinoma[19] | Radiotherapy (e.g., radioiodide therapy, external-beam radiation, or radium 223 therapy) and/or chemotherapeutics (e.g., cisplatin, carboplatin, or etoposide) |
| Neuroblastoma[20] | Chemotherapeutics (e.g., cyclophosphamide, doxorubicin, or vincristine) |

(C) Cancers wherein the dysregulation of a NTRK gene, a Trk protein, or expression or activity, or level of the same, includes overexpression of wildtype TrkA (autocrine activation), e.g., including:

| Cancer | Standard of care |
| --- | --- |
| Prostate Carcinoma[21,22] | Radiotherapy (e.g., radium 223 therapy) or chemotherapeutics (e.g. abiraterone, cabazitaxel, degarelix, denosumab, docetaxel, enzalutamide, leuprolide, prednisone, or sipuleucel-T) |
| Neuroblastoma[23] | Chemotherapeutics (e.g., cyclophosphamide, doxorubicin, or vincristine) |
| Pancreatic Carcinoma[24] | Chemotherapeutics as single agents (e.g., erlotinib, fluorouracil, gemcitabine, or mitomycin C) or combinations (e.g., gemcitabine-oxaliplatin) |
| Melanoma[25] | Chemotherapeutics (e.g., aldesleukin, dabrafenib, dacarbazine, interferon alfa-2b, ipilimumab, peginterferon alfa-2b, trametinib, or vemurafenib) |
| Head and Neck Squamous Cell Carcinoma[26] | Radiotherapy and/or chemotherapeutics (e.g., bleomycin, cetuximab, cisplatin, docetaxel, fluorouracil, or methotrexate) |
| Gastric Carcinoma[27] | Chemotherapeutics (e.g., docetaxel, doxorubicin, fluorouracil, mitomycin C, or trastuzumab) |

In some embodiments, the dysregulation of a NTRK gene, a Trk protein, or expression or activity, or level of the same, includes a translocation that results in the expression of a TrkB fusion protein, e.g., one of the TrkB fusion proteins shown in Table 12.

TABLE 12

Exemplary TrkB Fusion Proteins and Cancers

| Fusion Protein | Non-TrkB Fusion Partner | Non-limiting Exemplary Trk- and Synonyms of Associated Cancer(s) |
|---|---|---|
| NACC2-TrkB[10] | NACC Family Member 2, BEN and BTB (POZ) Domain Containing | Pilocytic Astrocytoma |
| QKI-TrkB[10] | QKI, KH Domain Containing, RNA Binding | Pilocytic Astrocytoma |
| AFAP1-TrkB[7] | Actin Filament Associated Protein 1 | Lower-grade Glioma, In vitro (murine Ba/F3 cells)[B], Pilocytic astrocytoma with anaplasia (PAA)[E] |
| PAN3-TrkB[7] | PAN3 Poly(A) Specific Ribonuclease Subunit | Head and Neck Squamous Cell Carcinoma |
| SQSTM1-TrkB[7] | Sequestosome 1 | Lower-Grade Glioma |
| TRIM24-TrkB[7] | Tripartite Motif Containing 24 | Lung adenocarcinoma |
| VCL-TrkB[11] | Vinculin | Pediatric gliomas |
| AGBL4-TrkB[11] | ATP/GTP Binding Protein-Like 4 | Pediatric gliomas |
| DAB2IP-TrkB | Disabled Homolog 2-Interacting Protein | |
| NTRK2-TERT[A] | Telomerase Reverse Transcriptase | Thyroid Cancer |
| TEL-TrkB[C] (ETV6) | ETS Variant 6 | In vitro (murine Ba/F3 cells) |
| QKI-TrkB[D] | Protein Quaking | Astrocytoma |

[A]PCT Patent Application Publication No. WO 2015/183836A1
[B]Drilon et al., *Ann Oncol.* 2016 May; 27(5): 920-6.
[C]Yuzugullu et al., *Cell Discov.* 2: 16030, 2016.
[D]Ni et al., *Neuro Oncol.* 2017 January; 19(1): 22-30.
[E]Lin et al., *Neuro-Oncol*, Vol. 18, Supp. Supplement 3, pp. iii58, Abstract Number: HG-48; 17th International Symposium on Pediatric Neuro-Oncology, ISPNO 2016. Liverpool, UK, 12 Jun. 2016-15 Jun. 2016.

In some embodiments, the dysregulation of a NTRK gene, a Trk protein, or expression or activity, or level of the same, includes at least one point mutation in a NTRK1 gene that results in the production of a TrkB protein that has one or more amino acid substitutions as compared to the wildtype TrkB protein (see, for example, the point mutations listed in Table 13.

TABLE 13

Activating TrkB Point Mutations[A]

| Point Mutation | Rationale | Exemplary Isoform in which Mutation is Present (if known) |
|---|---|---|
| A13T[C] | | Reference TrkB sequence |
| E142K[C] | | Reference TrkB sequence |
| R136H[C] | | Reference TrkB sequence |
| V619M[B] | | Unknown |
| F633L[B] | | NP_006171.2[D] (Corresponding to position 617 of Reference TrkB sequence) |
| G639R[B] | | NP_006171.2[D] (Corresponding to position 623 of Reference TrkB sequence) |
| G709C or G709A or G709S[B] | | NP_006171.2[D] (Corresponding to position 693 of Reference TrkB sequence) |

[A]Reference TrkB sequence is UniProtKB/Swiss-Prot: Q16620.1, and can be found at URL: www.ncbi.nlm.nih.gov/protein/2497560?report=genbank&log$=protalign&blast_rank=0&RID=0 (SEQ ID NO: 2)
[B]PCT Application No. WO2016196141A1.
[C]Bonanno et al., *Journal of Thoracic Oncology*, Vol. 11, No. 4, Supp. Suppl. 1, pp S67. Abstract Number: 28P; 6th European Lung Cancer Conference, ELCC 2016, Geneva, Switzerland.
[D]www.ncbi.nlm.nih.gov/protein/NP_006171.2

In some embodiments, the dysregulation of a NTRK gene, a Trk protein, or expression or activity, or level of the same, includes a translocation which results in the expression of a TrkC fusion protein, e.g., one of the TrkC fusion proteins shown in Table 14.

TABLE 14

Exemplary TrkC Fusion Proteins and Cancers

| Fusion Protein | Non-TrkB Fusion Partner | Non-limiting Exemplary Trk- and Synonyms of Associated Cancer(s) |
|---|---|---|
| ETV6-TrkC[11] (TEL; or chromosomal translocation t(12; 15) (p13; q25))[J] | ETS Variant 6 | Salivary Gland Cancer, Secretory Breast Carcinoma, Acute Myeloid Leukemia, Fibrosarcoma, Nephroma, Melanoma, Colorectal Cancer (CRC), Breast Cancer, Pediatric Gliomas, Thyroid Cancer (e.g., Papillary Thyroid Cancer), Infantile Fibrosarcoma, Soft Tissue Hemangioma, Gastrointestinal |

TABLE 14-continued

Exemplary TrkC Fusion Proteins and Cancers

| Fusion Protein | Non-TrkB Fusion Partner | Non-limiting Exemplary Trk- and Synonyms of Associated Cancer(s) |
|---|---|---|
| | | Stromal Tumor (GIST) (e.g., c-kit-negative GIST), Mammary Carcinoma (e.g., Mammary Analogue Secretory Carcinoma, Secretory Breast Carcinoma (SBSC))[K], Congenital Fibrosarcoma, Acute Myelogenous Leukemia, Polymorphous low-grade adenocarcinoma[D], ALK-negative inflammatory myofibroblastic tumors (IMT)[E], Infantile Fibrosarcoma (IFS)[F,M], Acinic cell carcinoma (AcCC)[G], Cellular mesoblastic nephroma[H], Promyelocytic leukemia[I], Burkitt Lymphoma[I], B-cell lymphoma[I], multiple myeloma[I], medulloblastoma[I], neuroblastoma[I], ovarian cancer[I], intestinal cancer[I], acute lymphblastic leukemia[K] |
| BTBD1-TrkC[11] | BTB (POZ) Domain Containing 1 | Pediatric Gliomas |
| LYN-TrkC[7] | V-Yes-1 Yamaguchi Sarcoma Viral Related Oncogene Homolog (also known as Lck/Yes-Related Novel Protein Tyrosine Kinase) | Head and Neck Squamous Cell Carcinoma |
| RBPMS-TrkC[7] | RNA Binding Protein with Multiple Splicing | Thyroid Cancer (e.g., Papillary Thyroid Cancer) |
| EML4-TrkC[A] | Echinoderm Microtubule-Associated Protein-Like 4 | Fibrosarcoma (e.g., Pediatric Fibrosarcoma[L]) |
| HOMER2-TrkC | Homer Protein Homolog 2 | Soft Tissue Sarcoma |
| TFG-TrkC | TRK-Fused Gene | Soft Tissue Solitary Fibrous Tumor |
| FAT1-TrkC | FAT Atypical Cadherin 1 | Cervical Squamous Cell Carcinoma ® |
| MYO5A-TrkC | Myosin VA | Spitz tumor[C] |
| MYH9-TrkC | Myosin Heavy Chain 9 | Spitz tumor[C] |

[A]Tannenbaum et al., *Cold Spring Harb. Mol. Case Stud.* 1: a000471, 2015.
[B]U.S. patent application Pub. No. 2015/0315657.
[C]Yeh et al., *J Pathol.* 240(3): 282-90, 2016
[D]Montalli et al., *J Oral Pathol Med.* doi: 10.1111/jop.12491, 2016
[E]Alassiri et al., *Am J Surg Pathol.*, Aug.; 40(8): 1051-61, 2016.
[F]Nagasubramanian et al., *Pediatr Blood Cancer.*, Aug.; 63(8): 1468-70, 2016.
[G]Chintakuntlawar et al., *Oral Surg Oral Med Oral Pathol Oral Radiol.* 2016 May; 121(5): 542-549.e1.
[H]U.S. Pat. No. US9511050B2.
[I]U.S. Pat. No. US9447135B2.
[J]Skalova et al., *Modern Pathology* 30, S27-S43, 2017.
[K]Hyrcza et al., Vol. 469, Supp. Supplement 1, pp. S17. Abstract Number: OFP-1997-7; 31st International Congress of the International Academy of Pathology and the 28th Congress of the European Society of Pathology, Cologne, Germany. 25-29 Sep. 2016.
[L]Sims et al., *Journal of Immunotherapy of Cancer*, Vol. 4, Supp. Supplement 1; Abstract Number: P280; 31st Annual Meeting and Associated Programs of the Society for Immunotherapy of Cancer, SITC 2016. National Harbor, MD; 9-13 Nov. 2016.
[K]Roberts et al., Blood, Vol. 128, No. 22. Abstract Number: 278, 58th Annual Meeting of the American Society of Hematology, ASH 2016. San Diego, CA, United States. 3 Dec. 2016-6 Dec. 2016.
[M]Pavlick et al., *Pediatr Blood Cancer*, doi: 10.1002/pbc.26433, 2017.

In some embodiments, the dysregulation of a NTRK gene, a Trk protein, or expression or activity, or level of the same, includes at least one point mutation in a NTRK1 gene that results in the production of a TrkC protein that has one or more amino acid substitutions as compared to the wildtype TrkC protein (see, for example, the point mutations listed in Table 15.

TABLE 15

Activating TrkC Point Mutations[A]

| Point Mutation | Rationale | Exemplary Isoform in which Mutation is Present (if known) |
|---|---|---|
| V603M[C] | | NP_001007157.1[D] |
| F617L[C] | | Reference TrkC sequence |

TABLE 15-continued

Activating TrkC Point Mutations[A]

| Point Mutation | Rationale | Exemplary Isoform in which Mutation is Present (if known) |
|---|---|---|
| G623R[B,C] | Steric Hinderance | Reference TrkC sequence |
| G696C or G696A or G696S[C] | | Reference TrkC sequence |

[A]Reference TrkC sequence is UniProtKB/Swiss-Prot: Q16288.2, and can be found at URL: www.ncbi.nlm.nih.gov/protein/134035335?report=genbank&log$=protalign&blast_rank=0&RID=0 (SEQ ID NO. 3)
[B]Drilon et al., Ann Oncol. 2016 May; 27(5): 920-6. doi: 10.1093/annonc/mdw042. Epub 2016 Feb. 15.
[C]PCT Application No. WO2016196141A1.
[D]www.ncbi.nlm.nih.gov/protein/NP_001007157

In some embodiments, a TRK-associated cancer has been identified as having one or more TRK inhibitor resistance mutations (that result in an increased resistance to a TRK inhibitor. Non-limiting examples of TRK inhibitor resistance mutations are listed in Tables 17-19.

TABLE 17

Exemplary TrkA Resistance Mutations

Amino acid position 517 (e.g., G517R)
Amino acid position 542 (e.g., A542V)
Amino acid position 568 (e.g., Q568x)
Amino acid position 573 (e.g., V573M)
Amino acid position 589 (e.g., F589L, F589C)
Amino acid position 595 (e.g., G595S, G595R[1])
Amino acid position 599 (e.g., D596V)
Amino acid position 600 (e.g., F600L)
Amino acid position 602 (e.g., R602x)
Amino acid position 646 (e.g., F646V)
Amino acid position 656 (e.g., C656Y, C656F)
Amino acid position 657 (e.g., L657V)
Amino acid position 667 (e.g., G667C[1], G667S)
Amino acid position 676 (e.g., Y676S)

[1]Russo et al., Acquired Resistance to the TRK Inhibitor Entrectinib in Colorectal Cancer, Cancer Discov. Jan; 6(1): 36-44, 2016.

TABLE 18

Exemplary TrkB Resistance Mutations

Amino acid position 545 (e.g., G545R)
Amino acid position 570 (e.g., A570V)
Amino acid position 596 (e.g., Q596E, Q596P)
Amino acid position 601 (e.g., V601G)
Amino acid position 617 (e.g., F617L, F617C, F617I)
Amino acid position 623 (e.g., G623S, G623R)
Amino acid position 624 (e.g., D624V)
Amino acid position 628 (e.g., F628x)
Amino acid position 630 (e.g., R630K)
Amino acid position 672 (e.g., F672x)
Amino acid position 682 (e.g., C682Y, C682F)
Amino acid position 683 (e.g., L683V)
Amino acid position 693 (e.g., G693S)
Amino acid position 702 (e.g., Y702x)

TABLE 19

Exemplary TrkC Resistance Mutations

Amino acid position 545 (e.g., G545R)
Amino acid position 570 (e.g., A570V)
Amino acid position 596 (e.g., Q596x)
Amino acid position 601 (e.g., V601)
Amino acid position 617 (e.g., F617x, F617L)
Amino acid position 623 (e.g., G623R[1])
Amino acid position 624 (e.g., D624V)
Amino acid position 628 (e.g., F628x)
Amino acid position 630 (e.g., R630x)
Amino acid position 675 (e.g., F675x)
Amino acid position 685 (e.g., C685Y, C684F)
Amino acid position 686 (e.g., L686V)
Amino acid position 696 (e.g., G696x, G696A)
Amino acid position 705 (e.g., Y705x)

[1]Drilon et al., What hides behind the MASC: clinical response and acquired resistance to entrectinib after ETV6-NTRK3 identification in a mammary analogue secretory carcinoma (MASC), Ann Oncol. 2016 May; 27(5): 920-6. doi: 10.1093/annonc/mdw042. Epub 2016 Feb. 15.

In some embodiments, provided herein is a method for treating a patient diagnosed with a Trk-associated cancer, comprising administering to the patient a therapeutically effective amount of a liquid formulation as provided herein. For example, the Trk-associated cancer can be selected from the group of: non-small cell lung cancer, papillary thyroid carcinoma, glioblastoma multiforme, acute myeloid leukemia, colorectal carcinoma, large cell neuroendocrine carcinoma, prostate cancer, neuroblastoma, pancreatic carcinoma, melanoma, head and neck squamous cell carcinoma, gastric carcinoma, Spitz cancer, papillary thyroid carcinoma, colon cancer, acute myeloid leukemia, gastrointestinal stromal tumor (GIST) (e.g., GIST testing wild type for KIT/PDGFR/BRAF/SDH), sarcoma, pediatric glioma, intrahepatic cholangicarcinoma, pilocytic astrocytoma, lower grade glioma, lung adenocarcinoma, salivary gland cancer, secretory breast cancer, fibrosarcoma, nephroma, and breast cancer.

In some embodiments, a Trk-associated cancer is selected from the group of: non-limiting examples of TRK-associated cancers include: Spitzoid melanoma, Spitz tumors (e.g., metastatic Spitz tumors), non-small cell lung cancer (NSCLC), thyroid carcinoma (e.g., papillary thyroid carcinoma (PTC)), acute myeloid leukemia (AML), sarcoma (e.g., undifferentiated sarcoma or adult soft tissue sarcoma), pediatric gliomas, colorectal cancer (CRC), glioblastoma multiforme (GBM), large cell neuroendocrine cancer (LC-NEC), thyroid cancer, intrahepatic cholangicarcinoma (ICC), pilocytic astrocytoma, lower-grade glioma, head and neck squamous cell carcinoma, adenocarcinoma (e.g., lung adenocarcinoma), salivary gland cancer, secretory breast carcinoma, breast cancer, acute myeloid leukemia, fibrosarcoma, nephroma, melanoma, bronchogenic carcinoma, B-cell cancer, Bronchus cancer, cancer of the oral cavity or pharynx, cancer of hematological tissues, cervical cancer, gastric cancer, kidney cancer, liver cancer, multiple myeloma, ovarian cancer, pancreatic cancer, salivary gland cancer, small bowel or appendix cancer, testicular cancer, urinary bladder cancer, uterine or endometrial cancer, inflammatory myofibroblastic tumors, gastrointestinal stromal tumor, non-Hodgkin's lymphoma, neuroblastoma, small cell lung cancer, squamous cell carcinoma, esophageal-gastric cancer, skin cancer, neoplasm (e.g., a melanocystic neoplasm), Spitz nevi, astrocytoma, medulloblastoma, glioma, large cell neuroendocrine tumors, mammary analogue secretory carconiomaa, nonparotid acinic cell carcinoma, bone cancer, and rectum carcinoma.

In some embodiments, the fibrosarcoma is infantile fibrosarcoma.

In some embodiments, the Trk-associated cancer is LMNAa-NTRK1 fusion soft tissue sarcoma or EVT6-NTRK3 fusion papillary thyroid cancer.

In some embodiments, the liquid formulations as described herein are useful for treating Trk-associated cancers in pediatric patients. For example, a liquid formulation as provided herein provided herein can be used to treat infantile sarcoma, neuroblastoma, congenital mesoblastic nephroma, brain low-grade glioma, and pontine glioma.

In some embodiments, the liquid formulations provided herein are useful for treating a Trk-associated cancer in combination with one or more additional therapeutic agents or therapies that work by the same or a different mechanism of action.

In some embodiments, the additional therapeutic agent(s) is selected from the group of: receptor tyrosine kinase-targeted therapeutic agents, including cabozantinib, crizotinib, erlotinib, gefitinib, imatinib, lapatinib, nilotinib, pazopanib, pertuzumab, regorafenib, sunitinib, and trastuzumab.

In some embodiments, the additional therapeutic agent(s) is selected from signal transduction pathway inhibitors, including, e.g., Ras-Raf-MEK-ERK pathway inhibitors (e.g., sorafenib, trametinib, or vemurafenib), PI3K-Akt-mTOR-S6K pathway inhibitors (e.g., everolimus, rapamycin, perifosine, or temsirolimus) and modulators of the apoptosis pathway (e.g., obataclax).

In some embodiments, the additional therapeutic agent(s) is selected from the group of: cytotoxic chemotherapeutics, including, e.g., arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, and vincristine.

In some embodiments, the additional therapeutic agent(s) is selected from the group of angiogenesis-targeted therapies, including e.g., aflibercept and bevacizumab.

In some embodiments, the additional therapeutic agent(s) is selected from the group of immune-targeted agents, e.g., including aldesleukin, ipilimumab, lambrolizumab, nivolumab, and sipuleucel-T.

In some embodiments, the additional therapeutic agent(s) is selected from agents active against the downstream Trk pathway, including, e.g., NGF-targeted biopharmaceuticals, such as NGF antibodies and panTrk inhibitors.

In some embodiments, the additional therapeutic agent or therapy is radiotherapy, including, e.g., radioiodide therapy, external-beam radiation, and radium 223 therapy.

In some embodiments, the additional therapeutic agent(s) includes any one of the above listed therapies or therapeutic agents which are standards of care in cancers wherein the cancer has a dysregulation of a NTRK gene, a Trk protein, or expression or activity, or level of the same.

Methods of detecting dysregulation of a NTRK gene, a Trk protein, or expression or activity, or level of the same, include, e.g., detection of NTRK gene translocations, e.g., using Fluorescent In Situ Hybridization (FISH) (e.g., as described in International Application Nos. PCT/US2013/061211 PCT/US2013/057495, which are incorporated herein by reference).

In some embodiments, provided herein is a method of treating cancer (e.g., a Trk-associated cancer) in a patient, comprising administering to said patient a liquid formulation as provided herein in combination with at least one additional therapy or therapeutic agent. In some embodiments, the at least one additional therapy or therapeutic agent is selected from radiotherapy (e.g., radioiodide therapy, external-beam radiation, or radium 223 therapy), cytotoxic chemotherapeutics (e.g., arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, or vincristine), tyrosine kinase targeted-therapeutics (e.g., afatinib, cabozantinib, cetuximab, crizotinib, dabrafenib, erlotinib, gefitinib, imatinib, lapatinib, nilotinib, pazopanib, panitumumab, pertuzumab, regorafenib, sunitinib, or trastuzumab), apoptosis modulators and signal transduction inhibitors (e.g. everolimus, perifosine, rapamycin, sorafenib, temsirolimus, trametinib, or vemurafenib), immune-targeted therapies (e.g., aldesleukin, interferon alfa-2b, ipilimumab, lambrolizumab, nivolumab, prednisone, or sipuleucel-T) and angiogenesis-targeted therapies (e.g., aflibercept or bevacizumab), wherein the amount of the liquid formulation as provided herein is, in combination with the additional therapy or therapeutic agent, effective in treating said cancer.

In some embodiments, the additional therapeutic agent is a different Trk inhibitor. In some embodiments, a receptor tyrosine kinase targeted therapeutic is a multikinase inhibitor (e.g., TRK-targeted therapeutic inhibitor) exhibiting TRK inhibition activity. In some embodiments, the TRK-targeted therapeutic inhibitor is selective for a TRK kinase. Exemplary TRK kinase inhibitors can exhibit inhibition activity ($IC_{50}$) against a TRK kinase of less than about 1000 nM, less than about 500 nM, less than about 200 nM, less than about 100 nM, less than about 50 nM, less than about 25 nM, less than about 10 nM, or less than about 1 nM as measured in an assay as described herein. In some embodiments, a TRK kinase inhibitor can exhibit inhibition activity ($IC_{50}$) against a TRK kinase of less than about 25 nM, less than about 10 nM, less than about 5 nM, or less than about 1 nM as measured in an assay. For example, a TRK inhibitor assay can be any of those provided in U.S. Pat. No. 8,933,084 (e.g., Example A or B).

Non-limiting examples of receptor tyrosine kinase (e.g., Trk) targeted therapeutic agents, include afatinib, cabozantinib, cetuximab, crizotinib, dabrafenib, entrectinib, erlotinib, gefitinib, imatinib, lapatinib, lestaurtinib, nilotinib, pazopanib, panitumumab, pertuzumab, sunitinib, trastuzumab, 1-((3S,4R)-4-(3-fluorophenyl)-1-(2-methoxyethyl) pyrrolidin-3-yl)-3-(4-methyl-3-(2-methylpyrimidin-5-yl)-1-phenyl-1H-pyrazol-5-yl)urea, AG 879, AR-772, AR-786, AR-256, AR-618, AZ-23, AZ623, DS-6051, Go 6976, GNF-5837, GTx-186, GW 441756, LOXO-101, MGCD516, PLX7486, RXDX101, TPX-0005, and TSR-011. Additional Trk targeted therapeutic agents include those described in U.S. Pat. Nos. 8,450,322; 8,513,263; 8,933,084; 8,791,123; 8,946,226; 8,450,322; 8,299,057; and 8,912,194; U.S. Publication No. 2016/0137654; 2015/0166564; 2015/0051222; 2015/0283132; and 2015/0306086; International Publication No. WO 2010/033941; WO 2010/048314; WO 2016/077841; WO 2011/146336; WO 2011/006074; WO 2010/033941; WO 2012/158413; WO 2014078454; WO 2014078417; WO 2014078408; WO 2014078378; WO 2014078372; WO 2014078331; WO 2014078328; WO 2014078325; WO 2014078323; WO 2014078322; WO 2015175788; WO 2009/013126; WO 2013/174876; WO 2015/124697; WO 2010/058006; WO 2015/017533; WO 2015/112806; WO 2013/183578; and WO 2013/074518, all of which are hereby incorporated by reference in their entireties.

Further examples of Trk inhibitors can be found in U.S. Pat. No. 8,637,516, International Publication No. WO 2012/034091, U.S. Pat. No. 9,102,671, International Publication No. WO 2012/116217, U.S. Publication No. 2010/0297115, International Publication No. WO 2009/053442, U.S. Pat. No. 8,642,035, International Publication No. WO 2009092049, U.S. Pat. No. 8,691,221, International Publication No. WO2006131952, all of which are incorporated by reference in their entireties herein. Exemplary Trk inhibitors include GNF-4256, described in *Cancer Chemother. Pharmacol.* 75(1):131-141, 2015; and GNF-5837 (N-[3-[[2,3-dihydro-2-oxo-3-(1H-pyrrol-2-ylmethylene)-1H-indol-6-yl] amino]-4-methylphenyl]-N'-[2-fluoro-5-(trifluoromethyl) phenyl]-urea), described in *ACS Med. Chem. Lett.* 3(2):140-145, 2012, each of which is incorporated by reference in its entirety herein.

Additional examples of Trk inhibitors include those disclosed in U.S. Publication No. 2010/0152219, U.S. Pat. No. 8,114,989, and International Publication No. WO 2006/123113, all of which are incorporated by reference in their entireties herein. Exemplary Trk inhibitors include AZ623, described in *Cancer* 117(6):1321-1391, 2011; AZD6918, described in *Cancer Biol. Ther.* 16(3):477-483, 2015; AZ64, described in *Cancer Chemother. Pharmacol.* 70:477-486, 2012; AZ-23 ((S)-5-Chloro-N2-(1-(5-fluoropyridin-2-yl) ethyl)-N4-(5-isopropoxy-1H-pyrazol-3-yl)pyrimidine-2,4-diamine), described in *Mol. Cancer Ther.* 8:1818-1827, 2009; and AZD7451; each of which is incorporated by reference in its entirety.

A Trk inhibitor can include those described in U.S. Pat. Nos. 7,615,383; 7,384,632; 6,153,189; 6,027,927; 6,025,166; 5,910,574; 5,877,016; and 5,844,092, each of which is incorporated by reference in its entirety.

Further examples of Trk inhibitors include CEP-751, described in *Int. J. Cancer* 72:672-679, 1997; CT327, described in *Acta Derm. Venereol.* 95:542-548, 2015; compounds described in International Publication No. WO 2012/034095; compounds described in U.S. Pat. No. 8,673,347 and International Publication No. WO 2007/022999; compounds described in U.S. Pat. No. 8,338,417; compounds described in International Publication No. WO 2016/027754; compounds described in U.S. Pat. No. 9,242,977; compounds described in U.S. Publication No. 2016/0000783; sunitinib (N-(2-diethylaminoethyl)-5-[(Z)-(5-fluoro-2-oxo-1H-indol-3-ylidene)methyl]-2,4-dimethyl-1H-pyrrole-3-carboxamide), as described in *PLoS One* 9:e95628, 2014; compounds described in International Publication No. WO 2011/133637; compounds described in U.S. Pat. No. 8,637,256; compounds described in *Expert. Opin. Ther. Pat.* 24(7):731-744, 2014; compounds described in *Expert Opin. Ther. Pat.* 19(3):305-319, 2009; (R)-2-phenylpyrrolidine substituted imidazopyridazines, e.g., GNF-8625, (R)-1-(6-(6-(2-(3-fluorophenyl)pyrrolidin-1-yl) imidazo[1,2-b]pyridazin-3-yl)-[2,4'-bipyridin]-2'-yl)piperidin-4-ol as described in *ACS Med. Chem. Lett.* 6(5):562-567, 2015; GTx-186 and others, as described in *PLoS One* 8(12):e83380, 2013; K252a ((9S-(9α,10β,12α))-2,3,9,10,11,12-hexahydro-10-hydroxy-10-(methoxycarbonyl)-9-methyl-9,12-epoxy-1H-diindolo[1,2,3-fg:3',2',1'-kl]pyrrolo[3,4-i][1,6]benzodiazocin-1-one), as described in *Mol. Cell Biochem.* 339(1-2):201-213, 2010; 4-aminopyrazolylpyrimidines, e.g., AZ-23 (((S)-5-chloro-N2-(1-(5-fluoropyridin-2-yl)ethyl)-N4-(5-isopropoxy-1H-pyrazol-3-yl)pyrimidine-2,4-diamine)), as described in *J. Med. Chem.* 51(15): 4672-4684, 2008; PHA-739358 (danusertib), as described in *Mol. Cancer Ther.* 6:3158, 2007; Go 6976 (5,6,7,13-tetrahydro-13-methyl-5-oxo-12H-indolo[2,3-a]pyrrolo[3,4-c]carbazole-12-propanenitrile), as described in *J. Neurochem.* 72:919-924, 1999; GW441756 ((3Z)-3-[(1-methylindol-3-yl)methylidene]-1H-pyrrolo[3,2-b]pyridin-2-one), as described in IJAE 115:117, 2010; milciclib (PHA-848125AC), described in *J. Carcinog.* 12:22, 2013; AG-879 ((2E)-3-[3,5-Bis(1,1-dimethylethyl)-4-hydroxyphenyl]-2-cyano-2-propenethioamide); altiratinib (N-(4-((2-(cyclopropanecarboxamido)pyridin-4-yl)oxy)-2,5-difluorophenyl)-N-(4-fluorophenyl)cyclopropane-1,1-dicarboxamide); cabozantinib (N-(4-((6,7-Dimethoxyquinolin-4-yl)oxy)phenyl)-N'-(4-fluorophenyl)cyclopropane-1,1-dicarboxamide); lestaurtinib ((5 S,6S,8R)-6-Hydroxy-6-(hydroxymethyl)-5-methyl-7,8,14,15-tetrahydro-5H-16-oxa-4b,8a,14-triaza-5,8-methanodibenzo[b,h]cycloocta[jkl]cyclopenta[e]-as-indacen-13(6H)-one); dovatinib (4-amino-5-fluoro-3-[6-(4-methylpiperazin-1-yl)-1H-benzimidazol-2-yl]quinolin-2 (1H)-one mono 2-hydroxypropanoate hydrate); sitravatinib (N-(3-fluoro-4-((2-(5-(((2-methoxyethyl)amino)methyl) pyridin-2-yl)thieno[3,2-b]pyridin-7-yl)oxy)phenyl)-N-(4-fluorophenyl)cyclopropane-1,1-dicarboxamide); ONO-5390556; regorafenib (4-[4-({[4-Chloro-3-(trifluoromethyl) phenyl]carbamoyl}amino)-3-fluorophenoxy]-N-methylpyridine-2-carboxamide hydrate); and VSR-902A; all of the references above are incorporated by reference in their entireties herein.

The ability of a Trk inhibitor to act as a TrkA, TrkB, and/or Trk C inhibitor may be tested using the assays described in Examples A and B in U.S. Pat. No. 8,513,263, which is incorporated herein by reference.

In some embodiments, signal transduction pathway inhibitors include Ras-Raf-MEK-ERK pathway inhibitors (e.g., binimetinib, selumetinib, encorafinib, sorafenib, trametinib, and vemurafenib), PI3K-Akt-mTOR-S6K pathway inhibitors (e.g. everolimus, rapamycin, perifosine, temsirolimus), and other kinase inhibitors, such as baricitinib, brigatinib, capmatinib, danusertib, ibrutinib, milciclib, quercetin, regorafenib, ruxolitinib, semaxanib, AP32788, BLU285, BLU554, INCB39110, INCB40093, INCB50465, INCB52793, INCB54828, MGCD265, NMS-088, NMS-1286937, PF 477736 ((R)-amino-N-[5,6-dihydro-2-(1-methyl-1H-pyrazol-4-yl)-6-oxo-1Hpyrrolo[4,3,2-ef][2,3] benzodiazepin-8-yl]-cyclohexaneacetamide), PLX3397, PLX7486, PLX8394, PLX9486, PRN1008, PRN1371, RXDX103, RXDX106, RXDX108, and TG101209 (N-tert-butyl-3-(5-methyl-2-(4-(4-methylpiperazin-1-yl)phenylamino)pyrimidin-4-ylamino)benzenesulfonamide).

Non-limiting examples of checkpoint inhibitors include ipilimumab, tremelimumab, nivolumab, pidilizumab, MPDL3208A, MEDI4736, MSB0010718C, BMS-936559, BMS-956559, BMS-935559 (MDX-1105), AMP-224, and pembrolizumab.

In some embodiments, cytotoxic chemotherapeutics are selected from arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, and vincristine.

Non-limiting examples of angiogenesis-targeted therapies include aflibercept and bevacizumab.

In some embodiments, immune-targeted agents are selected from aldesleukin, interferon alfa-2b, ipilimumab, lambrolizumab, nivolumab, prednisone, and sipuleucel-T.

Non-limiting examples of radiotherapy include radioiodide therapy, external-beam radiation, and radium 223 therapy.

Additional kinase inhibitors include those described in, for example, U.S. Pat. Nos. 7,514,446; 7,863,289; 8,026,247; 8,501,756; 8,552,002; 8,815,901; 8,912,204; 9,260,437; 9,273,051; U.S. Publication No. US 2015/0018336; International Publication No. WO 2007/002325; WO 2007/002433; WO 2008/080001; WO 2008/079906; WO 2008/079903; WO 2008/079909; WO 2008/080015; WO 2009/007748; WO 2009/012283; WO 2009/143018; WO 2009/143024; WO 2009/014637; 2009/152083; WO 2010/111527; WO 2012/109075; WO 2014/194127; WO 2015/112806; WO 2007/110344; WO 2009/071480; WO 2009/118411; WO 2010/031816; WO 2010/145998; WO 2011/092120; WO 2012/101032; WO 2012/139930; WO 2012/143248; WO 2012/152763; WO 2013/014039; WO 2013/102059; WO 2013/050448; WO 2013/050446; WO 2014/019908; WO 2014/072220; WO 2014/184069; and WO 2016/075224, all of which are hereby incorporated by reference in their entireties.

Further examples of kinase inhibitors include those described in, for example, WO 2016/081450; WO 2016/022569; WO 2016/011141; WO 2016/011144; WO 2016/

011147; WO 2015/191667; WO 2012/101029; WO 2012/113774; WO 2015/191666; WO 2015/161277; WO 2015/161274; WO 2015/108992; WO 2015/061572; WO 2015/058129; WO 2015/057873; WO 2015/017528; WO/2015/017533; WO 2014/160521; and WO 2014/011900, each of which is hereby incorporated by reference in its entirety.

Yet other additional therapeutic agents include RET inhibitors such as those described, for example, in U.S. Pat. Nos. 8,299,057; 8,399,442; 8,937,071; 9,006,256; and 9,035,063; U.S. Publication Nos. 2014/0121239; 2011/0053934; 2011/0301157; 2010/0324065; 2009/0227556; 2009/0130229; 2009/0099167; 2005/0209195; International Publication Nos. WO 2014/184069; WO 2014/072220; WO 2012/053606; WO 2009/017838; WO 2008/031551; WO 2007/136103; WO 2007/087245; WO 2007/057399; WO 2005/051366; and WO 2005/044835; and *J. Med. Chem.* 2012, 55 (10), 4872-4876.

These additional therapeutic agents may be administered with a liquid formulation as provided herein as part of the same or separate dosage forms, via the same or different routes of administration, and on the same or different administration schedules according to standard pharmaceutical practice known to one skilled in the art.

Also provided herein is (i) a pharmaceutical combination for treating cancer (e.g., a Trk-associated cancer) in a patient in need thereof, which comprises (a) a liquid formulation as provided herein, (b) an additional therapeutic agent and (c) optionally at least one additional additives for simultaneous, separate or sequential use for the treatment of a tumor disease, wherein the amounts of the liquid formulation as provided herein and of the additional therapeutic agent are together effective in treating said cancer; (ii) a pharmaceutical composition comprising such a combination; (iii) the use of such a combination for the preparation of a medicament for the treatment of cancer (e.g., a Trk-associated cancer); and (iv) a commercial package or product comprising such a combination as a combined preparation for simultaneous, separate or sequential use; and to a method of treatment of cancer (e.g., Trk-associated cancer) in a patient in need thereof.

Also provided are methods of treating a subject identified or diagnosed as having a Trk-associated cancer (e.g., a subject that has been identified or diagnosed as having a Trk-associated cancer through the use of a regulatory agency-approved, e.g., FDA-approved, kit for identifying dysregulation of a NTRK gene, a Trk protein, or expression or activity, or level of the same, in a subject or a biopsy sample from the subject) (e.g., any of the Trk-associated cancers described herein or known in the art) that include administering the subject a therapeutically effective amount of a liquid formulation as provided herein. Also provided is a liquid formulation as provided herein for use in treating a Trk-associated cancer in a subject identified or diagnosed as having a Trk-associated cancer (e.g., a subject that has been identified or diagnosed as having a Trk-associated cancer through the use of a regulatory agency-approved, e.g., FDA-approved, kit for identifying dysregulation of a NTRK gene, a Trk protein, or expression or activity, or level of the same, in a subject or a biopsy sample from the subject) (e.g., any of the Trk-associated cancers described herein or known in the art). Also provided is the use of a liquid formulation as provided herein for the manufacture of a medicament for treating a Trk-associated cancer in a subject identified or diagnosed as having a Trk-associated cancer (e.g., a subject that has been identified or diagnosed as having a Trk-associated cancer through the use of a regulatory agency-approved, e.g., FDA-approved, kit for identifying dysregulation of a NTRK gene, a Trk protein, or expression or activity, or level of the same, in a subject or a biopsy sample from the subject) (e.g., any of the Trk-associated cancers described herein or known in the art).

Also provided are methods of treating a subject (e.g., a subject suspected of having a Trk-associated cancer, a subject presenting with one or more symptoms of a Trk-associated cancer, or a subject having an elevated risk of developing a Trk-associated cancer) that include performing an assay (e.g., an assay that utilizes next generation sequencing, immunohistochemistry, break apart FISH, or dual-fusion FISH analysis) (e.g., using a regulatory agency-approved, e.g., FDA-approved, kit) on a sample obtained from the subject to determine whether the subject has dysregulation of a NTRK gene, a Trk protein, or expression or activity, or level of the same, and administering (e.g., specifically or selectively administering) a therapeutically effective amount of a liquid formulation as provided herein to a subject determined to have dysregulation of a NTRK gene, a Trk protein, or expression or activity, or levels of the same. Additional assays, non-limiting assays that may be used in these methods are described herein. Additional assays are also known in the art. Also provided is the use of a liquid formulation as provided herein for use in treating a Trk-associated cancer in a subject identified or diagnosed as having a Trk-associated cancer through a step of performing an assay (e.g., an in vitro assay) (e.g., an assay that utilizes next generation sequencing, immunohistochemistry, break apart FISH, or dual-fusion FISH analysis) (e.g., using a regulatory agency-approved, e.g., FDA-approved, kit) on a sample obtained from the subject to determine whether the subject has dysregulation of a NTRK gene, a Trk protein, or expression or activity, or level of the same, where the presence of dysregulation of a NTRK gene, a Trk protein, or expression or activity, or level of the same, identifies that the subject has a Trk-associated cancer. Also provided is the use of a liquid formulation as provided herein for the manufacture of a medicament for treating a Trk-associated cancer in a subject identified or diagnosed as having a Trk-associated cancer through a step of performing an assay (e.g., an in vitro assay) (e.g., an assay that utilizes next generation sequencing, immunohistochemistry, break apart FISH, or dual-fusion FISH analysis) (e.g., using a regulatory agency-approved, e.g., FDA-approved, kit) on a sample obtained from the subject to determine whether the subject has dysregulation of a NTRK gene, a Trk protein, or expression or activity, or level of the same, where the presence of dysregulation of a NTRK gene, a Trk protein, or expression or activity, or level of the same, identifies that the subject has a Trk-associated cancer. Some embodiments of any of the methods or uses described herein further include recording in the subject's clinical record (e.g., a computer readable medium) that the subject determined to have dysregulation of a NTRK gene, a Trk protein, or expression or activity, or level of the same, through the performance of the assay, should be administered a liquid formulation as provided herein.

In some embodiments of any of the methods or uses described herein, the subject has been identified or diagnosed as having a cancer with dysregulation of a NTRK gene, a Trk protein, or expression or activity, or level of the same (e.g., as determined using a regulatory agency-approved, e.g., FDA-approved, assay or kit). In some embodiments of any of the methods or uses described herein, the subject has a tumor that is positive for dysregulation of a NTRK gene, a Trk protein, or expression or activity, or level of the same (e.g., as determined using a regulatory agency-approved assay or kit). In some embodiments of any of the methods or uses described herein, the subject can be a subject with a tumor(s) that is positive for dysregulation of a NTRK gene, a Trk protein, or expression or activity, or level of the same (e.g., identified as positive using a regulatory agency-approved, e.g., FDA-approved, assay or kit). In some embodiments of any of the methods or uses described herein, the subject can be a subject whose tumors have dysregulation of a NTRK gene, a Trk protein, or expression or activity, or a level of the same (e.g., where the tumor is identified as such using a regulatory agency-approved, e.g., FDA-approved, kit or assay). In some embodiments of any of the methods or uses described herein, the subject is suspected of having a Trk-associated cancer. In some embodiments of any of the methods or uses described herein, the subject has a clinical record indicating that the subject has a tumor that has dysregulation of a NTRK gene, a Trk protein, or expression or activity, or level of the same (and optionally the clinical record indicates that the subject should be treated with any of the compositions provided herein).

Also provided are methods of treating a subject that include administering a therapeutically effective amount of a liquid formulation as provided herein to a subject having a clinical record that indicates that the subject has dysregulation of a NTRK gene, a Trk protein, or expression or activity, or level of the same. Also provided is the use of a liquid formulation as provided herein for the manufacture of a medicament for treating a Trk-associated cancer in a subject having a clinical record that indicates that the subject has dysregulation of a NTRK gene, a Trk protein, or expression or activity, or level of the same. Also provided is the use of a liquid formulation as provided herein for the manufacture of a medicament for treating a Trk-associated cancer in a subject having a clinical record that indicates that the subject has dysregulation of a NTRK gene, a Trk protein, or expression or activity, or level of the same. Some embodiments of these methods and uses can further include: a step of performing an assay (e.g., an in vitro assay) (e.g., an assay that utilizes next generation sequencing, immunohistochemistry, break apart FISH, or dual-fusion FISH analysis) (e.g., using a regulatory agency-approved, e.g., FDA-approved, kit) on a sample obtained from the subject to determine whether the subject has dysregulation of a NTRK gene, a Trk protein, or expression or activity, or level of the same, and recording information in a subject's clinical file (e.g., a computer-readable medium) that the subject has been identified to have dysregulation of a NTRK gene, a Trk protein, or expression or activity, or level of the same.

Also provided are methods (e.g., in vitro methods) of selecting a treatment for a subject that includes selecting a treatment including administration of a therapeutically effective amount of a liquid formulation as provided herein for a subject identified or diagnosed as having a Trk-associated cancer (e.g., a subject that has been identified or diagnosed as having a Trk-associated cancer through the use of a regulatory agency-approved, e.g., FDA-approved, kit for identifying dysregulation of a NTRK gene, a Trk protein, or expression or activity, or level of the same, in a subject or a biopsy sample from the subject) (e.g., any of the Trk-associated cancers described herein or known in the art). Some embodiments can further include administering the selected treatment to the subject identified or diagnosed as having a Trk-associated cancer. Some embodiments can further include a step of performing an assay (e.g., an in vitro assay) (e.g., an assay that utilizes next generation sequencing, immunohistochemistry, break apart FISH, or dual-fusion FISH analysis) (e.g., using a regulatory agency-approved, e.g., FDA-approved, kit) on a sample obtained from the subject to determine whether the subject has dysregulation of a NTRK gene, a Trk protein, or expression or activity, or level of the same, and identifying or diagnosing a subject determined to have dysregulation of a NTRK gene, a Trk protein, or expression or activity, or level of the same, as having a Trk-associated cancer.

Also provided are methods of selecting a treatment for a subject that include administration of a therapeutically effective amount of a liquid formulation as provided herein, wherein the methods include a step of performing an assay (e.g., an in vitro assay) (e.g., an assay that utilizes next generation sequencing, immunohistochemistry, break apart FISH, or dual-fusion FISH analysis) (e.g., using a regulatory agency-approved, e.g., FDA-approved, kit) on a sample obtained from the subject to determine whether the subject has dysregulation of a NTRK gene, a Trk protein, or expression or activity, or level of the same, and identifying or diagnosing a subject determined to have dysregulation of a NTRK gene, a Trk protein, or expression or activity, or level of the same, as having a Trk-associated cancer, and selecting a therapeutic treatment including administration of a therapeutically effective amount of a liquid formulation as provided herein for the subject identified or diagnosed as having a Trk-associated cancer. Some embodiments further include administering the selected treatment to the subject identified or diagnosed as having a Trk-associated cancer.

Also provided are methods of selecting a subject for treatment including administration of a therapeutically effective amount of a liquid formulation as provided herein that include selecting, identifying, or diagnosing a subject having a Trk-associated cancer, and selecting the subject for treatment including administration of a therapeutically effective amount of a liquid formulation as provided herein. In some embodiments, identifying or diagnosing a subject as having a Trk-associated cancer can include a step of performing an assay (e.g., an in vitro assay) (e.g., an assay that utilizes next generation sequencing, immunohistochemistry, break apart FISH, or dual-fusion FISH) (e.g., using a regulatory agency-approved, e.g., FDA-approved, kit) on a sample obtained from the subject to determine whether the subject has dysregulation of a NTRK gene, a Trk protein, or expression or activity, or level of the same, and identifying or diagnosing a subject determined to have dysregulation of a NTRK gene, a Trk protein, or expression or activity, or level of the same, as having a Trk-associated cancer. In some embodiments, the selecting a treatment can be used as part of a clinical study that includes administration of various treatments of a Trk-associated cancer.

In some embodiments of any of the methods or uses described herein, an assay used determine whether the subject has dysregulation of a NTRK gene, a Trk protein, or expression or activity, or level of the same, using a sample (e.g., a biological sample or a biopsy sample (e.g., a paraffin-embedded biopsy sample) from a subject (e.g., a subject suspected of having a Trk-associated cancer, a subject having one or more symptoms of a Trk-associated cancer, and/or a subject that has an increased risk of developing a Trk-associated cancer) can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR). As is well-known in the art, the assays are typically performed, e.g., with at least one labelled nucleic acid probe or at least one labelled antibody or antigen-binding fragment thereof. Assays can utilize other detection methods known in the art for detecting dysregulation of a NTRK gene, a Trk protein, or expression or activity, or levels of the same (see, e.g., the references cited herein).

In some embodiments, a liquid formulation as provided herein is useful for treating chronic and acute pain, including pain associated with cancer, surgery, and bone fracture. A liquid formulation as provided herein may be useful in the treatment of multiple types of pain including inflammatory pain, neuropathic pain, and pain associated with cancer, surgery, and bone fracture. A liquid formulation as provided herein can also be useful for treating cancers including neuroblastoma, ovarian, pancreatic and colorectal cancer. A liquid formulation as provided herein is also useful for treating inflammation and certain infectious diseases. In addition, a liquid formulation as provided herein may also be used to treat interstitial cystitis (IC), painful bladder syndrome (PBS), urinary incontinence, asthma, anorexia, atopic dermatitis, and psoriasis. A liquid formulation as provided herein may also be used to treat demyelination and dysmyelination by promoting myelination, neuronal survival, and oligodendrocyte differentiation via blocking Sp35-TrkA interaction. A liquid formulation as provided herein may be useful in the treatment of multiple types of pain including inflammatory pain, neuropathic pain, surgical pain and pain associated with cancer. A liquid formulation as provided herein may be useful in the treatment of bone-related diseases (such as those involving bone resorption). Examples of bone-related diseases include metastatic bone disease, treatment-induced bone loss, osteoporosis, rheumatoid arthritis, ankylosing spondylitis, Paget's disease, and periodontal disease. The osteoporosis may be attributed to (1) menopause in women, (2) aging in men or women, (3) suboptimal bone growth during childhood and adolescence that resulted in failure to reach peak bone mass, and/or (4) bone loss secondary to other disease conditions, eating disorders, medications and/or medical treatments. Other osteolytic diseases that can be treated according to the methods provided herein are more localized. A particular example is metastatic tumor-induced osteolysis. In this condition, bone cancers or bone metastases induce localized osteolysis that causes pain, bone weakness and fractures. Such localized osteolysis also permits tumors to grow larger by creating more space for them in the bone and releasing growth factors from the bone matrix. Cancers presently known to cause tumor-induced osteolysis include hematological malignancies (e.g., myeloma and lymphoma) and solid tumors (e.g., breast, prostate, lung, renal and thyroid), all of which the present disclosure contemplates treating. As used herein, the term treatment includes prophylaxis as well as treatment of an existing condition.

Accordingly, also provided herein is a method of treating diseases or medical conditions in a subject in need thereof, wherein said disease or condition is treatable with an inhibitor of TrkA and/or TrkB (e.g., a Trk-associated cancer), comprising administering to the subject a liquid formulation as provided herein in an amount effective to treat or prevent said disorder. In a particular embodiment, provided herein is a method of treating pain, cancer, inflammation, neurodegenerative disease or *Trypanosoma cruzi* infection in a mammal, which comprises administering to said mammal a therapeutically effective amount of a liquid formulation as provided herein. In another embodiment, provided herein is a method of treating osteolytic disease in a mammal, which comprises administering to said subject in need thereof a therapeutically effective amount of a liquid formulation as provided herein.

A liquid formulation as provided herein can be used in combination with one or more additional drugs that work by the same or a different mechanism of action. Such conjoint treatment may be achieved by way of the simultaneous, sequential or separate administration of the individual components of the treatment. Examples include anti-inflammatory compounds, steroids (e.g., dexamethasone, cortisone and fluticasone), analgesics such as NSAIDs (e.g., aspirin, ibuprofen, indomethacin, and ketoprofen), and opioids (such as morphine), and chemotherapeutic agents.

In the field of medical oncology it is normal practice to use a combination of different forms of treatment to treat each patient with cancer. In medical oncology the other component(s) of such conjoint treatment in addition to compositions provided herein may be, for example, surgery, radiotherapy, chemotherapy, signal transduction inhibitors and/or monoclonoal antibodies. Compounds of Formula (I) therefore may also be useful as adjuvants to cancer treatment, that is, they can be used in combination with one or more additional therapies or therapeutic agents, for example a chemotherapeutic agent that works by the same or by a different mechanism of action.

Accordingly, a liquid formulation as provided herein can be administered in combination with one or more agents selected from mitotic inhibitors, alkylating agents, antimetabolites, antisense DNA or RNA, intercalating antibiotics, growth factor inhibitors, signal transduction inhibitors, cell cycle inhibitors, enzyme inhibitors, retinoid receptor modulators, proteasome inhibitors, topoisomerase inhibitors, biological response modifiers, anti-hormones, angiogenesis inhibitors, cytostatic agents anti-androgens, targeted antibodies, HMG-CoA reductase inhibitors, and prenyl-protein transferase inhibitors.

In some embodiments of any the methods described herein, the liquid formulations provided herein are administered in combination with a therapeutically effective amount of at least one additional therapeutic agent selected from one or more additional therapies or therapeutic (e.g., chemotherapeutic) agents.

Non-limiting examples of additional therapeutic agents include: other receptor tyrosine kinase-targeted therapeutic agents (e.g., TRK kinase inhibitors), kinase targeted therapeutics, signal transduction pathway inhibitors, checkpoint inhibitors, modulators of the apoptosis pathway (e.g. obataclax); cytotoxic chemotherapeutics, angiogenesis-targeted therapies, immune-targeted agents, and radiotherapy.

In the methods of treatment described herein the liquid formulations provided herein can be especially useful in treating a subject with dysphagia (e.g., difficulty swallowing). For example, the liquid formulations provided herein can be useful in a method of treating cancer in a subject with an oropharyngeal dysphagia.

Where the compound disclosed herein has at least one chiral center, the compounds may accordingly exist as enantiomers. Where the compounds possess two chiral centers, the compounds may additionally exist as diastereomers. That is, the compound of Formula I, in addition to having the desired configuration designated by the nomenclature "(S)—N-(5-((R)-2-(2,5-difluorophenyl)-pyrrolidin-1-yl)-pyrazolo[1,5-a]pyrimidin-3-yl)-3-hydroxypyrrolidine-1-carboxamide hydrogen sulfate" (hereinafter referred to as the (S,R) isomer), it may also be present in minor amounts as the isomer (R)—N-(5-((R)-2-(2,5-difluorophenyl)-pyrrolidin-1-yl)-pyrazolo[1,5-a]pyrimidin-3-yl)-3-hydroxypyrrolidine-1-carboxamide hydrogen sulfate (hereinafter referred to as the (R,R) isomer) and/or may also be present in minor amounts as the (S)—N-(5-((S)-2-(2,5-difluorophenyl)-pyrrolidin-1-yl)-pyrazolo[1,5-a]pyrimidin-3-yl)-3-hydroxypyrrolidine-1-carboxamide hydrogen sulfate (hereinafter referred to as the (S,S) isomer), and/or may be present in minor amounts as the isomer (R)—N-(5-((S)-2-(2,5-difluorophenyl)-pyrrolidin-1-yl)-pyrazolo[1,5-a]pyrimidin-3-yl)-3-hydroxypyrrolidine-1-carboxamide hydrogen sulfate" (hereinafter referred to as the (R,S) isomer). It is to be understood that all such isomers and mixtures thereof are encompassed within the scope of the present invention. Preferably, wherein the compound is present as the (S,R) isomer, the (S,R) isomer is present at an excess of greater than or equal to about 80%, more preferably at an excess of greater than or equal to about 90%, more preferably still at an excess of greater than or equal to about 95%, more preferably still at an excess of greater than or equal to about 98%, more preferably at an excess of greater than or equal to about 99%.

It will be appreciated that crystalline form (I-HS) contains two centers of asymmetry and may therefore be prepared and isolated in a mixture of isomers such as a racemic or diastereomeric mixture, or in an enantiomerically pure form. Where stereochemistry is specified by a solid wedge or dashed line representing a particular configuration, then that stereoisomer is so specified and defined.

As used herein, the term "pharmaceutically acceptable salts" refers to salts that retain the desired biological activity of the subject compound and exhibit minimal undesired toxicological effects. These pharmaceutically acceptable salts may be prepared in situ during the final isolation and purification of the compound, or by separately reacting the purified compound in its free acid or free base form with a suitable base or acid, respectively. In some embodiments, pharmaceutically acceptable salts may be preferred over the respective free base or free acid because such salts impart greater stability or solubility to the molecule thereby facilitating formulation into a dosage form. Basic compounds are generally capable of forming pharmaceutically acceptable acid addition salts by treatment with a suitable acid. Suitable acids include pharmaceutically acceptable inorganic acids and pharmaceutically acceptable organic acids. Representative pharmaceutically acceptable acid addition salts include hydrochloride, hydrobromide, nitrate, methylnitrate, sulfate, bisulfate, sulfamate, phosphate, acetate, hydroxyacetate, phenylacetate, propionate, butyrate, isobutyrate, valerate, maleate, hydroxymaleate, acrylate, fumarate, malate, tartrate, citrate, salicylate, p-aminosalicyclate, glycollate, lactate, heptanoate, phthalate, oxalate, succinate, benzoate, o-acetoxybenzoate, chlorobenzoate, methylbenzoate, dinitrobenzoate, hydroxybenzoate, methoxybenzoate, mandelate, tannate, formate, stearate, ascorbate, palmitate, oleate, pyruvate, pamoate, malonate, laurate, glutarate, glutamate, estolate, methanesulfonate (mesylate), ethanesulfonate (esylate), 2-hydroxyethanesulfonate, benzenesulfonate (besylate), p-aminobenzenesulfonate, p-toluenesulfonate (tosylate), napthalene-2-sulfonate, Ethanedisulfonate, and 2,5-dihydroxybenzoate.

As used herein, unless otherwise noted, the term "isolated form" shall mean that the compound is present in a form which is separate from any solid mixture with another compound(s), solvent system or biological environment. In some embodiments, the crystalline form (I-HS) is present as an isolated form.

As used herein, unless otherwise noted, the term "substantially pure form" shall mean that the mole percent of impurities in the isolated compound or crystalline form is less than about 5 mole percent, preferably less than about 2 mole percent, more preferably, less than about 0.5 mole percent, most preferably, less than about 0.1 mole percent. In some embodiments, the crystalline form (I-HS) is present as a substantially pure form.

As used herein, unless otherwise noted, the term "substantially free of other amorphous, polymorph or crystalline form(s)" when used to described crystalline form (I-HS) shall mean that mole percent of other amorphous, polymorph or crystalline form(s) of the isolated base of crystalline form (I-HS) is less than about 5 mole percent, preferably less than about 2 mole percent, more preferably, less than about 0.5 mole percent, most preferably less than about 0.1 mole percent. In some embodiments, the crystalline form (I-HS) is present as a form substantially free of other amorphous, polymorph or crystalline form(s).

The terms "polymorph" and "polymorphic form" refer to different crystalline forms of a single compound. That is, polymorphs are distinct solids sharing the same molecular formula, yet each polymorph may have distinct solid state physical properties. Therefore, a single compound may give rise to a variety of polymorphic forms where each form has different and distinct solid state physical properties, such as different solubility profiles, dissolution rates, melting point temperatures, flowability, and/or different X-ray diffraction peaks. The differences in physical properties may affect pharmaceutical parameters such as storage stability, compressibility and density (which can be important in formulation and product manufacturing), and dissolution rate (which can be an important factor in bioavailability). Techniques for characterizing polymorphic forms include, but are not limited to, X-ray powder diffractometry (XRPD), differential scanning calorimetry (DSC), thermal gravimetric analysis (TGA), single-crystal X-ray diffractometry (XRD), vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility measurements, dissolution measurements, elemental analysis and Karl Fischer analysis.

The term "amorphous" means a solid in a solid state that is a non-crystalline state. Amorphous solids are disordered arrangements of molecules and therefore possess no distinguishable crystal lattice or unit cell and consequently have no definable long range ordering. The solid state form of a solid may be determined by polarized light microscopy, X-ray powder diffraction ("XRPD"), differential scanning calorimetry ("DSC"), or other standard techniques known to those of skill in the art.

As used herein, unless otherwise noted, the terms "treating," "treatment," and the like, shall include the management and care of a subject or patient (preferably mammal, more preferably human) for the purpose of combating a disease, condition, or disorder and includes the administration of a disclosed compound to alleviate the symptoms or complications, or reduce the rate of progression of the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

As used herein, the term "Trk-associated cancer" shall be defined to include cancers associated with or having dysregulation of a NTRK gene, a Trk protein, or expression or activity, or level of the same (e.g., any of types of dysregulation of a NTRK gene, a Trk protein, or expression or activity, or level of the same, described herein). Non-limiting examples of a Trk-associated cancer are described herein.

As used herein, the term "pain" shall be defined to include acute, chronic, inflammatory and neuropathic pain, including diabetic neuropathy. Further, the pain may be centrally mediated, peripherally mediated, caused by structural tissue injury, caused by soft tissue injury or caused by progressive disease. Any centrally mediated, peripherally mediated, structural tissue injury, soft tissue injury or progressive disease related pain may be acute or chronic.

As used herein, unless otherwise noted, pain shall include inflammatory pain, centrally mediated pain, peripherally mediated pain, visceral pain, structural related pain, cancer pain, soft tissue injury related pain, progressive disease related pain, neuropathic pain, acute pain from acute injury, acute pain from trauma, acute pain from surgery, headache, dental pain, back pain (preferably lower back pain), chronic pain from neuropathic conditions and chronic pain from post-stroke conditions.

Some embodiments include methods for the treatment of pain, wherein the pain is acute pain. Some embodiments include methods for the treatment of pain, wherein the pain is chronic pain. Some embodiments include methods for the treatment of pain, wherein the pain is neuropathic pain, including diabetic neuropathy. Some embodiments include methods for the treatment of pain, wherein the pain is inflammatory pain.

In some embodiments, the pain is selected from the group consisting of osteoarthritis, rheumatoid arthritis, fibromyalgia, headache, toothache, burn, sunburn, animal bite (such as dog bite, cat bite, snake bite, spider bite, insect sting, and the like), neurogenic bladder, benign prostatic hypertrophy, interstitial cystitis, rhinitis, contact dermatitis/hypersensitivity, itch, eczema, pharyngitis, mucositis, enteritis, cellulites, causalgia, sciatic neuritis, mandibular joint neuralgia, peripheral neuritis, polyneuritis, stump pain, phantom limb pain, post-operative ileus, cholecystitis, postmastectomy pain syndrome, oral neuropathic pain, Charcot's pain, reflex sympathetic dystrophy, Guillain-Barre syndrome, meralgia paresthetica, burning-mouth syndrome, post-herpetic neuralgia, trigeminal neuralgia, peripheral neuropathy, bilateral peripheral neuropathy, diabetic neuropathy, postherpetic neuralgia, trigeminal neuralgia, optic neuritis, postfebrile neuritis, migrating neuritis, segmental neuritis, Gombault's neuritis, neuronitis, cervicobrachial neuralgia, cranial neuralgia, geniculate neuralgia, glossopharyngial neuralgia, migrainous neuralgia, idiopathic neuralgia, intercostals neuralgia, mammary neuralgia, Morton's neuralgia, nasociliary neuralgia, occipital neuralgia, red neuralgia, Sluder's neuralgia, splenopalatine neuralgia, supraorbital neuralgia, vidian neuralgia, inflammatory bowel disease, irritable bowel syndrome, labor, childbirth, menstrual cramps, cancer, back pain, lower back pain and carpal tunnel syndrome pain.

Acute pain includes pain caused by acute injury, trauma, illness or surgery (for example, open-chest surgery (including open-heart or bypass surgery)). Acute pain also includes, and is not limited to, headache, post-operative pain, kidney stone pain, gallbladder pain, gallstone pain, obstetric pain, rheumatological pain, dental pain or pain caused by sports-medicine injuries, carpal tunnel syndrome, burns, musculoskeletal sprains and strains, musculotendinous strain, cervicobrachial pain syndromes, dyspepsia, gastric ulcer, duodenal ulcer, dysmenorrhea or endometriosis.

Chronic pain includes pain caused by an inflammatory condition, osteoarthritis, rheumatoid arthritis or as sequela to disease, acute injury or trauma. Chronic pain also includes, and is not limited to, headache, upper back pain or lower back pain (selected from back pain resulting from systematic, regional or primary spine disease (selected from radiculopathy)), bone pain (selected from bone pain due to osteoarthritis, osteoporosis, bone metastases or unknown reasons), pelvic pain, spinal cord injury-associated pain, cardiac chest pain, non-cardiac chest pain, central post-stroke pain, myofascial pain, cancer pain, AIDS pain, sickle cell pain, geriatric pain or pain caused by headache, migraine, trigeminal neuralgia, temporomandibular joint syndrome, fibromyalgia syndrome, osteoarthritis, rheumatoid arthritis, gout, fibrositis or thoracic outlet syndromes.

Neuropathic pain includes pain resulting from chronic or debilitating conditions or disorders. The chronic or debilitating conditions or disorders which can lead to neuropathic pain include, but are not limited to, painful diabetic peripheral neuropathy, post-herpetic neuralgia, trigeminal neuralgia, post-stroke pain, multiple sclerosis-associated pain, neuropathies-associated pain such as in idiopathic or post-traumatic neuropathy and mononeuritis, HIV-associated neuropathic pain, cancer-associated neuropathic pain, carpal tunnel-associated neuropathic pain, spinal cord injury-associated pain, complex regional pain syndrome, fibromyalgia-associated neuropathic pain, lumbar and cervical pain, reflex sympathic dystrophy, phantom limb syndrome and other chronic and debilitating condition-associated pain syndromes.

"Acute neurodegenerative disorders or diseases" include, but are not limited to, various types of acute neurodegenerative disorders associated with neuron death or damage including cerebrovascular insufficiency, focal brain trauma, diffuse brain damage, and spinal cord injury, that is, cerebral ischemia or infarction including embolic occlusion and thrombotic occlusion, reperfusion following acute ischemia, perinatal hypoxic-ischemic injury, cardiac arrest, as well as intracranial hemorrhage of any type (including, but not limited to, epidural, subdural, subarachnoid and intracerebral), and intracranial and intravertebral lesions (including, but not limited to, contusion, penetration, shear, compression and laceration), and whiplash shaken infant syndrome. In some embodiments, the acute neurodegenerative disorder is a result of stroke, acute ischemic injury, head injury or spinal injury.

"Chronic neurodegenerative disorders or diseases" include, but are not limited to, Alzheimer's disease, Pick's disease, diffuse Lewy body disease, progressive supranuclear palsy (Steel-Richardson syndrome), multisystem degeneration (Shy-Drager syndrome), chronic epileptic conditions associated with neurodegeneration, motor neuron diseases including amyotrophic lateral sclerosis, degenerative ataxias, cortical basal degeneration, ALS-Parkinson's-Dementia complex of Guam, subacute sclerosing panencephalitis, Huntington's disease, Parkinson's disease, synucleinopathies (including multiple system atrophy), primary progressive aphasia, striatonigral degeneration, Machado-Joseph disease/spinocerebellar ataxia type 3 and olivopontocerebellar degenerations, Gilles De La Tourette's disease, bulbar and pseudobulbar palsy, spinal and spinobulbar muscular atrophy (Kennedy's disease), multiple sclerosis, primary lateral sclerosis, familial spastic paraplegia, Werdnig-Hoffmann disease, Kugelberg-Welander disease, Tay-Sach's disease, Sandhoff disease, familial spastic disease, Wohlfart-Kugelberg-Welander disease, spastic paraparesis, progressive multifocal leukoencephalopathy, familial dysautonomia (Riley-Day syndrome), and prion diseases (including, but not limited to Creutzfeldt-Jakob, Gerstmann- Straussler-Scheinker disease, Kuru and fatal familial insomnia). In some embodiments, the chronic neurodegenerative disorder is selected from Alzheimer's disease, Parkinson's disease, multiple sclerosis or cerebral palsy.

The term "subject" as used herein, refers to an animal, preferably a mammal, most preferably a human, who has been the object of treatment, observation or experiment. In some embodiments, the subject has experienced and/or exhibited at least one symptom of the disease or disorder to be treated and/or prevented. In some embodiments, the patient is from birth through the first 28 days of life, from 29 days of age to less than two years of age, from two years of age to less than 12 years of age, (12 years of age through 21 years of age (up to, but not including, the twenty-second birthday), from 22 years of age to 35 years of age, from 35 years of age to 65 years of age, or greater than 65 years of age. In some embodiments, a patient is a pediatric patient (i.e. a patient under the age of 21 years at the time of diagnosis or treatment). The term "pediatric" can be further divided into various subpopulations including: neonates (from birth through the first 28 days of life); infants (29 days of age to less than two years of age); children (two years of age to less than 12 years of age); and adolescents (12 years of age through 21 years of age (up to, but not including, the twenty-second birthday)). Berhman R E, Kliegman R, Arvin A M, Nelson W E. Nelson *Textbook of Pediatrics,* 15th Ed. Philadelphia: W.B. Saunders Company, 1996; Rudolph A M, et al. *Rudolph's Pediatrics,* 21st Ed. New York: McGraw-Hill, 2002; and Avery M D, First L R. *Pediatric Medicine,* 2nd Ed. Baltimore: Williams & Wilkins; 1994. In some embodiments, the patient is an elderly patient (e.g., a patient of more than 65 years of age).

In some embodiments, the subject has been identified or diagnosed as having a cancer with dysregulation of a NTRK gene, a Trk protein, or expression or activity, or level of the same (e.g., as determined using a regulatory agency-approved, e.g., FDA-approved, assay or kit). In some embodiments, the subject has a tumor that is positive for dysregulation of a NTRK gene, a Trk protein, or expression or activity, or level of the same (e.g., as determined using a regulatory agency-approved assay or kit). The subject can be a subject with a tumor(s) that is positive for dysregulation of a NTRK gene, a Trk protein, or expression or activity, or level of the same (e.g., identified as positive using a regulatory agency-approved, e.g., FDA-approved, assay or kit). The subject can be a subject whose tumors have dysregulation of a NTRK gene, a Trk protein, or expression or activity, or a level of the same (e.g., where the tumor is identified as such using a regulatory agency-approved, e.g., FDA-approved, kit or assay). In some embodiments, the subject is suspected of having a Trk-associated cancer. In some embodiments, the subject has a clinical record indicating that the subject has a tumor that has dysregulation of a NTRK gene, a Trk protein, or expression or activity, or level of the same (and optionally the clinical record indicates that the subject should be treated with any of the compositions provided herein).

The term "Trk" or "Trk protein" includes any of the Trk proteins described herein (e.g., a TrkA, a TrkB, or a TrkC protein).

The term "NTRK gene" includes any of the NTRK genes described herein (e.g., a NTRK1, a NTRK2, or a NTRK3 gene).

The term "wildtype" or "wild-type" describes a nucleic acid (e.g., a NTRK gene or a Trk mRNA) or protein (e.g., a Trk protein) that is found in a subject that does not have a Trk-associated cancer (and optionally also does not have an increased risk of developing a Trk-associated cancer or condition and/or is not suspected of having a Trk-associated cancer or condition) or is found in a cell or tissue from a subject that does not have a Trk-associated cancer or condition (and optionally also does not have an increased risk of developing a Trk-associated cancer or condition and/or is not suspected of having a Trk-associated cancer or condition).

The term "regulatory agency" is a country's agency for the approval of the medical use of pharmaceutical agents with the country. For example, a non-limiting example of a regulatory agency is the U.S. Food and Drug Administration (FDA).

The phrase "dysregulation of a NTRK gene, a Trk protein, or expression or activity, or level of the same" is a genetic mutation (e.g., a NTRK gene translocation that results in the expression of a fusion protein, a deletion in a NTRK gene that results in the expression of a Trk protein that includes a deletion of at least one amino acid as compared to the wild-type Trk protein, or a mutation in a NTRK gene that results in the expression of a Trk protein with one or more point mutations, an alternative spliced version of a Trk mRNA that results in a Trk protein that results in the deletion of at least one amino acid in the Trk protein as compared to the wild-type Trk protein), or a NTRK gene duplication that results in overexpression of a Trk protein) or an autocrine activity resulting from the overexpression of a NTRK gene a cell, that results in a pathogenic increase in the activity of a kinase domain of a Trk protein (e.g., a constitutively active kinase domain of a Trk protein) in a cell. For example, a dysregulation of a NTRK gene, a Trk protein, or expression or activity, or level of the same, can be a mutation in a NTRK1, NTRK2, or NTRK3 gene that encodes a Trk protein that is constitutively active or has increased activity as compared to a protein encoded by a NTRK1, NTRK2, or NTRK3 gene that does not include the mutation. For example, a dysregulation of a NTRK gene, a Trk protein, or expression or activity, or level of the same, can be the result of a gene translocation which results in the expression of a fusion protein that contains a first portion of TrkA, TrkB, or TrkC that includes a functional kinase domain, and a second portion of a partner protein (i.e., that is not TrkA, TrkB, or TrkC). A gene encoding a fusion protein can include, e.g., the following exons of a wild-type NTRK1 gene: exons 10-19, exons 12-19, exons 12-19, exons 13-19, exons 14-19, or exons 15-19. A gene encoding a fusion protein can include, e.g., the following exons of a wild-type NTRK2 gene: exons 12-21, exons 13-21, exons 15-21, exons 16-21, or exons 17-21. A gene encoding a fusion protein can include, e.g., the following exons of a wild-type NTRK3 gene: exons 17-22 or exons 16-22. Non-limiting examples of fusion proteins that are a result of a NTRK gene translocation are described in Tables 1, 3, and 4.

A dysregulation of a NTRK gene, a Trk protein, or expression or activity, or level of the same, can, e.g., include a mutation(s) in a NTRK1, NTRK2, or NTRK3 gene that results in a TrkA, TrkB, or TrkC containing at least one (e.g., two, three, four, or five) point mutations (e.g., one of more of the point mutations listed in Table 6). A dysregulation of a NTRK gene, a Trk protein, or expression or activity, or level of the same, can, e.g., include a mutation in a NTRK2 gene that results in a TrkB protein including a point mutation of V673M. A dysregulation of a NTRK gene, a Trk protein, or expression or activity, or level of the same, can, e.g., include a mutation in a NTRK3 gene that results in a TrkC protein including a point mutation of H677Y.

A dysregulation of a NTRK gene, a Trk protein, or expression or activity, or level of the same, can be a mutation in a NTRK1, NTRK2, or NTRK3 gene that results in a deletion of one or more contiguous amino acids (e.g., at least two, at least three, at least four, at least 5, at least 6, at least 7, at least 8, at least 9, at least 10, at least 15, at least 20, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 210, at least 220, at least 230, at least 240, at least 250, at least 260, at least 270, at least 280, at least 290, at least 300, at least 310, at least 320, at least 330, at least 340, at least 350, at least 360, at least 370, at least 380, at least 390, or at least 400 amino acids) in the TrkA, TrkB, or TrkC protein (except for the deletion of amino acids in the kinase domain of TrkA, TrkB, or TrkC that would result in inactivation of the kinase domain). In some embodiments, dysregulation of a NTRK gene, a Trk protein, or expression or activity, or level of the same, can include a deletion in a NTRK1 gene that results in a TrkA protein that lacks the NGF-binding site or exon 10, which includes the NGF binding site, the latter of which is associated with acute myeloid leukemia.

In some examples, a dysregulation of a NTRK gene, a Trk protein, or expression or activity, or level of the same, can include an alternate spliced form of a Trk mRNA, e.g., a TrkAIII spliced variant or an alternative spliced form of a TrkA mRNA that results in the production of a TrkA protein that lacks the amino acids encoded by exon 10. In some examples, a dysregulation of a NTRK gene, a Trk protein, or expression or activity, or level of the same, includes an amplification of a NTRK gene (e.g., one, two, three, or four additional copies of the NTRK gene) that can result, e.g., in an autocrine expression of a NTRK gene in a cell.

The term "Trk-associated cancer or tumor" is a cancer that is associated with dysregulation of a NTRK gene, a Trk protein, or expression or activity, or level of the same (e.g., a cancer that is associated with at least one example (e.g., two, three, four, or five examples) of dysregulation of a NTRK gene, a Trk protein, or expression or activity, or level of the same, described herein).

The term "mammal" as used herein, refers to a warm-blooded animal that has or is at risk of developing a disease described herein and includes, but is not limited to, guinea pigs, dogs, cats, rats, mice, hamsters, and primates, including humans.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In particular, a therapeutically effective amount, when administered to a subject in need of such treatment, is sufficient to (i) treat or prevent a particular disease, condition, or disorder which can be treated with an inhibitor of TrkA and/or TrkB, (ii) attenuate, ameliorate, or eliminate one or more symptoms of the particular disease, condition, or disorder, or (iii) prevent or delay the onset of one or more symptoms of the particular disease, condition, or disorder described herein. The amount of crystalline form (I-HS) that will correspond to such a therapeutically effective amount will vary depending upon factors such the disease condition and its severity, the identity (e.g., weight) of the mammal in need of treatment, but can nevertheless be routinely determined by one skilled in the art.

As used herein, the term "composition" is intended to encompass a product comprising the specified ingredients in the specified amounts, as well as any product which results, directly or indirectly, from combinations of the specified ingredients in the specified amounts.

To provide a more concise description, some of the quantitative expressions given herein are not qualified with the term "about." It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

In some embodiments, the term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

The term "about" preceding one or more peak positions in an X-ray powder diffraction pattern means that all of the peaks of the group which it precedes are reported in terms of angular positions (two theta) with an allowable variability of ±0.3°. The variability of ±0.3° is intended to be used when comparing two powder X-ray diffraction patterns. In practice, if a diffraction pattern peak from one pattern is assigned a range of angular positions (two theta) which is the measured peak position±0.3° and if those ranges of peak positions overlap, then the two peaks are considered to have the same angular position. For example, if a peak from one pattern is determined to have a position of 11.00, for comparison purposes the allowable variability allows the peak to be assigned a position in the range of 10.7°-11.3°.

The term "about" preceding a value for DSC, TGA, TG, or DTA, which are reported as degrees Celsius, have an allowable variability of ±5° C.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any range therein.

In some embodiments, a liquid formulation as provided herein contains, per unit dosage unit, about 20 mg, about 30 mg, about 40 mg, about 50 mg, about 100 mg, about 150 mg, about 200 mg, about 250 mg, about 300 mg, about 400 mg, or about 500 mg of a compound of Formula (I), a pharmaceutically acceptable salt thereof, or a combination thereof. The dosages, however, may be varied depending upon the requirement of the patients, the severity of the condition being treated and the compound being employed. In some embodiments, the dosages are administered once daily (QD) or twice daily (BID).

The daily dosage of a compound of Formula (I), a pharmaceutically acceptable salt thereof, or a combination thereof in a liquid formulation as described herein may be varied over a wide range from 1.0 to 10,000 mg per adult human per day, or higher, or any range therein. For oral administration, the compositions are preferably provided in the form of tablets containing, 0.01, 0.05, 01, 0.5, 1.0, 2.5, 5.0, 10.0, 15.0, 25.0, 500, 100, 150, 200, 250 and 500 milligrams of the active ingredient for the symptomatic adjustment of the dosage to the patient to be treated. An effective amount of the drug is ordinarily supplied at a dosage level of from about 0.1 mg/kg to about 1000 mg/kg of body weight per day, or any range therein. The range can be from about 0.5 to about 500 mg/kg of body weight per day, or any range therein. The range can be from about 1.0 to about 250 mg/kg of body weight per day, or any range therein. The range can be from about 0.1 to about 100 mg/kg of body weight per day, or any range therein. In an example, the range may be from about 0.1 to about 50.0 mg/kg of body weight per day, or any amount or range therein. In another example, the range may be from about 0.1 to about 15.0 mg/kg of body weight per day, or any range therein. In yet another example, the range may be from about 0.5 to about 7.5 mg/kg of body weight per day, or any amount or range therein. A liquid formulation as provided herein may be administered on a regimen of 1 to 4 times per day or in a single daily dose.

Optimal dosages to be administered may be readily determined by those skilled in the art, and will vary with the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts. For example, determining proper dosages for pediatric patients can be determined using known methods, including weight, age, and models such as Simrcyp4 Pediatric Simulation modeling (CERTARA, Princeton, N.J.) which can be used to establish a pharmacokinetic approach for dosing that takes into account patient age, ontogeny of the clearance pathways that a compound of formula (I), a pharmaceutically acceptable salt thereof, or a combination thereof, and body surface area (BSA).

The liquid formulations provided herein can be administered through a number of different routes including oral administration, intranasal administration, and administration through an enteral feeding or gastrostomy tube.

Acronyms found in the specification have the following meanings:

| | |
|---|---|
| ATP | adenosine triphosphate |
| DI | deionized |
| EtOH | ethanol |
| GC | gas chromatography |
| MOPS | 3-(N-morpholino)-propanesulfonic acid |
| MTBE | methyl tert-butyl ether |
| PDA | photodiode array |
| RRT | relative retention time |
| RT | room temperature |
| THF | tetrahydrofuran |
| TMB | 3,3',5,5'-tetramethylbenzidine |

The following examples illustrate the invention and are set forth to aid in the understanding of the invention, and are not intended and should not be construed to limit in any way the invention set forth in the claims which follow thereafter.

In the examples described below, unless otherwise indicated all temperatures are set forth in degrees Celsius. Reagents were purchased from commercial suppliers such as Sigma-Aldrich Chemical Company, EMD, JT Baker, or Pharco-Aaper, and were used without further purification unless otherwise indicated. Tetrahydrofuran (THF), heptane and other organic solvents were purchased from commercial suppliers, such as Sigma-Aldrich Chemical Company, ACROS, Alfa-Aesar, Lancaster, TCI, or Maybridge, and used as received.

One skilled in the art will recognize that, where not otherwise specified, the reaction step(s) is performed under suitable conditions, according to known methods, to provide the desired product. One skilled in the art will also recognize that wherein a reaction step as disclosed herein may be carried out in a variety of solvents or solvent systems, said reaction step may also be carried out in a mixture of the suitable solvents or solvent systems. One skilled in the art will recognize that, in the specification and claims as presented herein, wherein a reagent or reagent class/type (e.g. base, solvent, etc.) is recited in more than one step of a process, the individual reagents are independently selected for each reaction step and may be the same of different from each other. For example, wherein two steps of a process recite an organic or inorganic base as a reagent, the organic or inorganic base selected for the first step may be the same or different than the organic or inorganic base of the second step.

The reactions set forth below were done generally under a positive pressure of nitrogen (unless otherwise stated) in "ACS grade" solvents, and the reaction flasks were typically fitted with rubber septa for the introduction of substrates and reagents via syringe or addition funnel.

Two reversed-phase high performance liquid chromatography (HPLC) systems were used for in-process monitoring and analysis, using acetonitrile and water/trifluoroacetic acid as mobile phases. One system employed an Agilent Zorbax Extend C18 column at 264 nm, while the other system (hereinafter, "TRK1PM1 HPLC") included a Waters Xbridge Phenyl Column at 268 nm. Unless otherwise specified, the former system was used. The silica for both systems was stirred in a flask with the compound, and then filtered through a polypropylene cloth before being analyzed.

Figure 7:
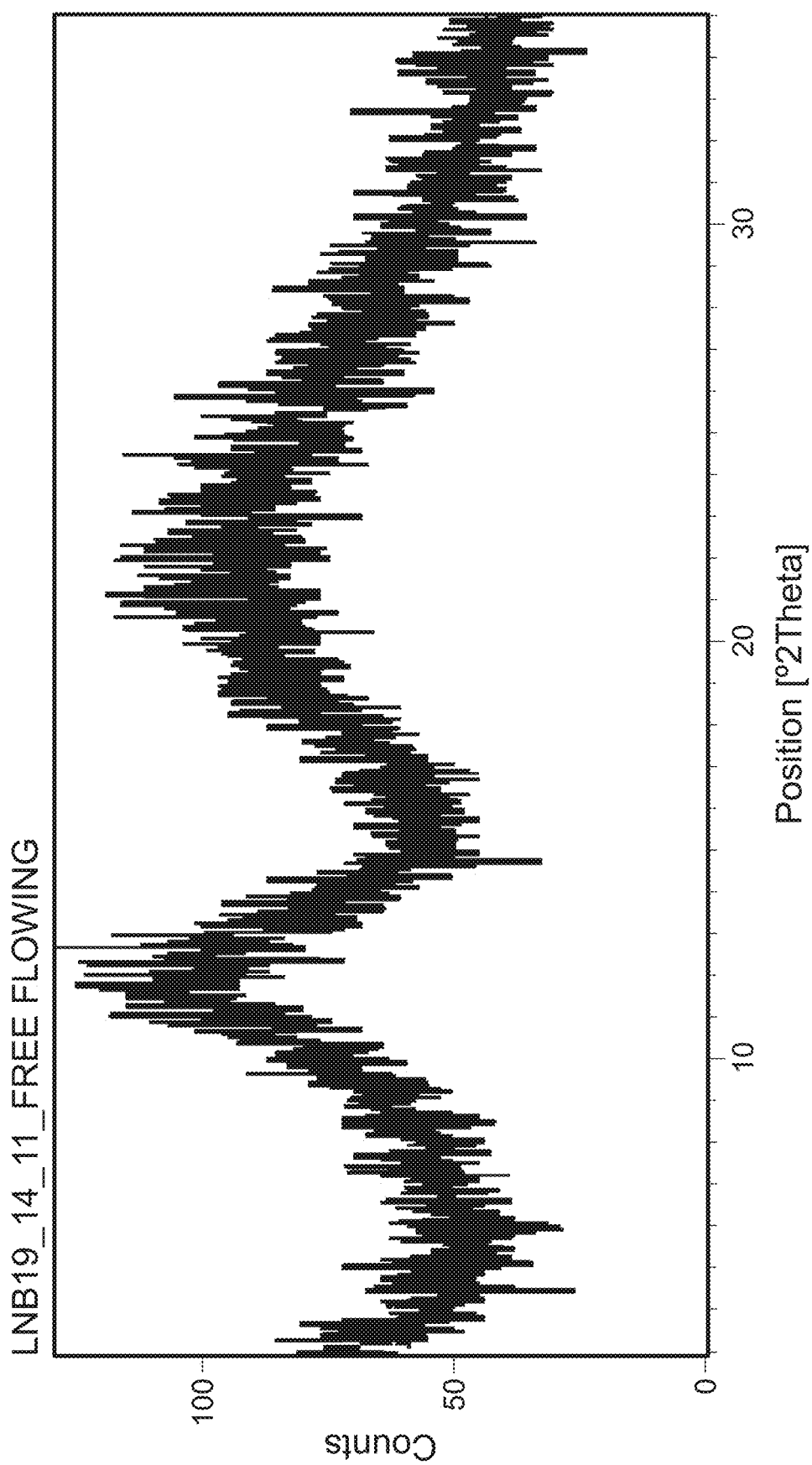
FIG. 7 illustrates an XRPD pattern of the amorphous freebase form of a compound of Formula I, according to one embodiment.

Amorphous Freebase Form of Compound of Formula I:

About 1 gram of (S)—N-(5-((R)-2-(2,5-difluorophenyl)pyrrolidin-1-yl)-pyrazolo[1,5-a]pyrimidin-3-yl)-3-hydroxypyrrolidine-1-carboxamide is dissolved in minimum amount of water and cooled to a temperature of about −26° Celsius followed by drying in the freeze dryer for 24 hours. About 20 mg of the amorphous material obtained from the freeze dryer was weighed in a vial, to which 5 volume aliquots of an appropriate solvent system was added. The mixture was checked for dissolution and if no dissolution was apparent, the mixture was heated to about 40° Celsius and checked again. This procedure was continued until dissolution was observed or until 100 volumes of solvent had been added. The XRPD pattern of the amorphous material obtained from the freeze drying experiment is shown in FIG. 7.

Amorphous hydrogen sulfate salt of compound of Formula I was prepared as described in Example 14A in WO 2010/048314 (see Example 3). The XRPD patterns of the two different lots of amorphous material prepared by this method are show in FIG. 28.

Also provided herein is a process for the preparation of crystalline form (I-HS). In some embodiments, the process comprises the steps as shown in Scheme 1.

In some embodiments, provided herein is a process for the preparation of crystalline form (I-HS), comprising:

(a) adding concentrated sulfuric acid to a solution of (S)—N-(5-((R)-2-(2,5-difluorophenyl)pyrrolidin-1-yl)-pyrazolo[1,5-a]pyrimidin-3-yl)-3-hydroxypyrrolidine-1-carboxamide in EtOH to form the hydrogen sulfate salt of (S)—N-(5-((R)-2-(2,5-difluorophenyl)pyrrolidin-1-yl)-pyrazolo[1,5-a]pyrimidin-3-yl)-3-hydroxypyrrolidine-1-carboxamide;

(b) adding heptane to the solution in Step (a) to form a slurry;

(c) filtering the slurry to isolate (S)—N-(5-((R)-2-(2,5-difluorophenyl)pyrrolidin-1-yl)-pyrazolo[1,5-a]pyrimidin-3-yl)-3-hydroxypyrrolidine-1-carboxamide hydrogen sulfate;

(d) mixing said (S)—N-(5-((R)-2-(2,5-difluorophenyl)pyrrolidin-1-yl)-pyrazolo[1,5-a]pyrimidin-3-yl)-3-hydroxypyrrolidine-1-carboxamide hydrogen sulfate with a 5:95 w/w solution of water/2-butanone;

(e) heating the mixture from step (d) at about 65-70° C. with stirring until the weight percent of ethanol is about 0.5% to form a slurry of the crystalline form of (S)—N-(5-((R)-2-(2,5-difluorophenyl)pyrrolidin-1-yl)-pyrazolo[1,5-a]pyrimidin-3-yl)-3-hydroxypyrrolidine-1-carboxamide hydrogen sulfate; and (f) isolating the crystalline form of (S)—N-(5-((R)-2-(2,5-difluorophenyl)pyrrolidin-1-yl)-pyrazolo[1,5-a]pyrimidin-3-yl)-3-hydroxypyrrolidine-1-carboxamide hydrogen sulfate by filtration.

In some embodiments, the above method further comprises: (b1) seeding the solution from step (a) with (S)—N-(5-((R)-2-(2,5-difluorophenyl)pyrrolidin-1-yl)-pyrazolo[1,5-a]pyrimidin-3-yl)-3-hydroxypyrrolidine-1-carboxamide hydrogen sulfate at room temperature and allowing the solution to stir until a slurry forms.

In some embodiments, provided herein is a process for the preparation of crystalline form (I-HS), comprising:

(a) reacting 5-chloro-3-nitropyrazolo[1,5-a]pyrimidine with (R)-2-(2,5-difluorophenyl)-pyrrolidine (R)-2-hydroxysuccinate in the presence of a base to form (R)-5-(2-(2,5-difluorophenyl)pyrrolidin-1-yl)-3-nitropyrazolo[1,5-a]pyrimidine;

(b) treating said (R)-5-(2-(2,5-difluorophenyl)pyrrolidin-1-yl)-3-nitropyrazolo[1,5-a]pyrimidine with Zn and hydrochloric acid to form (R)-5-(2-(2,5-difluorophenyl)pyrrolidin-1-yl)pyrazolo[1,5-a]pyrimidin-3-amine;

(c) treating said (R)-5-(2-(2,5-difluorophenyl)pyrrolidin-1-yl)pyrazolo[1,5-a]pyrimidin-3-amine with a base and phenyl chloroformate to form phenyl (R)-(5-(2-(2,5-difluorophenyl)pyrrolidin-1-yl)pyrazolo[1,5-a]pyrimidin-3-yl)carbamate;

(d) reacting said phenyl (R)-(5-(2-(2,5-difluorophenyl)pyrrolidin-1-yl)pyrazolo[1,5-a]pyrimidin-3-yl)carbamate with (S)-pyrrolidin-3-ol to form (S)—N-(5-((R)-2-(2,5-difluorophenyl)pyrrolidin-1-yl)pyrazolo[1,5-a]pyrimidin-3-yl)-3-hydroxypyrrolidine-1-carboxamide;

(e) adding sulfuric acid to said (S)—N-(5-((R)-2-(2,5-difluorophenyl)pyrrolidin-1-yl)pyrazolo[1,5-a]pyrimidin-3-yl)-3-hydroxypyrrolidine-1-carboxamide form (S)—N-(5-((R)-2-(2,5-difluorophenyl)pyrrolidin-1-yl)-pyrazolo[1,5-a]pyrimidin-3-yl)-3-hydroxypyrrolidine-1-carboxamide hydrogen sulfate; and (f) isolating the crystalline form of (S)—N-(5-((R)-2-(2,5-difluorophenyl)pyrrolidin-1-yl)-pyrazolo[1,5-a]pyrimidin-3-yl)-3-hydroxypyrrolidine-1-carboxamide hydrogen sulfate.

In some embodiments of the above step (a), the base is an amine base, such as triethylamine.

In some embodiments of the above step (c), the base is an alkali metal base, such as an alkali metal carbonate, such as potassium carbonate.

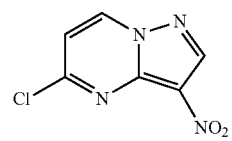

Preparation A

Preparation of 5-chloro-3-nitropyrazolo[1,5-a]pyrimidine

Step A—Preparation of Sodium pyrazolo[1,5-a]pyrimidin-5-olate

A solution of 1H-pyrazol-5-amine and 1,3-dimethylpyrimidine-2,4(1H,3H)-dione (1.05 equiv.) were charged to a round bottom flask outfitted with a mechanical stirrer, a steam pot, a reflux condenser, a J-Kem temperature probe and an N2 adaptor for positive N2 pressure control. Under mechanical stirring the solids were suspended with 4 vol. (4 mL/g) of absolute EtOH under a nitrogen atmosphere, then charged with 2.1 equivalents of NaOEt (21 wt % solution in EtOH), and followed by line-rinse with 1 vol. (1 mL/g) of absolute EtOH. The slurry was warmed to about 75° Celsius and stirred at gentle reflux until less than 1.5 area % of 1H-pyrazol-5-amine was observed by TRK1PM1 HPLC to follow the progression of the reaction using 20 μL of slurry diluted in 4 mL deionized water and 5 μL injection at 220 nm.

After 1 additional hour, the mixture was charged with 2.5 vol. (2.5 mL/g) of heptane and then refluxed at 700 Celsius for 1 hour. The slurry was then cooled to room temperature overnight. The solid was collected by filtration on a tabletop funnel and polypropylene filter cloth. The reactor was rinsed and charged atop the filter cake with 4 vol. (4 mL/g) of heptane with the cake pulled and the solids being transferred to tared drying trays and oven-dried at 45° Celsius under high vacuum until their weight was constant. Pale yellow solid sodium pyrazolo[1,5-a]-pyrimidin-5-olate was obtained in 93-96% yield (corrected) and larger than 99.5 area % observed by HPLC (1 mg/mL dilution in deionized water, TRK1PM1 at 220 nm).

Step B—Preparation of 3-nitropyrazolo[15-a]pyrimidin-5(4H)-one

A tared round bottom flask was charged with sodium pyrazolo[1,5-a]pyrimidin-5-olate that was dissolved at 40-45° Celsius in 3.0 vol. (3.0 mL/g) of deionized water, and then concentrated under high vacuum at 650 Celsius in a water-bath on a rotary evaporator until 2.4× weight of starting material was observed (1.4 vol/1.4 mL/g deionized water content). Gas chromatography (GC) for residual EtOH (30 μL of solution dissolved in ~1 mL MeOH) was performed showing less than 100 ppm with traces of ethyl nitrate fumes being observed below upon later addition of HNO₃. In some cases, the original solution was charged with an additional 1.5 vol. (1.5 mL/g) of DI water, then concentrated under high vacuum at 650 Celsius in a water-bath on a rotary evaporator until 2.4× weight of starting material was observed (1.4 vol/1.4 mL/g DI water content). Gas chromatograph for residual EtOH (30 µL of solution dissolved in about 1 mL MeOH) was performed showing <<100 ppm of residual EtOH without observing any ethyl nitrate fumes below upon later addition of HNO₃.

A round bottom vessel outfitted with a mechanical stirrer, a steam pot, a reflux condenser, a J-Kem temperature probe and an N2 adaptor for positive N2 pressure control was charged with 3 vol. (3 mL/g, 10 equiv) of >90 wt % HNO₃ and cooled to about 10° Celsius under a nitrogen atmosphere using external ice-water cooling bath under a nitrogen atmosphere. Using a pressure equalizing addition funnel, the HNO₃ solution was charged with the 1.75-1.95 volumes of a deionized water solution of sodium pyrazolo[1,5-a]pyrimidin-5-olate (1.16-1.4 mL DI water/g of sodium pyrazolo[1,5-a]pyrimidin-5-olate) at a rate to maintain 35-40° Celsius internal temperature under cooling. Two azeotropes were observed without any ethyl nitrate fumes. The azeotrope flask, the transfer line (if applicable) and the addition funnel were rinsed with 2×0.1 vol. (2×0.1 mL/g) deionized water added to the reaction mixture. Once the addition was complete, the temperature was gradually increased to about 45-50° Celsius for about 3 hours with HPLC showing >99.5 area % conversion of sodium pyrazolo[1,5-a]pyrimidin-5-olate to 3-nitropyrazolo[1,5-a]pyrimidin-5(4H)-one.

Step C—Preparation of 5-chloro-3-nitropyrazolo[1,5-a]pyrimidine 3-nitropyrazolo[1,5-a]pyrimidin-5(4H)-one was charged to a round bottom flask outfitted with a mechanical stirrer, a heating mantle, a reflux condenser, a J-Kem temperature probe and an N2 adaptor for positive N2 pressure control. Under mechanical stirring the solids were suspended with 8 volumes (8 mL/g) of CH₃CN, and then charged with 2,6-lutitine (1.05 equiv) followed by warming the slurry to about 50° Celsius. Using a pressure equalizing addition funnel, the mixture was dropwise charged with 0.33 equivalents of POCl₃. This charge yielded a thick, beige slurry of a trimer that was homogenized while stirring until a semi-mobile mass was observed. An additional 1.67 equivalents of POCl₃ was charged to the mixture while allowing the temperature to stabilize, followed by warming the reaction mixture to a gentle reflux (78° Celsius). Some puffing was observed upon warming the mixture that later subsided as the thick slurry got thinner.

The reaction mixture was allowed to reflux until complete dissolution to a dark solution and until HPLC (20 µL diluted in 5 mL of CH₃CN, TRK1PM1 HPLC, 5 µL injection, 268 nm) confirmed that no more trimer (RRT 0.92) was present with less than 0.5 area % of 3-nitropyrazolo[1,5-a]pyrimidin-5(4H)-one (RRT 0.79) being observed by manually removing any interfering and early eluting peaks related to lutidine from the area integration. On a 1.9 kg scale, 0 area % of the trimer, 0.25 area % of 3-nitropyrazolo[1,5-a]pyrimidin-5(4H)-one, and 99.5 area % of 5-chloro-3-nitropyrazolo[1,5-a]pyrimidine was observed after 19 hours of gentle reflux using TRK1PM1 HPLC at 268 nm Preparation B

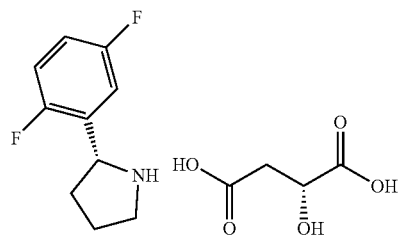

Preparation of (R)-2-(2,5-difluorophenyl)-pyrrolidine (R)-2-hydroxysuccinate

Step A—Preparation of tert-butyl (4-(2,5-difluorophenyl)-4-oxobutyl)-carbamate 2-bromo-1,4-difluorobenzene (1.5 eq.) was dissolved in 4 volumes of THF (based on weight of tert-butyl 2-oxopyrrolidine-1-carboxylate) and cooled to about 5° Celsius. A solution of 2.0 M iPrMgCl in THF (1.4 eq.) was added over 2 hours to the mixture while maintaining a reaction temperature below 25° Celsius. The solution was allowed to cool to about 5° Celsius and stirred for 1 hour (GC analysis confirmed Grignard formation). A solution of tert-butyl 2-oxopyrrolidine-1-carboxylate (1.0 eq.) in 1 volume of THF was added over about 30 min while maintaining a reaction temperature below 25° Celsius. The reaction was stirred at about 50 Celsius for 90 min (tert-butyl 2-oxopyrrolidine-1-carboxylate was confirmed to be less than 0.5 area % by HPLC). The reaction was quenched with 5 volumes of 2 M aqueous HCl while maintaining a reaction temperature below 45° Celsius. The reaction was then transferred to a separatory funnel adding 10 volumes of heptane and removing the aqueous layer. The organic layer was washed with 4 volumes of saturated aqueous NaCl followed by addition of 2×1 volume of saturated aqueous NaCl. The organic layer was solvent-switched to heptane (<1% wt THF confirmed by GC) at a distillation temperature of 35-55° Celsius and distillation pressure of 100-200 mm Hg for 2×4 volumes of heptane being added with a minimum distillation volume of about 7 volumes. The mixture was then diluted to 10 volumes with heptane while heating to about 55° Celsius yielded a denser solid with the mixture being allowed to cool to room temperature overnight. The slurry was cooled to less than 5° Celsius and filtered through polypropylene filter cloth. The wet cake was washed with 2×2 volumes of heptane. The solids were dried under vacuum at 550 Celsius until the weight was constant, yielding tert-butyl (4-(2,5-difluorophenyl)-4-oxobutyl)-carbamate as a white solid at about 75% to 85% theoretical yield.

Step B—Preparation of 5-(2,5-difluorophenyl)-3,4-dihydro-2H-pyrrole tert-butyl (4-(2,5-difluorophenyl)-4-oxobutyl)-carbamate was dissolved in 5 vol. of toluene with 2.2 eq. of 12M HCl being added observing a mild exotherm and gas evolution. The reaction was heated to 650 Celsius for 12-24 hours and monitored by HPLC. Upon completion the reaction was cooled to less than 15° Celsius with an ice/water bath. The pH was adjusted to about 14 with 3 equivalents of 2M aqueous NaOH (4.7 vol.). The reaction was stirred at room temperature for 1-2 hours. The mixture was transferred to a separatory funnel with toluene. The aqueous layer was removed and the organic layer was washed with 3 volumes of saturated aqueous NaCl. The organic layer was concentrated to an oil and redissolved in 1.5 volumes of heptane. The resulting suspension was filtered through a GF/F filter paper and concentrated to a light yellow oil of 5-(2,5-difluorophenyl)-3,4-dihydro-2H-pyrrole with a 90% to 100% theoretical yield.

Step C—Preparation of (R)-2-(2,5-difluorophenyl)-pyrrolidine

Chloro-1,5-cyclooctadiene iridium dimer (0.2 mol %) and (R)-2-(2-(diphenylphosphino)phenyl)-4-isopropyl-4,5-dihydrooxazole (0.4 mol %) were suspended in 5 volumes of MTBE (based on 5-(2,5-difluorophenyl)-3,4-dihydro-2H-pyrrole) at room temperature. The mixture was stirred for 1 hour and most of the solids dissolved with the solution turning dark red. The catalyst formation was monitored using an HPLC/PDA detector. The reaction was cooled to less than 50 Celsius and 5-(2,5-difluorophenyl)-3,4-dihydro-2H-pyrrole (1.0 eq.) was added using a 0.5 volumes of MTBE rinse. Diphenylsilane (1.5 eq.) was added over about 20 minutes while maintaining a reaction temperature below 10° Celsius. The reaction was stirred for 30 minutes below 10° Celsius and then allowed to warm to room temperature. The reaction was stirred overnight at room temperature. The completion of the reaction was confirmed by HPLC and then cooled to less than 5° Celsius. The reaction was quenched with 5 volumes of 2M aqueous HCl maintaining temperature below 20° Celsius. After 10 minutes the ice/water bath was removed and the reaction temperature was allowed to increase to room temperature while stirring for 2 hours. The mixture was transferred to a separatory funnel with 3 volumes of MTBE. The aqueous layer was washed with 3.5 volumes of MTBE followed by addition of 5 volumes of MTBE to the aqueous layer while adjusting the pH to about 14 by adding 0.75 volumes of aqueous 50% NaOH. The organic layer was washed with 5 volumes of aqueous saturated NaCl, then concentrated to an oil, and diluted with 3 volumes of MTBE. The solution was filtered through a polypropylene filter cloth and rinsed with 1 volume of MTBE. The filtrate was concentrated to an oil of (R)-2-(2,5-difluorophenyl)-pyrrolidine with a 95% to 100% theoretical yield and with 75-85% ee.

Step D—Preparation of (R)-2-(2,5-difluorophenyl)-pyrrolidine (R)-2-hydroxy-succinate (R)-2-(2,5-difluorophenyl)-pyrrolidine (1.0 eq.) was transferred to a round bottom flask charged with 15 volumes (corrected for potency) of EtOH (200 prf). D-malic acid (1.05 eq.) was added and the mixture was heated to 650 Celsius. The solids all dissolved at about 64° Celsius. The solution was allowed to cool to RT. At about 55° Celsius the solution was seeded with (R)-2-(2,5-difluorophenyl)-pyrrolidine (R)-2-hydroxy-succinate (about 50 mg, >97% ee) and stirred at room temperature overnight. The suspension was then filtered through a polypropylene filter cloth and washed with 2×1 volumes of EtOH (200 prf). The solids were dried under vacuum at 550 Celsius, yielding (R)-2-(2,5-difluorophenyl)-pyrrolidine (R)-2-hydroxy-succinate with a 75% to 90% theoretical yield and with >96% ee.

Referring to Scheme 1, suitable bases include tertiary amine bases, such as triethylamine, and K$_2$CO$_3$. Suitable solvents include ethanol, heptane and tetrahydrofuran (THF). The reaction is conveniently performed at temperatures between 5° Celsius and 50° Celsius. The reaction progress was generally monitored by HPLC TRK1PM1.

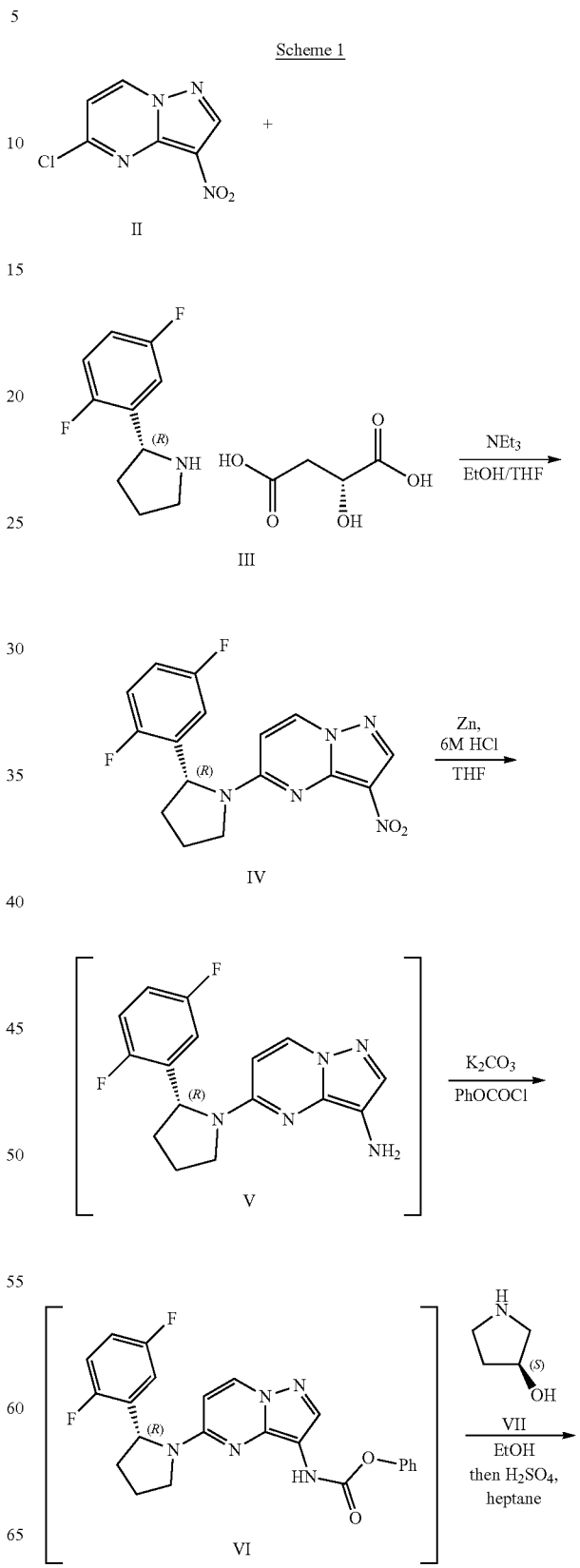

-continued

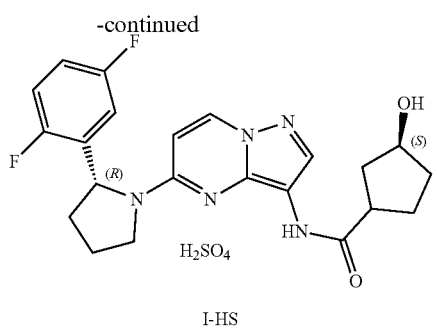

I-HS

Compounds II (5-chloro-3-nitropyrazolo[1,5-a]pyrimidine) and III ((R)-2-(2,5-difluorophenyl)-pyrrolidine (R)-2-hydroxysuccinate, 1.05 eq.) were charged to a round bottom flask outfitted with a mechanical stirrer, a J-Kem temperature probe and an N2 adaptor for positive N2 pressure control. A solution of 4:1 EtOH:THF (10 mL/g of compound II) was added and followed by addition of triethylamine (NEt$_3$, 3.50 eq.) via addition funnel with the temperature reaching about 40° Celsius during addition. Once the addition was complete, the reaction mixture was heated to 500 Celsius and stirred for 0.5-3 hours to yield compound IV.

To a round bottom flask equipped with a mechanical stirrer, a J-Kem temperature probe, and an N2 inlet compound IV was added and followed by addition of tetrahydrofuran (10 mL/g of compound IV). The solution was cooled to less than 5° Celsius in an ice bath, and Zn (9-10 eq.) was added. 6M HCl (9-10 eq.) was then added dropwise at such a rate to keep the temperature below 30° Celsius (for 1 kg scale the addition took about 1.5 hours). Once the exotherm subsided, the reaction was allowed to warm to room temperature and was stirred for 30-60 min until compound IV was not detected by HPLC. At this time, a solution of potassium carbonate (K$_2$CO$_3$, 2.0 eq.) in water (5 mL/g of compound IV) was added all at once and followed by rapid dropwise addition of phenyl chloroformate (PhOCOCl, 1.2 eq.). Gas evolution (CO$_2$) was observed during both of the above additions, and the temperature increased to about 30° Celsius after adding phenyl chloroformate. The carbamate formation was stirred at room temperature for 30-90 min. HPLC analysis immediately followed to run to ensure less than 1 area % for the amine being present and high yield of compound VI in the solution.

To the above solution amine VII ((S)-pyrrolidin-3-ol, 1.1 eq. based on theoretical yield for compound VI) and EtOH (10 mL/g of compound VI) was added. Compound VII was added before or at the same time as EtOH to avoid ethyl carbamate impurities from forming. The above EtOH solution was concentrated to a minimum volume (4-5 mL/g) using the batch concentrator under reduced pressure (THF levels should be <5% by GC), and EtOH (10 mL/g of compound VI) was back-added to give a total of 10 mL/g. The reaction was then heated at 500 Celsius for 9-19 hours or until HPLC shows that compound VI is less than 0.5 area %. The reaction was then cooled to room temperature, and sulfuric acid (H$_2$SO$_4$, 1.0 eq. to compound VI) was added via addition funnel to yield compound I-HS with the temperature usually exotherming at about 30° Celsius.

Example 1

Preparation of Crystalline Form (I-HS) (Method 1)

(S)—N-(5-((R)-2-(2,5-difluorophenyl)pyrrolidin-1-yl)-pyrazolo[1,5-a]pyrimidin-3-yl)-3-hydroxypyrrolidine-1-carboxamide (0.500 g, 1.17 mmol) was dissolved in EtOH (2.5 mL) and cooled to about 5° Celsius. Concentrated sulfuric acid (0.0636 mL, 1.17 mmol) was added to the cooled solution and stirred for about 10 min, while warming to room temperature. Methyl tert-butyl ether (MTBE) (2 mL) was slowly added to the mixture, resulting in the product gumming out. EtOH (2.5 mL) was then added to the mixture and heated to about reflux until all solids were dissolved. Upon cooling to room temperature and stirring for about 1 hour, some solids formed. After cooling to about 5° Celsius, the solids were filtered and washed with MTBE. After filtration and drying at air for about 15 minutes, (S)—N-(5-((R)-2-(2,5-difluorophenyl)pyrrolidin-1-yl)-pyrazolo[1,5-a]pyrimidin-3-yl)-3-hydroxypyrrolidine-1-carboxamide hydrogen sulfate was isolated as a solid.

Example 2

Preparation of Crystalline Form (I-HS) (Method 2)

Concentrated sulfuric acid (392 mL) was added to a solution of 3031 g of (S)—N-(5-((R)-2-(2,5-difluorophenyl)pyrrolidin-1-yl)-pyrazolo[1,5-a]pyrimidin-3-yl)-3-hydroxypyrrolidine-1-carboxamide in 18322 mL EtOH to form the hydrogen sulfate salt. The solution was seeded with 2 g of (S)—N-(5-((R)-2-(2,5-difluorophenyl)pyrrolidin-1-yl)-pyrazolo[1,5-a]pyrimidin-3-yl)-3-hydroxypyrrolidine-1-carboxamide hydrogen sulfate and the solution was stirred at room temperature for at least 2 hours to form a slurry of the hydrogen sulfate salt. Heptane (20888 g) was added and the slurry was stirred at room temperature for at least 60 min. The slurry was filtered and the filter cake was washed with 1:1 heptane/EtOH. The solids were then dried under vacuum at ambient temperature (oven temperature set at 150 Celsius).

The dried hydrogen sulfate salt (6389 g from 4 combined lots) was added to a 5:95 w/w solution of water/2-butanone (total weight 41652 g). The mixture was heated at about 680 Celsius with stirring until the weight percent of ethanol was about 0.5%, during which time a slurry formed. The slurry was filtered, and the filter cake was washed with a 5:95 w/w solution of water/2-butanone. The solids were then dried under vacuum at ambient temperature (oven temperature set at 150 Celsius) to provide the crystalline form of (S)—N-(5-((R)-2-(2,5-difluorophenyl)-pyrrolidin-1-yl)-pyrazolo[1,5-a]pyrimidin-3-yl)-3-hydroxypyrrolidine-1-carboxamide hydrogen sulfate.

Example 3

Preparation of Amorphous Form AM(HS)

To a solution of (S)—N-(5-((R)-2-(2,5-difluorophenyl)pyrrolidin-1-yl)pyrazolo[1,5-a]pyrimidin-3-yl)-3-hydroxypyrrolidine-1-carboxamide (9.40 g, 21.94 mmol) in MeOH (220 mL) was slowly added sulfuric acid (0.1 M in MeOH, 219.4 mL, 21.94 mmol) at ambient temperature under rapid stirring. After 30 minutes, the reaction was first concentrated by rotary evaporator to near dryness, then on high vacuum for 48 h to provide amorphous form of (S)—N-(5-((R)-2-(2,5-difluorophenyl)pyrrolidin-1-yl)pyrazolo[1,5-a]pyrimidin-3-yl)-3-hydroxypyrrolidine-1-carboxamide sulfate (11.37 g, 21.59 mmol, 98.43% yield). LCMS (apci m/z 429.1, M+H).

Example 4

Preparation of Crystalline HCl Salt of Formula I

A mixture of (S)—N-(5-((R)-2-(2,5-difluorophenyl)pyrrolidin-1-yl)pyrazolo[1,5-a]pyrimidin-3-yl)-3-hydroxypyrrolidine-1-carboxamide (0.554 g, 1.29 mmol) in EtOH (6 mL, 200 proof) and MTBE (10 mL) was heated to 50° C. while stirring to obtain a solution, followed by addition of hydrogen chloride (conc.) (0.108 mL, 1.29 mmol) in one portion. The reaction mixture was then allowed to cool to ambient temperature first, then cooled to about 5° C. in an ice-water bath with stirring to induce crystallization. The suspension was stirred for 4 h in the ice-water bath before it was vacuum-filtered, with the filter cake rinsed with MTBE and dried under vacuum at 55° C. to constant weight, yielding crystalline (S)—N-(5-((R)-2-(2,5-difluorophenyl) pyrrolidin-1-yl)pyrazolo[1,5-a]pyrimidin-3-yl)-3-hydroxypyrrolidine-1-carboxamide hydrochloride (0.534 g, 89% yield). LCMS (apci m/z 429.2, M+H).

Preparation of Crystalline HBr Salt of Formula I

A mixture of (S)—N-(5-((R)-2-(2,5-difluorophenyl)pyrrolidin-1-yl)pyrazolo[1,5-a]pyrimidin-3-yl)-3-hydroxypyrrolidine-1-carboxamide (0.505 g, 1.18 mmol) in EtOH (6 mL, 200 proof) and MTBE (10 mL) was heated to 50° C. while stirring to obtain a solution, followed by addition of hydrogen bromide (33% aq.) (0.213 mL, 1.18 mmol) in one portion. The reaction mixture was heated to reflux to obtain a mostly clear solution with small amount of oily residue on glass wall of reaction vessel. Upon cooled to ambient temperature, precipitation appeared and the oily residue solidified. The mixture was heated to 50° C. again, then allowed to cool to room temperature and stirred for overnight. The suspension was vacuum-filtered, with the filter cake rinsed with MTBE and dried under vacuum at 55° C. to constant weight, yielding crystalline (S)—N-(5-((R)-2-(2,5-difluorophenyl)pyrrolidin-1-yl)pyrazolo[1,5-a]pyrimidin-3-yl)-3-hydroxypyrrolidine-1-carboxamide hydrobromide (0.51 g, 85% yield). LCMS (apci m/z 429.3, M+H).

Preparation of Crystalline Mesylate Salt of Formula I

A mixture of (S)—N-(5-((R)-2-(2,5-difluorophenyl)pyrrolidin-1-yl)pyrazolo[1,5-a]pyrimidin-3-yl)-3-hydroxypyrrolidine-1-carboxamide (0.532 g, 1.24 mmol) in EtOH (2.7 mL, 200 proof) and MTBE (5.3 mL) was heated to 50° C. while stirring to obtain a solution, followed by addition of methanesulfonic acid (0.076 mL, 1.24 mmol) in one portion. The reaction mixture was heated to reflux to obtain a mostly clear solution with small amount of particulates. Upon cooled to ambient temperature, precipitation appeared along with some oily residue. Additional EtOH (0.5 mL, 200-proof) and methanesulfonic acid (0.010 mL) were added to obtain a solution. The reaction mixture was heated to 50° C. again, then allowed to cool to room temperature and stirred for 1 h. The suspension was vacuum-filtered, with the filter cake rinsed with MTBE and dried under vacuum at 55° C. to constant weight, yielding crystalline (S)—N-(5-((R)-2-(2,5-difluorophenyl)pyrrolidin-1-yl)pyrazolo[1,5-a]pyrimidin-3-yl)-3-hydroxypyrrolidine-1-carboxamide methanesulfonate (0.51 g, 78% yield). LCMS (apci m/z 429.4, M+H).

Preparation of Crystalline Camsylate Salt of Formula I

A mixture of (S)—N-(5-((R)-2-(2,5-difluorophenyl)pyrrolidin-1-yl)pyrazolo[1,5-a]pyrimidin-3-yl)-3-hydroxypyrrolidine-1-carboxamide (0.500 g, 1.17 mmol) and S-(+)-camphorsulfonic acid (0.271 g, 1.17 mmol) in EtOH (3 mL, 200 proof) and MTBE (5 mL) was heated to reflux while stirring to obtain a solution. Upon cooled to ambient temperature, precipitation appeared. The suspension was stirred at room temperature for overnight, then vacuum-filtered, with the filter cake rinsed with MTBE and dried under vacuum at 55° C. to constant weight, yielding crystalline (S)—N-(5-((R)-2-(2,5-difluorophenyl)pyrrolidin-1-yl)pyrazolo[1,5-a]pyrimidin-3-yl)-3-hydroxypyrrolidine-1-carboxamide ((1S,4R)-7,7-dimethyl-2-oxobicyclo[2.2.1]heptan-1-yl)methanesulfonate.

Example 5

Infantile Fibrosarcoma with NTRK3-ETV6 Fusion Successfully Treated with a Liquid Formulations of (S)—N-(5-((R)-2-(2,5-difluorophenyl)-pyrrolidin-1-yl)-pyrazolo[1,5-a]pyrimidin-3-yl)-3-hydroxypyrrolidine-1-carboxamide Materials and Methods A multicenter pediatric phase 1 dose-escalation study in patients with advanced solid or primary CNS tumors was initiated in December 2015 (ClinicalTrials.gov Identifier: NCT02637687) to evaluate the safety and tolerability of Compound I-HS (i.e., the hydrogen sulfate salt of (S)—N-(5-((R)-2-(2,5-difluorophenyl)pyrrolidin-1-yl)-pyrazolo[1,5-a]pyrimidin-3-yl)-3-hydroxypyrrolidine-1-carboxamide). Eligibility criteria included age 1-21 years regardless of the presence of a known TRK alteration, as well as those patients aged 1 month of age or greater with a known NTRK fusion and a diagnosis of infantile fibrosarcoma or congenital mesoblastic nephroma. An oral liquid formulation of Compound I-HS was developed for patients unable to swallow capsules. Simcyp® Pediatric Simulation modeling (CERTARA, Princeton, N.J.) was utilized to establish a pharmacokinetic approach for dosing that takes into account patient age, ontogeny of the clearance pathways that eliminate Compound I-HS, and body surface area (BSA). The pediatric dose selected for the initial cohort was predicted to equal the exposure achieved in adult patients taking a dose of 100 mg BID, the recommended Phase 2 adult dose. Cycles are measured in 28-day increments with continuous dosing. Response assessments by appropriate imaging modalities are scheduled every eight weeks. Patients continue on therapy until evidence of disease progression or intolerable toxicity.

A kit was provided that included a sealed graduated amber bottle containing 7.6 g of Compound I-HS; a sealed bottle containing 51 g CAVASOL® W7 HP Pharma; a sealed bottle containing 500 g trisodium citrate dihydrate; a sealed bottle containing 100 mL sterile water; a sealed pint (~473 mL) bottle of ORA-Sweet® SF; a funnel; a 28-mm press-in bottle adaptor; a box containing 56 units of 1-mL single use dosing syringes; a box containing 56 units of 5-mL single use dosing syringes; a drug product label indicating the concentration of Compound I-HS (20 mg/mL); and compounding instructions.

Figure 9:
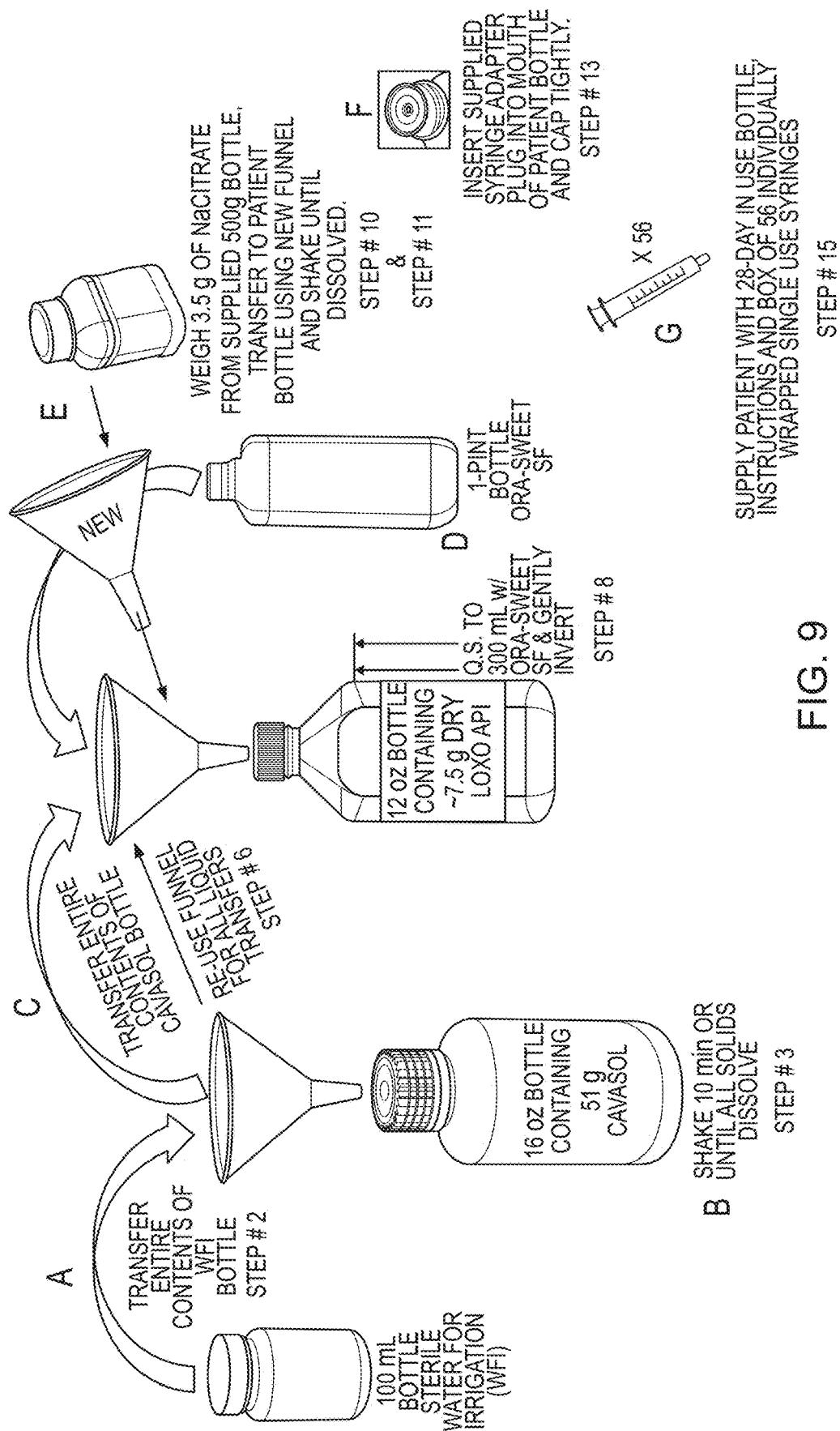
FIG. 9 is pictogram of pediatric solution formulation compounding instructions for the crystalline form (I-HS).

A liquid solution was prepared as shown in FIG. 9. First, the seal (cap) was removed from the bottle containing CAVASOL® W7 HP Pharma. Next, using the funnel, the contents of the 100 mL bottle of sterile water to were added to the bottle containing CAVASOL® W7 HP Pharma. The bottle with its cap was then closed and the bottle containing CAVASOL® W7 HP Pharma and sterile water was shaken until all of the CAVASOL® W7 HP was dissolved. Ten minutes was allowed to pass for full dissolution of the CAVASOL® W7 HP Pharma. The bottom and sides of the bottle were inspected to make sure all CAVASOL® W7 HP Pharma dissolved and was not clumped on the bottom or clinging to the sides. Next, the bottle was allowed to stand without agitation for approximately five minutes to allow the bubbles created from dissolved CAVASOL® W7 HP Pharma to dissipate. The seal (cap) from the graduated bottle containing Compound I-HS was then removed. Using the same funnel from earlier, the CAVASOL® W7 HP Pharma solution was added to the graduated bottle containing Compound I-HS. The bottle was capped and shaken by hand until dissolved. Bubbles were allowed to come to surface and a clear red solution resulted. Using the same funnel from earlier, q.s. to 300 mL with the supplied ORA-Sweet® SF. The graduated bottle was capped and gently inverted 10 times to mix the ORA-Sweet® SF with the Compound I-HS/CAVASOL® W7 HP solution while being careful not to introduce too many bubbles into the formulation. Next, 3.5 g trisodium citrate dihydrate from the provided container of Trisodium Citrate Dihydrate was weighed and added, using the second funnel in the kit, to the liquid formulation and, subsequently, the bottle was capped and the bottle was inverted ten times. The bubbles were allowed to rise to the top and the contents of the bottle were inspected to make sure all of the trisodium citrate dihydrate was fully dissolved; if it was not, the bottle was inverted an additional 10 times. Subsequently, the cap on the graduated bottle was removed and the provided 28-mm press-in bottle adaptor (syringe adaptor) was inserted in the bottle. The bottle was then closed by securely placing the cap on the bottle. The liquid formulation was then administered the desired amount of Compound I-HS using a 1 mL or 5 mL syringe, depending on patient dosing regimen.

Results

An otherwise healthy female was born with a large, vascular, right-sided neck mass extending to the face that was initially diagnosed and treated as a Rapidly Involuting Congenital Hemangioma. At 6 months of age, the mass grew rapidly and surgical excision/debulking revealed the diagnosis of IFS confirmed by an ETV6 translocation by fluorescent in situ hybridization (FISH). Within the first 7 days post-operatively, the tumor rapidly progressed, encroaching the oral cavity. Chemotherapy with vincristine, actinomycin-D and cyclophosphamide was initiated but the patient experienced disease progression during cycle 1. A new chemotherapy regimen comprised of ifosfamide and doxorubicin (ID) was started concurrently with debulking surgery and a tracheostomy was placed-for oropharyngeal obstruction. Two additional courses of ID and four courses of ifosfamide and etoposide had minimal impact on the tumor. The tumor progressed to involve the base of skull, mastoids and cervical vasculature. Gross surgical resection was performed in October 2015 by a team of multidisciplinary surgeons but clear surgical margins could not be achieved.

Figure 10:
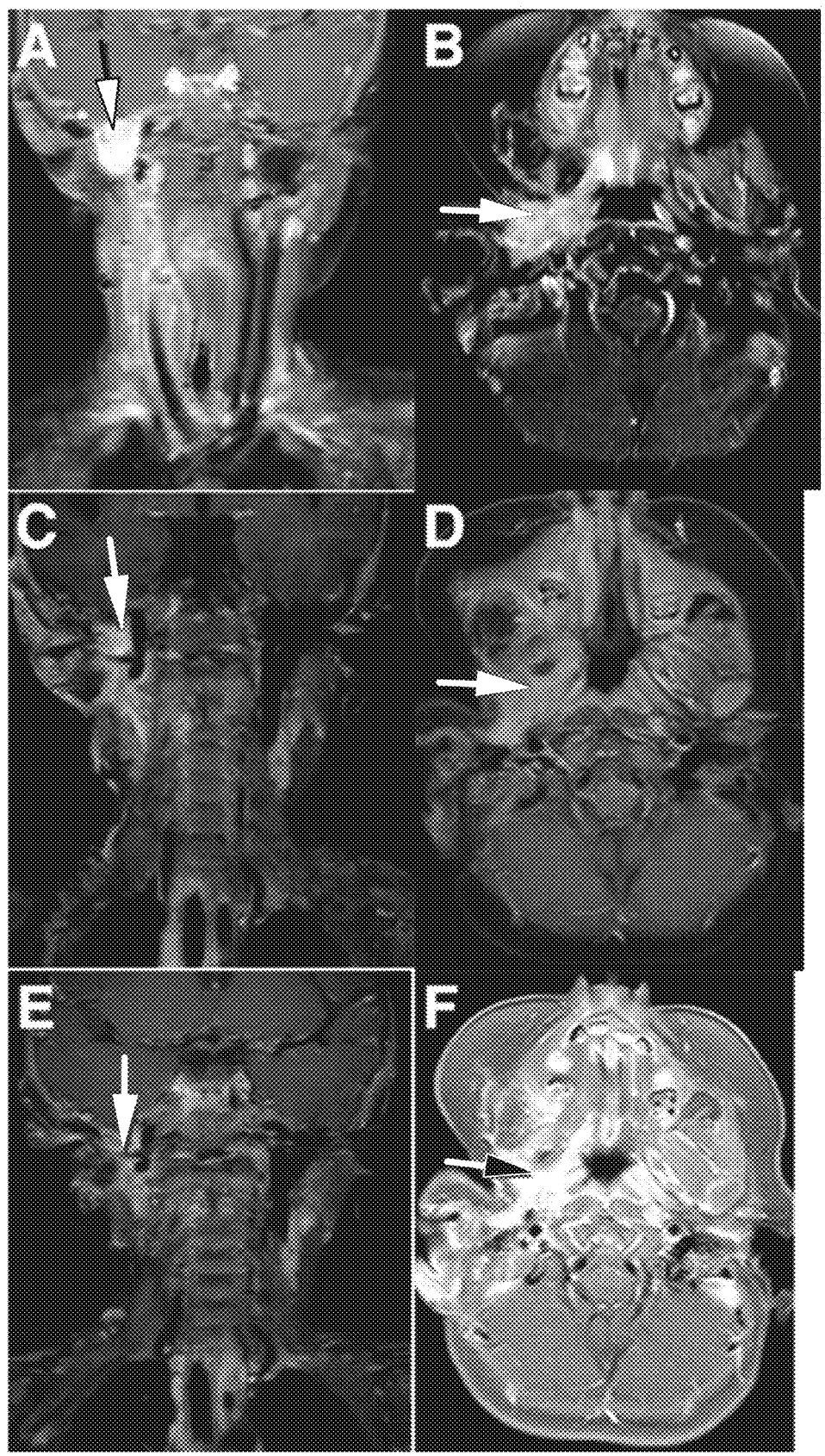
FIG. 10 is set of six MR images showing the brain in neck of the patient diagnosed with infantile fibrosarcoma. (A) and (B) are MR images of the brain and neck showing a 20 mm×19 mm×18 mm hyperenhancing mass involving the skull base of the middle cranial fossa, just anterior and inferior to the inner ear structures five weeks following surgical resection. (C) and (D) are MR images of the brain and neck showing a significant interval reduction in the size and enhancement of the mass by more than 90% from baseline at the end of cycle 1 (day 28) where the patient was administered the hydrogen sulfate salt of (S)—N-(5-((R)-2-(2,5-difluorophenyl)pyrrolidin-1-yl)-pyrazolo[1,5-a]pyrimidin-3-yl)-3-hydroxypyrrolidine-1-carboxamide BID. (E) and (F) are MR images of the brain and neck taken at the end of Cycle 2, which confirmed the size reduction and showed continued decrease in enhancement, confirming partial response.

Five weeks following surgical resection, an MR of the brain and neck showed a 20 mm×19 mm×18 mm hyperenhancing mass involving the skull base of the middle cranial fossa, just anterior and inferior to the inner ear structures FIG. 10A and FIG. 10B. Further chemotherapy was determined to be futile due to lack of response to all standard regimens. Repeat surgical resection was deemed not possible. Therapeutic radiotherapy was possible, but based on the age of the patient and location of the disease, it was expected to produce devastating long-term sequelae.

At the age of 16 months, the patient enrolled on the Phase 1 pediatric study of the oral, selective TRK inhibitor Compound I-HS. The parents noted improved engagement and playfulness throughout cycle 1. At the end of cycle 1 (day 28), an MR of the brain and neck showed a significant interval reduction in the size and enhancement of the mass by more than 90% from baseline FIG. 10C and FIG. 10D. Repeat scans at the end of Cycle 2 confirmed the size reduction and showed continued decrease in enhancement, confirming partial response FIG. 10E and FIG. 10F. During the first two cycles, the patient experienced fever and PCR-confirmed influenza A (considered not related) but no adverse events related to Compound I-HS.

Example 6

A Liquid Formulations of (S)—N-(5-((R)-2-(2,5-difluorophenyl)-pyrrolidin-1-yl)-pyrazolo[1,5-a]pyrimidin-3-yl)-3-hydroxypyrrolidine-1-carboxamide A liquid formulation of (S)—N-(5-((R)-2-(2,5-difluorophenyl)-pyrrolidin-1-yl)-pyrazolo[1,5-a]pyrimidin-3-yl)-3-hydroxypyrrolidine-1-carboxamide was prepared with the components listed in Table 16.

TABLE 16

A liquid formulations of (S)-N-(5-((R)-2-(2,5-difluorophenyl)-pyrrolidin-1-yl)-pyrazolo[1,5-a]pyrimidin-3-yl)-3-hydroxypyrrolidine-1-carboxamide.

| Material Name | % Weight (a) | Total Formulation Weight in grams (b) | Theoretical Quantity Required (a × b)/100 | Amount per bottle[1] |
|---|---|---|---|---|
| Compound I-HS API | 2.05% | 171,648 | 3,518.8 grams[1][2] | 1.47 g |
| Purified Water, USP | 33.55% | | 57,587.9 grams | 24.01 g |
| KLEPTOSE ® HPB Parenteral Grade EP, USP | 14.55% | | 24.974.8 grams | 10.48 g |
| ORA-SWEET ® | 48.51% | | 83.266.4 grams | 34.93 g |
| Sodium Citrate, Dihydrate. Granular, USP (Spectrum) | 0.94% | | 1.613.5 grams (1.694.2 grams)[3] | 0.68 g |
| 231a12 Natural Masking Type Flavor (Abelei) | 0.10% | | 171.6 grams | 0.07 g |
| 231a39 Natural Bitterness Masking Type Flavor (Abelei) | 0.20% | | 343.3 grams | 0.14 g |

TABLE 16-continued

A liquid formulations of (S)-N-(5-((R)-2-(2,5-difluorophenyl)-pyrrolidin-1-yl)-pyrazolo[1,5-a]pyrimidin-3-yl)-3-hydroxypyrrolidine-1-carboxamide.

| Material Name | % Weight (a) | Total Formulation Weight in grams (b) | Theoretical Quantity Required (a × b)/100 | Amount per bottle[1] |
|---|---|---|---|---|
| Bitterness Masking Flavor, Nat (FONA - Liquid) | 0.05% | | 85.8 grams | 0.04 g |
| FONATECH ® Taste Modifier Flavor, Nat | 0.05% | | 85.8 grams | 0.04 g |

[1]Includes an API correction factor of 0.8137. Calculation: Free base molecular weight/salt formula weight = 428.44/526.51. Density of the liquid formulation is 1.2 mg/mL.
[2]Label claim = 3,518.8 grams Salt Form API × 0.8137/171,648 grams total formulation * 1.2 g/mL density * 1,000 mg/g.
[3]Includes an additional 5% of the total amount of Sodium Citrate added to the formulation for pH adjustment, as needed.

REFERENCES

1. Wiesner et al., *Nature Comm.* 5:3116, 2014.
2. Vaishnavi et al., *Nature Med.* 19:1469-1472, 2013.
3. Greco et al., *Mol. Cell. Endocrinol.* 28:321, 2010.
4. Kim et al., *PloS ONE* 9(3):e91940, 2014.
5. Vaishnavi et al., *Nature Med.* 19:1469-1472, 2013.
6. Fernandez-Cuesta et al., "Cross-entity mutation analysis of lung neuroendocrine tumors sheds light into their molecular origin and identifies new therapeutic targets," *AACR Annual Meeting* 2014, Abstract, April 2014.
7. Stransky et al., *Nature Comm.* 5:4846, 2014.
8. Ross et al., *Oncologist* 19:235-242, 2014.
9. Doebele et al., *J. Clin. Oncol.* 32:5s, 2014.
10. Jones et al., *Nature Genetics* 45:927-932, 2013.
11. Wu et al., *Nature Genetics* 46:444-450, 2014.
12. WO 2013/059740
13. Zheng et al., "Anchored multiplex PCR for targeted next-generation sequencing," *Nature Med.*, published online on Nov. 10, 2014.
14. Caria et al., *Cancer Genet. Cytogenet.* 203:21-29, 2010.
15. Frattini et al., *Nature Genet.* 45:1141-1149, 2013.
16. Martin-Zanca et al., *Nature* 319:743, 1986.
17. Meyer et al., *Leukemia* 21: 2171-2180, 2007.
18. Reuther et al., *Mol. Cell. Biol.* 20:8655-8666, 2000.
19. Marchetti et al., *Human Mutation* 29(5):609-616, 2008.
20. Tacconelli et al., *Cancer Cell* 6:347, 2004.
21. Walch et al., *Clin. Exp. Metastasis* 17: 307-314, 1999.
22. Papatsoris et al., *Expert Opin. Invest. Drugs* 16(3):303-309, 2007.
23. Van Noesel et al., *Gene* 325: 1-15, 2004.
24. Zhang et al., *Oncology Reports* 14: 161-171, 2005.
25. Truzzi et al., *J Invest. Dermatol.* 128(8):2031, 2008.
26. Kolokythas et al., *J. Oral Maxillofacial Surgery* 68(6): 1290-1295, 2010.
27. Ni et al., *Asian Pacific Journal of Cancer Prevention* 13:1511, 2012.

What is claimed:

1. A liquid formulation comprising:
(S)—N-(5-((R)-2-(2,5-difluorophenyl)-pyrrolidin-1-yl)-pyrazolo[1,5-a]pyrimidin-3-yl)-3-hydroxypyrrolidine-1-carboxamide having the formula (I):

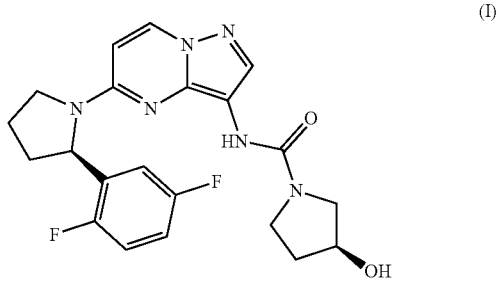 [SMILES: O=C(Nc1cnn2ccc(N3CCC[C@@H]3c3cc(F)ccc3F)nc12)N1CC[C@H](O)C1]

a pharmaceutically acceptable salt thereof, or a combination thereof;
hydroxypropyl-β-cyclodextrin;
sodium citrate; and
a sweetener;
wherein:
the formulation has a pH of about 2.5 to about 5.5; and
the compound of formula (I), the pharmaceutically acceptable salt thereof, or the combination thereof has a concentration of about 20 mg/mL to about 30 mg/mL in the liquid formulation.

2. The liquid formulation of claim 1, wherein the liquid formulation is prepared from the hydrogen sulfate salt of the compound of formula (I).

3. The liquid formulation of claim 1, wherein hydroxypropyl-β-cyclodextrin is present in the liquid formulation in an amount from about 13 wt. % to about 17 wt. %.

4. The liquid formulation of claim 3, wherein hydroxypropyl-β-cyclodextrin is present in the liquid formulation in an amount of about 15 wt. %.

5. The liquid formulation of claim 1, wherein sodium citrate includes at least one of sodium citrate monohydrate and sodium citrate dihydrate.

6. The liquid formulation of claim 5, wherein sodium citrate includes sodium citrate dihydrate.

7. The liquid formulation of claim 6, wherein sodium citrate dihydrate is present in the liquid formulation in an amount from about 0.7 wt. % to about 1.5 wt. %.

8. The liquid formulation of claim 7, wherein sodium citrate dihydrate is present in the liquid formulation in an amount of about 1.1 wt. %.

9. The liquid formulation of claim 1, wherein the sweetener includes sucrose, glycerin, sorbitol, and flavoring.

10. The liquid formulation of claim 9, wherein the sweetener further includes citric acid and sodium phosphate.

11. The liquid formulation of claim 10, wherein the sweetener further includes methylparaben and potassium sorbate.

12. The liquid formulation of claim 11, wherein the sweetener is present in the liquid formulation in an amount from about 45 wt. % to about 55 wt. %.

13. The liquid formulation of claim 12, wherein the sweetener is present in the liquid formulation in an amount of about 50 wt. %.

14. The liquid formulation of claim 9, further comprising a bitterness masking agent.

15. The liquid formulation of claim 14, wherein the bitterness masking agent is present in the liquid formulation in an amount from about 0.2 wt. % to about 0.5 wt. %.

16. The liquid formulation of claim 15, wherein the bitterness masking agent is present in the liquid formulation in an amount of about 0.4 wt. %.

17. The liquid formulation of claim 1, wherein the sweetener includes sucralose.

18. The liquid formulation of claim 17, further comprising a flavoring agent.

19. The liquid formulation of claim 18, wherein the flavoring agent is a berry flavoring agent.

20. The liquid formulation of claim 18, wherein the flavoring agent is present in the liquid formulation in an amount from about 0.01 wt. % to about 0.1 wt. %.

21. A liquid formulation comprising:
(S)—N-(5-((R)-2-(2,5-difluorophenyl)-pyrrolidin-1-yl)-pyrazolo[1,5-a]pyrimidin-3-yl)-3-hydroxypyrrolidine-1-carboxamide having the formula (I):

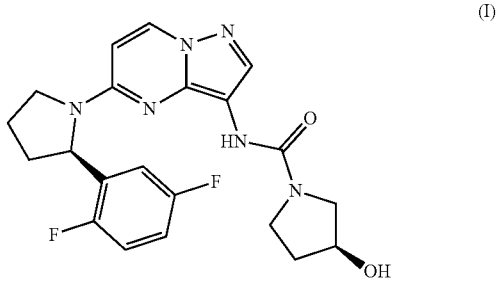 [SMILES: O=C(Nc1cnn2ccc(N3CCC[C@@H]3c3cc(F)ccc3F)nc12)N1CC[C@H](O)C1]

a pharmaceutically acceptable salt thereof, or a combination thereof;
hydroxypropyl-β-cyclodextrin present in an amount from about 13 wt. % to about 17 wt. %;
sodium citrate dihydrate present in an amount from about 0.7 wt. % to about 1.5 wt. %;
a sweetener that includes sucrose, glycerin, sorbitol, and flavoring, wherein the sweetener is buffered with citric acid and sodium phosphate, wherein the sweetener is preserved with methylparaben and potassium sorbate, and wherein the sweetener is present in an amount from about 45 wt. % to about 55 wt. %; and
a bitterness masking agent present in the liquid formulation in an amount from about 0.2 wt. % to about 0.5 wt. %;
wherein:
the formulation has a pH of about 2.5 to about 5.5; and
the compound of formula (I), the pharmaceutically acceptable salt thereof, or the combination thereof has a concentration of about 20 mg/mL to about 30 mg/mL in the liquid formulation.

22. A liquid formulation comprising:
(S)—N-(5-((R)-2-(2,5-difluorophenyl)-pyrrolidin-1-yl)-pyrazolo[1,5-a]pyrimidin-3-yl)-3-hydroxypyrrolidine-1-carboxamide having the formula (I):

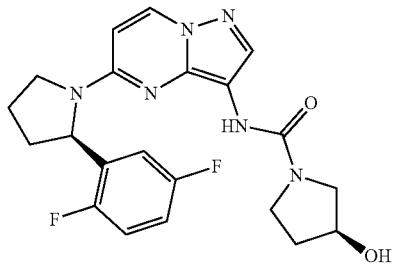

(I)

a pharmaceutically acceptable salt thereof, or a combination thereof;

hydroxypropyl-β-cyclodextrin present in an amount from about 13 wt. % to about 17 wt. %;

sodium citrate dihydrate present in an amount from about 0.7 wt. % to about 1.5 wt. %;

a sweetener that includes sucrose; and a flavoring agent present in an amount from about 0.01 wt. % to about 0.1 wt. %;

wherein:

the formulation has a pH of about 2.5 to about 5.5; and the compound of formula (I), the pharmaceutically acceptable salt thereof, or the combination thereof has a concentration of about 20 mg/mL to about 30 mg/mL in the liquid formulation.

* * * * *

SEQUENCE LISTING

```
<160> NUMBER OF SEQ ID NOS: 3

<210> SEQ ID NO 1
<211> LENGTH: 796
<212> TYPE: PRT
<213> ORGANISM: Homo sapiens

<400> SEQUENCE: 1

Met Leu Arg Gly Gly Arg Arg Gly Gln Leu Gly Trp His Ser Trp Ala
1               5                   10                  15

Ala Gly Pro Gly Ser Leu Leu Ala Trp Leu Ile Leu Ala Ser Ala Gly
            20                  25                  30

Ala Ala Pro Cys Pro Asp Ala Cys Cys Pro His Gly Ser Ser Gly Leu
        35                  40                  45

Arg Cys Thr Arg Asp Gly Ala Leu Asp Ser Leu His His Leu Pro Gly
    50                  55                  60

Ala Glu Asn Leu Thr Glu Leu Tyr Ile Glu Asn Gln Gln His Leu Gln
65                  70                  75                  80

His Leu Glu Leu Arg Asp Leu Arg Gly Leu Gly Glu Leu Arg Asn Leu
                85                  90                  95

Thr Ile Val Lys Ser Gly Leu Arg Phe Val Ala Pro Asp Ala Phe His
            100                 105                 110

Phe Thr Pro Arg Leu Ser Arg Leu Asn Leu Ser Phe Asn Ala Leu Glu
```

```
            115                 120                 125
Ser Leu Ser Trp Lys Thr Val Gln Gly Leu Ser Leu Gln Glu Leu Val
130                 135                 140

Leu Ser Gly Asn Pro Leu His Cys Ser Cys Ala Leu Arg Trp Leu Gln
145                 150                 155                 160

Arg Trp Glu Glu Glu Gly Leu Gly Gly Val Pro Glu Gln Lys Leu Gln
                165                 170                 175

Cys His Gly Gln Gly Pro Leu Ala His Met Pro Asn Ala Ser Cys Gly
                180                 185                 190

Val Pro Thr Leu Lys Val Gln Val Pro Asn Ala Ser Val Asp Val Gly
                195                 200                 205

Asp Asp Val Leu Leu Arg Cys Gln Val Glu Gly Arg Gly Leu Glu Gln
210                 215                 220

Ala Gly Trp Ile Leu Thr Glu Leu Glu Gln Ser Ala Thr Val Met Lys
225                 230                 235                 240

Ser Gly Gly Leu Pro Ser Leu Gly Leu Thr Leu Ala Asn Val Thr Ser
                245                 250                 255

Asp Leu Asn Arg Lys Asn Val Thr Cys Trp Ala Glu Asn Asp Val Gly
                260                 265                 270

Arg Ala Glu Val Ser Val Gln Val Asn Val Ser Phe Pro Ala Ser Val
                275                 280                 285

Gln Leu His Thr Ala Val Glu Met His His Trp Cys Ile Pro Phe Ser
290                 295                 300

Val Asp Gly Gln Pro Ala Pro Ser Leu Arg Trp Leu Phe Asn Gly Ser
305                 310                 315                 320

Val Leu Asn Glu Thr Ser Phe Ile Phe Thr Glu Phe Leu Glu Pro Ala
                325                 330                 335

Ala Asn Glu Thr Val Arg His Gly Cys Leu Arg Leu Asn Gln Pro Thr
                340                 345                 350

His Val Asn Asn Gly Asn Tyr Thr Leu Leu Ala Ala Asn Pro Phe Gly
                355                 360                 365

Gln Ala Ser Ala Ser Ile Met Ala Ala Phe Met Asp Asn Pro Phe Glu
370                 375                 380

Phe Asn Pro Glu Asp Pro Ile Pro Val Ser Phe Ser Pro Val Asp Thr
385                 390                 395                 400

Asn Ser Thr Ser Gly Asp Pro Val Glu Lys Lys Asp Glu Thr Pro Phe
                405                 410                 415

Gly Val Ser Val Ala Val Gly Leu Ala Val Phe Ala Cys Leu Phe Leu
                420                 425                 430

Ser Thr Leu Leu Leu Val Leu Asn Lys Cys Gly Arg Arg Asn Lys Phe
                435                 440                 445

Gly Ile Asn Arg Pro Ala Val Leu Ala Pro Glu Asp Gly Leu Ala Met
                450                 455                 460

Ser Leu His Phe Met Thr Leu Gly Gly Ser Ser Leu Ser Pro Thr Glu
465                 470                 475                 480

Gly Lys Gly Ser Gly Leu Gln Gly His Ile Ile Glu Asn Pro Gln Tyr
                485                 490                 495

Phe Ser Asp Ala Cys Val His His Ile Lys Arg Arg Asp Ile Val Leu
                500                 505                 510

Lys Trp Glu Leu Gly Glu Gly Ala Phe Gly Lys Val Phe Leu Ala Glu
                515                 520                 525

Cys His Asn Leu Leu Pro Glu Gln Asp Lys Met Leu Val Ala Val Lys
530                 535                 540
```

```
Ala Leu Lys Glu Ala Ser Glu Ser Ala Arg Gln Asp Phe Gln Arg Glu
545                 550                 555                 560

Ala Glu Leu Leu Thr Met Leu Gln His Gln His Ile Val Arg Phe Phe
                565                 570                 575

Gly Val Cys Thr Glu Gly Arg Pro Leu Leu Met Val Phe Glu Tyr Met
            580                 585                 590

Arg His Gly Asp Leu Asn Arg Phe Leu Arg Ser His Gly Pro Asp Ala
        595                 600                 605

Lys Leu Leu Ala Gly Gly Glu Asp Val Ala Pro Gly Pro Leu Gly Leu
    610                 615                 620

Gly Gln Leu Leu Ala Val Ala Ser Gln Val Ala Ala Gly Met Val Tyr
625                 630                 635                 640

Leu Ala Gly Leu His Phe Val His Arg Asp Leu Ala Thr Arg Asn Cys
                645                 650                 655

Leu Val Gly Gln Gly Leu Val Val Lys Ile Gly Asp Phe Gly Met Ser
            660                 665                 670

Arg Asp Ile Tyr Ser Thr Asp Tyr Tyr Arg Val Gly Gly Arg Thr Met
        675                 680                 685

Leu Pro Ile Arg Trp Met Pro Pro Glu Ser Ile Leu Tyr Arg Lys Phe
    690                 695                 700

Thr Thr Glu Ser Asp Val Trp Ser Phe Gly Val Val Leu Trp Glu Ile
705                 710                 715                 720

Phe Thr Tyr Gly Lys Gln Pro Trp Tyr Gln Leu Ser Asn Thr Glu Ala
                725                 730                 735

Ile Asp Cys Ile Thr Gln Gly Arg Glu Leu Glu Arg Pro Arg Ala Cys
            740                 745                 750

Pro Pro Glu Val Tyr Ala Ile Met Arg Gly Cys Trp Gln Arg Glu Pro
        755                 760                 765

Gln Gln Arg His Ser Ile Lys Asp Val His Ala Arg Leu Gln Ala Leu
    770                 775                 780

Ala Gln Ala Pro Pro Val Tyr Leu Asp Val Leu Gly
785                 790                 795

<210> SEQ ID NO 2
<211> LENGTH: 822
<212> TYPE: PRT
<213> ORGANISM: Homo sapiens

<400> SEQUENCE: 2

Met Ser Ser Trp Ile Arg Trp His Gly Pro Ala Met Ala Arg Leu Trp
1               5                   10                  15

Gly Phe Cys Trp Leu Val Val Gly Phe Trp Arg Ala Ala Phe Ala Cys
                20                  25                  30

Pro Thr Ser Cys Lys Cys Ser Ala Ser Arg Ile Trp Cys Ser Asp Pro
            35                  40                  45

Ser Pro Gly Ile Val Ala Phe Pro Arg Leu Glu Pro Asn Ser Val Asp
        50                  55                  60

Pro Glu Asn Ile Thr Glu Ile Phe Ile Ala Asn Gln Lys Arg Leu Glu
65                  70                  75                  80

Ile Ile Asn Glu Asp Asp Val Glu Ala Tyr Val Gly Leu Arg Asn Leu
                85                  90                  95

Thr Ile Val Asp Ser Gly Leu Lys Phe Val Ala His Lys Ala Phe Leu
            100                 105                 110

Lys Asn Ser Asn Leu Gln His Ile Asn Phe Thr Arg Asn Lys Leu Thr
```

-continued

```
            115                 120                 125
Ser Leu Ser Arg Lys His Phe Arg His Leu Asp Leu Ser Glu Leu Ile
130                 135                 140
Leu Val Gly Asn Pro Phe Thr Cys Ser Cys Asp Ile Met Trp Ile Lys
145                 150                 155                 160
Thr Leu Gln Glu Ala Lys Ser Ser Pro Asp Thr Gln Asp Leu Tyr Cys
                165                 170                 175
Leu Asn Glu Ser Ser Lys Asn Ile Pro Leu Ala Asn Leu Gln Ile Pro
                180                 185                 190
Asn Cys Gly Leu Pro Ser Ala Asn Leu Ala Ala Pro Asn Leu Thr Val
                195                 200                 205
Glu Glu Gly Lys Ser Ile Thr Leu Ser Cys Ser Val Ala Gly Asp Pro
210                 215                 220
Val Pro Asn Met Tyr Trp Asp Val Gly Asn Leu Val Ser Lys His Met
225                 230                 235                 240
Asn Glu Thr Ser His Thr Gln Gly Ser Leu Arg Ile Thr Asn Ile Ser
                245                 250                 255
Ser Asp Asp Ser Gly Lys Gln Ile Ser Cys Val Ala Glu Asn Leu Val
                260                 265                 270
Gly Glu Asp Gln Asp Ser Val Asn Leu Thr Val His Phe Ala Pro Thr
                275                 280                 285
Ile Thr Phe Leu Glu Ser Pro Thr Ser Asp His His Trp Cys Ile Pro
290                 295                 300
Phe Thr Val Lys Gly Asn Pro Lys Pro Ala Leu Gln Trp Phe Tyr Asn
305                 310                 315                 320
Gly Ala Ile Leu Asn Glu Ser Lys Tyr Ile Cys Thr Lys Ile His Val
                325                 330                 335
Thr Asn His Thr Glu Tyr His Gly Cys Leu Gln Leu Asp Asn Pro Thr
                340                 345                 350
His Met Asn Asn Gly Asp Tyr Thr Leu Ile Ala Lys Asn Glu Tyr Gly
                355                 360                 365
Lys Asp Glu Lys Gln Ile Ser Ala His Phe Met Gly Trp Pro Gly Ile
                370                 375                 380
Asp Asp Gly Ala Asn Pro Asn Tyr Pro Asp Val Ile Tyr Glu Asp Tyr
385                 390                 395                 400
Gly Thr Ala Ala Asn Asp Ile Gly Asp Thr Thr Asn Arg Ser Asn Glu
                405                 410                 415
Ile Pro Ser Thr Asp Val Thr Asp Lys Thr Gly Arg Glu His Leu Ser
                420                 425                 430
Val Tyr Ala Val Val Val Ile Ala Ser Val Val Gly Phe Cys Leu Leu
                435                 440                 445
Val Met Leu Phe Leu Leu Lys Leu Ala Arg His Ser Lys Phe Gly Met
                450                 455                 460
Lys Gly Pro Ala Ser Val Ile Ser Asn Asp Asp Asp Ser Ala Ser Pro
465                 470                 475                 480
Leu His His Ile Ser Asn Gly Ser Asn Thr Pro Ser Ser Glu Gly Gly
                485                 490                 495
Gly Pro Asp Ala Val Ile Gly Met Thr Lys Ile Pro Val Ile Glu
                500                 505                 510
Asn Pro Gln Tyr Phe Gly Ile Thr Asn Ser Gln Leu Lys Pro Asp Thr
                515                 520                 525
Phe Val Gln His Ile Lys Arg His Asn Ile Val Leu Lys Arg Glu Leu
530                 535                 540
```

Gly Glu Gly Ala Phe Gly Lys Val Phe Leu Ala Glu Cys Tyr Asn Leu
545                 550                 555                 560

Cys Pro Glu Gln Asp Lys Ile Leu Val Ala Val Lys Thr Leu Lys Asp
                565                 570                 575

Ala Ser Asp Asn Ala Arg Lys Asp Phe His Arg Glu Ala Glu Leu Leu
                580                 585                 590

Thr Asn Leu Gln His Glu His Ile Val Lys Phe Tyr Gly Val Cys Val
            595                 600                 605

Glu Gly Asp Pro Leu Ile Met Val Phe Glu Tyr Met Lys His Gly Asp
        610                 615                 620

Leu Asn Lys Phe Leu Arg Ala His Gly Pro Asp Ala Val Leu Met Ala
625                 630                 635                 640

Glu Gly Asn Pro Pro Thr Glu Leu Thr Gln Ser Gln Met Leu His Ile
                645                 650                 655

Ala Gln Gln Ile Ala Ala Gly Met Val Tyr Leu Ala Ser Gln His Phe
                660                 665                 670

Val His Arg Asp Leu Ala Thr Arg Asn Cys Leu Val Gly Glu Asn Leu
            675                 680                 685

Leu Val Lys Ile Gly Asp Phe Gly Met Ser Arg Asp Val Tyr Ser Thr
        690                 695                 700

Asp Tyr Tyr Arg Val Gly Gly His Thr Met Leu Pro Ile Arg Trp Met
705                 710                 715                 720

Pro Pro Glu Ser Ile Met Tyr Arg Lys Phe Thr Thr Glu Ser Asp Val
                725                 730                 735

Trp Ser Leu Gly Val Val Leu Trp Glu Ile Phe Thr Tyr Gly Lys Gln
                740                 745                 750

Pro Trp Tyr Gln Leu Ser Asn Asn Glu Val Ile Glu Cys Ile Thr Gln
            755                 760                 765

Gly Arg Val Leu Gln Arg Pro Arg Thr Cys Pro Gln Glu Val Tyr Glu
        770                 775                 780

Leu Met Leu Gly Cys Trp Gln Arg Glu Pro His Met Arg Lys Asn Ile
785                 790                 795                 800

Lys Gly Ile His Thr Leu Leu Gln Asn Leu Ala Lys Ala Ser Pro Val
                805                 810                 815

Tyr Leu Asp Ile Leu Gly
            820

<210> SEQ ID NO 3
<211> LENGTH: 839
<212> TYPE: PRT
<213> ORGANISM: Homo sapiens

<400> SEQUENCE: 3

Met Asp Val Ser Leu Cys Pro Ala Lys Cys Ser Phe Trp Arg Ile Phe
1               5                   10                  15

Leu Leu Gly Ser Val Trp Leu Asp Tyr Val Gly Ser Val Leu Ala Cys
                20                  25                  30

Pro Ala Asn Cys Val Cys Ser Lys Thr Glu Ile Asn Cys Arg Arg Pro
            35                  40                  45

Asp Asp Gly Asn Leu Phe Pro Leu Leu Glu Gly Gln Asp Ser Gly Asn
        50                  55                  60

Ser Asn Gly Asn Ala Ser Ile Asn Ile Thr Asp Ile Ser Arg Asn Ile
65                  70                  75                  80

Thr Ser Ile His Ile Glu Asn Trp Arg Ser Leu His Thr Leu Asn Ala

```
                     85                  90                  95
Val Asp Met Glu Leu Tyr Thr Gly Leu Gln Lys Leu Thr Ile Lys Asn
            100                 105                 110

Ser Gly Leu Arg Ser Ile Gln Pro Arg Ala Phe Ala Lys Asn Pro His
            115                 120                 125

Leu Arg Tyr Ile Asn Leu Ser Ser Asn Arg Leu Thr Thr Leu Ser Trp
            130                 135                 140

Gln Leu Phe Gln Thr Leu Ser Leu Arg Glu Leu Gln Leu Glu Gln Asn
145                 150                 155                 160

Phe Phe Asn Cys Ser Cys Asp Ile Arg Trp Met Gln Leu Trp Gln Glu
                165                 170                 175

Gln Gly Glu Ala Lys Leu Asn Ser Gln Asn Leu Tyr Cys Ile Asn Ala
            180                 185                 190

Asp Gly Ser Gln Leu Pro Leu Phe Arg Met Asn Ile Ser Gln Cys Asp
            195                 200                 205

Leu Pro Glu Ile Ser Val Ser His Val Asn Leu Thr Val Arg Glu Gly
            210                 215                 220

Asp Asn Ala Val Ile Thr Cys Asn Gly Ser Gly Ser Pro Leu Pro Asp
225                 230                 235                 240

Val Asp Trp Ile Val Thr Gly Leu Gln Ser Ile Asn Thr His Gln Thr
                245                 250                 255

Asn Leu Asn Trp Thr Asn Val His Ala Ile Asn Leu Thr Leu Val Asn
                260                 265                 270

Val Thr Ser Glu Asp Asn Gly Phe Thr Leu Thr Cys Ile Ala Glu Asn
            275                 280                 285

Val Val Gly Met Ser Asn Ala Ser Val Ala Leu Thr Val Tyr Tyr Pro
            290                 295                 300

Pro Arg Val Val Ser Leu Glu Glu Pro Glu Leu Arg Leu Glu His Cys
305                 310                 315                 320

Ile Glu Phe Val Val Arg Gly Asn Pro Pro Pro Thr Leu His Trp Leu
                325                 330                 335

His Asn Gly Gln Pro Leu Arg Glu Ser Lys Ile Ile His Val Glu Tyr
            340                 345                 350

Tyr Gln Glu Gly Glu Ile Ser Glu Gly Cys Leu Leu Phe Asn Lys Pro
            355                 360                 365

Thr His Tyr Asn Asn Gly Asn Tyr Thr Leu Ile Ala Lys Asn Pro Leu
            370                 375                 380

Gly Thr Ala Asn Gln Thr Ile Asn Gly His Phe Leu Lys Glu Pro Phe
385                 390                 395                 400

Pro Glu Ser Thr Asp Asn Phe Ile Leu Phe Asp Glu Val Ser Pro Thr
                405                 410                 415

Pro Pro Ile Thr Val Thr His Lys Pro Glu Glu Asp Thr Phe Gly Val
            420                 425                 430

Ser Ile Ala Val Gly Leu Ala Ala Phe Ala Cys Val Leu Leu Val Val
            435                 440                 445

Leu Phe Val Met Ile Asn Lys Tyr Gly Arg Arg Ser Lys Phe Gly Met
            450                 455                 460

Lys Gly Pro Val Ala Val Ile Ser Gly Glu Glu Asp Ser Ala Ser Pro
465                 470                 475                 480
```

```
Leu His His Ile Asn His Gly Ile Thr Thr Pro Ser Ser Leu Asp Ala
                485                 490                 495

Gly Pro Asp Thr Val Val Ile Gly Met Thr Arg Ile Pro Val Ile Glu
            500                 505                 510

Asn Pro Gln Tyr Phe Arg Gln Gly His Asn Cys His Lys Pro Asp Thr
        515                 520                 525

Tyr Val Gln His Ile Lys Arg Arg Asp Ile Val Leu Lys Arg Glu Leu
    530                 535                 540

Gly Glu Gly Ala Phe Gly Lys Val Phe Leu Ala Glu Cys Tyr Asn Leu
545                 550                 555                 560

Ser Pro Thr Lys Asp Lys Met Leu Val Ala Val Lys Ala Leu Lys Asp
                565                 570                 575

Pro Thr Leu Ala Ala Arg Lys Asp Phe Gln Arg Glu Ala Glu Leu Leu
            580                 585                 590

Thr Asn Leu Gln His Glu His Ile Val Lys Phe Tyr Gly Val Cys Gly
        595                 600                 605

Asp Gly Asp Pro Leu Ile Met Val Phe Glu Tyr Met Lys His Gly Asp
    610                 615                 620

Leu Asn Lys Phe Leu Arg Ala His Gly Pro Asp Ala Met Ile Leu Val
625                 630                 635                 640

Asp Gly Gln Pro Arg Gln Ala Lys Gly Glu Leu Gly Leu Ser Gln Met
                645                 650                 655

Leu His Ile Ala Ser Gln Ile Ala Ser Gly Met Val Tyr Leu Ala Ser
            660                 665                 670

Gln His Phe Val His Arg Asp Leu Ala Thr Arg Asn Cys Leu Val Gly
        675                 680                 685

Ala Asn Leu Leu Val Lys Ile Gly Asp Phe Gly Met Ser Arg Asp Val
    690                 695                 700

Tyr Ser Thr Asp Tyr Tyr Arg Leu Phe Asn Pro Ser Gly Asn Asp Phe
705                 710                 715                 720

Cys Ile Trp Cys Glu Val Gly Gly His Thr Met Leu Pro Ile Arg Trp
                725                 730                 735

Met Pro Pro Glu Ser Ile Met Tyr Arg Lys Phe Thr Thr Glu Ser Asp
            740                 745                 750

Val Trp Ser Phe Gly Val Ile Leu Trp Glu Ile Phe Thr Tyr Gly Lys
        755                 760                 765

Gln Pro Trp Phe Gln Leu Ser Asn Thr Glu Val Ile Glu Cys Ile Thr
    770                 775                 780

Gln Gly Arg Val Leu Glu Arg Pro Arg Val Cys Pro Lys Glu Val Tyr
785                 790                 795                 800

Asp Val Met Leu Gly Cys Trp Gln Arg Glu Pro Gln Gln Arg Leu Asn
                805                 810                 815

Ile Lys Glu Ile Tyr Lys Ile Leu His Ala Leu Gly Lys Ala Thr Pro
            820                 825                 830

Ile Tyr Leu Asp Ile Leu Gly
        835
```